United States Patent
Shin et al.

(10) Patent No.: US 11,472,966 B2
(45) Date of Patent: Oct. 18, 2022

(54) COATING COMPOSITION, ORGANIC LIGHT-EMITTING DIODE USING SAME AND METHOD FOR PREPARING SAME

(71) Applicant: LG Chem, Ltd., Seoul (KR)

(72) Inventors: Hyeonah Shin, Daejeon (KR); Sungkyoung Kang, Daejeon (KR); Kwanghyun Kim, Daejeon (KR); Jaesoon Bae, Daejeon (KR); Jaechol Lee, Daejeon (KR); Jae Hak Jeong, Daejeon (KR); Chung Whan Lee, Daejeon (KR); Hyungil Park, Daejeon (KR)

(73) Assignee: LG Chem, Ltd.

(*) Notice: Subject to any disclaimer, the term of this patent is extended or adjusted under 35 U.S.C. 154(b) by 729 days.

(21) Appl. No.: 16/469,923

(22) PCT Filed: Sep. 14, 2018

(86) PCT No.: PCT/KR2018/010845
§ 371 (c)(1),
(2) Date: Jun. 14, 2019

(87) PCT Pub. No.: WO2019/066338
PCT Pub. Date: Apr. 4, 2019

(65) Prior Publication Data
US 2019/0338140 A1    Nov. 7, 2019

(30) Foreign Application Priority Data

Sep. 26, 2017 (KR) ........................ 10-2017-0124472
Sep. 13, 2018 (KR) ........................ 10-2018-0109381

(51) Int. Cl.
C09D 4/00 (2006.01)
C07C 217/78 (2006.01)
(Continued)

(52) U.S. Cl.
CPC ............. C09D 4/00 (2013.01); C07C 217/78 (2013.01); H01L 51/006 (2013.01);
(Continued)

(58) Field of Classification Search
CPC . C09D 4/00; C09D 4/06; H01L 51/005–0074; H01L 51/50–5096
See application file for complete search history.

(56) References Cited

U.S. PATENT DOCUMENTS

2007/0102695 A1   5/2007   Inbasekaran et al.
2013/0137818 A1   5/2013   Schulte et al.
(Continued)

FOREIGN PATENT DOCUMENTS

| CN | 105733562 A | 7/2016 |
| JP | H11144875 A | 5/1999 |

(Continued)

OTHER PUBLICATIONS

International Search Report for Application No. PCT/KR2018/010845 dated Dec. 19, 2018, 2 pages.
(Continued)

*Primary Examiner* — Vu A Nguyen
(74) *Attorney, Agent, or Firm* — Lerner, David, Littenberg, Krumholz & Mentlik, LLP

(57) ABSTRACT

The present specification relates to a coating composition comprising a compound represented by Chemical Formula 1; and an ionic compound comprising an anion group represented by Chemical Formula 10, an organic light emitting device using the same, and a method for manufacturing the same.

19 Claims, 1 Drawing Sheet

```
701
601
501
401
301
201
101
```

(51) Int. Cl.
  *H01L 51/00*  (2006.01)
  *H01L 51/50*  (2006.01)
  *H01L 51/56*  (2006.01)

(52) U.S. Cl.
  CPC .......... *H01L 51/0039* (2013.01); *H01L 51/56* (2013.01); *C07C 2603/18* (2017.05); *H01L 51/0003* (2013.01); *H01L 51/0026* (2013.01); *H01L 51/506* (2013.01); *H01L 51/5088* (2013.01)

(56) References Cited

U.S. PATENT DOCUMENTS

| | | | |
|---|---|---|---|
| 2015/0094437 A1 | 4/2015 | Caille et al. | |
| 2016/0013417 A1* | 1/2016 | Oyamada | H01L 51/0036 438/46 |
| 2016/0163982 A1 | 6/2016 | Ishihara et al. | |

FOREIGN PATENT DOCUMENTS

| | | |
|---|---|---|
| JP | 2000178281 A | 6/2000 |
| JP | 2010021422 A | 1/2010 |
| KR | 20090114716 A | 11/2009 |
| KR | 101217942 B1 | 12/2012 |
| KR | 20130106255 A | 9/2013 |
| KR | 20140005862 A | 1/2014 |
| KR | 20140107594 A | 9/2014 |
| KR | 20150034379 A | 4/2015 |
| KR | 20150093995 A | 8/2015 |
| KR | 20160041124 A | 4/2016 |
| KR | 20160067728 A | 6/2016 |

OTHER PUBLICATIONS

International Search Report for Application No. PCT/KR2018/010841, dated Dec. 20, 2018, pp. 1-2.

* cited by examiner

| 701 |
| 601 |
| 501 |
| 401 |
| 301 |
| 201 |
| 101 |

COATING COMPOSITION, ORGANIC LIGHT-EMITTING DIODE USING SAME AND METHOD FOR PREPARING SAME

CROSS-REFERENCE TO RELATED APPLICATIONS

This application is a national phase entry under 35 U.S.C. § 371 of International Application No. PCT/KR2018/010845, filed Sep. 14, 2018, which claims priority to Korean Patent Application No. 10-2017-0124472, filed Sep. 26, 2017, and Korean Patent Application No. 10-2018-0109381, filed Sep. 13, 2018, the disclosures of which are incorporated herein by reference.

TECHNICAL FIELD

The present specification relates to a coating composition, an organic light emitting device formed using the coating composition, and a method for manufacturing the same.

BACKGROUND ART

An organic light emission phenomenon is one of examples converting current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer comprising a hole injection layer, a hole transfer layer, a light emitting layer and an electron transfer layer.

A deposition process has been normally used in the art for manufacturing an organic light emitting device. However, manufacturing an organic light emitting device using a deposition process has a problem of high material loss, and in order to resolve such a problem, technologies for manufacturing a device through a solution process capable of increasing production efficiency with low material loss have been developed, and development of materials usable in a solution process has been required.

Materials used in an organic light emitting device for a solution process need to have properties as follows.

First, a storable homogeneous solution needs to be formed. Commercialized materials for a deposition process have favorable crystallinity, and are not well-dissolved in a solution, or crystals are readily caught even when forming a solution. Therefore, a concentration gradient of the solution may change depending on the storage time or possibility of forming a defective device is high.

Second, materials used in the solution process need to have excellent coatability when forming a thin film so that a thin film with a uniform thickness is formed without causing holes or aggregation.

Third, layers going through the solution process need to have tolerance for solvents and materials used in the process forming other layers, and excellent current efficiency and excellent lifetime properties are required when manufacturing an organic light emitting device.

Accordingly, development of new compositions has been required in the art.

DISCLOSURE

Technical Problem

The present specification is directed to providing a coating composition usable in an organic light emitting device for a solution process, an organic light emitting device comprising the same, and a method for manufacturing the same.

Technical Solution

One embodiment of the present specification provides a coating composition comprising a compound represented by the following Chemical Formula 1; and an ionic compound comprising an anion group represented by the following Chemical Formula 10.

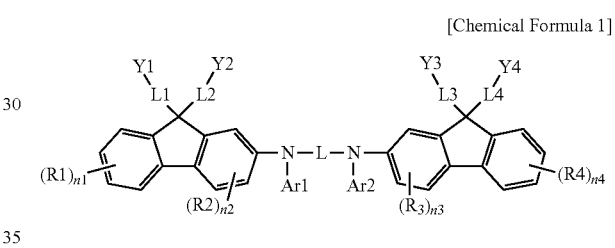

[Chemical Formula 1]

In Chemical Formula 1,

L and L1 to L4 are the same as or different from each other, and each independently a substituted or unsubstituted arylene group, Ar1 and Ar2 are the same as or different from each other, and each independently a substituted or unsubstituted aryl group; or a substituted or unsubstituted heteroaryl group, R1 to R4 are the same as or different from each other, and each independently hydrogen; deuterium; a substituted or unsubstituted alkyl group; a substituted or unsubstituted alkoxy group; a substituted or unsubstituted aryl group; or a substituted or unsubstituted heteroaryl group, Y1 to Y4 are the same as or different from each other, and each independently —(R201)s; or —X-A, and two or more of Y1 to Y4 are —X-A, R201 is hydrogen; deuterium; a halogen group; a substituted or unsubstituted alkyl group; a substituted or unsubstituted alkoxy group; a substituted or unsubstituted aryl group; or a substituted or unsubstituted aryloxy group, s is an integer of 0 to 5, and when s is 2 or greater, two or more R201s are the same as or different from each other, X is O or S, A is a functional group crosslinkable by heat or light, n1 and n4 are each independently an integer of 0 to 4, n2 and n3 are each independently an integer of 0 to 3, and when n1 to n4 are each 2 or greater, substituents in the parentheses are the same as or different from each other,

[Chemical Formula 10]

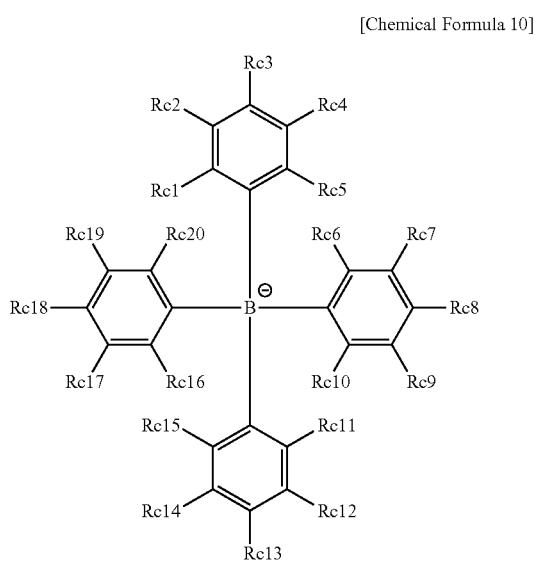

in Chemical Formula 10, at least one of Rc1 to Rc20 is F, a cyano group, or a substituted or unsubstituted fluoroalkyl group, at least one of the remaining Rc1 to Rc20 is a functional group crosslinkable by heat or light, the remaining Rc1 to Rc20 are the same as or different from each other, and each independently hydrogen; deuterium; a nitro group; —C(O)$R_{100}$; —O$R_{101}$; —S$R_{102}$; —$SO_3R_{103}$; —COO$R_{104}$; —OC(O)$R_{105}$; —C(O)N$R_{106}R_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, and $R_{100}$ to $R_{107}$ are the same as or different from each other, and each independently hydrogen; deuterium; or a substituted or unsubstituted alkyl group.

In addition, one embodiment of the present specification provides an organic light emitting device comprising a first electrode; a second electrode; and one or more organic material layers provided between the first electrode and the second electrode, wherein one or more layers of the organic material layers comprise the coating composition; or a cured material thereof.

Lastly, one embodiment of the present specification provides a method for manufacturing an organic light emitting device comprising preparing a substrate; forming a first electrode on the substrate; forming one or more organic material layers on the first electrode; and forming a second electrode on the organic material layer, wherein the forming of organic material layers comprises forming one or more organic material layers using the coating composition.

Advantageous Effects

A coating composition according to one embodiment of the present disclosure can be used in a solution process, and therefore, large area devices can be manufactured. The compound can be used as a material of an organic material layer of an organic light emitting device, and low driving voltage, high light emission efficiency and long lifetime properties can be provided.

In addition, by forming a thin film completely cured from heat treatment at less than 220° C. or UV treatment, the compound according to one embodiment of the present specification forms a stable thin film not damaged from a next solution process.

Moreover, solubility increases by using the compound of the present disclosure, which has an advantage of widening solvent selection when preparing a coating composition of a solution process.

DESCRIPTION OF DRAWINGS

The FIGURE illustrates an example of an organic light emitting device according to one embodiment of the present specification.

101: Substrate
201: Anode
301: Hole Injection Layer
401: Hole Transfer Layer
501: Light Emitting Layer
601: Electron Transfer Layer
701: Cathode

MODE FOR DISCLOSURE

Hereinafter, the present specification will be described in detail.

One embodiment of the present specification provides a coating composition comprising a compound represented by the following Chemical Formula 1; and an ionic compound comprising an anion group represented by the following Chemical Formula 10.

[Chemical Formula 1]

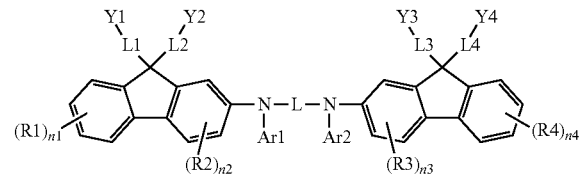

In Chemical Formula 1,

L and L1 to L4 are the same as or different from each other, and each independently a substituted or unsubstituted arylene group, Ar1 and Ar2 are the same as or different from each other, and each independently a substituted or unsubstituted aryl group; or a substituted or unsubstituted heteroaryl group, R1 to R4 are the same as or different from each other, and each independently hydrogen; deuterium; a substituted or unsubstituted alkyl group; a substituted or unsubstituted alkoxy group; a substituted or unsubstituted aryl group; or a substituted or unsubstituted heteroaryl group, Y1 to Y4 are the same as or different from each other, and each independently —(R201)s; or —X-A, and two or more of Y1 to Y4 are —X-A, R201 is hydrogen; deuterium; a halogen group; a substituted or unsubstituted alkyl group; a substituted or unsubstituted alkoxy group; a substituted or unsubstituted aryl group; or a substituted or unsubstituted aryloxy group, s is an integer of 0 to 5, and when s is 2 or greater, two or more R201s are the same as or different from each other, X is O or S, A is a functional group crosslinkable by heat or light, n1 and n4 are each independently an integer of 0 to 4, n2 and n3 are each independently an integer of 0 to 3, and when n1 to n4 are each 2 or greater, substituents in the parentheses are the same as or different from each other,

[Chemical Formula 10]

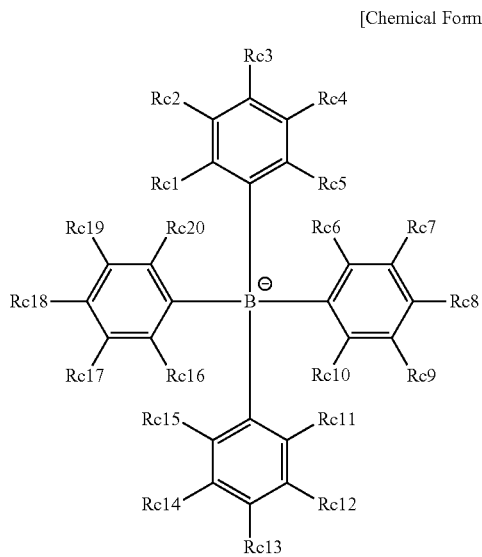

in Chemical Formula 10, at least one of Rc1 to Rc20 is F, a cyano group, or a substituted or unsubstituted fluoroalkyl group, at least one of the remaining Rc1 to Rc20 is a functional group crosslinkable by heat or light, the remaining Rc1 to Rc20 if available are the same as or different from each other, and each independently hydrogen; deuterium; a nitro group; —C(O)R$_{100}$; —OR$_{101}$; —SR$_{102}$; —SO$_3$R$_{103}$; COOR$_{104}$; —OC(O)R$_{105}$; —C(O)NR$_{106}$R$_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, and R$_{100}$ to R$_{107}$ are the same as or different from each other, and each independently hydrogen; deuterium; or a substituted or unsubstituted alkyl group.

The compound represented by Chemical Formula 1 according to one embodiment of the present disclosure forms a stable thin film completely cured from heat treatment or UV treatment by comprising an oxygen (O) or sulfur (S) atom in the compound. Specifically, the compound represented by Chemical Formula 1 according to one embodiment of the present disclosure described above has high affinity with hydrocarbon series and/or ether series solvents and thereby has solvent selectivity (orthogonality) by comprising an alkyl group, an alkoxy group or an aryloxy group in the compound, and may prevent migration to other layers by having tolerance for solvents used when forming layers other than an organic material layer comprising the compound using a solution process.

In addition, excellent coatability, low driving voltage, high light emission efficiency and long lifetime properties may be provided.

In the present specification, a description of a certain member being placed "on" another member comprises not only a case of the one member adjoining the another member but a case of still another member being present between the two members.

In the present specification, a description of a certain part "comprising" certain constituents means capable of further comprising other constituents, and does not exclude other constituents unless particularly stated on the contrary.

The compound represented by Chemical Formula 1 according to one embodiment of the present specification preferably comprises compounds having solubility for proper organic solvents.

In addition, with the compound represented by Chemical Formula 1 according to one embodiment of the present specification, an organic light emitting device may be manufactured using a solution coating method, and therefore, large area devices may be manufactured.

In the present specification, the "functional group crosslinkable by heat or light" may mean a reactive substituent crosslinking compounds by being exposed to heat or light. The crosslinkage may be produced by linking radicals produced while carbon-carbon multiple bonds or cyclic structures are disintegrated by heat treatment or light irradiation.

Hereinafter, substituents of the present specification will be described in detail.

In the present specification,

means a site bonding to other substituents or bonding sites.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents each independently selected from the group consisting of deuterium; a halogen group; a cyano group; a nitro group; a hydroxyl group; a silyl group; a boron group; an alkyl group; a cycloalkyl group; an alkoxy group; an aryloxy group; an aryl group; and a heterocyclic group, or being unsubstituted, or being substituted with a substituent linking two or more substituents among the substituents illustrated above, or being unsubstituted. For example, "a substituent linking two or more substituents" may comprise a biphenyl group. In other words, a biphenyl group may be an aryl group, or interpreted as a substituent linking two phenyl groups.

In the present specification, the halogen group is fluorine (F), chlorine (Cl), bromine (Br) or iodine (I).

In the present specification, the silyl group may be represented by a chemical formula of —SiR$_a$R$_b$R$_c$, and R$_a$, R$_b$ and R$_c$ may each independently be hydrogen; a substituted or unsubstituted alkyl group; or a substituted or unsubstituted aryl group. Specific examples of the silyl group may include a trimethylsilyl group, a triethylsilyl group, a tert-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by a chemical formula of —$BR_dR_e$, and $R_d$ and $R_e$ may each independently be hydrogen; a substituted or unsubstituted alkyl group; or a substituted or unsubstituted aryl group. Specific examples of the boron group may include a trimethylboron group, a triethylboron group, a tert-butyldimethylboron group, a triphenylboron group, a phenylboron group and the like, but are not limited thereto.

In the present specification, the alkyl group may be linear or branched, and although not particularly limited thereto, the number of carbon atoms may be from 1 to 60, and according to one embodiment, the number of carbon atoms of the alkyl group may be from 1 to 30. According to another embodiment, the number of carbon atoms of the alkyl group is from 1 to 10. Specific examples of the alkyl group may include a methyl group, an ethyl group, a propyl group, an isopropyl group, an n-butyl group, an isobutyl group, a tert-butyl group, an n-pentyl group, an n-hexyl group, an n-heptyl group and the like, but are not limited thereto.

In the present specification, the cycloalkyl group is not particularly limited, but may have 3 to 60 carbon atoms, and according to one embodiment, the number of carbon atoms of the cycloalkyl group is from 3 to 40. According to another embodiment, the number of carbon atoms of the cycloalkyl group is from 3 to 20. Specific examples of the cycloalkyl group may include a cyclopropyl group, a cyclobutyl group, a cyclopentyl group, a cyclohexyl group, a cycloheptyl group, a cyclooctyl group and the like, but are not limited thereto.

In the present specification, the alkoxy group may be linear, branched or cyclic. The number of carbon atoms of the alkoxy group is not particularly limited, but may be from 1 to 20. Specific examples of the alkoxy group may include a methoxy group, an ethoxy group, an n-propoxy group, an n-butoxy group, a tert-butoxy group, an n-pentyloxy group, an n-hexyloxy group, an n-octyloxy group, an n-nonyloxy group, an n-decyloxy group and the like, but are not limited thereto.

In the present specification, the number of carbon atoms of the aryloxy group is not particularly limited, but may be from 6 to 60. Descriptions on the aryl group to provide below are applied to the aryl group in the aryloxy group.

In the present specification, the aryl group is not particularly limited, but may have 6 to 60 carbon atoms, and may be a monocyclic aryl group or a polycyclic aryl group.

According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the polycyclic aryl group may include a naphthyl group, an anthracenyl group, a phenanthrenyl group, a pyrenyl group, a perylenyl group, a triphenyl group, a chrysenyl group, a fluorenyl group and the like, but are not limited thereto.

In the present specification, the fluorenyl group may be substituted, and two substituents may bond to each other to form a spiro structure.

When the fluorenyl group is substituted, spirofluorenyl groups such as

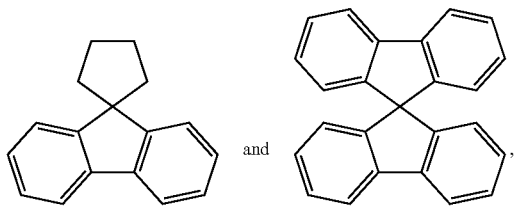

and substituted fluorenyl groups such as

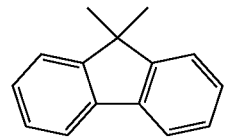

(9,9-dimethylfluorenyl group) and

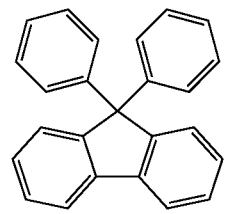 [SMILES: c1ccc(C2(c3ccccc3)c3ccccc3-c3ccccc32)cc1]

(9,9-diphenylfluorenyl group) may be included. However, the structure is not limited thereto.

In the present specification, the heterocyclic group is a heterocyclic group including one or more of N, O, P, S, Si or Se as a heteroatom, and although not particularly limited thereto, the number of carbon atoms may be from 2 to 60. According to one embodiment, the number of carbon atoms of the heterocyclic group is from 2 to 30. According to another embodiment, the number of carbon atoms of the heterocyclic group is from 2 to 20. Examples of the heterocyclic group may include a pyridyl group, a pyrrole group, a pyrimidyl group, a pyridazinyl group, a furanyl group, a thiophene group, a benzothiophene group, a benzofuran group, a dibenzothiophene group, a dibenzofuran group and the like, but are not limited thereto.

In the present specification, descriptions on the heterocyclic group provided above may be applied to the heteroaryl group except for being aromatic.

In the present specification, descriptions on the aryl group provided above are applied to the arylene group except for being divalent.

In the present specification, descriptions on the aryl group provided above are applied to the aryl group in the aryloxy group.

According to one embodiment of the present specification, L is a substituted or unsubstituted arylene group having 6 to 60 carbon atoms.

In another embodiment, L is a substituted or unsubstituted arylene group having 6 to 30 carbon atoms.

According to another embodiment, L is a substituted or unsubstituted phenylene group; or a substituted or unsubstituted biphenylylene group. When L is a substituted or unsubstituted phenylene group; or a substituted or unsubstituted biphenylylene group, a conjugate structure that the phenylene group or the biphenylylene group has allows an energy level suitable for hole injection and hole transfer by enabling holes to smoothly migrate, and a manufactured organic light emitting device has low driving voltage, high light emission efficiency and excellent lifetime properties.

According to one embodiment of the present specification, L may be represented by the following Chemical Formula 1-A or 1-B.

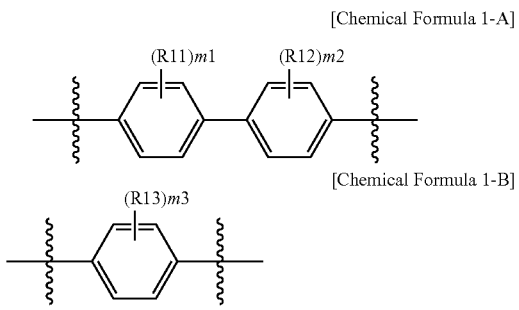

[Chemical Formula 1-A]

[Chemical Formula 1-B]

In Chemical Formulae 1-A and 1-B,

R11 to R13 are the same as or different from each other, and each independently hydrogen; deuterium; a substituted or unsubstituted alkyl group; a substituted or unsubstituted alkoxy group; a substituted or unsubstituted aryl group; or a substituted or unsubstituted heteroaryl group, m1 to m3 are each independently an integer of 0 to 4, and when m1 to m3 are 2 or greater, substituents in the parentheses are the same as or different from each other.

In one embodiment of the present specification, R11 to R13 are the same as or different from each other, and each independently hydrogen; deuterium; a substituted or unsubstituted alkyl group having 1 to 60 carbon atoms; a substituted or unsubstituted alkoxy group having 1 to 20 carbon atoms; a substituted or unsubstituted aryl group having 6 to 60 carbon atoms; or a substituted or unsubstituted heteroaryl group having 2 to 60 carbon atoms.

According to another embodiment, R11 to R13 are the same as or different from each other, and each independently hydrogen; deuterium; a substituted or unsubstituted alkyl group having 1 to 30 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms.

According to another embodiment, R11 to R13 are the same as or different from each other, and each independently hydrogen; deuterium; a substituted or unsubstituted alkyl group having 1 to 30 carbon atoms; a substituted or unsubstituted aryl group having 6 to 30 carbon atoms; or a substituted or unsubstituted heteroaryl group having 2 to 30 carbon atoms.

In another embodiment, R11 to R13 are the same as or different from each other, and each independently hydrogen; deuterium; a substituted or unsubstituted methyl group; a substituted or unsubstituted ethyl group; a substituted or unsubstituted n-propyl group; a substituted or unsubstituted n-butyl group; a substituted or unsubstituted tert-butyl group; a substituted or unsubstituted phenyl group; a substituted or unsubstituted biphenyl group; or a substituted or unsubstituted dibenzofuran group.

According to another embodiment, R11 to R13 are the same as or different from each other, and each independently hydrogen; deuterium; a methyl group; an ethyl group; an n-propyl group; an n-butyl group; a tert-butyl group; a phenyl group; a biphenyl group; or a dibenzofuran group.

In another embodiment, R11 to R13 are hydrogen.

According to one embodiment of the present specification, m1 to m3 are each independently 0 or 1.

In one embodiment of the present specification, Ar1 and Ar2 are the same as or different from each other, and each independently a substituted or unsubstituted aryl group having 6 to 60 carbon atoms; or a substituted or unsubstituted heteroaryl group having 2 to 60 carbon atoms.

According to another embodiment, Ar1 and Ar2 are the same as or different from each other, and each independently a substituted or unsubstituted aryl group having 6 to 30 carbon atoms; or a substituted or unsubstituted heteroaryl group having 2 to 30 carbon atoms.

In one embodiment of the present specification, Art and Ar2 are the same as or different from each other, and each independently a substituted or unsubstituted aryl group having 6 to 30 carbon atoms.

According to another embodiment, Ar1 and Ar2 are the same as or different from each other, and each independently a substituted or unsubstituted phenyl group; a substituted or unsubstituted biphenyl group; a substituted or unsubstituted terphenyl group; or a substituted or unsubstituted naphthyl group.

In another embodiment, Ar1 and Ar2 are the same as or different from each other, and each independently a phenyl group; a biphenyl group; a terphenyl group; or a naphthyl group.

In one embodiment of the present specification, R1 to R4 are the same as or different from each other, and each independently hydrogen; deuterium; a substituted or unsubstituted alkyl group having 1 to 60 carbon atoms; a substituted or unsubstituted alkoxy group having 1 to 20 carbon atoms; a substituted or unsubstituted aryl group having 6 to 60 carbon atoms; or a substituted or unsubstituted heteroaryl group having 2 to 60 carbon atoms.

According to another embodiment, R1 to R4 are the same as or different from each other, and each independently hydrogen; deuterium; a substituted or unsubstituted alkyl group having 1 to 30 carbon atoms; a substituted or unsubstituted aryl group having 6 to 30 carbon atoms; or a substituted or unsubstituted heteroaryl group having 2 to 30 carbon atoms.

In another embodiment, R1 to R4 are the same as or different from each other, and each independently hydrogen; deuterium; a substituted or unsubstituted methyl group; a substituted or unsubstituted ethyl group; a substituted or unsubstituted phenyl group; a substituted or unsubstituted biphenyl group; a substituted or unsubstituted dibenzothiophene group; or a substituted or unsubstituted dibenzofuran group.

According to another embodiment, R1 to R4 are the same as or different from each other, and each independently hydrogen; deuterium; a methyl group; an ethyl group; a phenyl group; a biphenyl group; a dibenzothiophene group; or a dibenzofuran group.

In another embodiment, R2 and R3 are hydrogen, and R1 and R4 are a phenyl group.

In another embodiment, R1 to R4 are hydrogen.

According to one embodiment of the present specification, n1 to n4 are each independently 0 or 1.

According to one embodiment of the present specification, Y1 to Y4 are the same as or different from each other, and each independently —(R201)s; or —X-A, and two or more of Y1 to Y4 are —X-A.

In another embodiment, Y1 to Y4 are the same as or different from each other, and each independently —(R201)s; or —X-A, and two of Y1 to Y4 are —X-A.

According to another embodiment, Y1 and Y4 are the same as or different from each other, and each independently —X-A, and Y2 and Y3 are —(R201)s.

In another embodiment, Y1 and Y2 are the same as or different from each other, and each independently —X-A, and Y3 and Y4 are —(R201)s.

According to another embodiment, Y1, Y2 and Y4 are the same as or different from each other, and each independently —X-A, and Y3 is —(R201)s.

In another embodiment, Y1 to Y4 are the same as or different from each other, and each independently —X-A.

In one embodiment of the present specification, X is O or S.

According to one embodiment of the present specification, A is a functional group crosslinkable by heat or light.

The functional group crosslinkable by heat or light may be any one of the following structures.

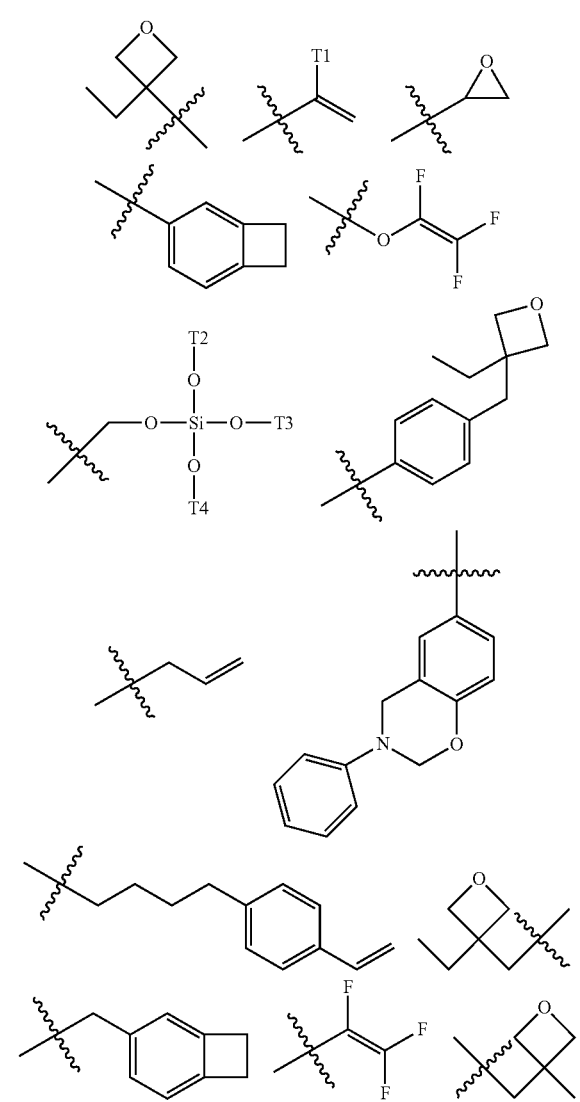

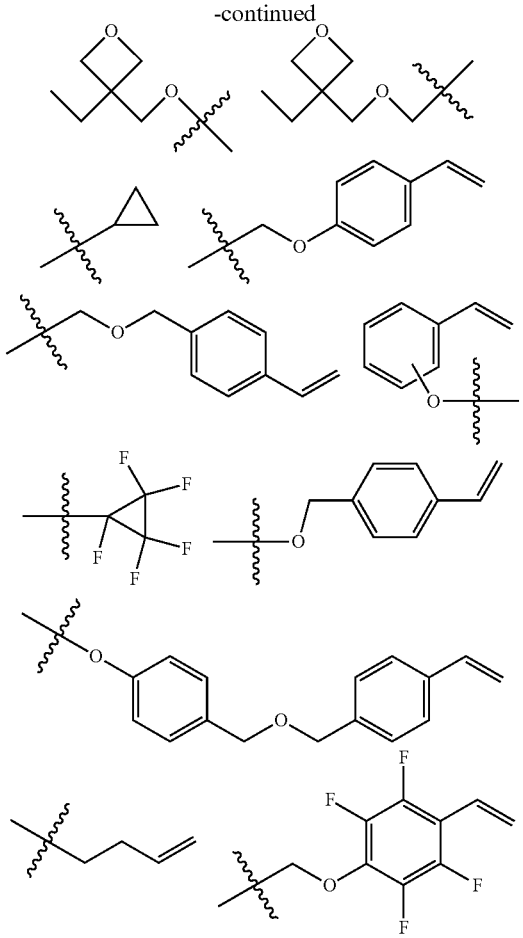

In the structures,

T1 is hydrogen; or a substituted or unsubstituted alkyl group having 1 to 6 carbon atoms, and T2 to T4 are the same as or different from each other, and each independently a substituted or unsubstituted alkyl group having 1 to 6 carbon atoms.

In one embodiment of the present specification, T1 is hydrogen; a substituted or unsubstituted methyl group; a substituted or unsubstituted ethyl group; a substituted or unsubstituted n-propyl group; a substituted or unsubstituted n-butyl group; or a substituted or unsubstituted tert-butyl group.

In another embodiment, T1 is hydrogen; a methyl group; an ethyl group; an n-propyl group; an n-butyl group; or a tert-butyl group.

According to one embodiment of the present specification, T2 to T4 are the same as or different from each other, and each independently a substituted or unsubstituted methyl group; a substituted or unsubstituted ethyl group; a substituted or unsubstituted n-propyl group; a substituted or unsubstituted n-butyl group; or a substituted or unsubstituted tert-butyl group.

In another embodiment, T2 to T4 are the same as or different from each other, and each independently a methyl group; an ethyl group; an n-propyl group; an n-butyl group; or a tert-butyl group.

According to one embodiment of the present specification, s is an integer of 0 to 2, and when s is 2, two R201s are the same as or different from each other.

In one embodiment of the present specification, R201 is hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted aryloxy group having 4 to 30 carbon atoms.

In one embodiment of the present specification, R201 is hydrogen; deuterium; a halogen group; an alkyl group having 1 to 20 carbon atoms; an alkoxy group having 1 to 20 carbon atoms unsubstituted or substituted with an alkoxy group having 1 to 20 carbon atoms; an aryl group having 6 to 30 carbon atoms; or an aryloxy group having 6 to 30 carbon atoms.

According to another embodiment, R201 is hydrogen; deuterium; fluorine (—F); a substituted or unsubstituted methyl group; a substituted or unsubstituted butyl group; a substituted or unsubstituted methoxy group; a substituted or unsubstituted ethoxy group; a substituted or unsubstituted ethylhexyloxy group; or a substituted or unsubstituted phenyloxy group.

In another embodiment, R201 is hydrogen; deuterium; fluorine (—F); a methyl group; a butyl group; a methoxy group; an ethoxy group unsubstituted or substituted with an alkoxy group having 1 to 20 carbon atoms; an ethylhexyloxy group; or a phenyloxy group.

According to another embodiment, R201 is hydrogen; deuterium; fluorine (—F); a methyl group; a tert-butyl group; a methoxy group; an ethoxy group unsubstituted or substituted with an ethoxy group; a 2-ethylhexyloxy group; or a phenyloxy group.

According to one embodiment of the present specification, L1 to L4 are the same as or different from each other, and each independently a substituted or unsubstituted arylene group having 6 to 60 carbon atoms.

According to another embodiment, L1 to L4 are the same as or different from each other, and each independently a substituted or unsubstituted arylene group having 6 to 30 carbon atoms.

In another embodiment, L1 to L4 are the same as or different from each other, and each independently an arylene group having 6 to 30 carbon atoms unsubstituted or substituted with one or more substituents selected from the group consisting of a halogen group, a substituted or unsubstituted alkyl group having 1 to 20 carbon atoms, a substituted or unsubstituted alkoxy group having 1 to 20 carbon atoms and a substituted or unsubstituted aryloxy group having 6 to 30 carbon atoms.

In another embodiment, L1 to L4 are the same as or different from each other, and each independently an arylene group having 6 to 30 carbon atoms unsubstituted or substituted with one or more substituents selected from the group consisting of a halogen group, an alkyl group having 1 to 20 carbon atoms, an alkoxy group having 1 to 20 carbon atoms unsubstituted or substituted with an alkoxy group having 1 to 20 carbon atoms, and an aryloxy group having 6 to 30 carbon atoms.

According to another embodiment, L1 to L4 are the same as or different from each other, and each independently a phenylene group unsubstituted or substituted with one or more substituents selected from the group consisting of a halogen group, a substituted or unsubstituted alkyl group having 1 to 20 carbon atoms, a substituted or unsubstituted alkoxy group having 1 to 20 carbon atoms and a substituted or unsubstituted aryloxy group having 6 to 30 carbon atoms; or a naphthylene group unsubstituted or substituted with one or more substituents selected from the group consisting of a halogen group, a substituted or unsubstituted alkyl group having 1 to 20 carbon atoms, a substituted or unsubstituted alkoxy group having 1 to 20 carbon atoms and a substituted or unsubstituted aryloxy group having 6 to 30 carbon atoms.

In another embodiment, L1 to L4 are the same as or different from each other, and each independently a phenylene group unsubstituted or substituted with one or more substituents selected from the group consisting of fluorine (—F), a substituted or unsubstituted methyl group, a substituted or unsubstituted tert-butyl group, a substituted or unsubstituted methoxy group, a substituted or unsubstituted ethoxy group, a substituted or unsubstituted 2-ethylhexyloxy group and a substituted or unsubstituted phenyloxy group; or a naphthylene group unsubstituted or substituted with one or more substituents selected from the group consisting of fluorine (—F), a substituted or unsubstituted methyl group, a substituted or unsubstituted tert-butyl group, a substituted or unsubstituted methoxy group, a substituted or unsubstituted ethoxy group, a substituted or unsubstituted 2-ethylhexyloxy group and a substituted or unsubstituted phenyloxy group.

According to another embodiment, L1 to L4 are the same as or different from each other, and each independently a phenylene group; a naphthylene group; a fluorophenylene group; a methylphenylene group; a dimethylphenylene group; a tert-butylphenylene group; a methoxyphenylene group; an ethoxyethoxyphenylene group; a phenyloxyphenylene group; or a 2-ethylhexyloxyphenylene group.

According to one embodiment of the present specification, Chemical Formula 1 may be represented by any one of the following Chemical Formulae 2 to 5.

[Chemical Formula 2]

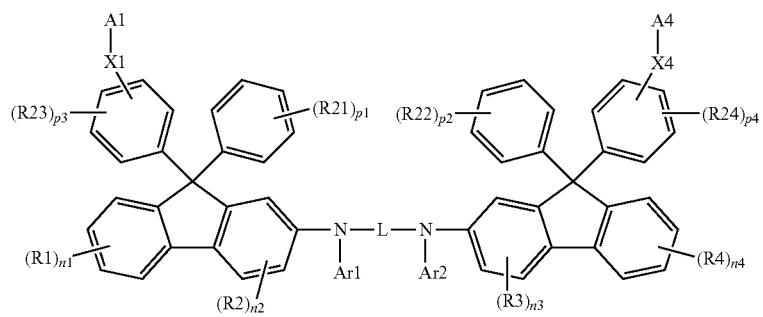

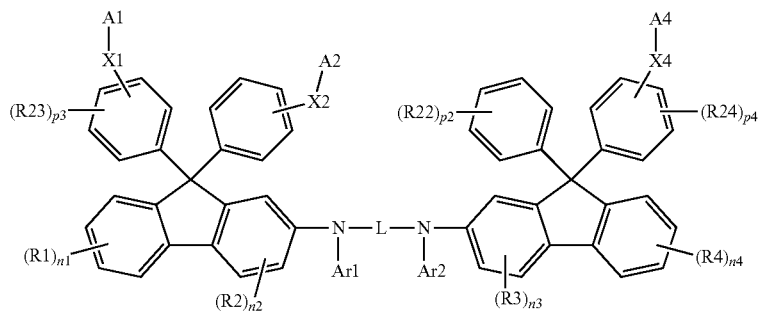

[Chemical Formula 3]

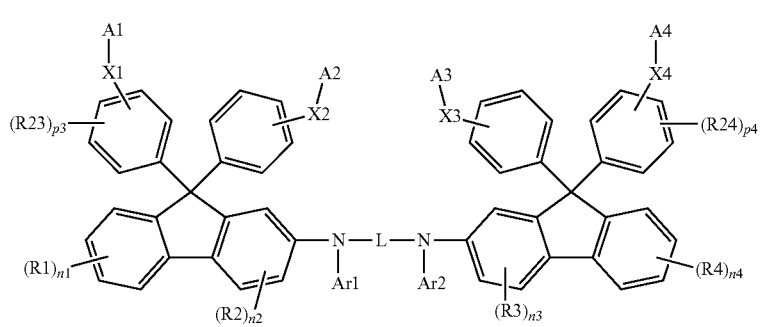

[Chemical Formula 4]

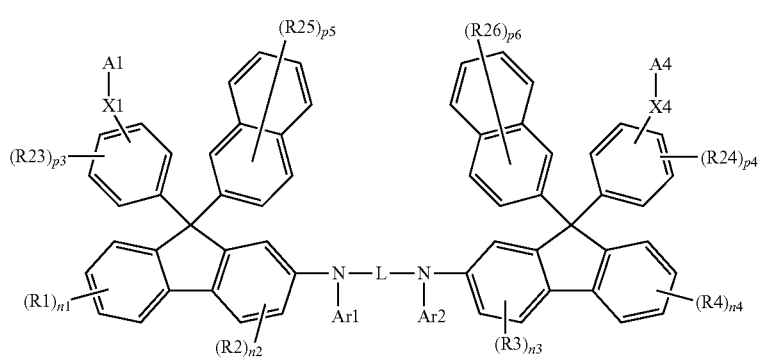

[Chemical Formula 5]

In Chemical Formulae 2 to 5,

R1 to R4, n1 to n4, Ar1, Ar2 and L have the same definitions as in Chemical Formula 1, X1 to X4 are the same as or different from each other, and each independently O or S, A1 to A4 are the same as or different from each other, and each independently a functional group crosslinkable by heat or light, R21 to R26 are the same as or different from each other, and each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group, p1 and p2 are each independently an integer of 0 to 5,
p3 and p4 are each independently an integer of 0 to 4,
p5 and p6 are each independently an integer of 0 to 7, and when p1 to p6 are each 2 or greater, substituents in the parentheses are the same as or different from each other.

According to one embodiment of the present specification, R21 to R26 are the same as or different from each other, and each independently hydrogen; a substituted or unsubstituted alkyl group having 1 to 20 carbon atoms; a substituted or unsubstituted alkoxy group having 1 to 20 carbon atoms; a substituted or unsubstituted aryloxy group having 6 to 30 carbon atoms; a substituted or unsubstituted aryl group having 6 to 30 carbon atoms; or a substituted or unsubstituted heteroaryl group having 2 to 30 carbon atoms.

According to another embodiment, R21 to R26 are the same as or different from each other, and each independently hydrogen; fluorine (—F); a substituted or unsubstituted methyl group; a substituted or unsubstituted tert-butyl group; a substituted or unsubstituted methoxy group; a substituted or unsubstituted ethoxy group; a substituted or unsubstituted hexyloxy group; or a substituted or unsubstituted phenyloxy group.

In another embodiment, R21 to R26 are each independently hydrogen; fluorine (—F); a methyl group; a tert-butyl group; a methoxy group; an ethoxyethoxy group; a 2-ethylhexyloxy group; or a phenyloxy group.

According to another embodiment, p1 to p6 are each independently 0 or 1.

In one embodiment of the present specification, Chemical Formula 1 may be represented by any one of the following Compounds 1 to 140.

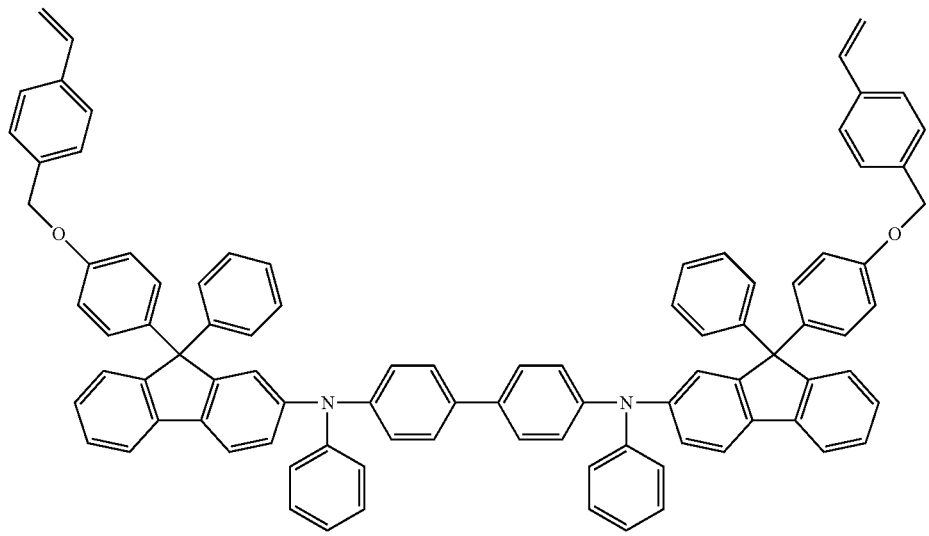
Compound 1
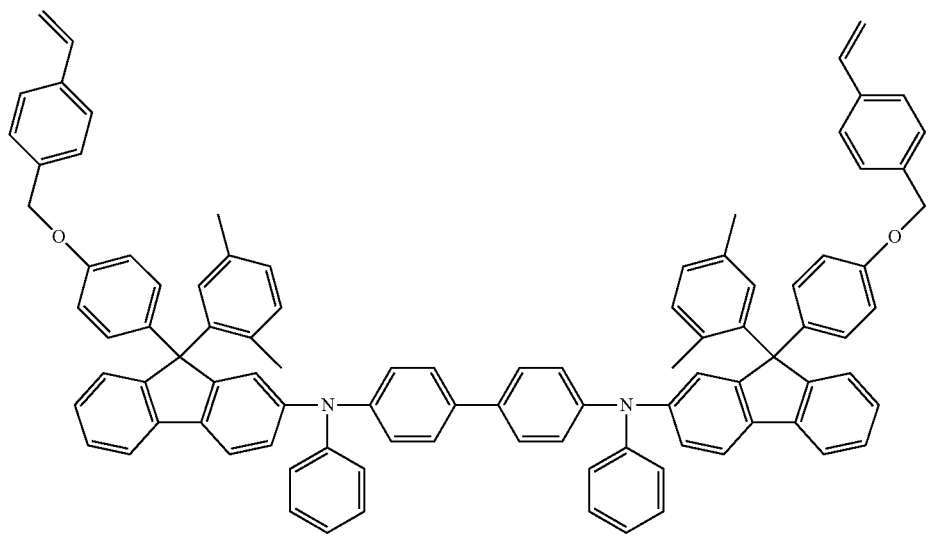
Compound 2
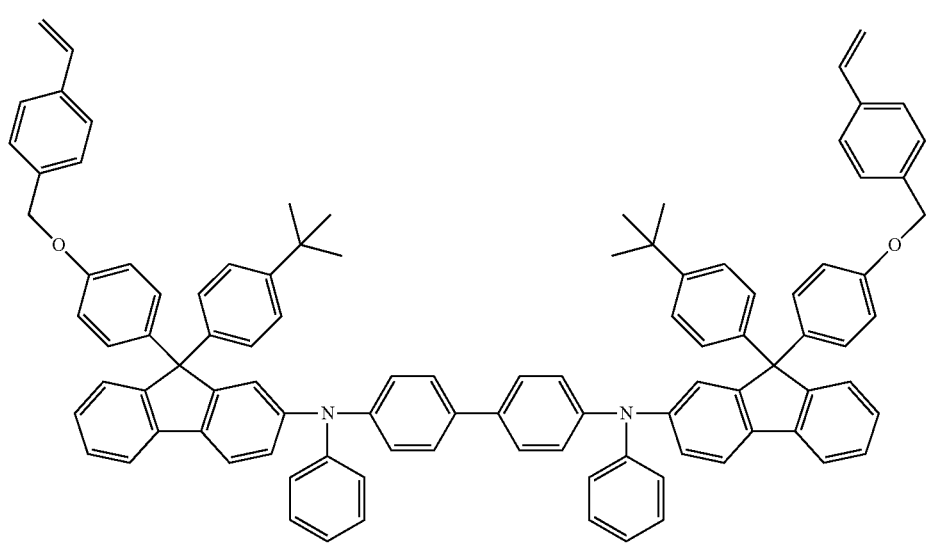
Compound 3

-continued
Compound 4
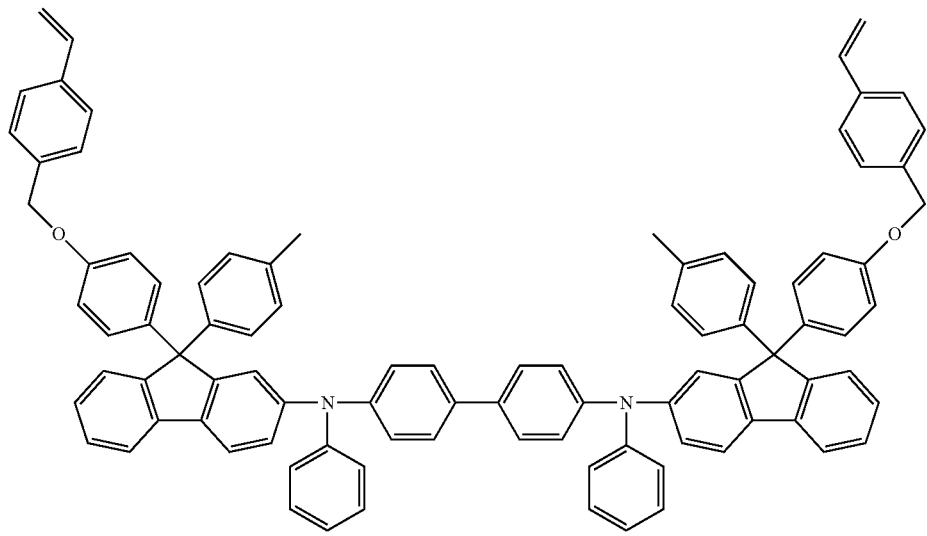
Compound 5
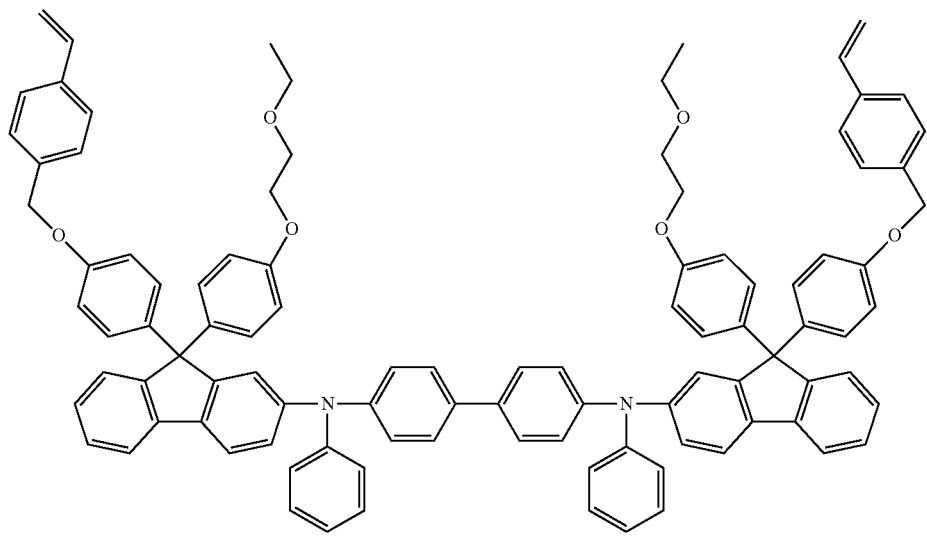
Compound 6
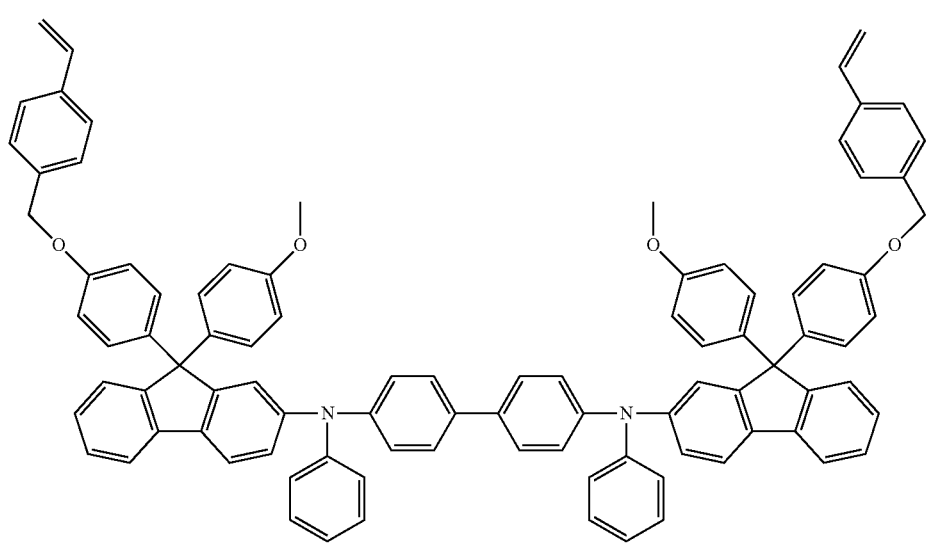

-continued
Compound 7
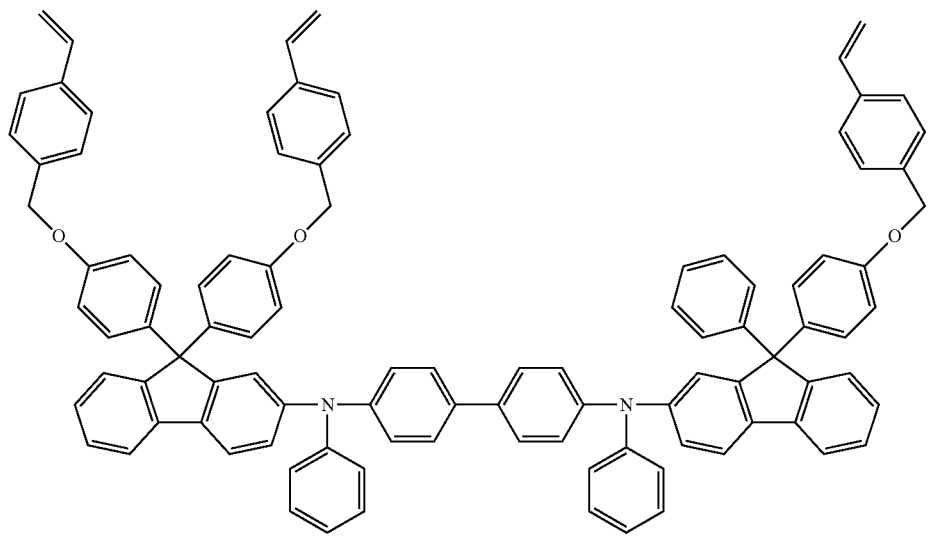
Compound 8
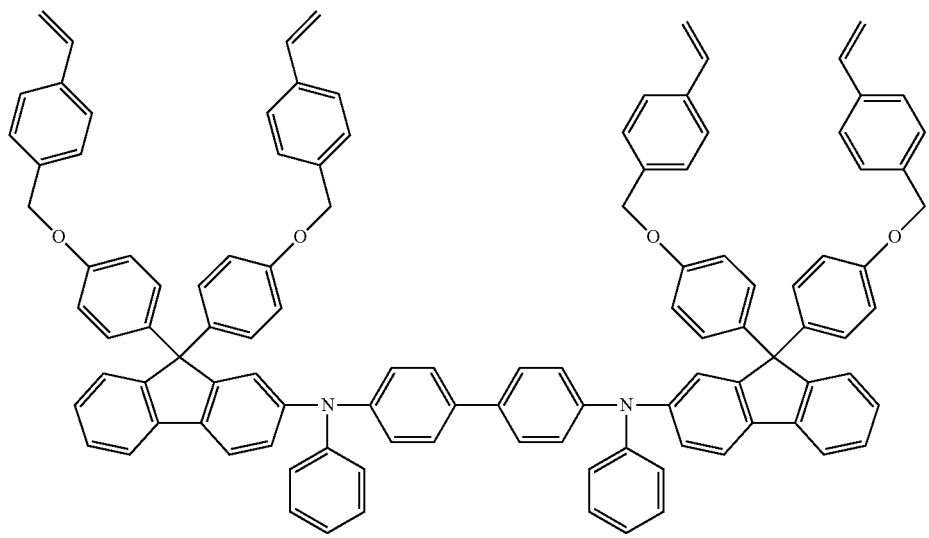
Compound 9
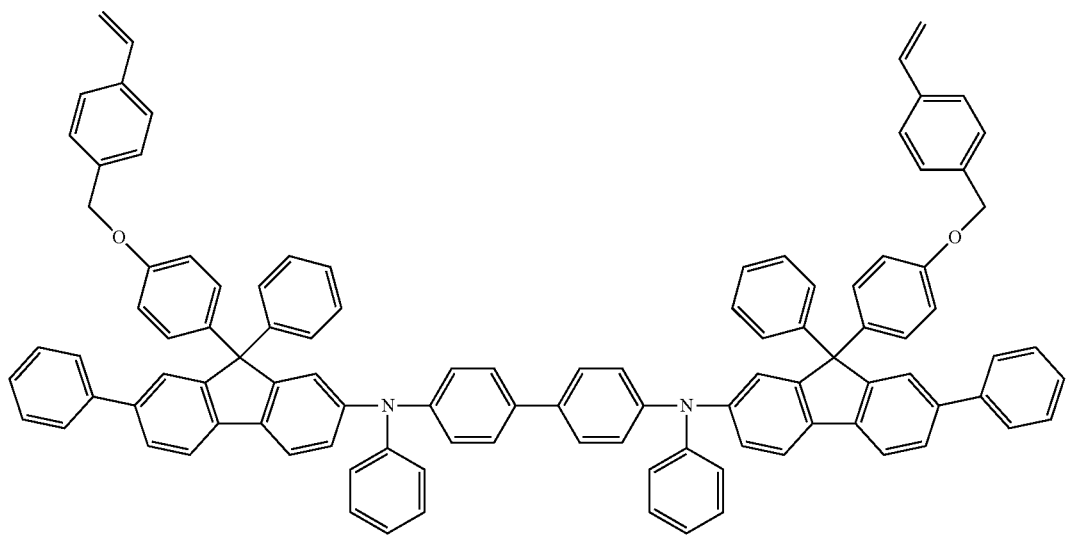

-continued
Compound 10
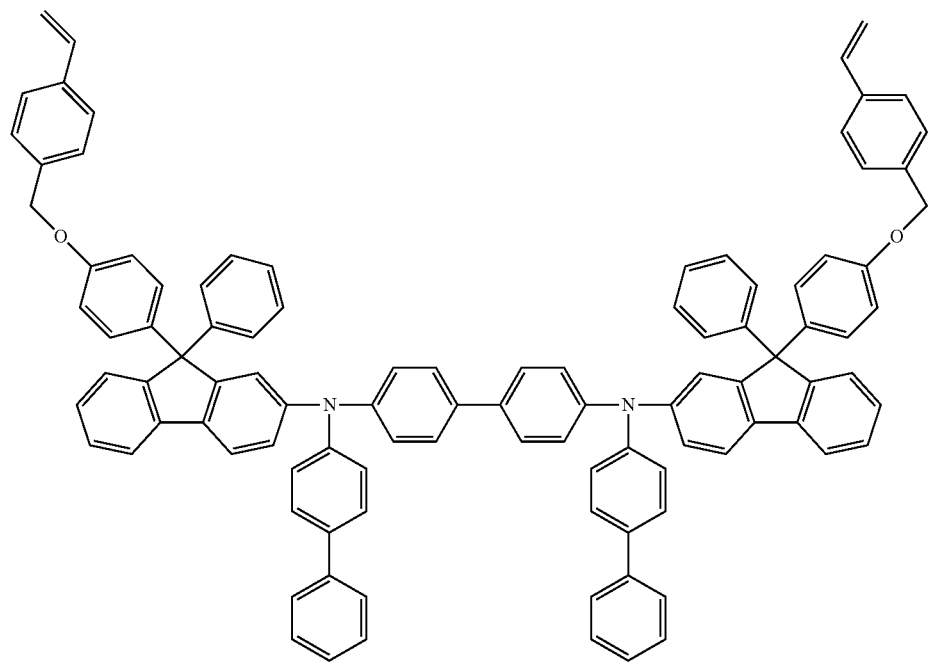
Compound 11
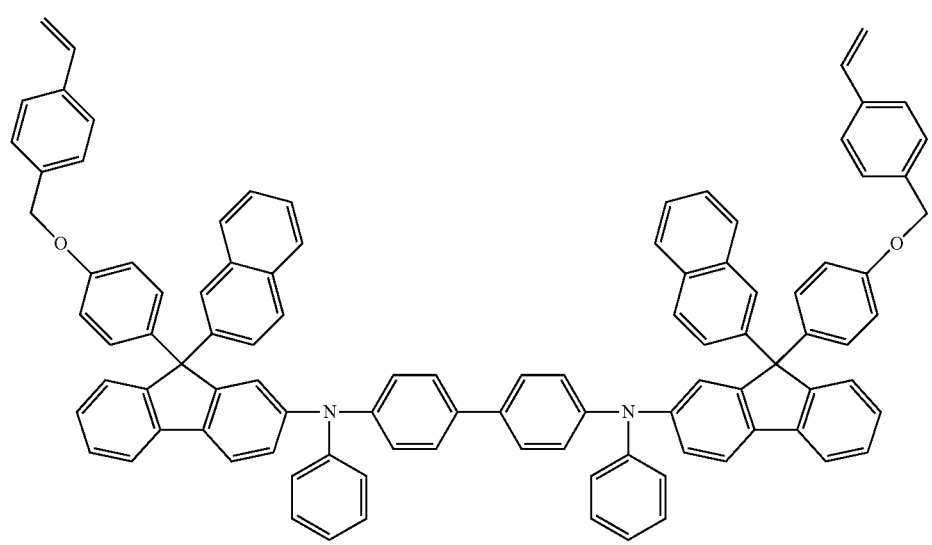

Compound 12
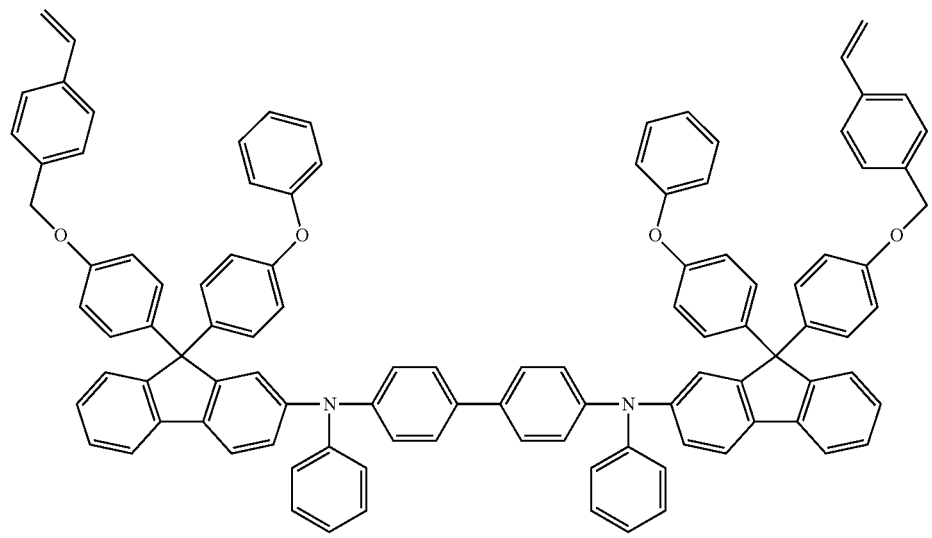
Compound 13
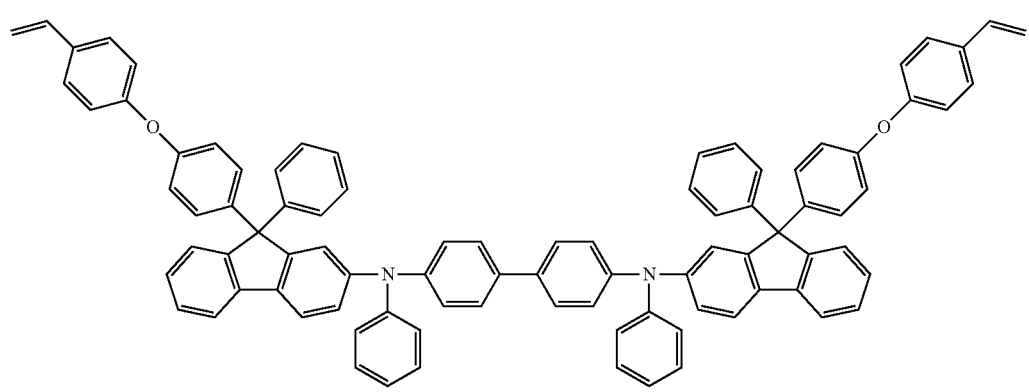
Compound 14
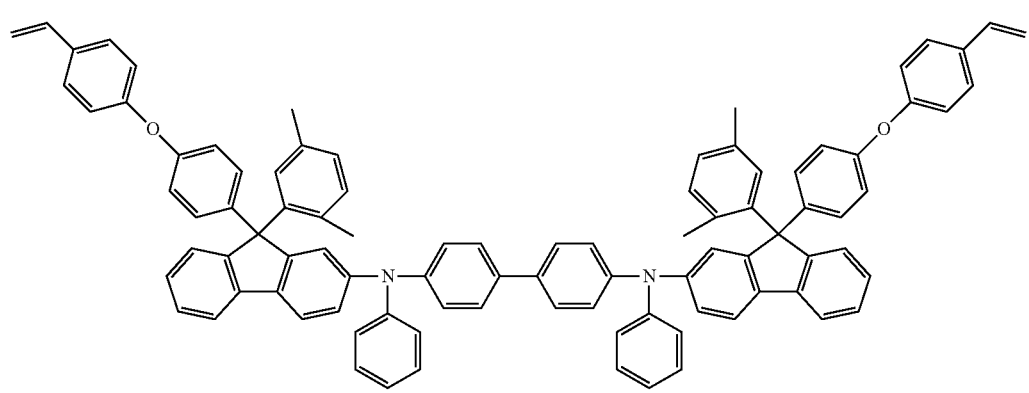

-continued
Compound 15
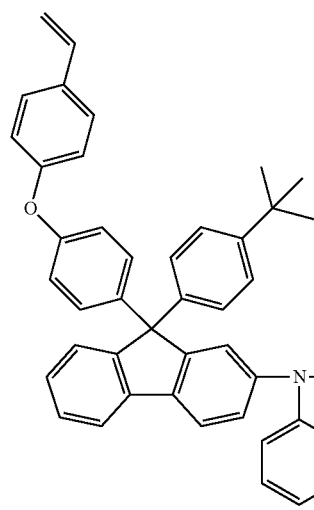
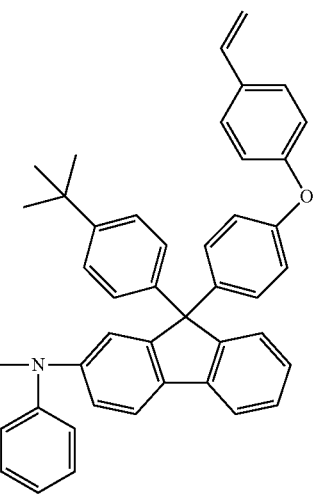
Compound 16
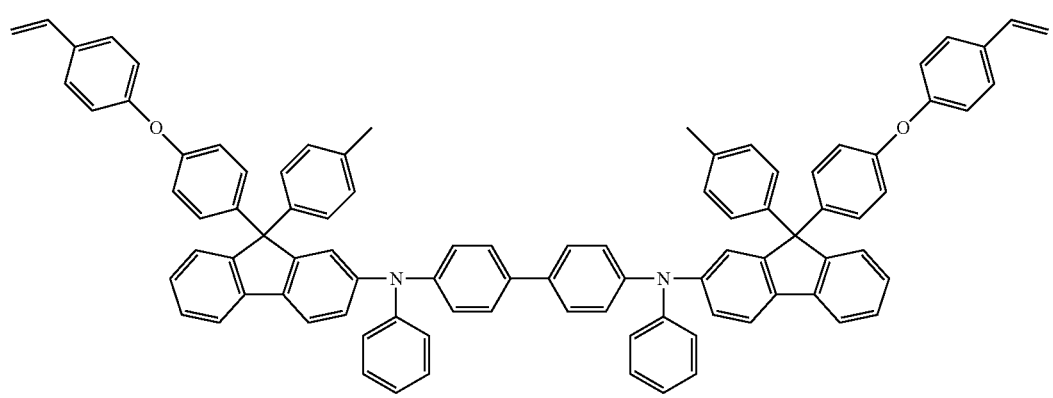
Compound 17
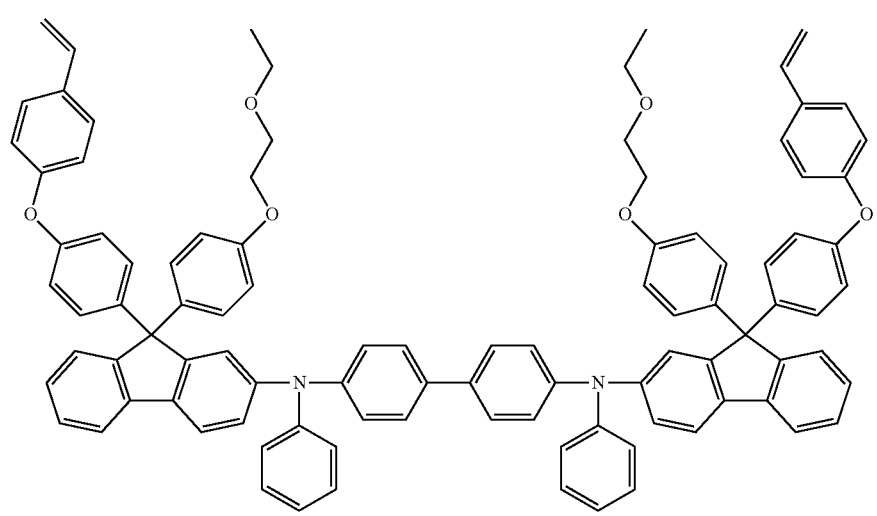

-continued
Compound 18
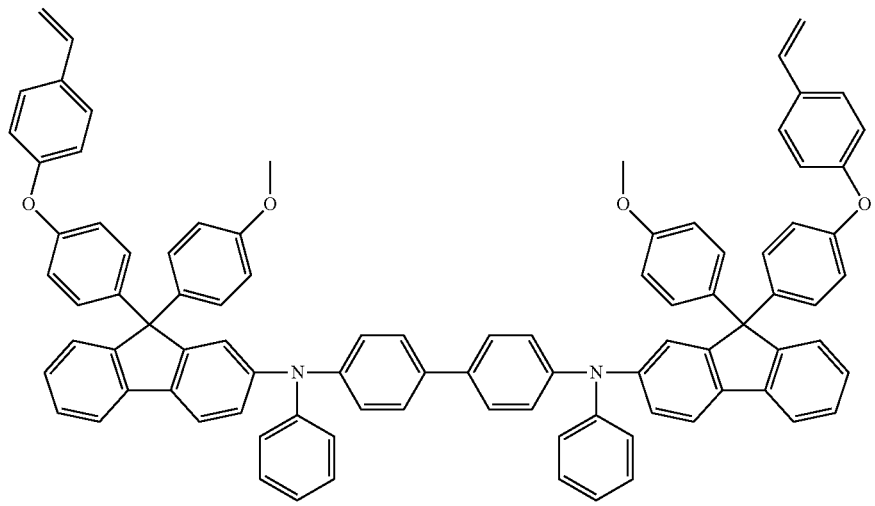
Compound 19
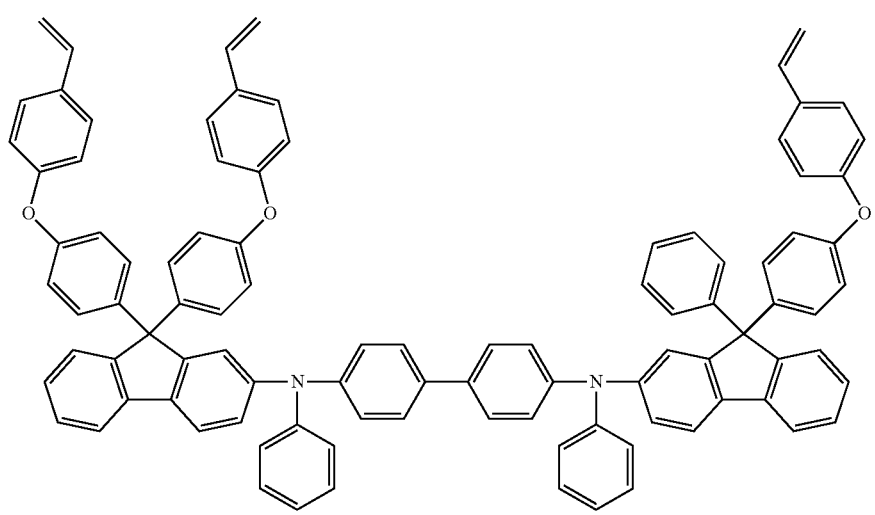
Compound 20
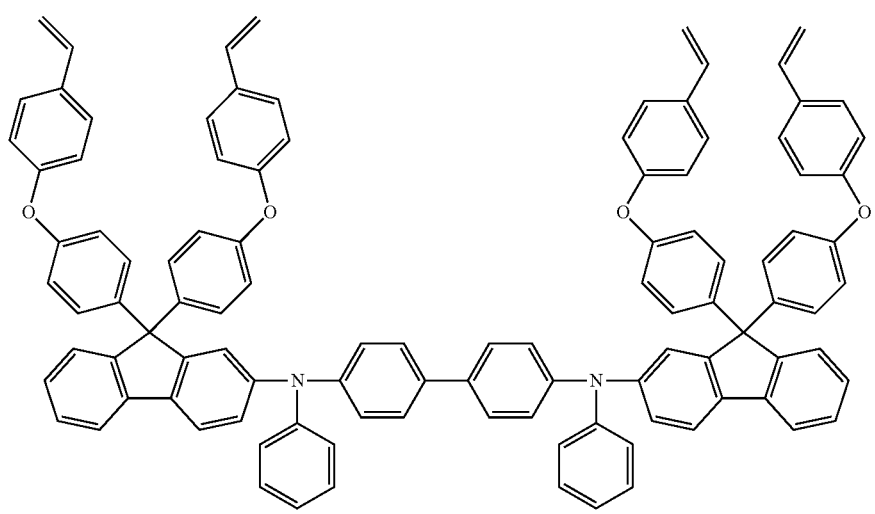

Compound 21
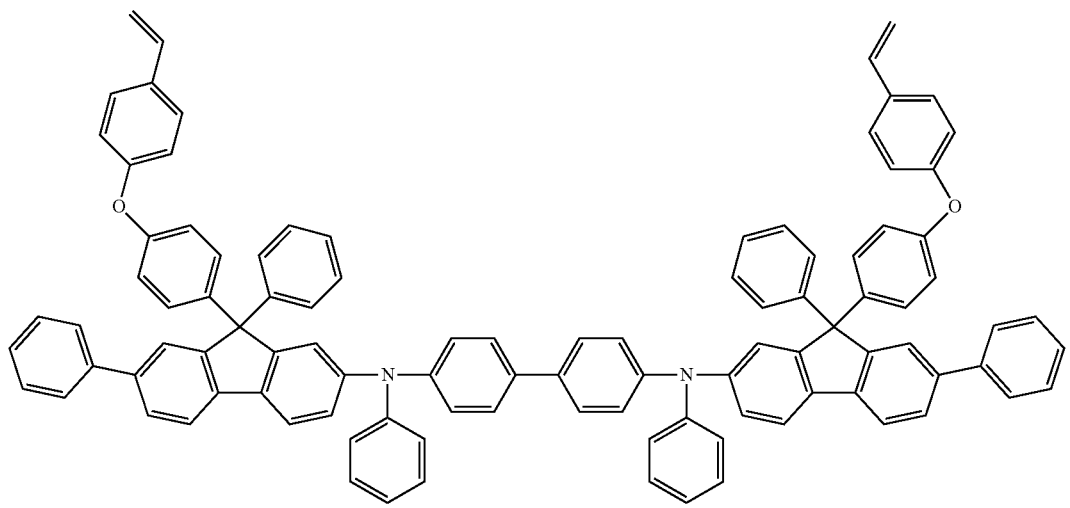
Compound 22
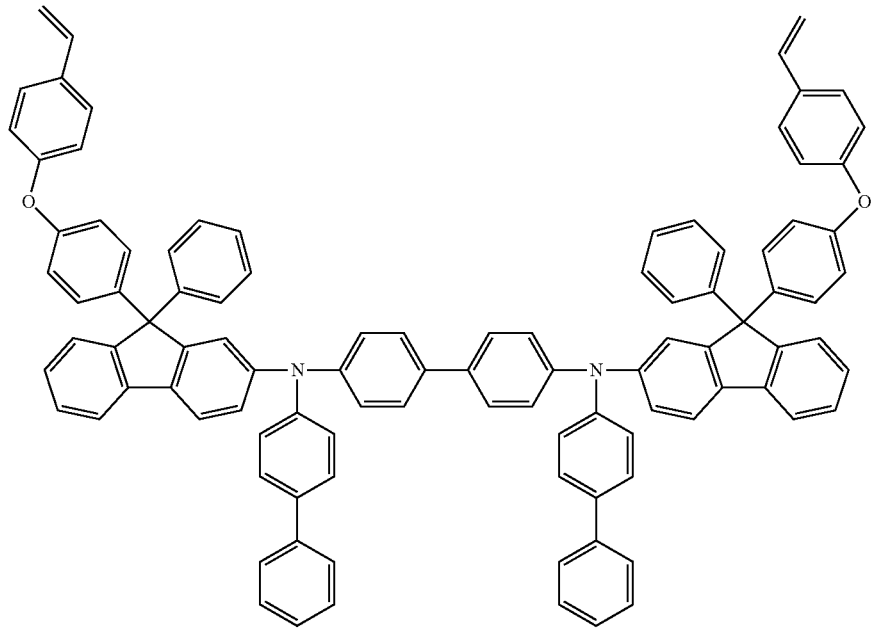
Compound 23
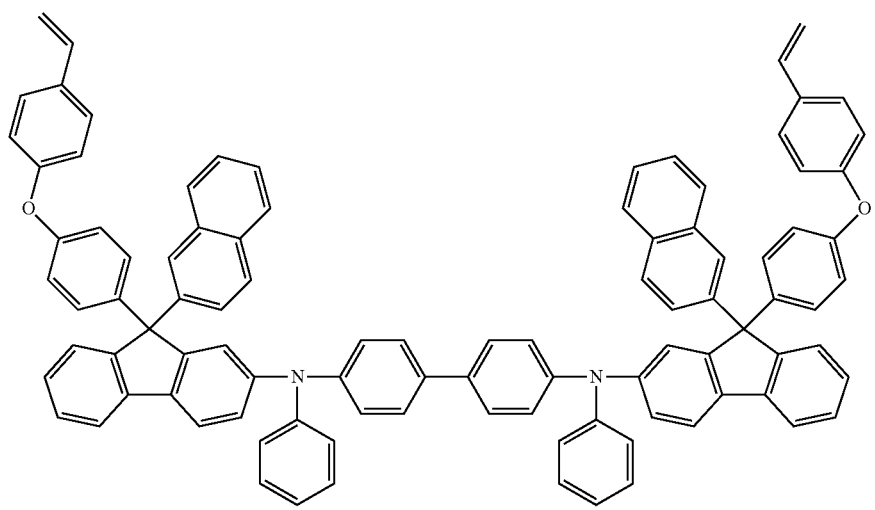

-continued
Compound 24
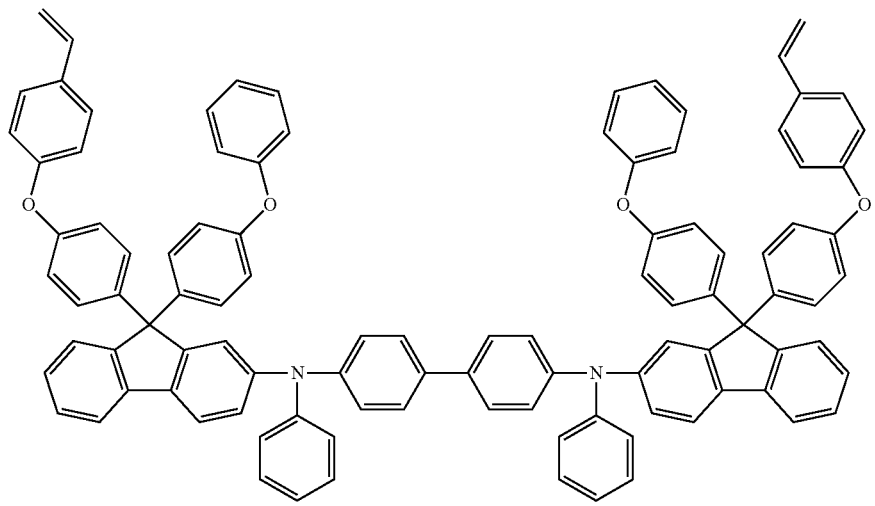
Compound 25
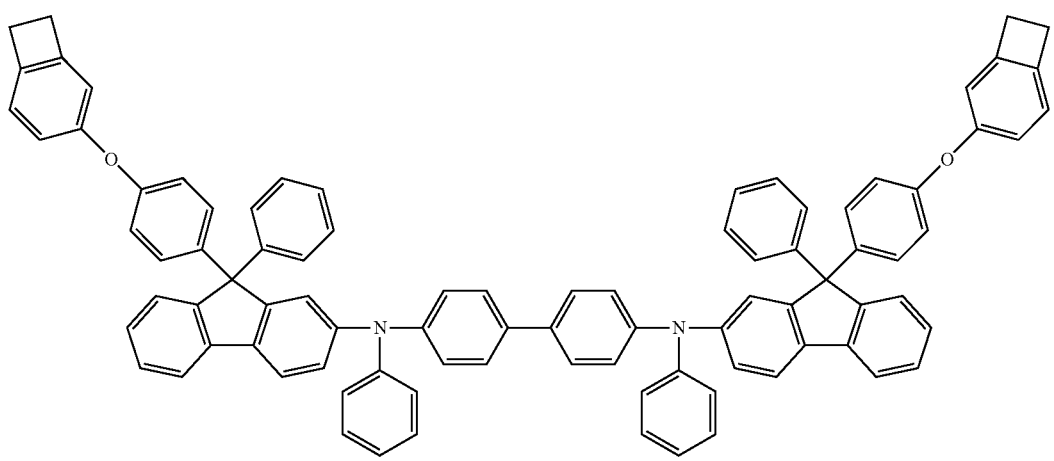
Compound 26
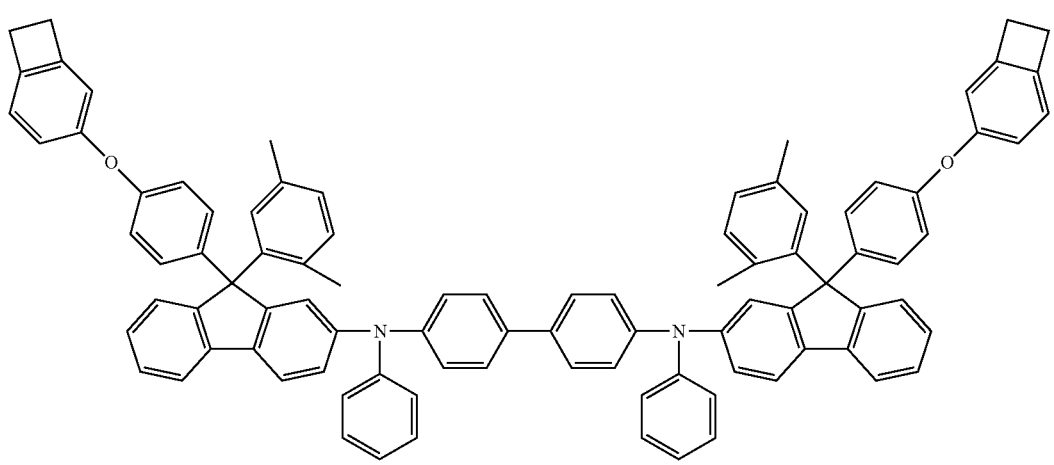

Compound 27
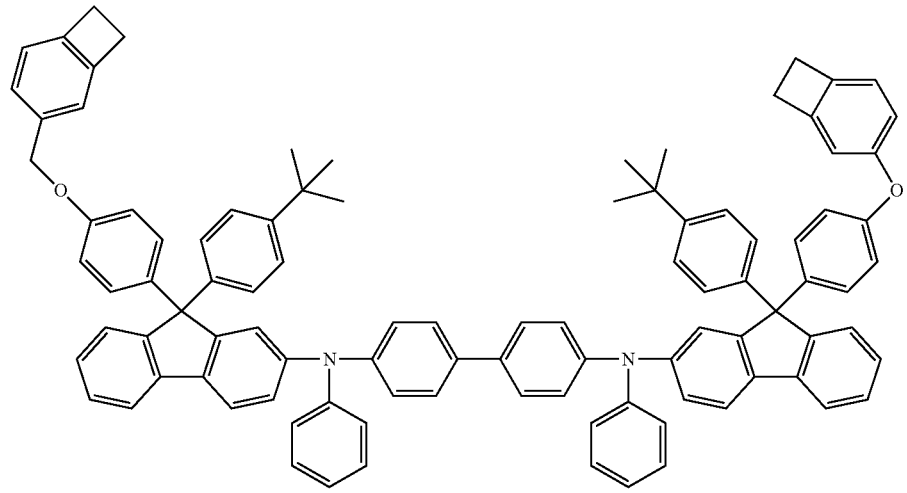
Compound 28
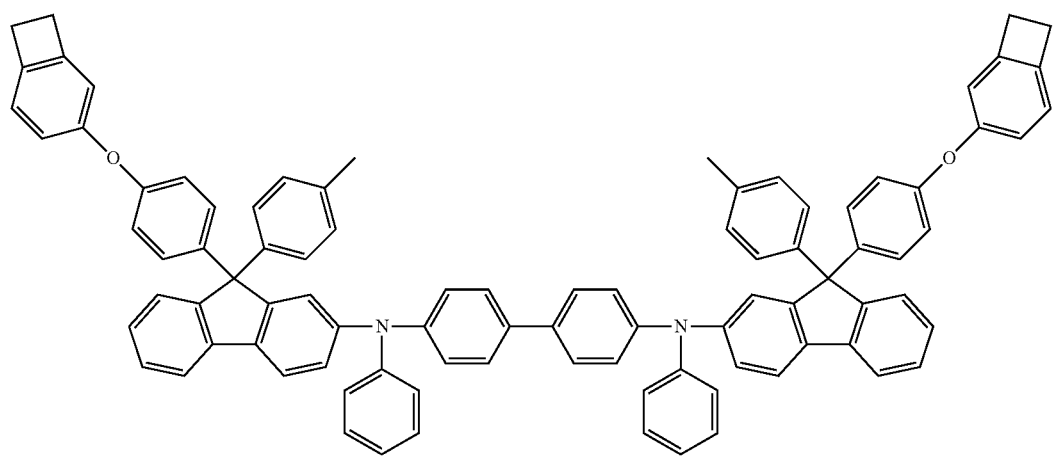
Compound 29
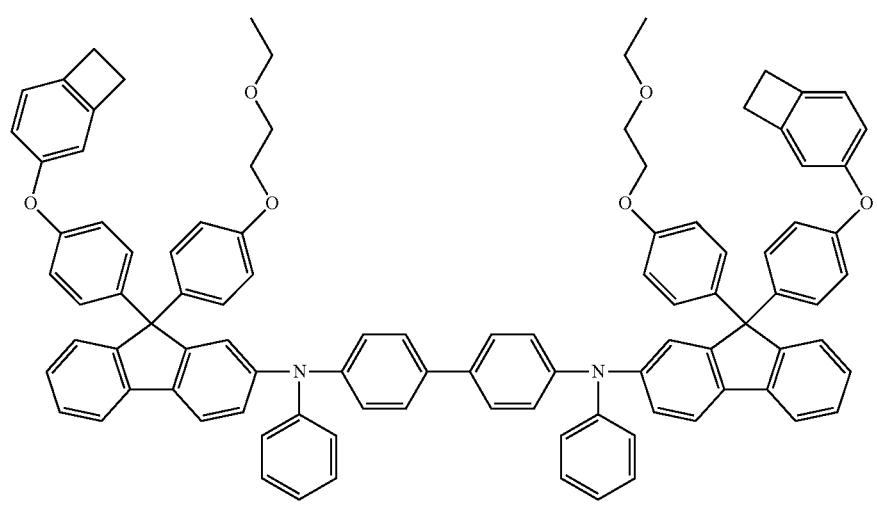

-continued
Compound 30
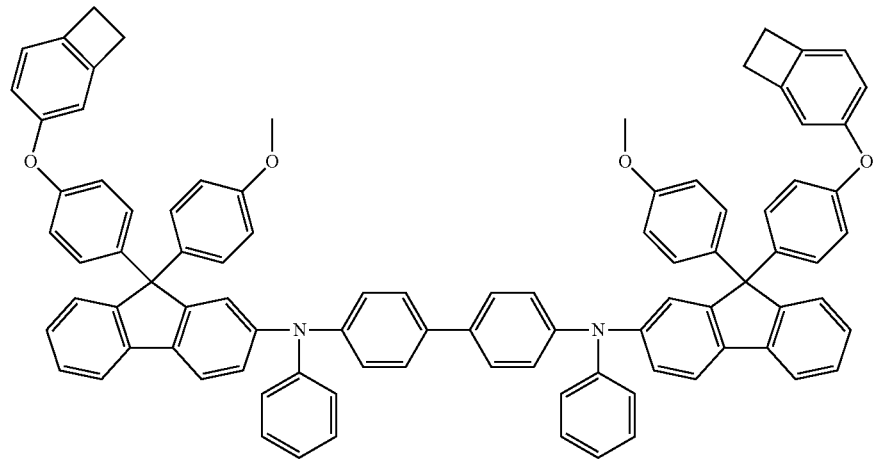
Compound 31
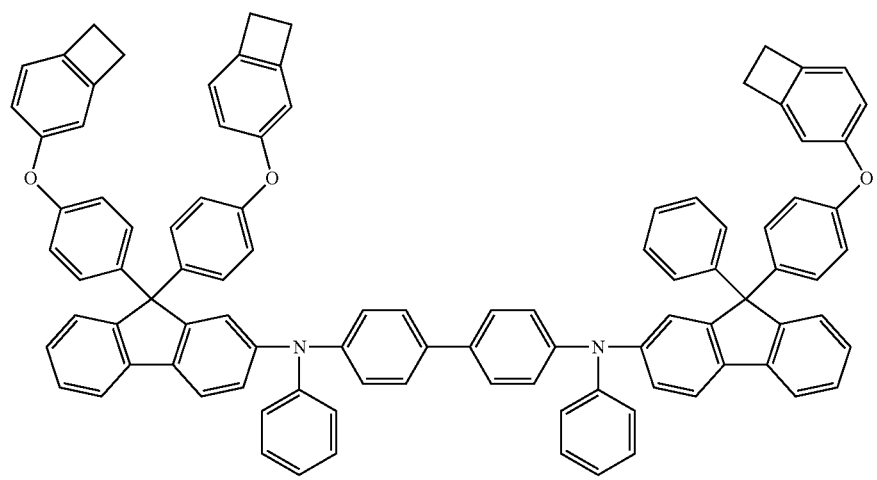
Compound 32
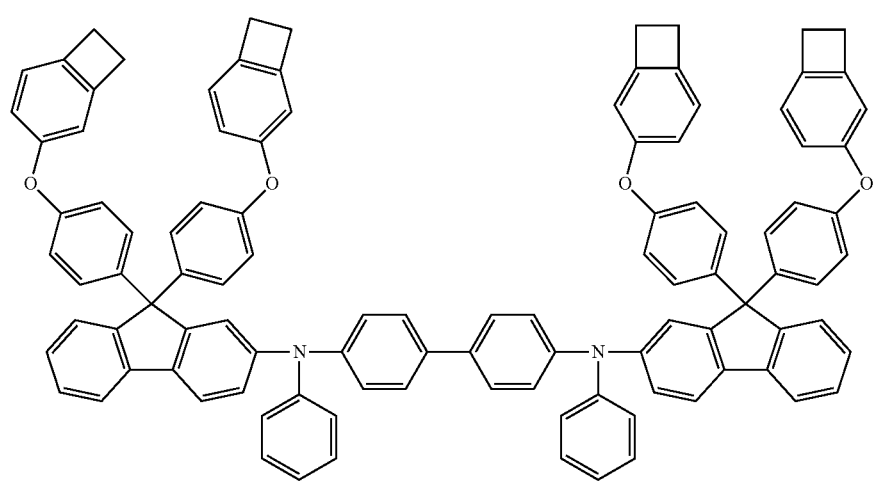

-continued
Compound 33
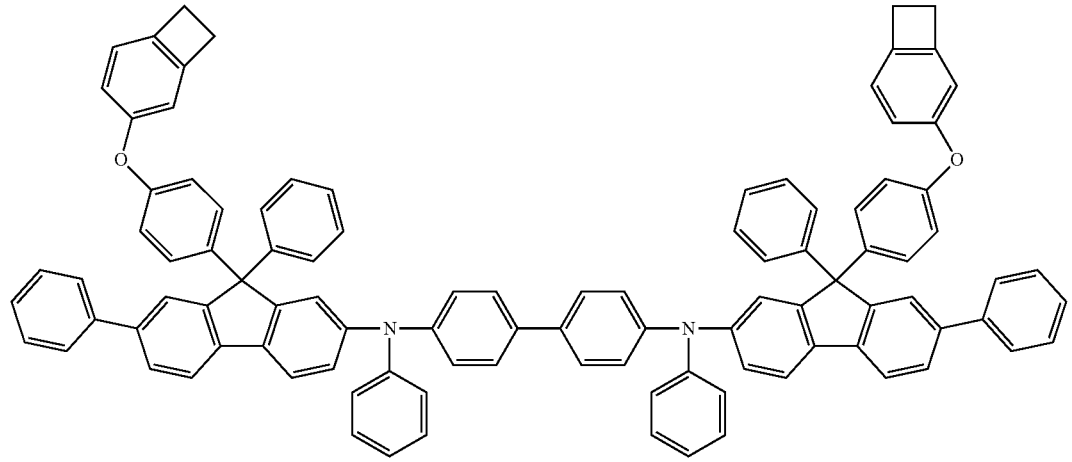
Compound 34
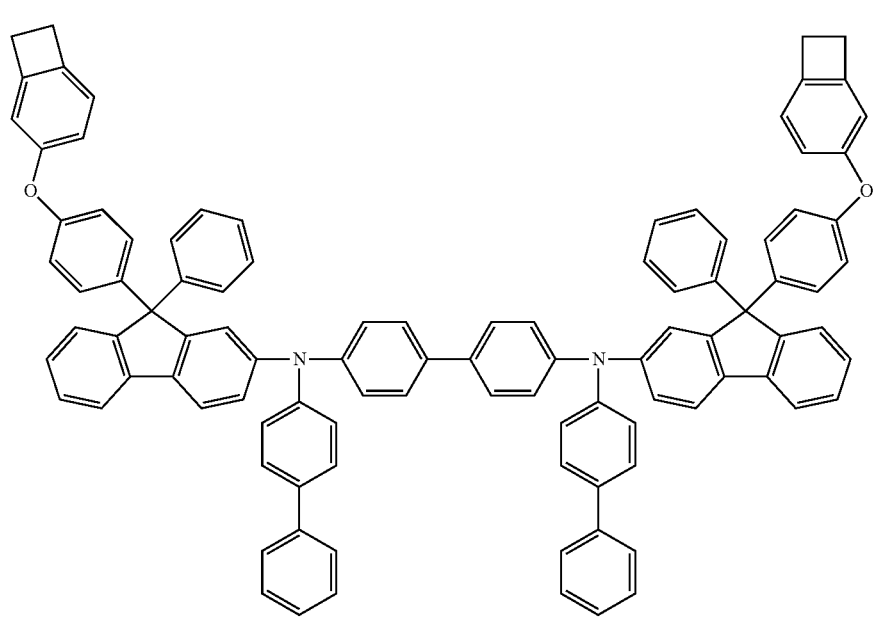
Compound 35
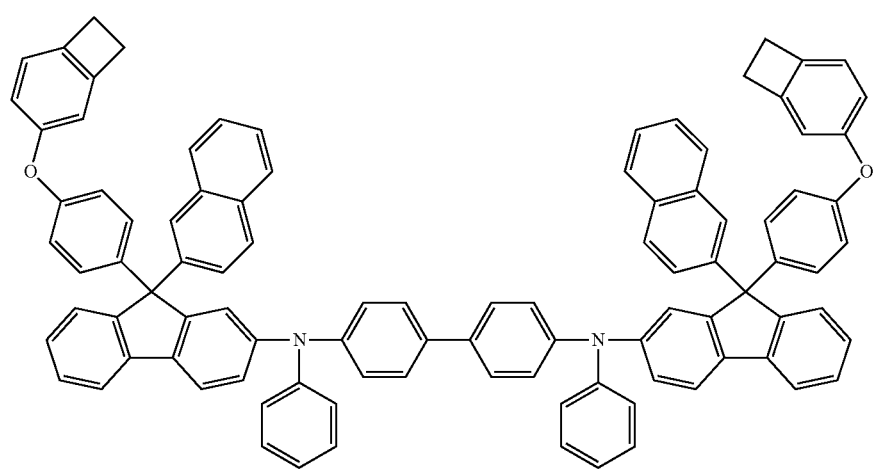

Compound 36
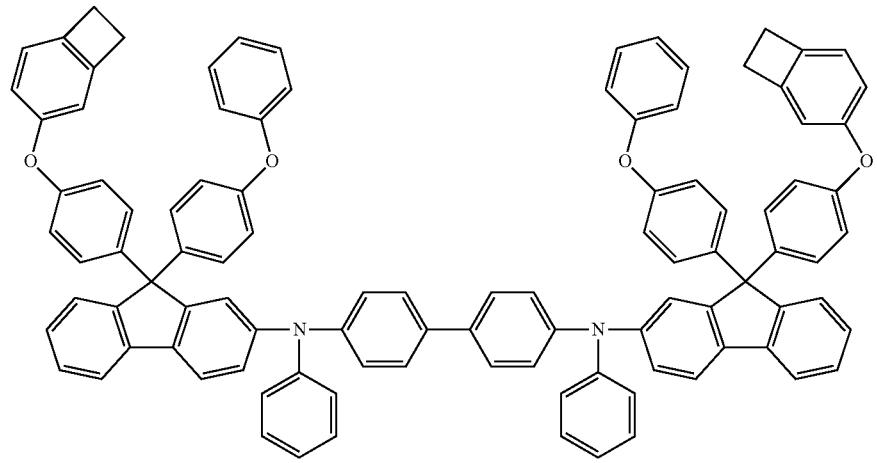
Compound 37
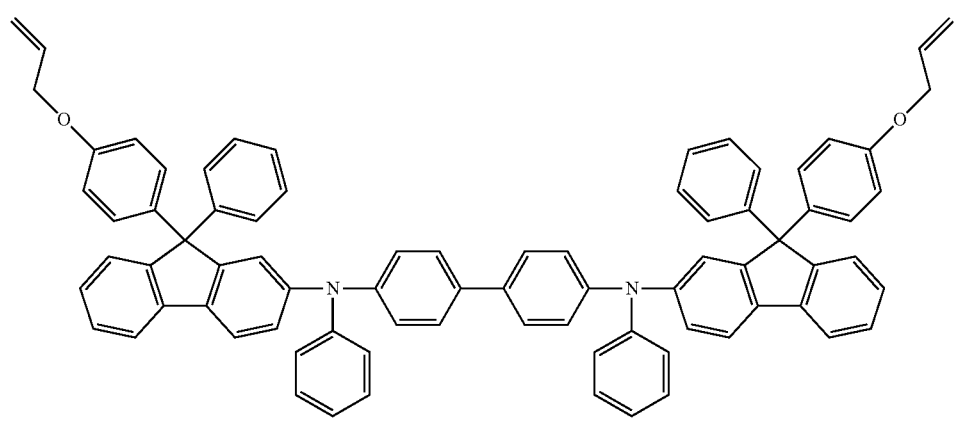
Compound 38
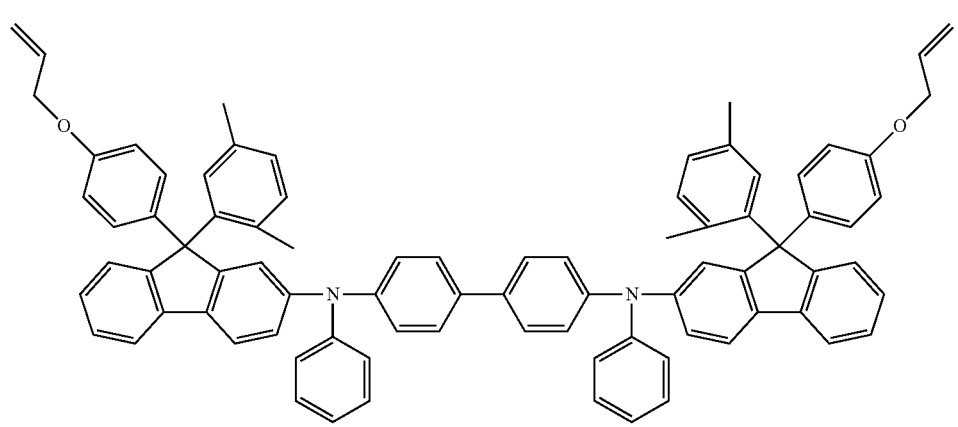

Compound 39
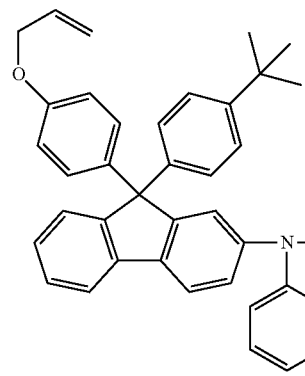
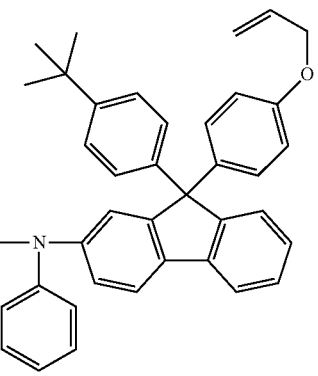
Compound 40
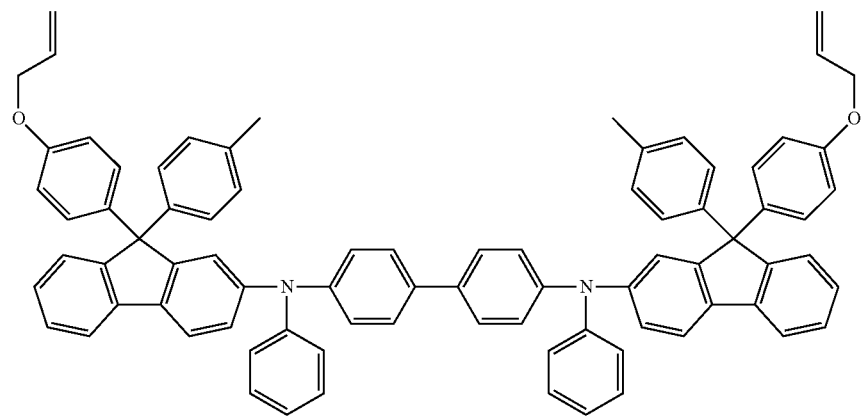
Compound 41
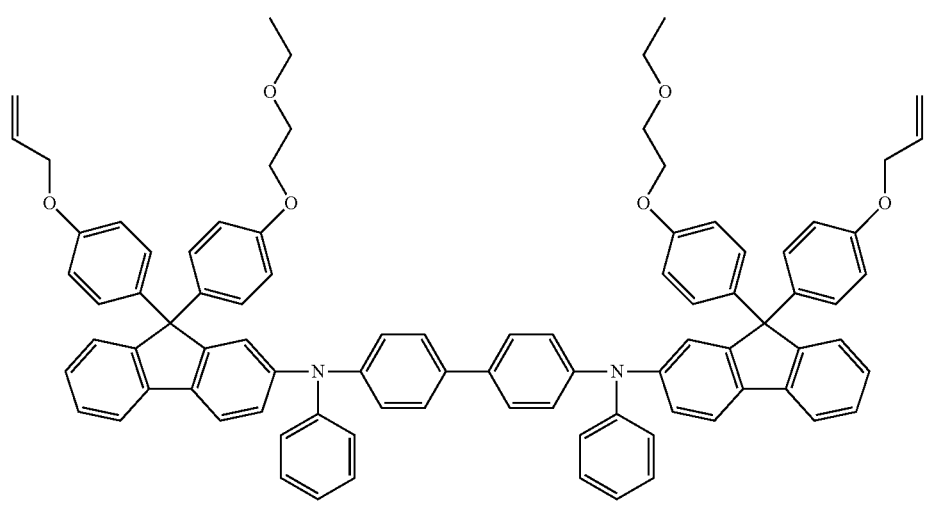

-continued
Compound 42
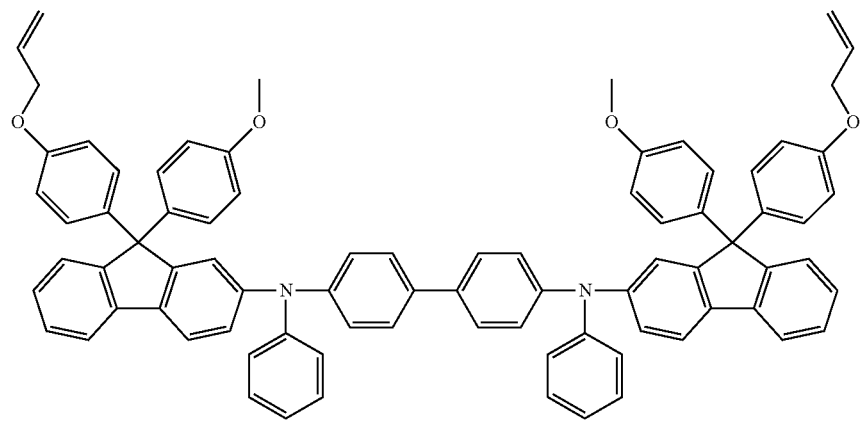
Compound 43
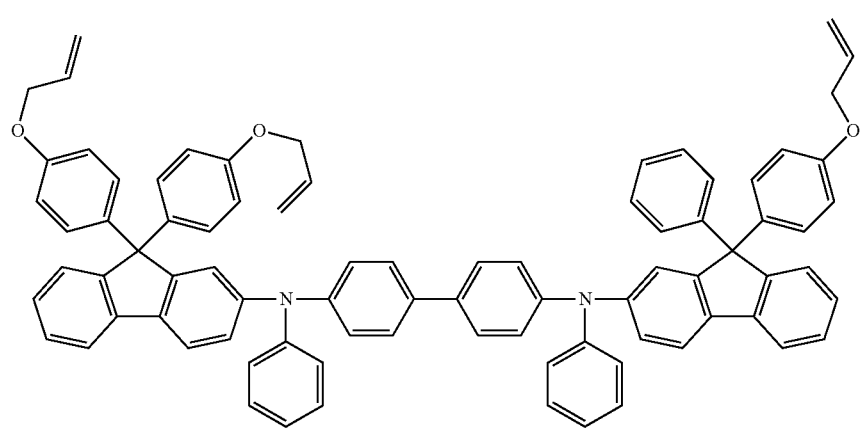
Compound 44
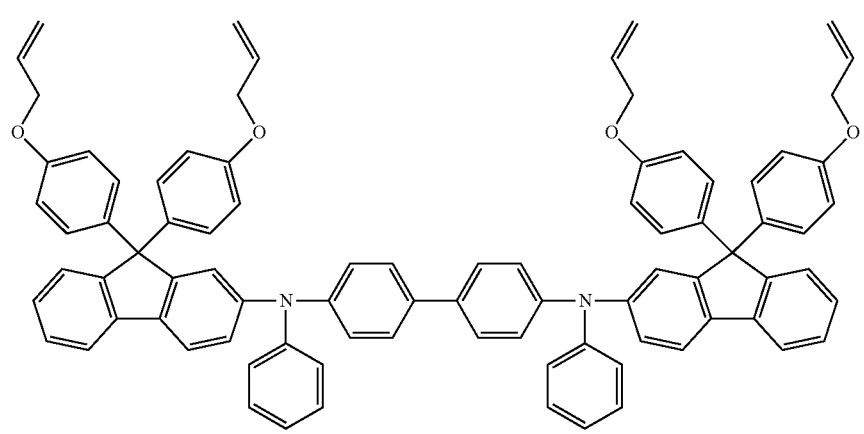

Compound 45
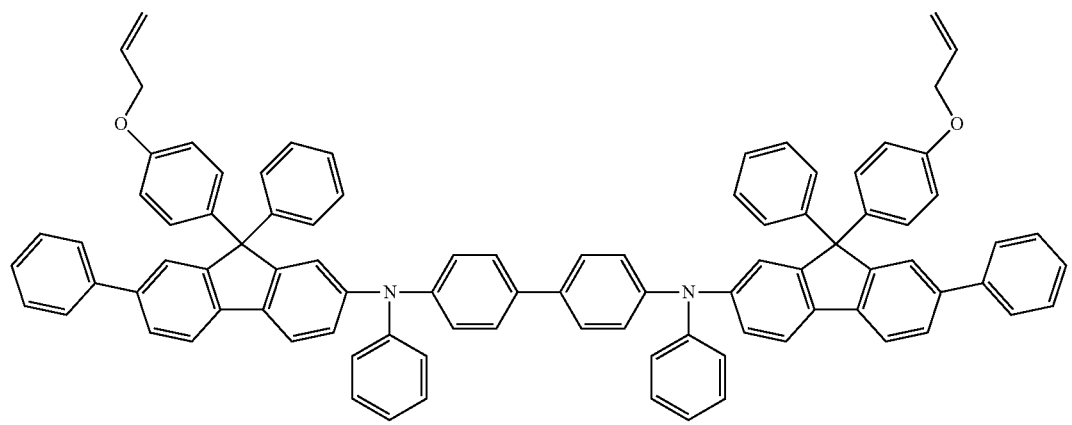
Compound 46
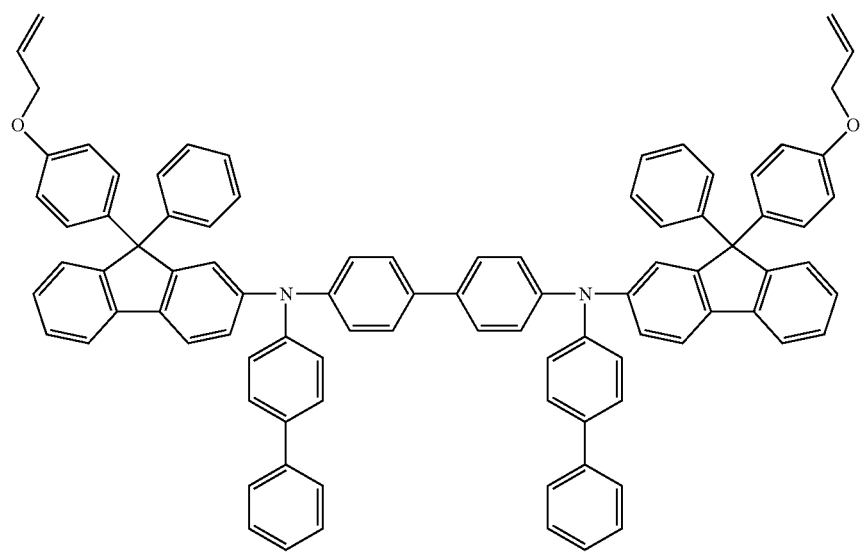
Compound 47
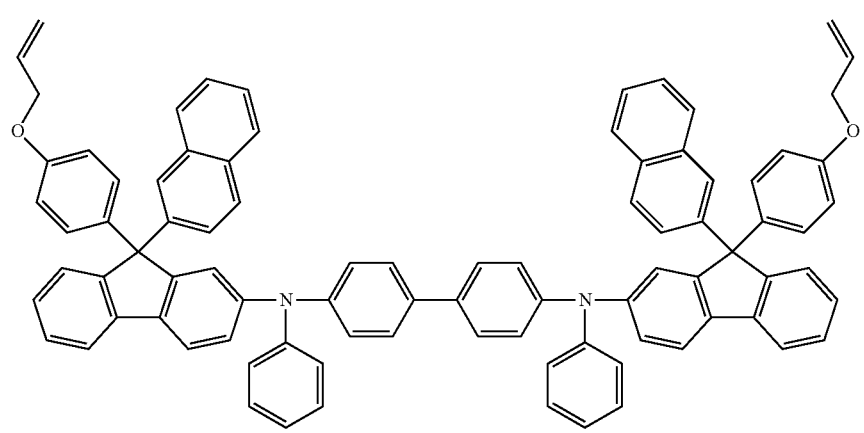

Compound 48
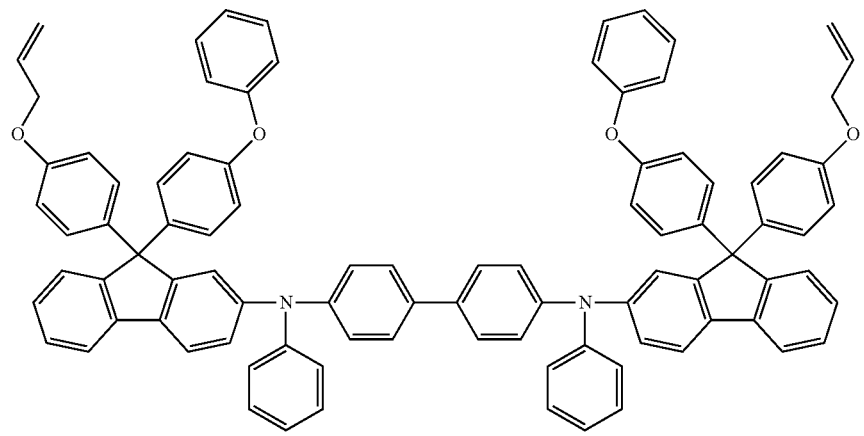
Compound 49
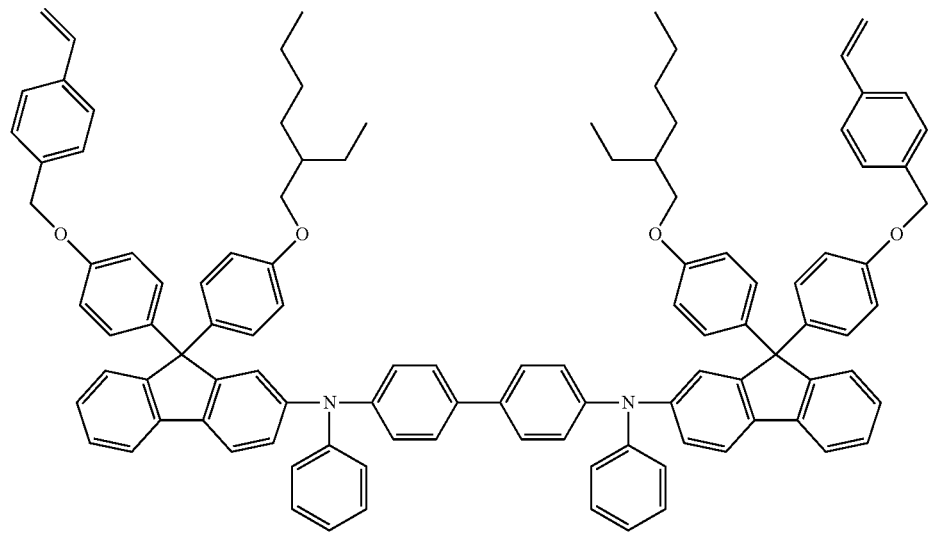
Compound 50
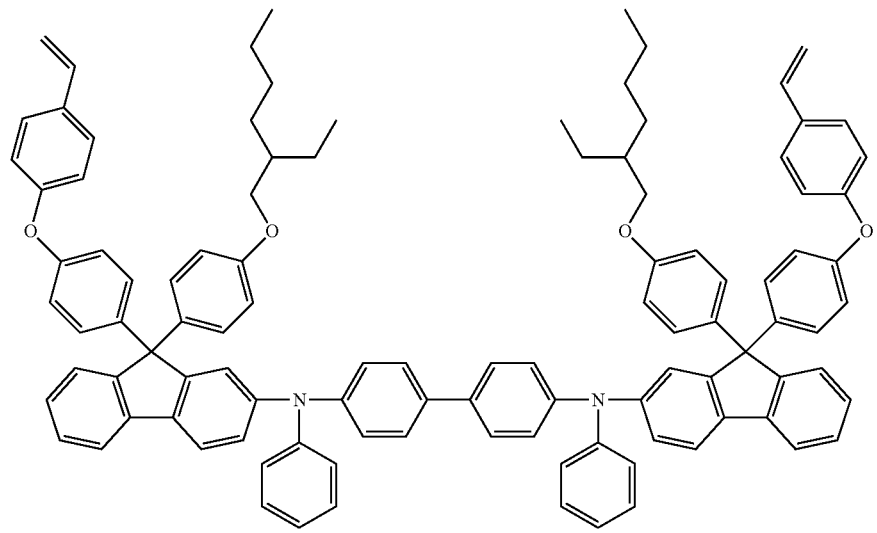

-continued
Compound 51
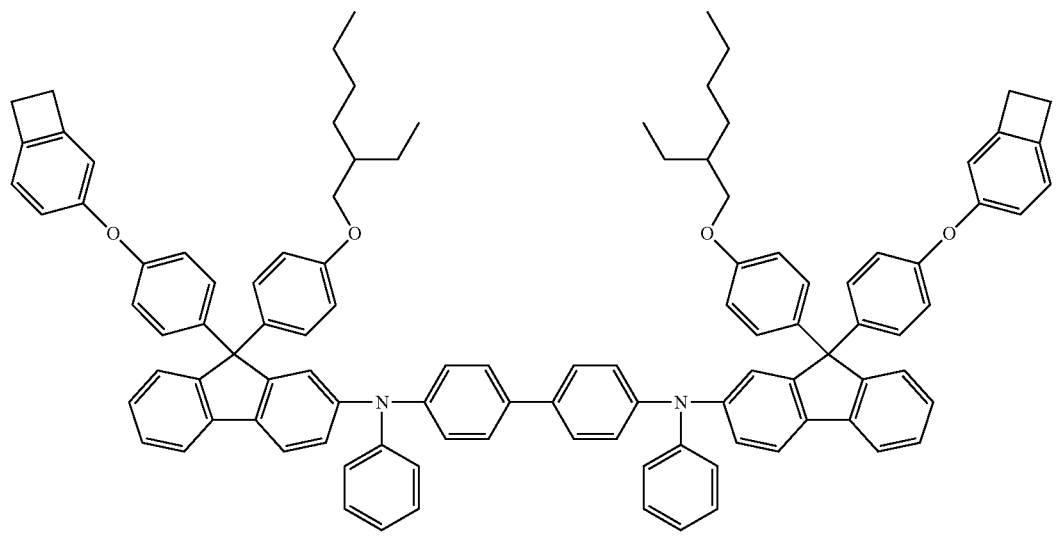
Compound 52
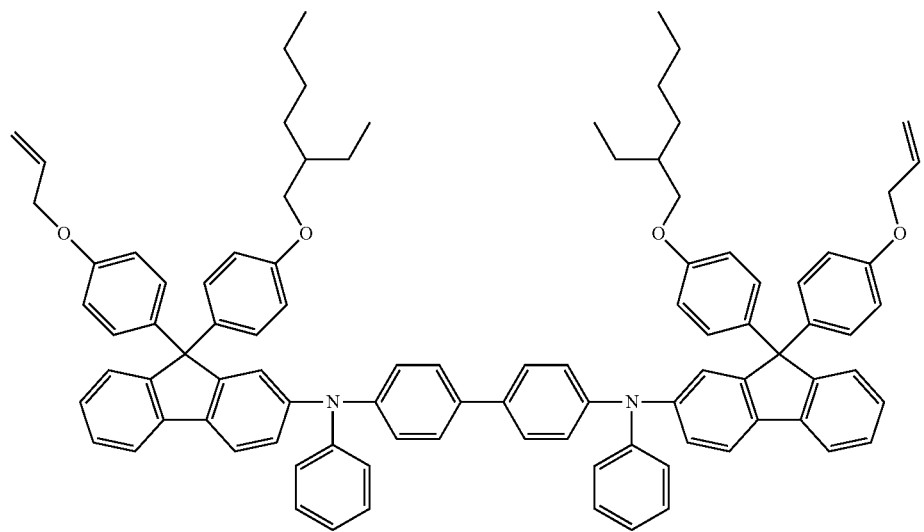
Compound 53
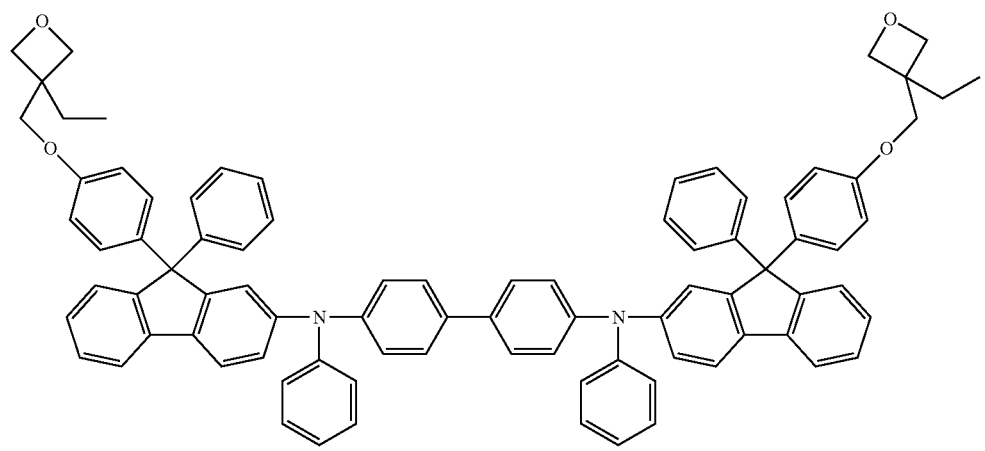

-continued
Compound 54
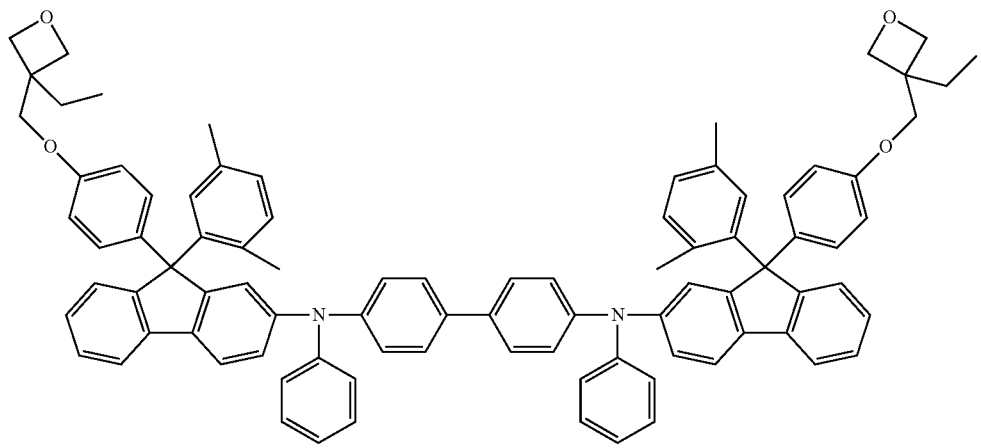
Compound 55
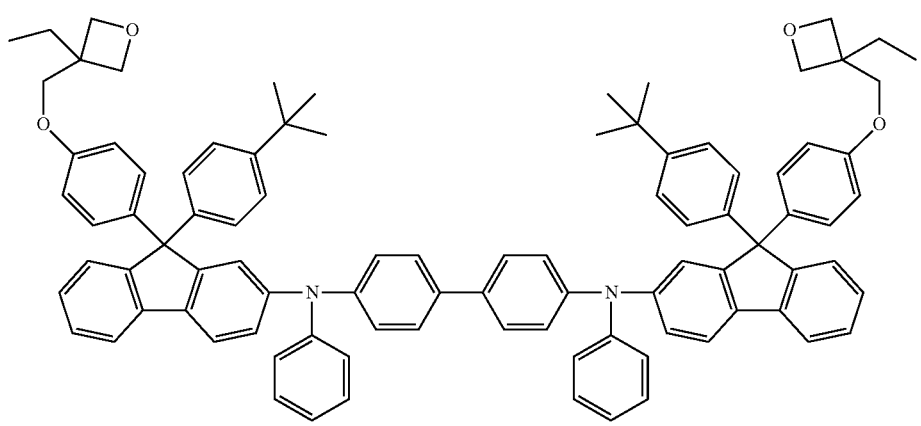
Compound 56
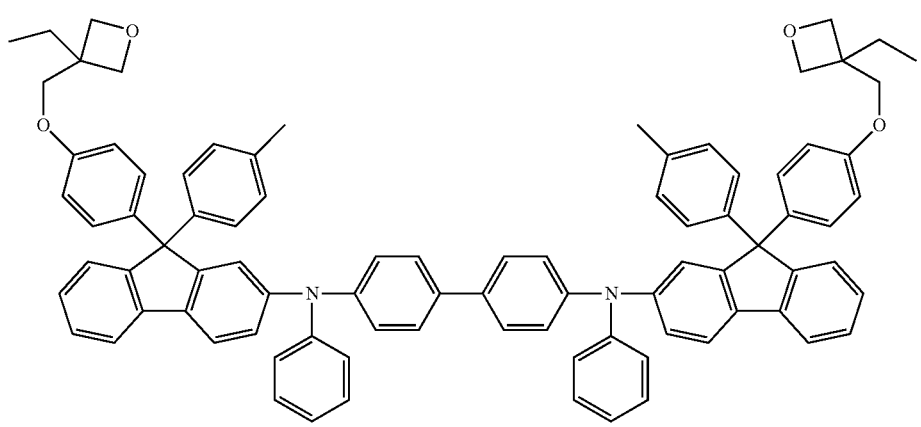

-continued
Compound 57
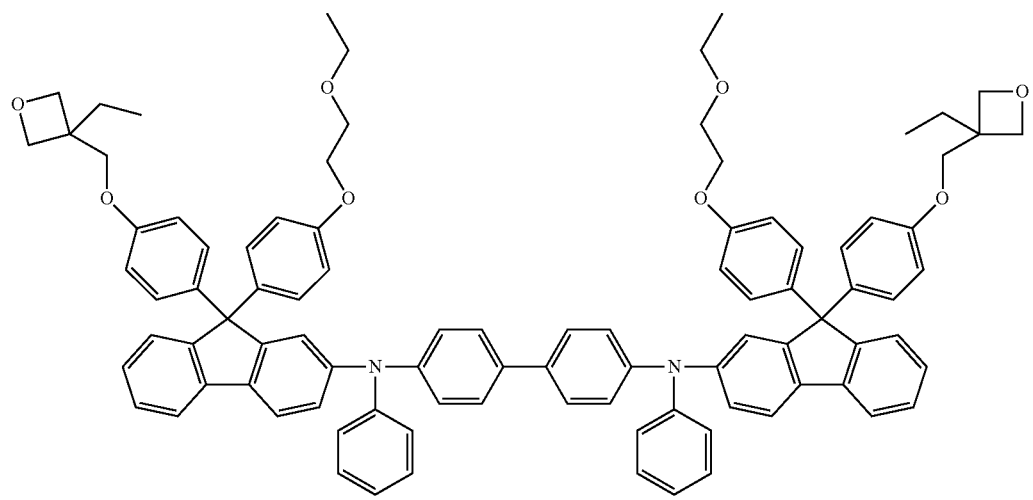
Compound 58
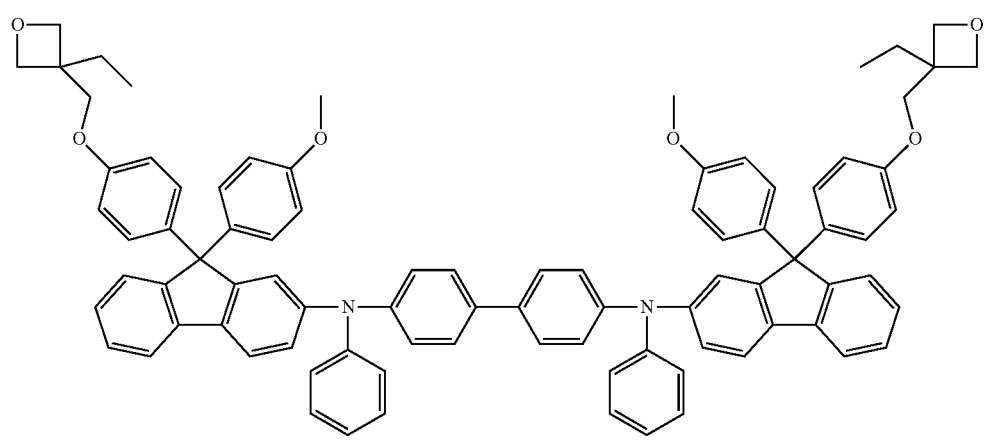
Compound 59
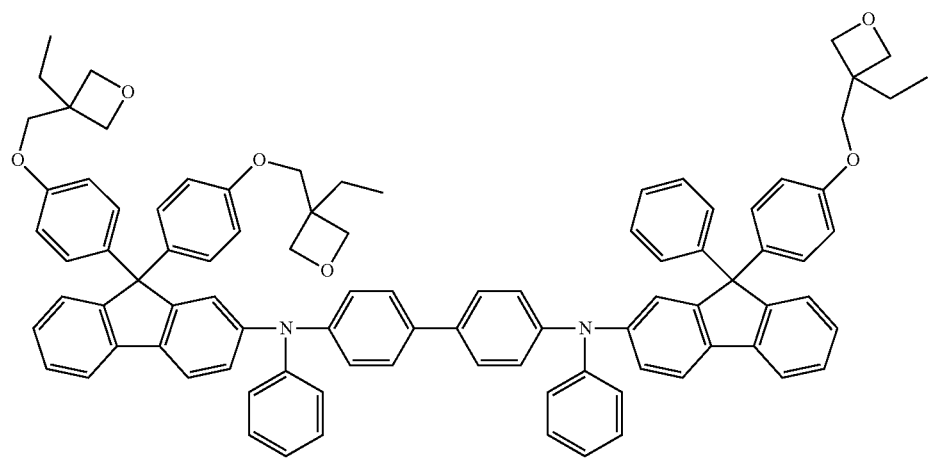

Compound 60
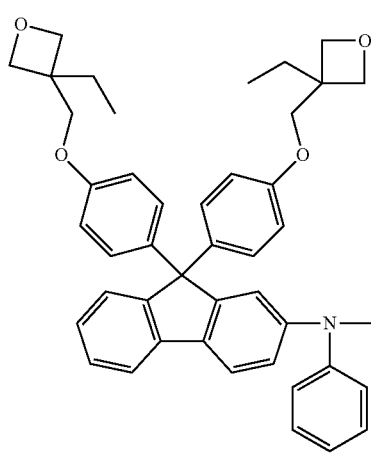 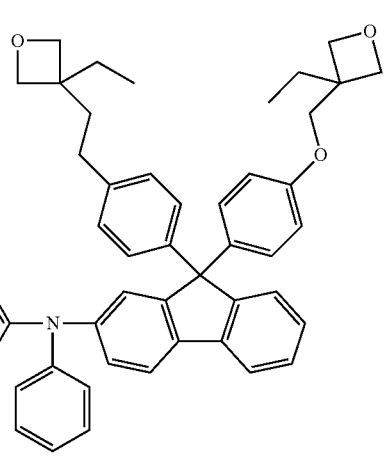
Compound 61
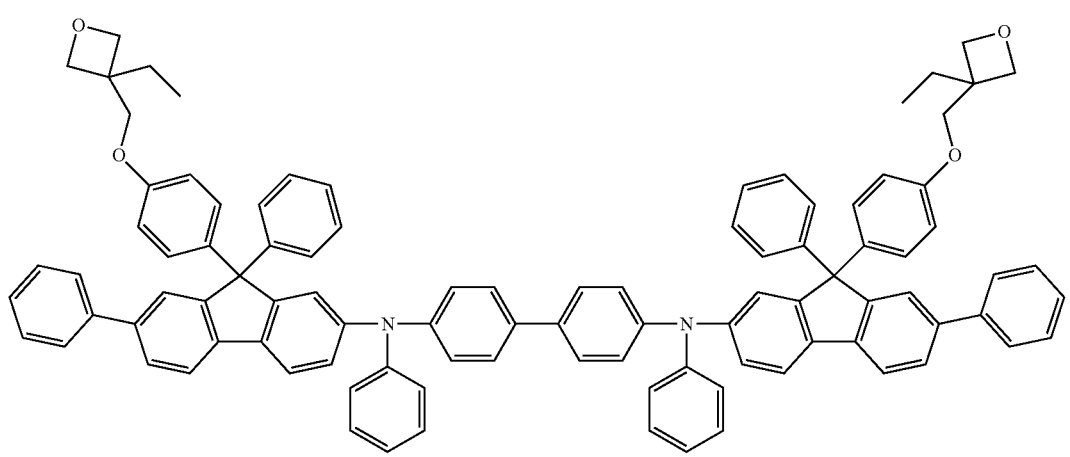
Compound 62
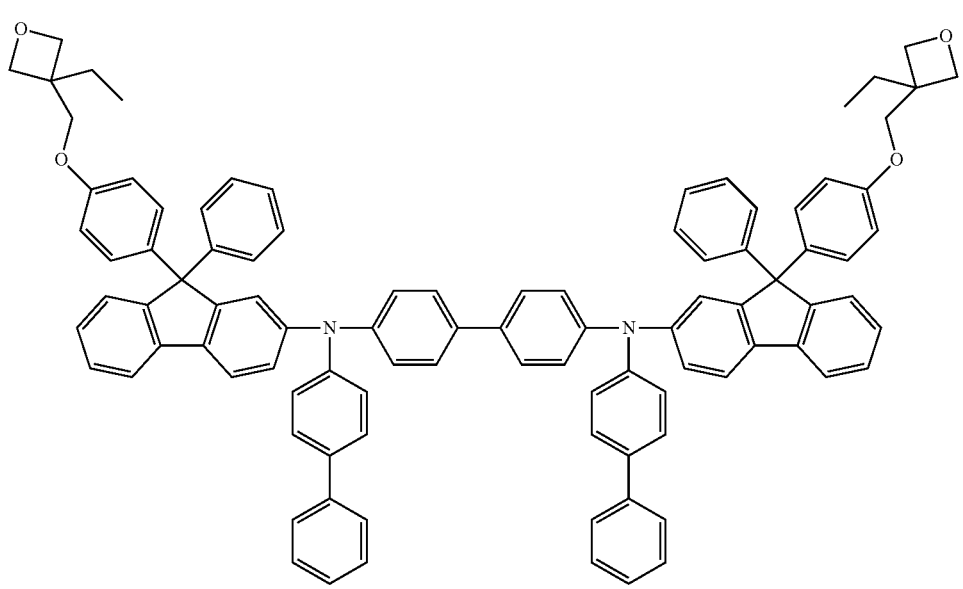

Compound 63
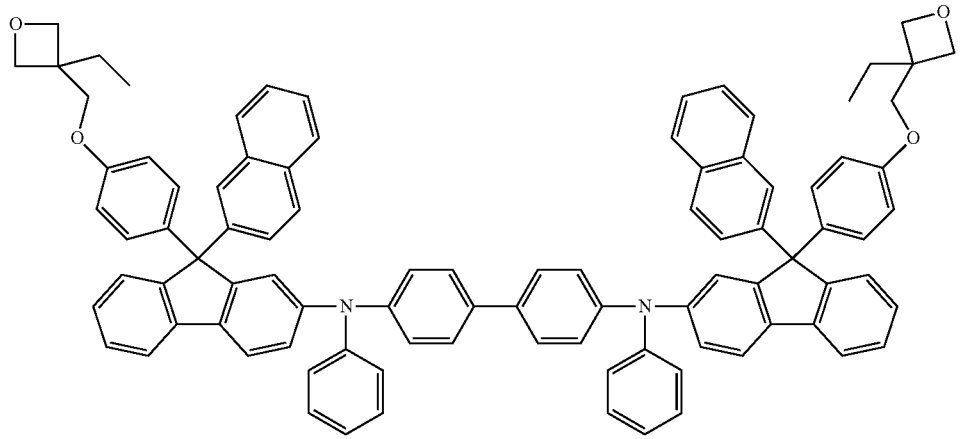
Compound 64
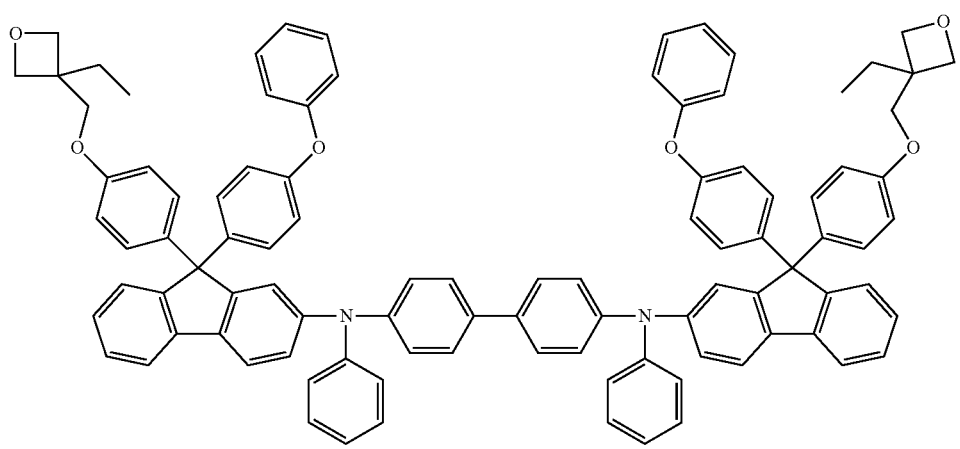
Compound 65
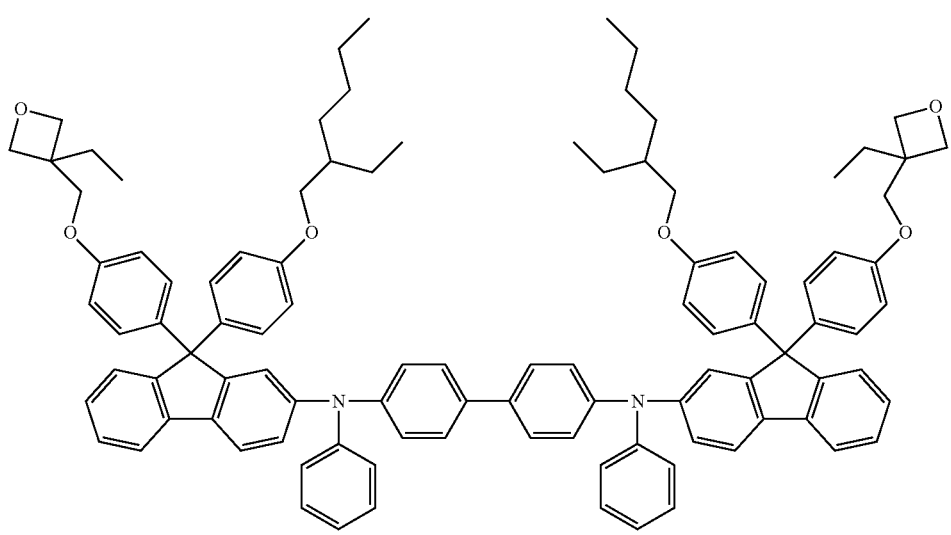

-continued
Compound 66
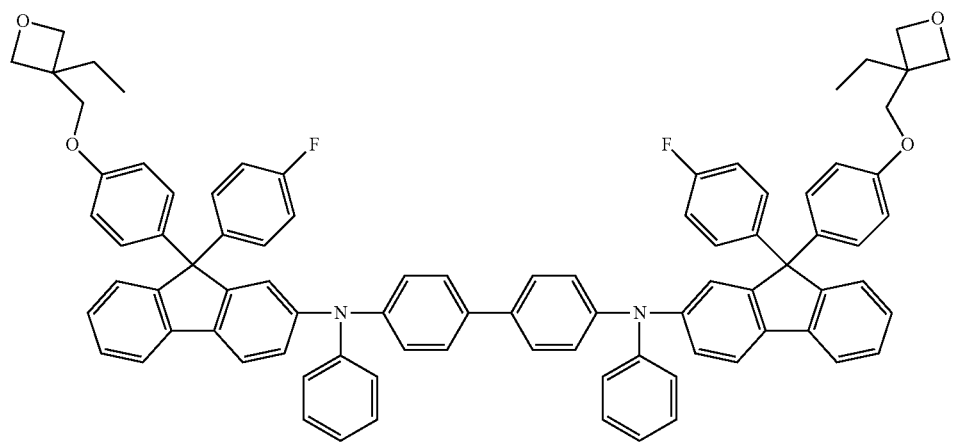
Compound 67
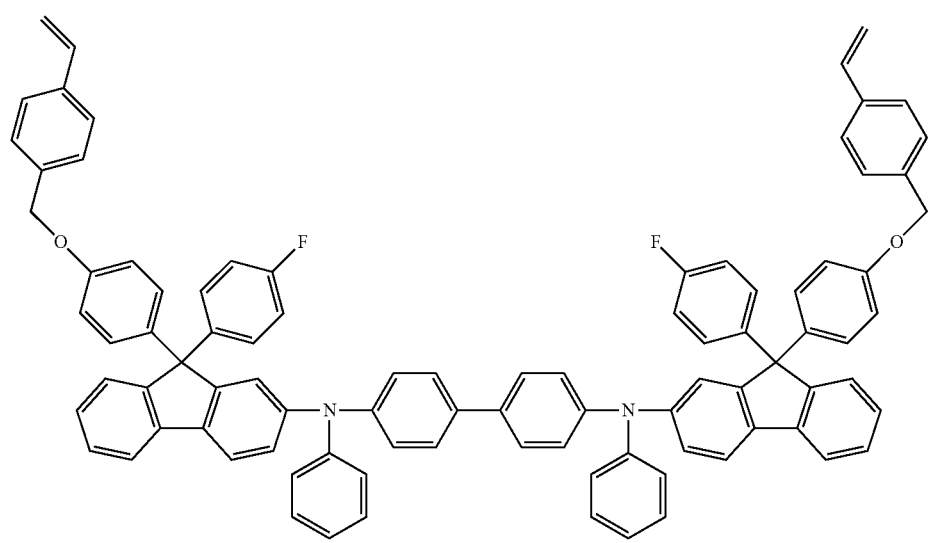
Compound 68
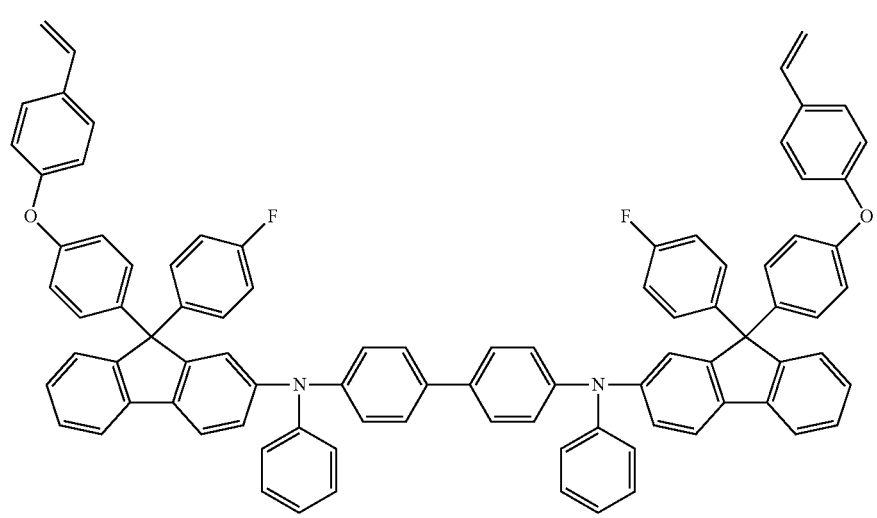

Compound 69
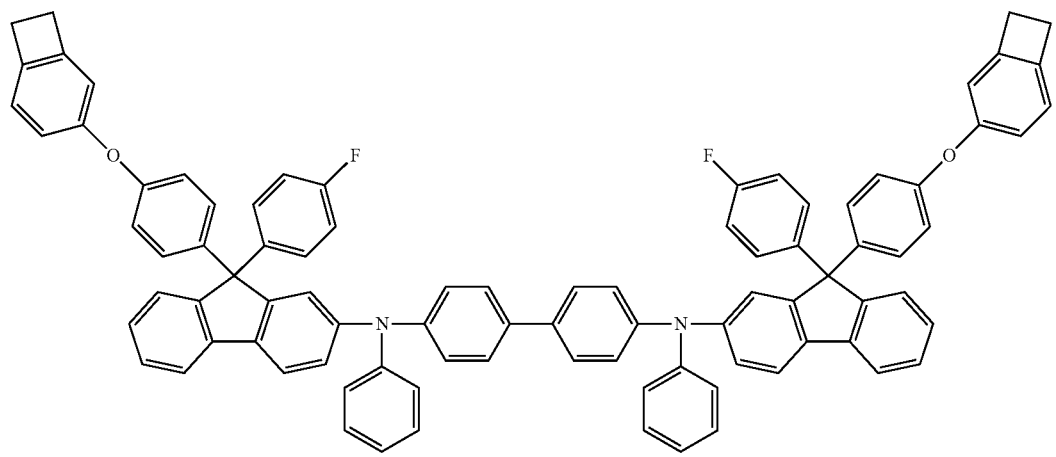
Compound 70
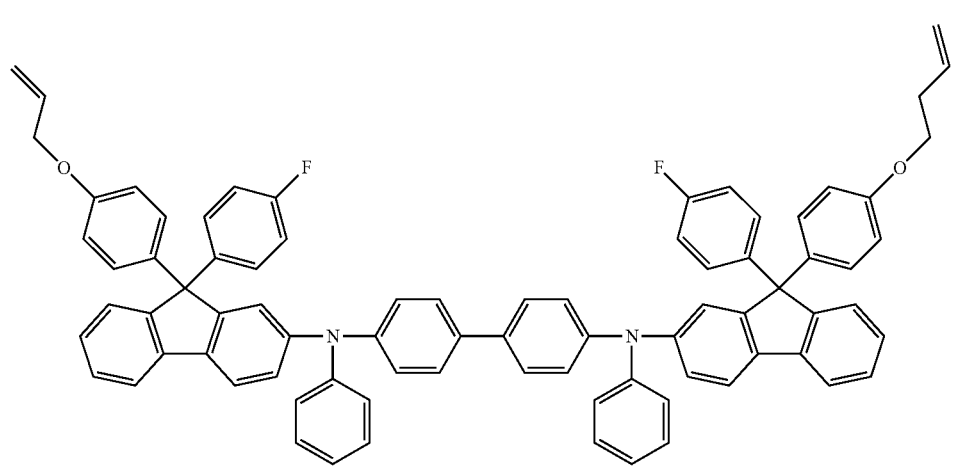
Compound 71
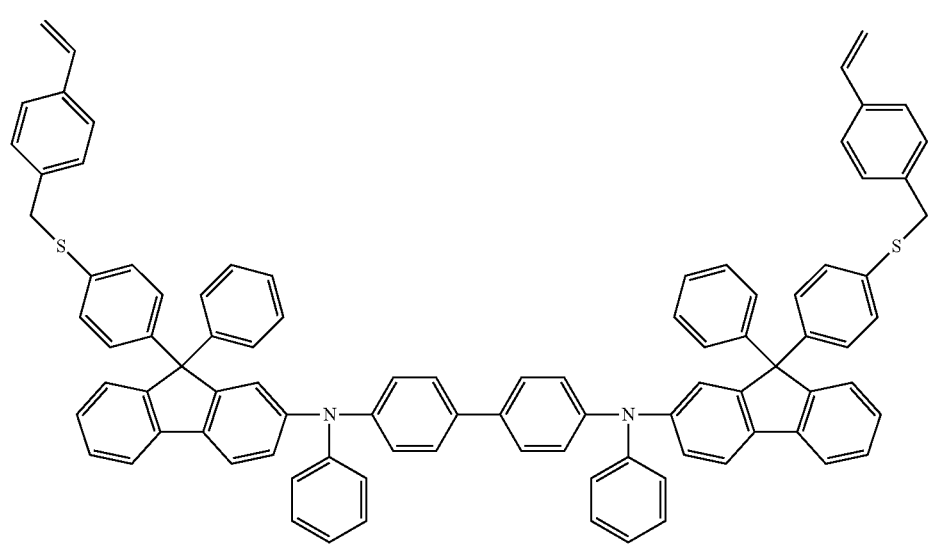

Compound 72
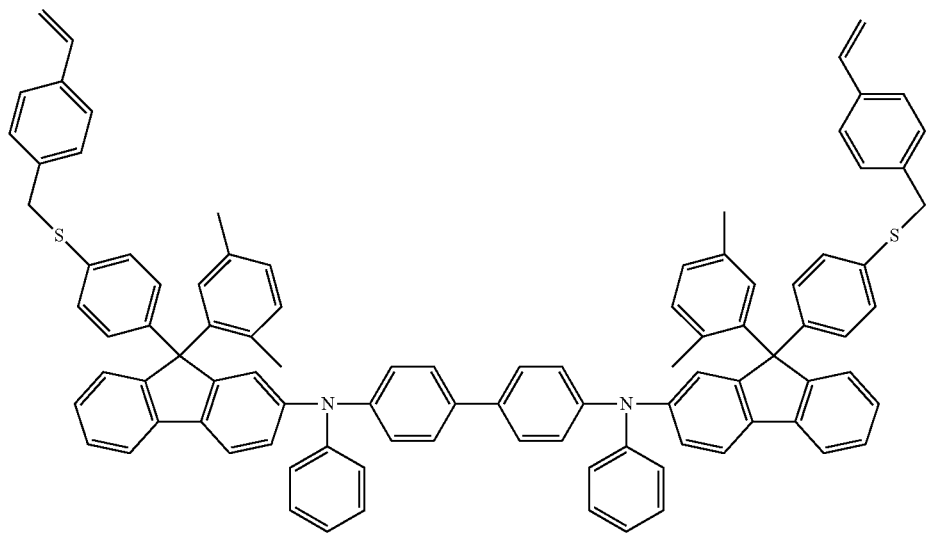
Compound 73
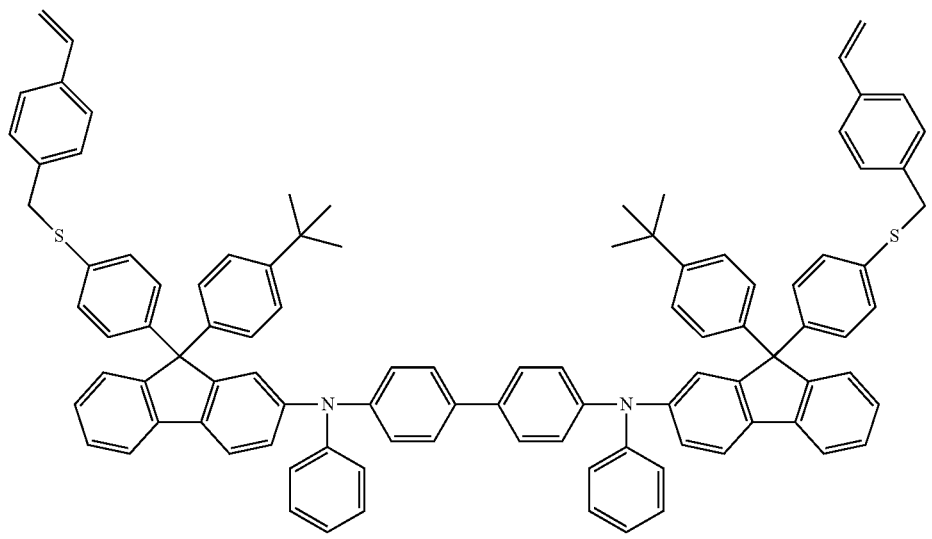
Compound 74
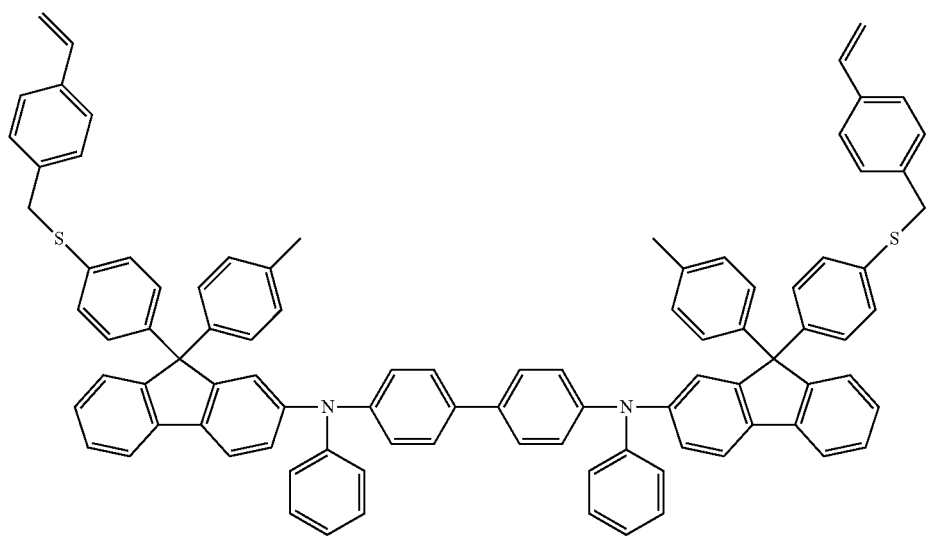

Compound 75
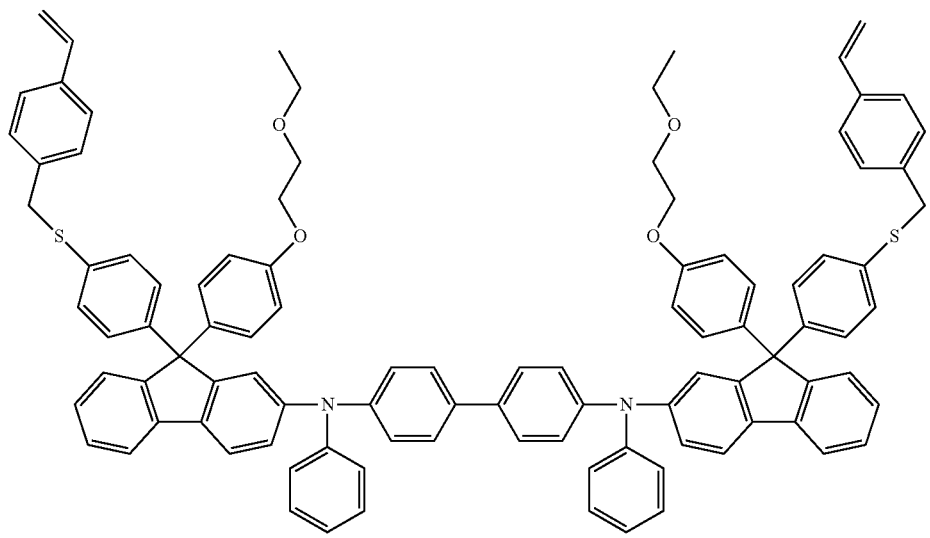
Compound 76
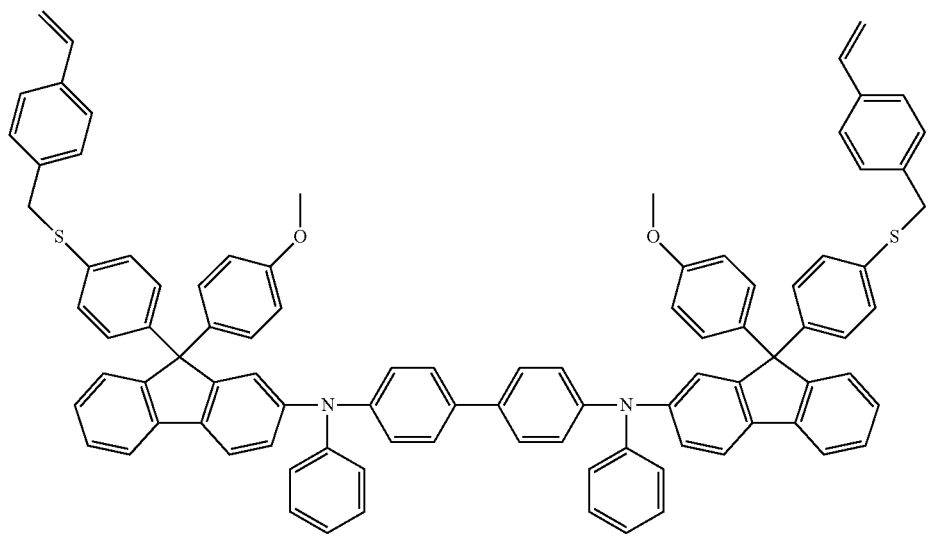
Compound 77
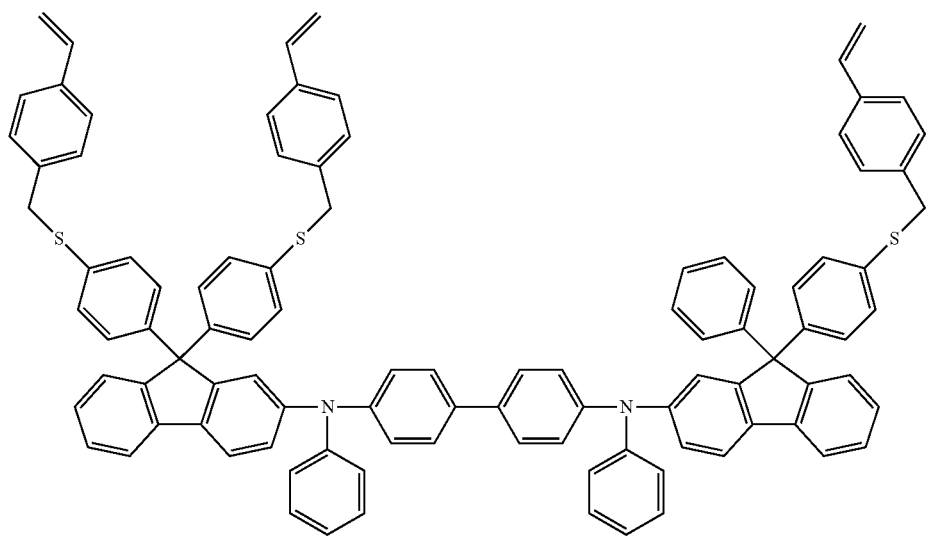

Compound 78
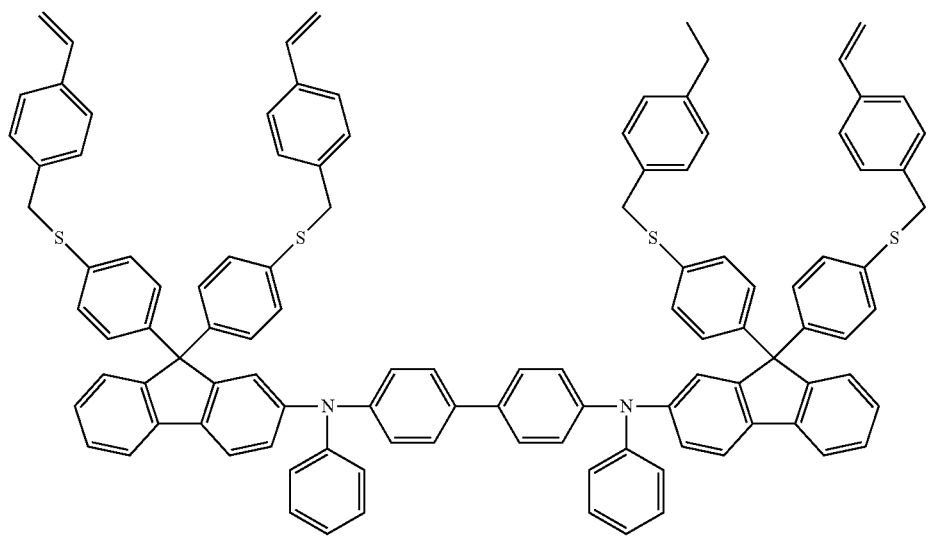
Compound 79
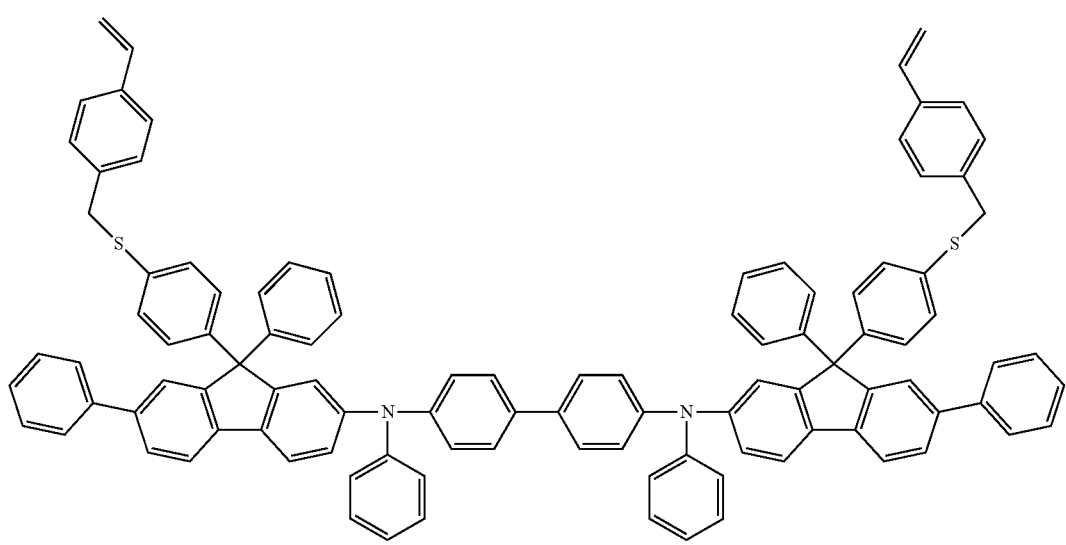

Compound 80
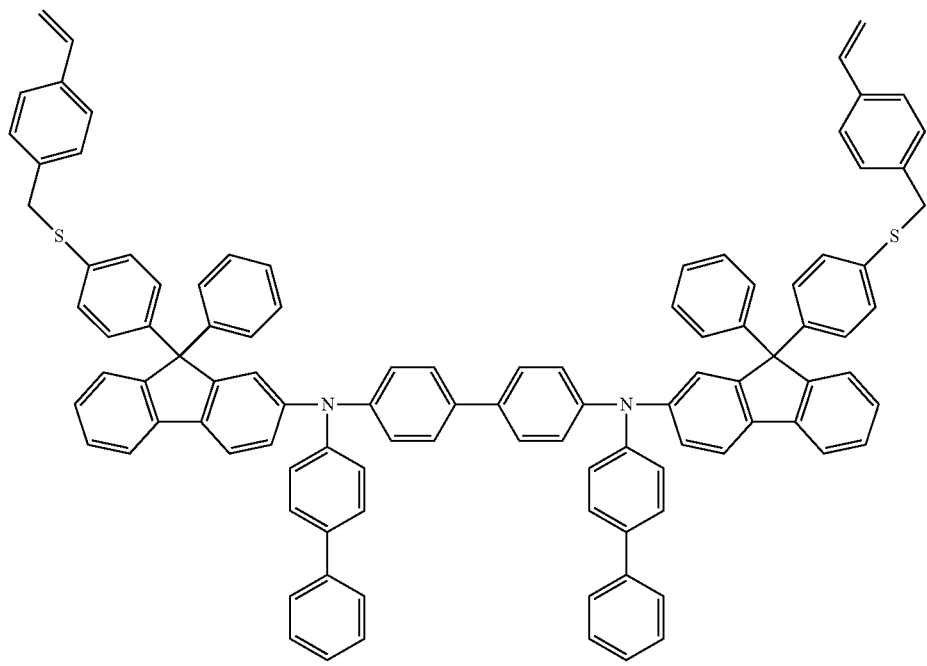
Compound 81
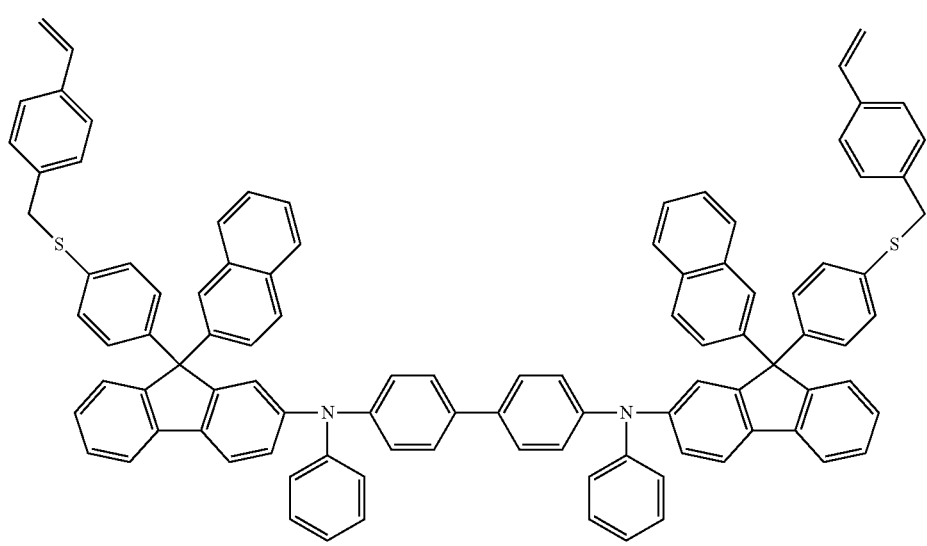

-continued
Compound 82
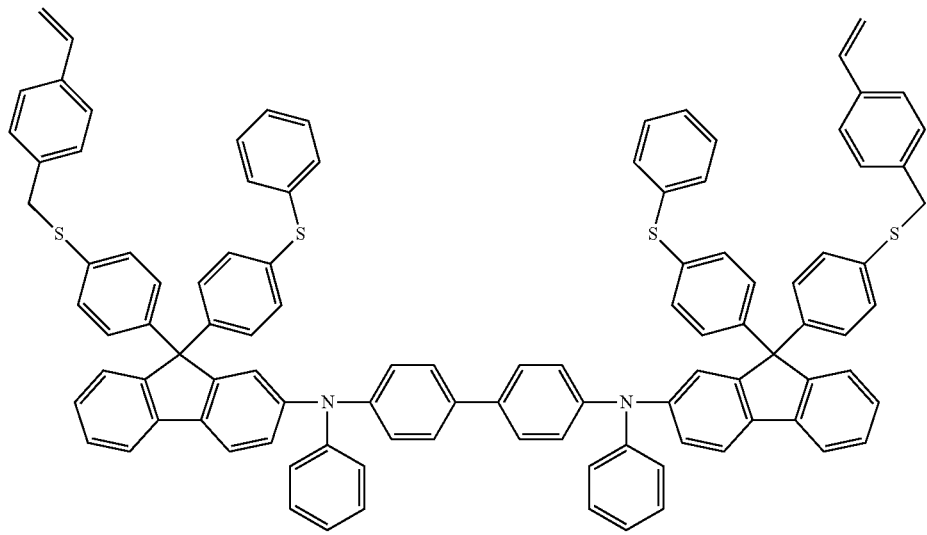
Compound 83
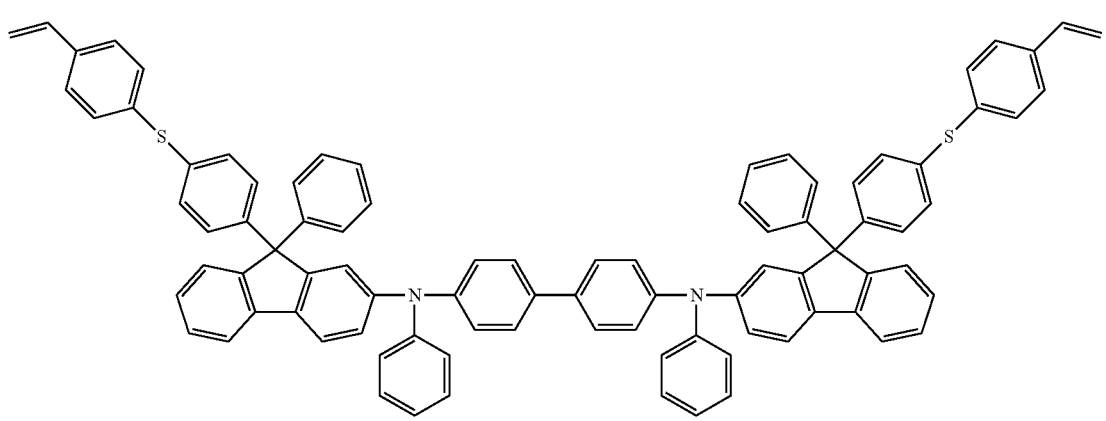
Compound 84
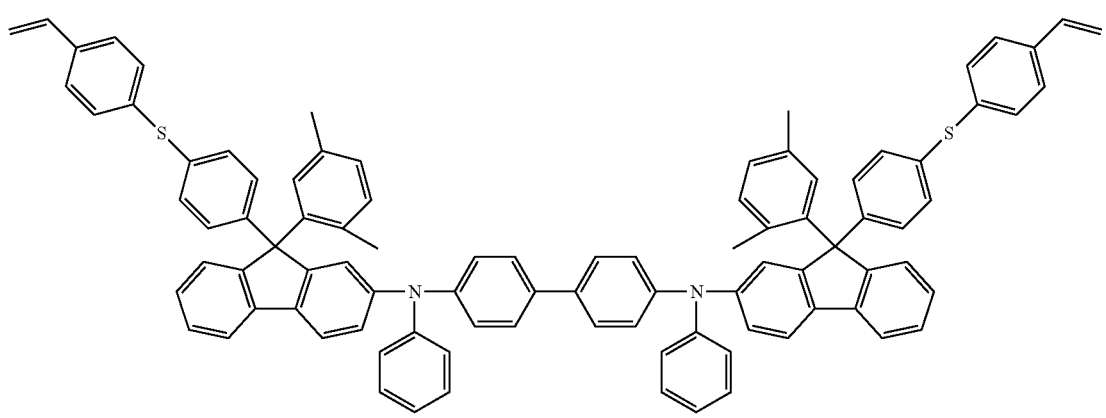

-continued
Compound 85
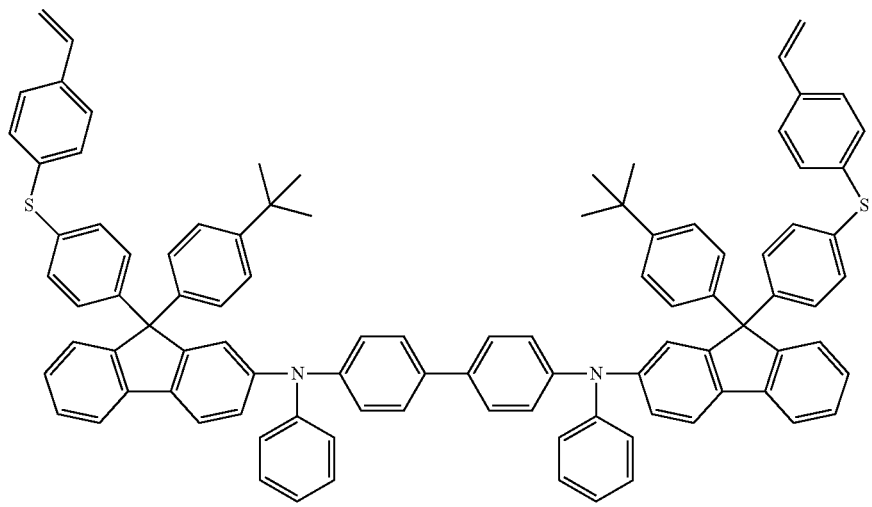
Compound 86
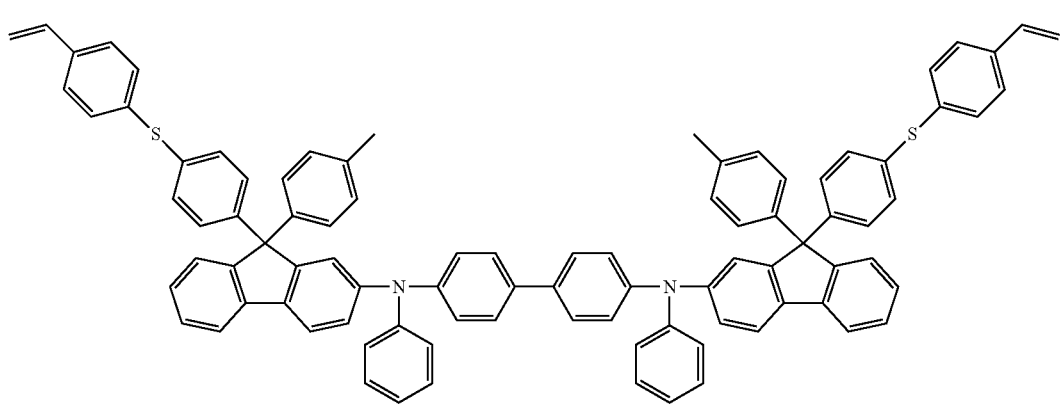
Compound 87
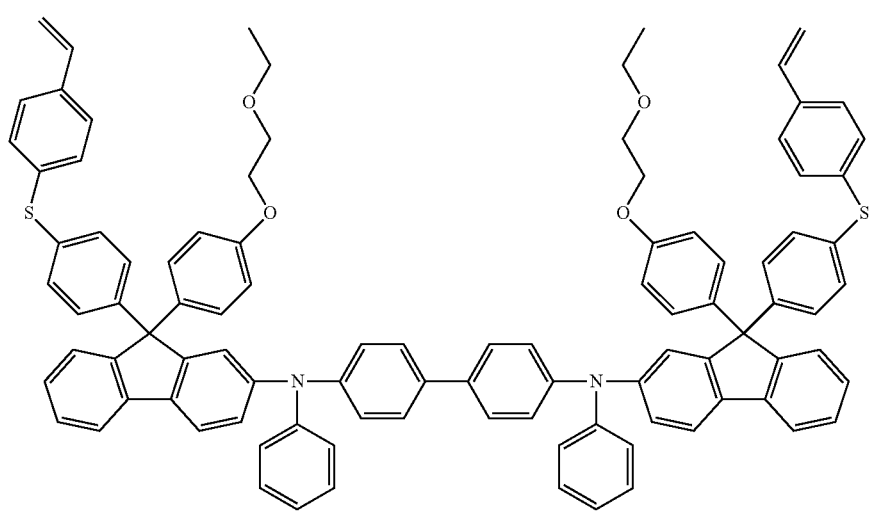

-continued
Compound 88
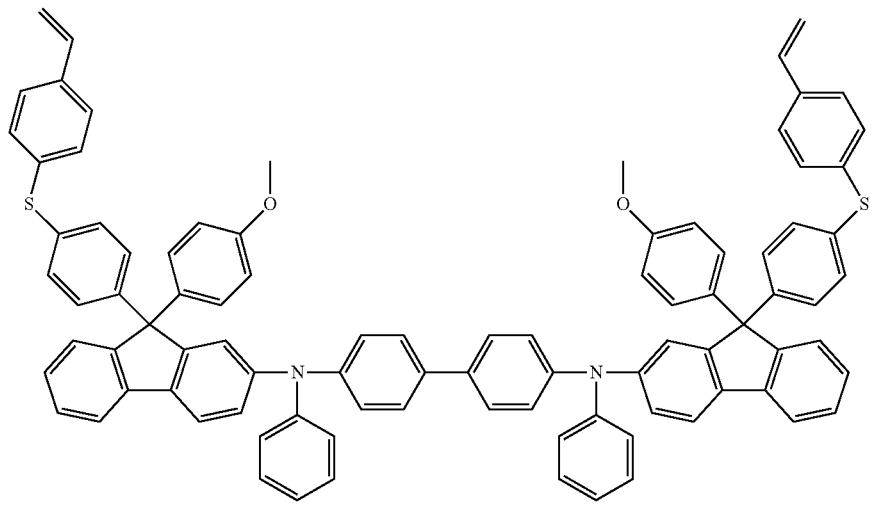
Compound 89
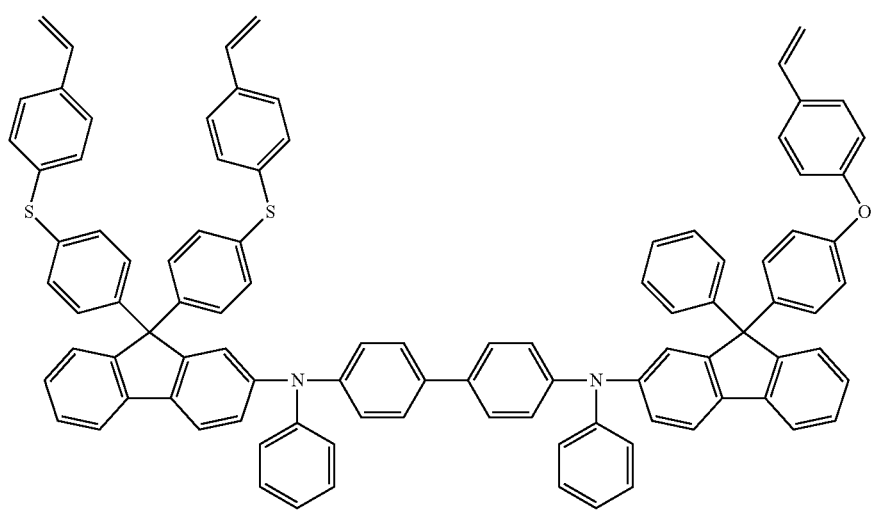
Compound 90
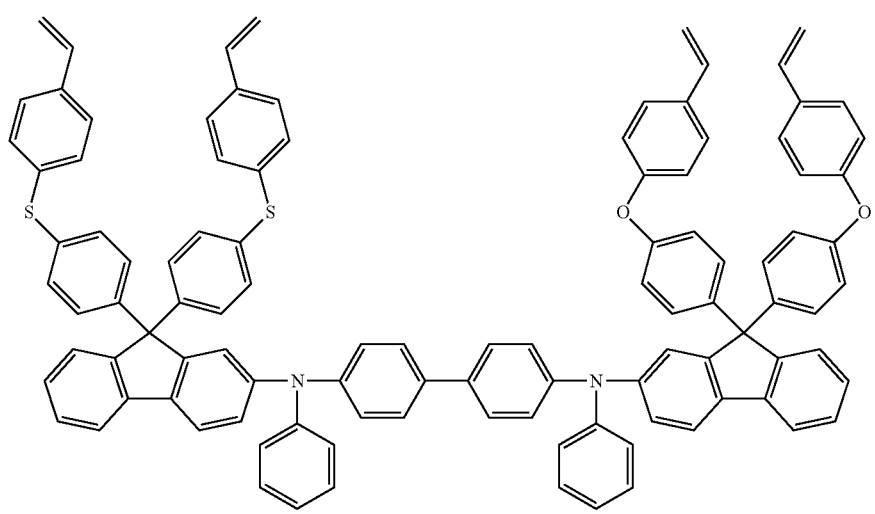

-continued
Compound 91
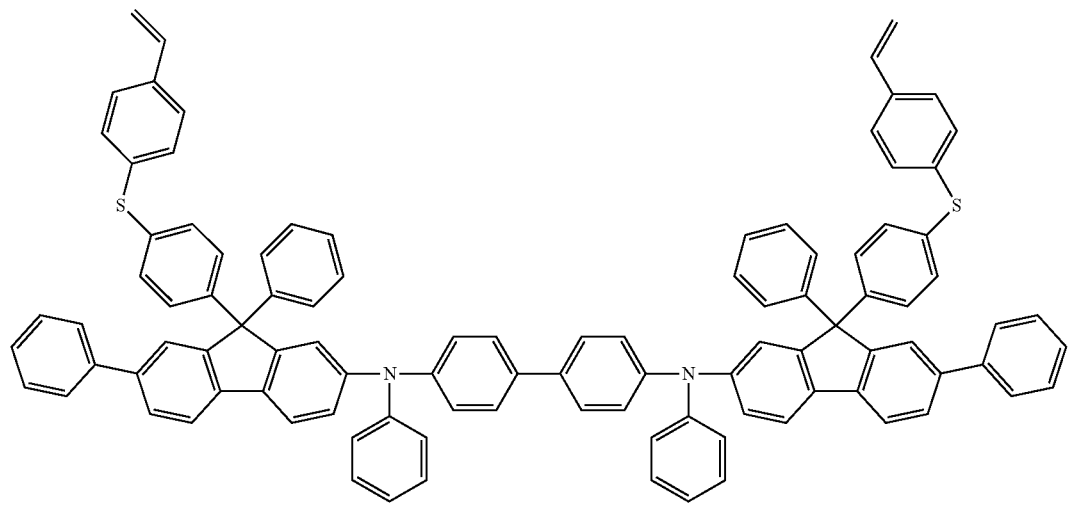
Compound 92
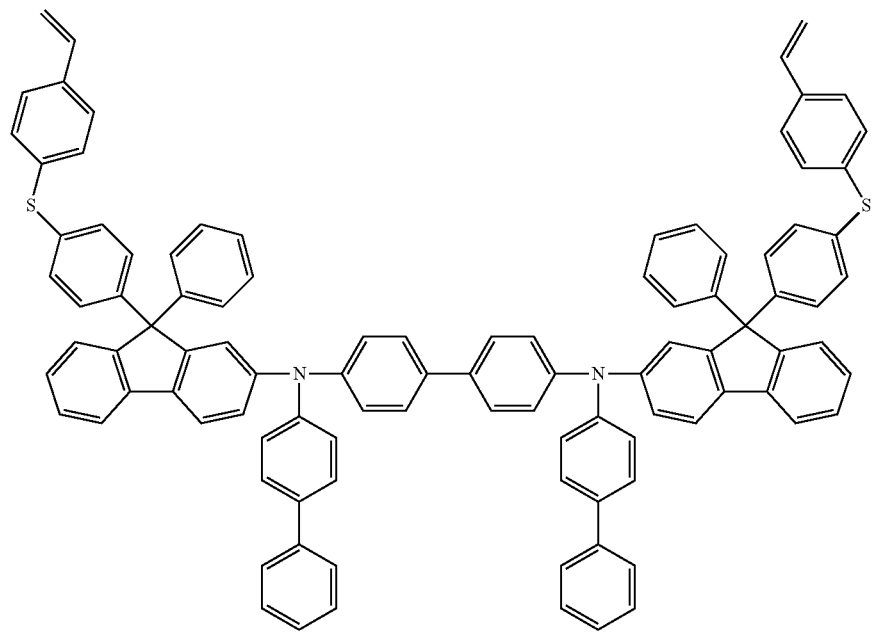
Compound 93
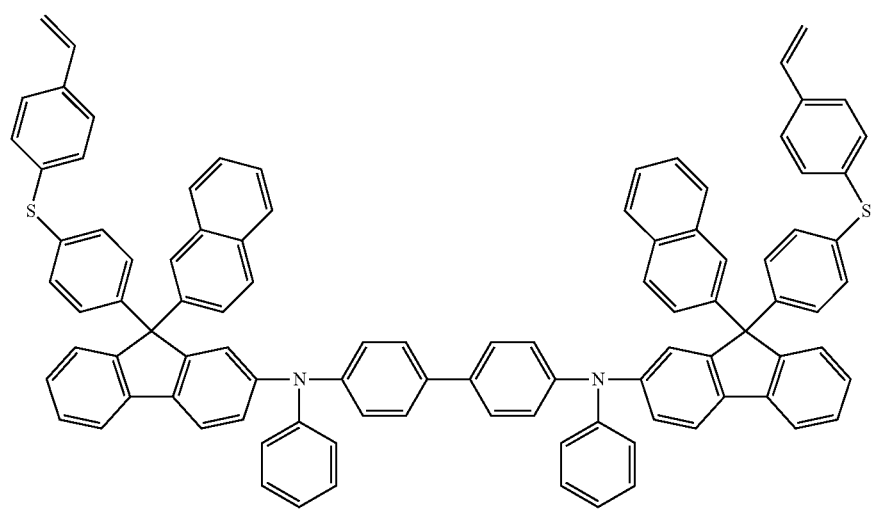

Compound 94
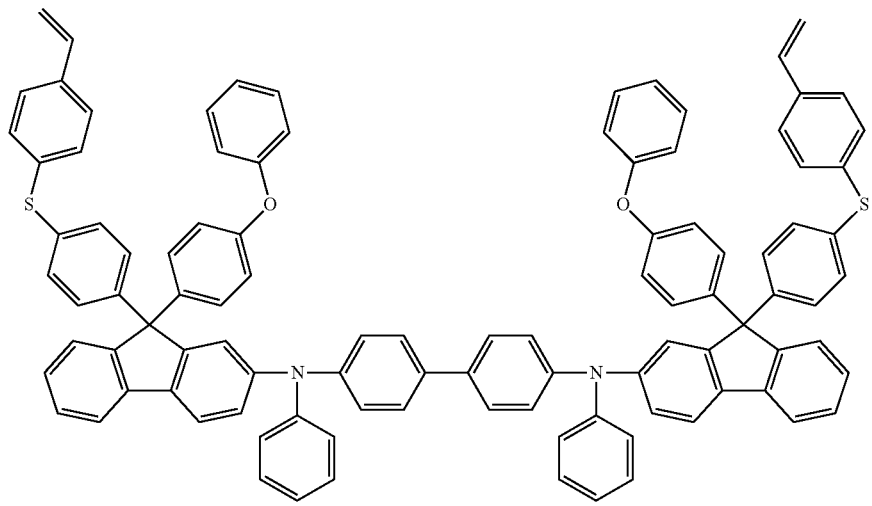
Compound 95
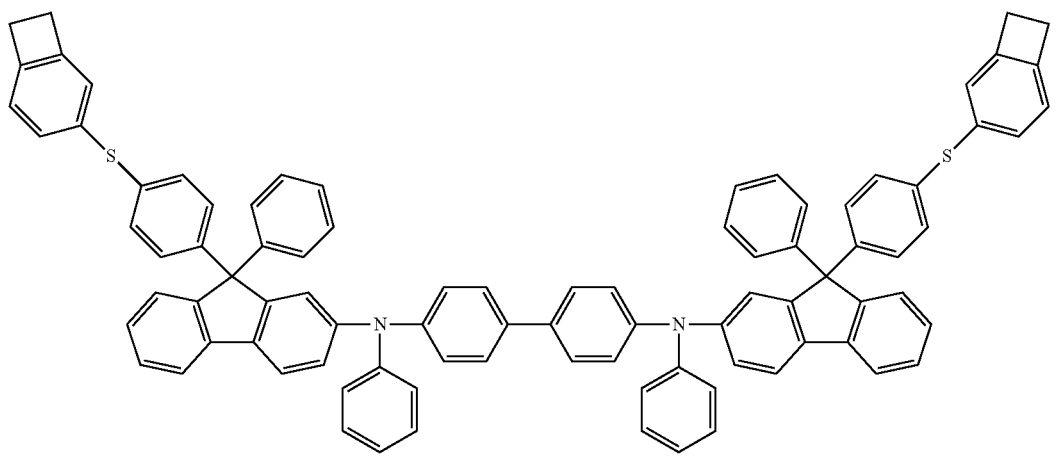
Compound 96
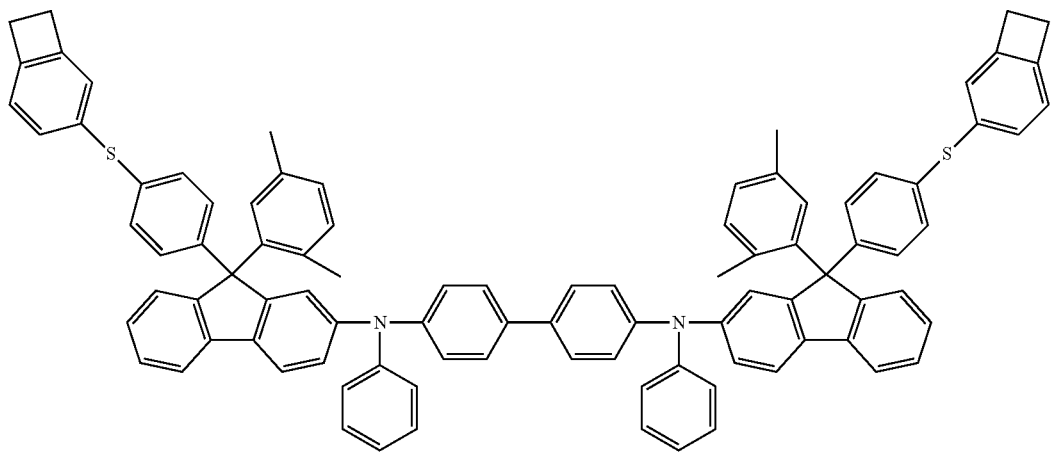

Compound 97
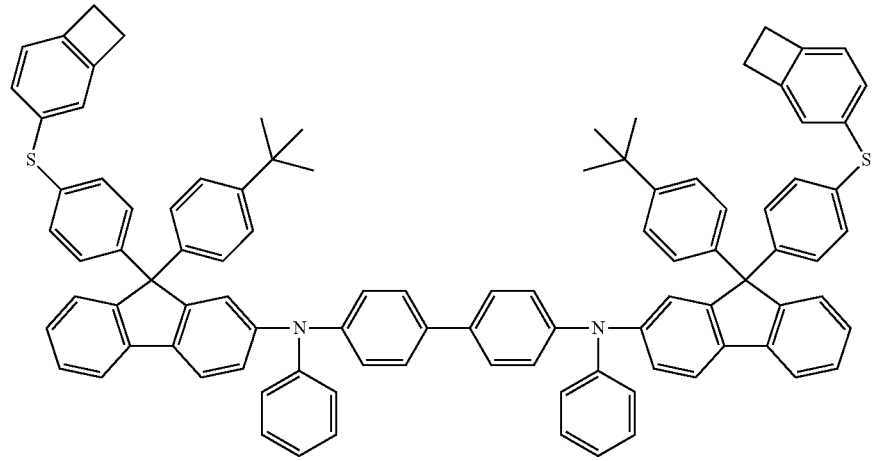
Compound 98
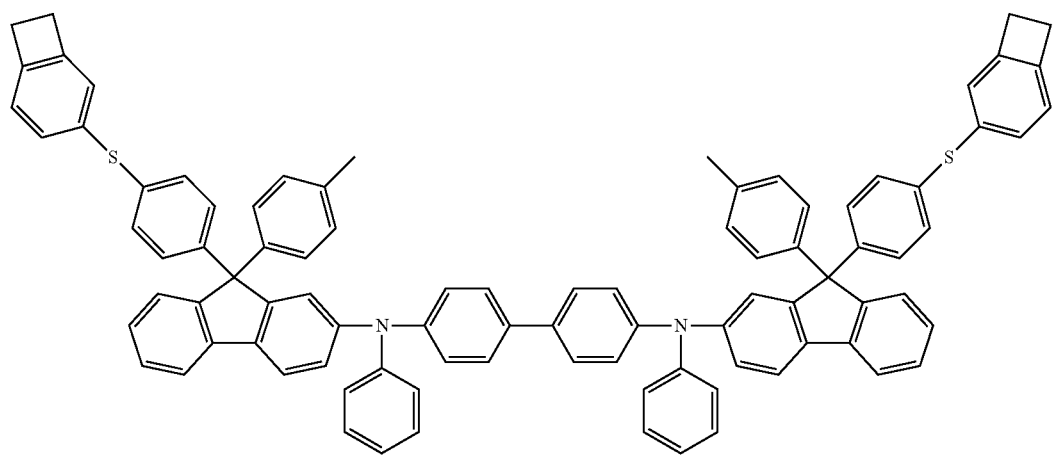
Compound 99
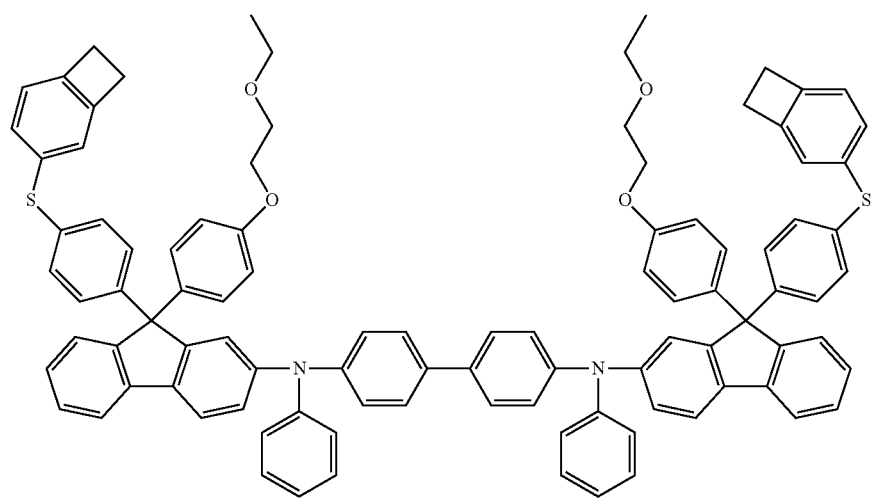

Compound 100
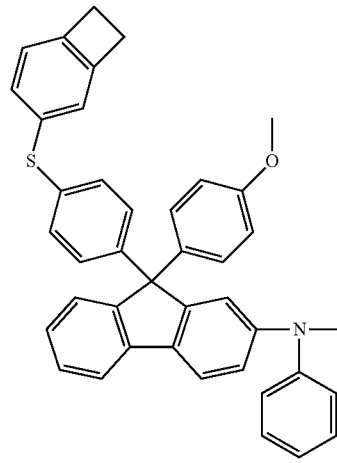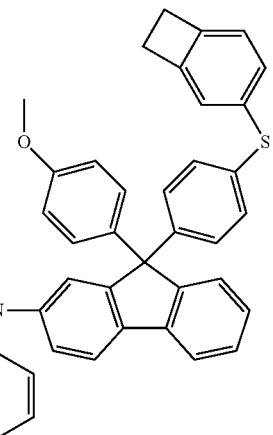
Compound 101

Compound 102
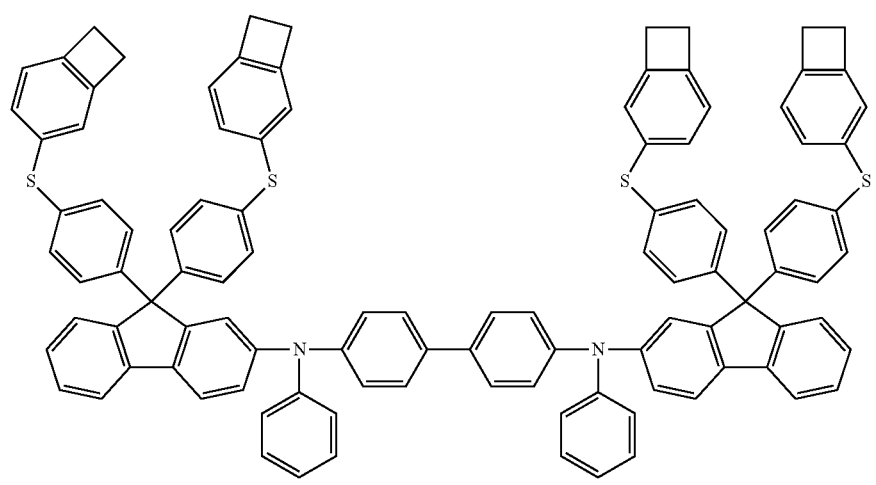

Compound 103
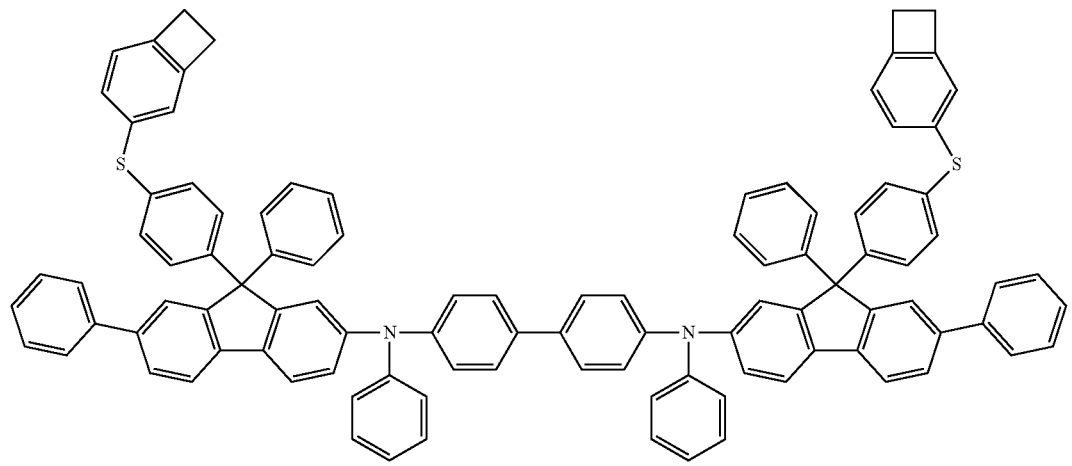
Compound 104
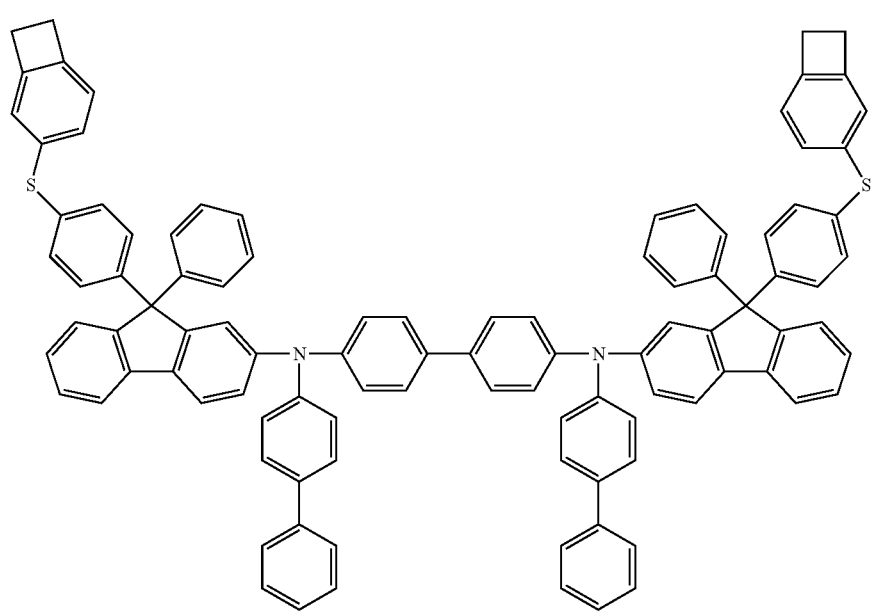
Compound 105
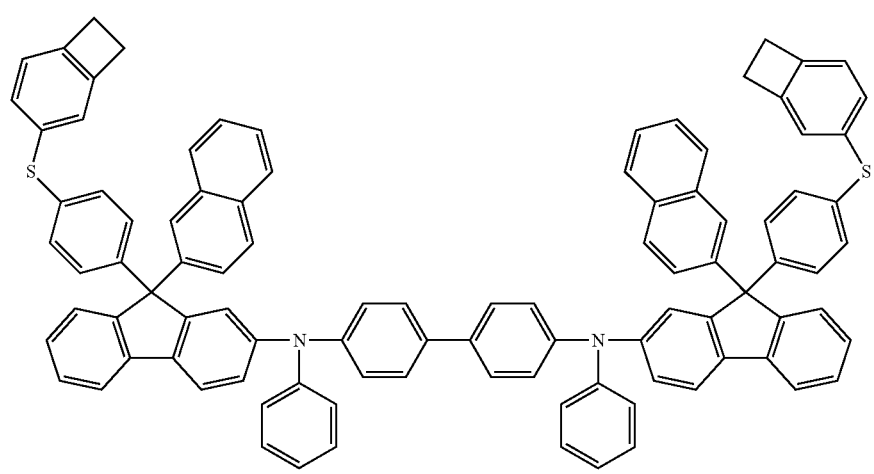

-continued
Compound 106
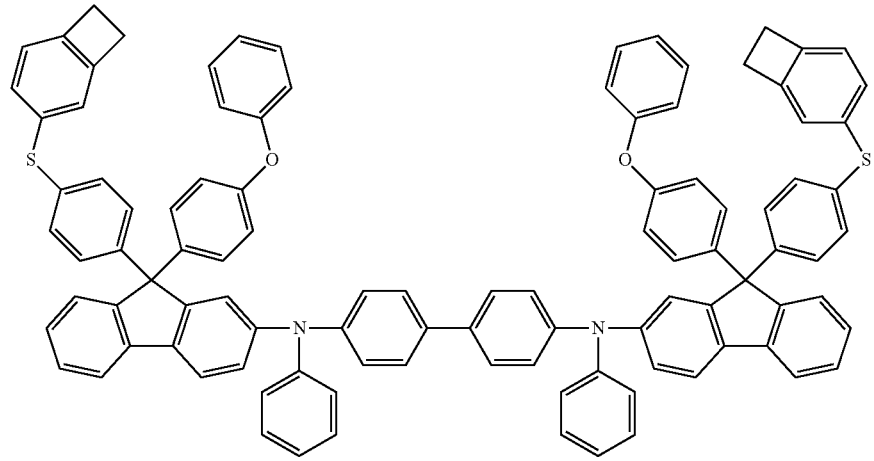
Compound 107
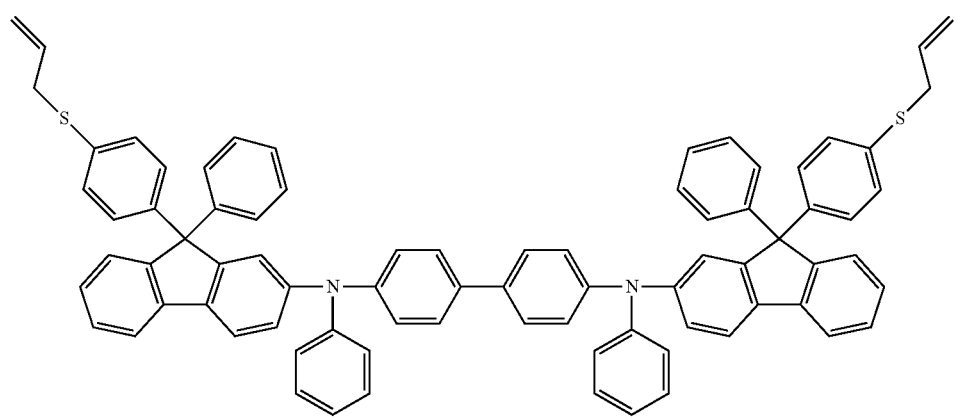
Compound 108
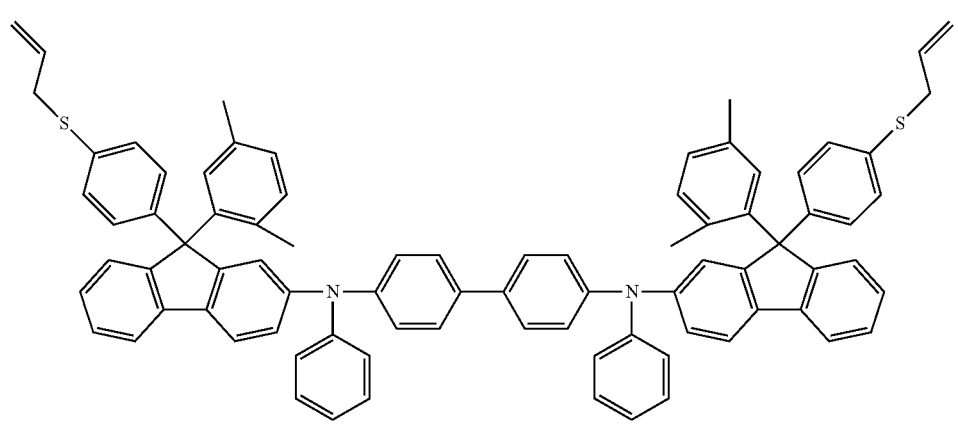

Compound 109
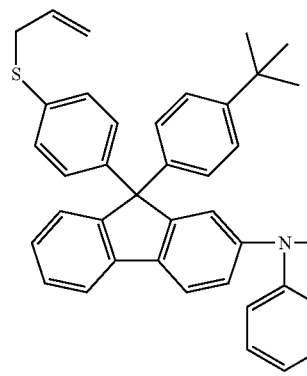 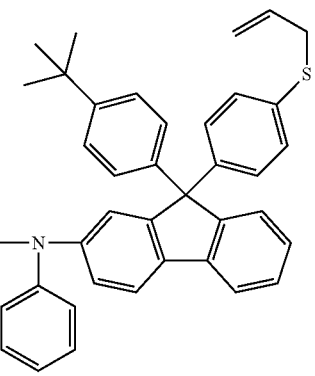
Compound 110
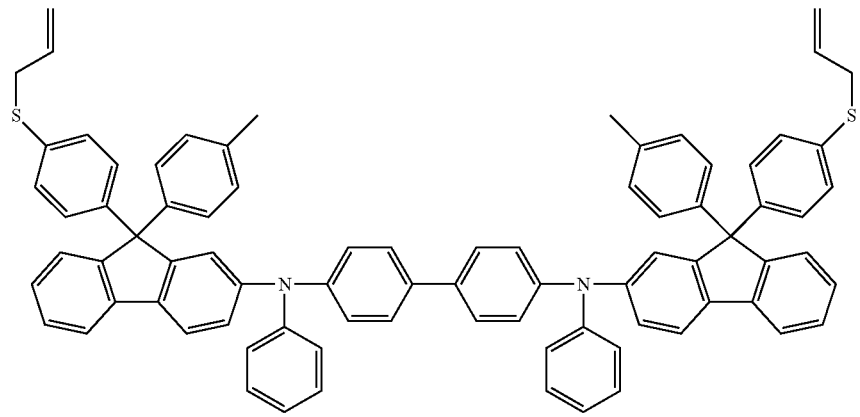
Compound 111
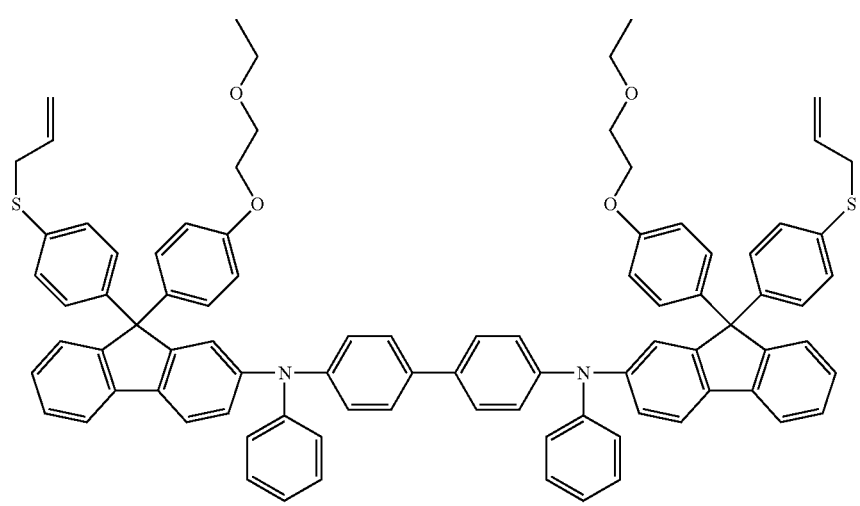

-continued
Compound 112
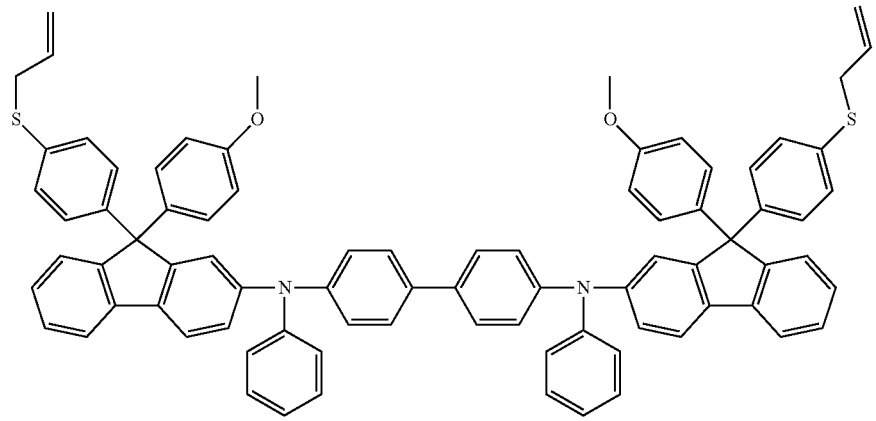
Compound 113
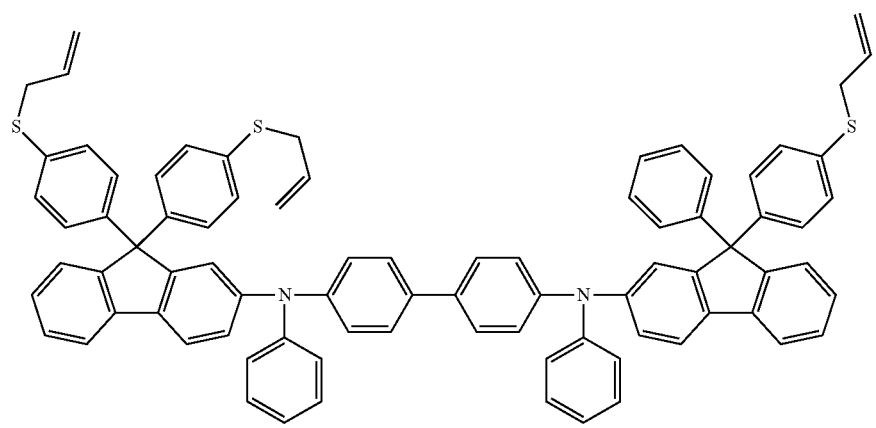
Compound 114
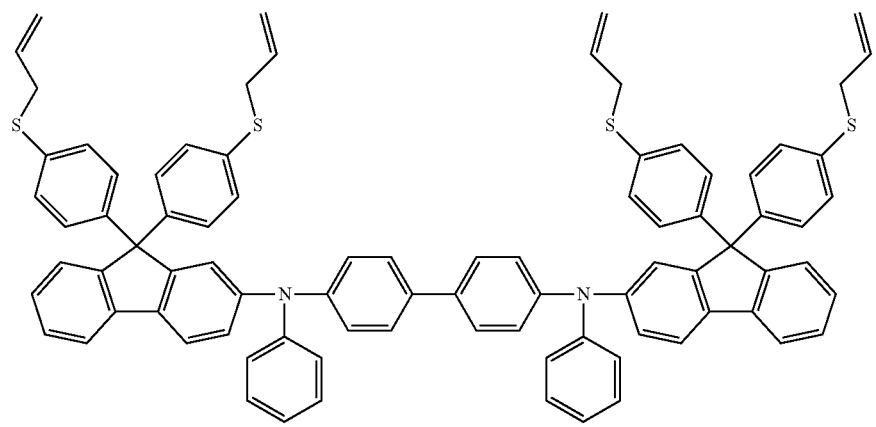

-continued
Compound 115
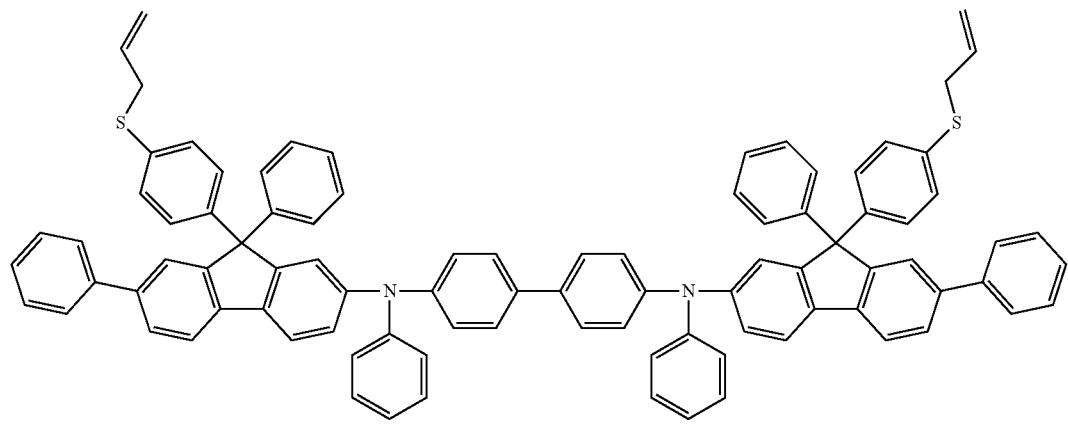
Compound 116
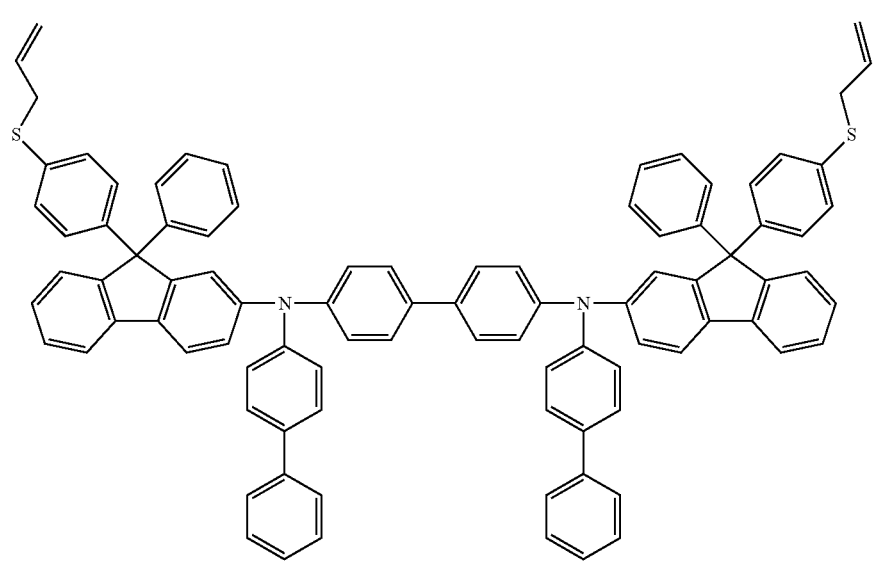
Compound 117
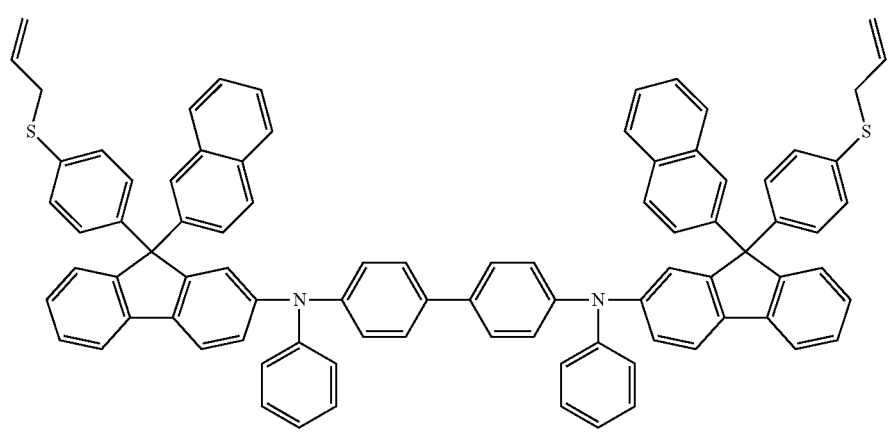

Compound 118
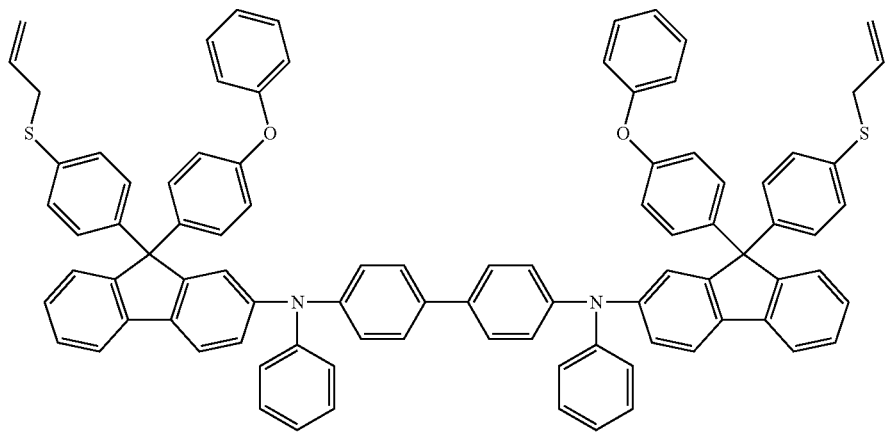
Compound 119
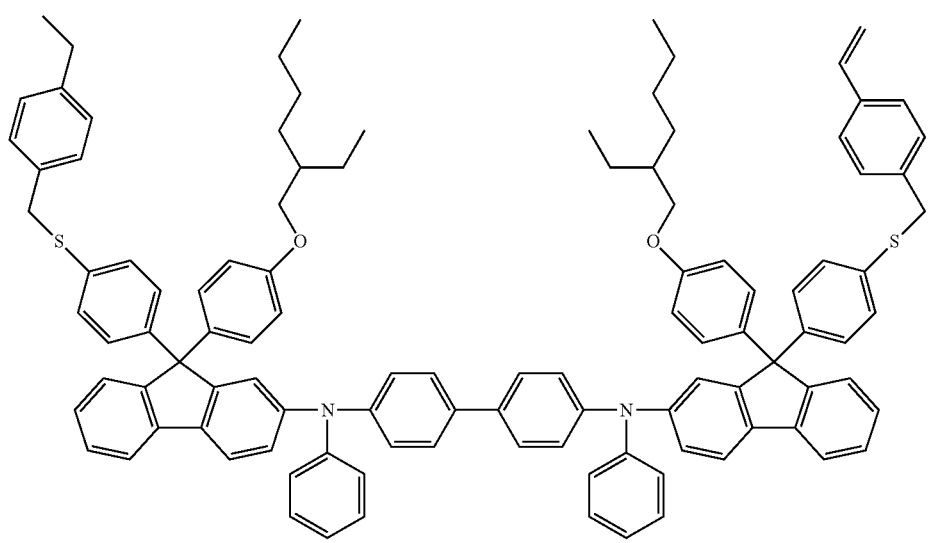
Compound 120
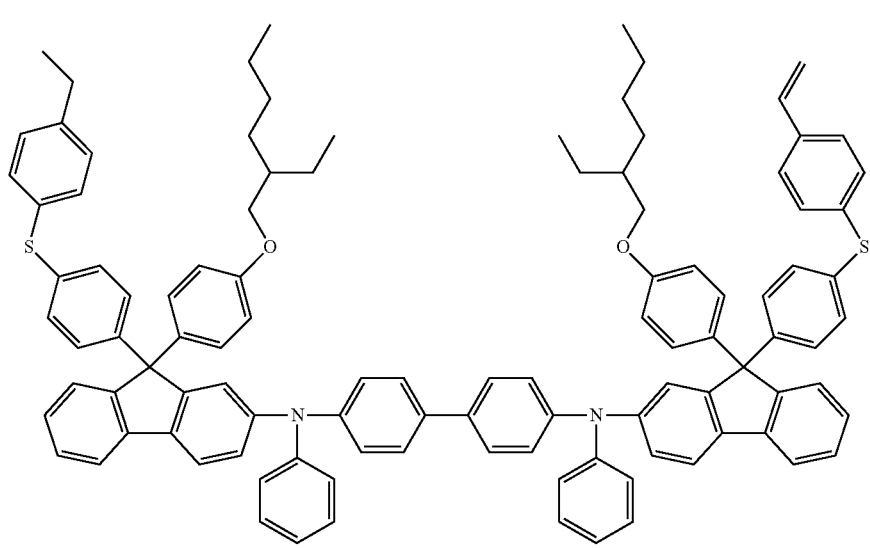

Compound 121
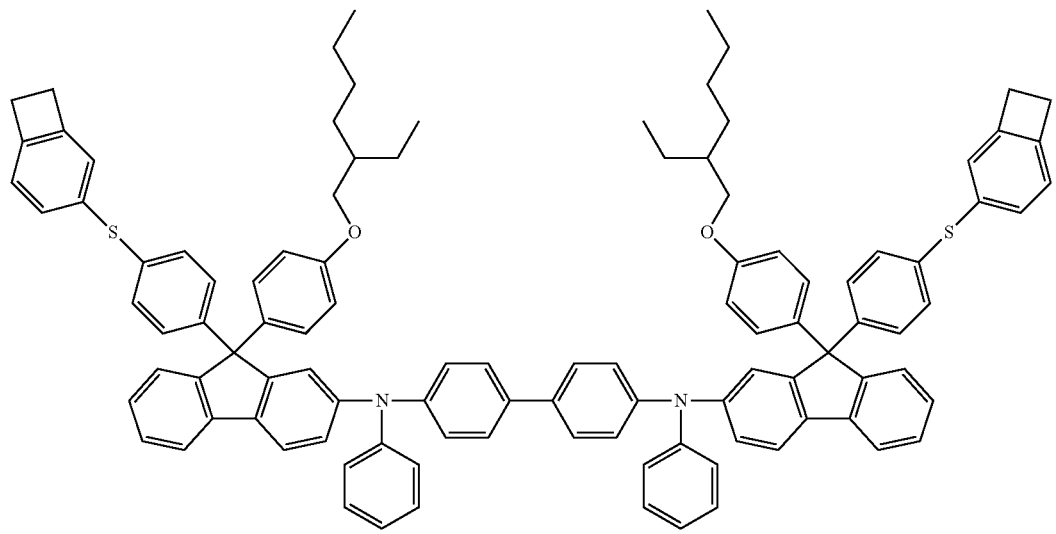
Compound 122
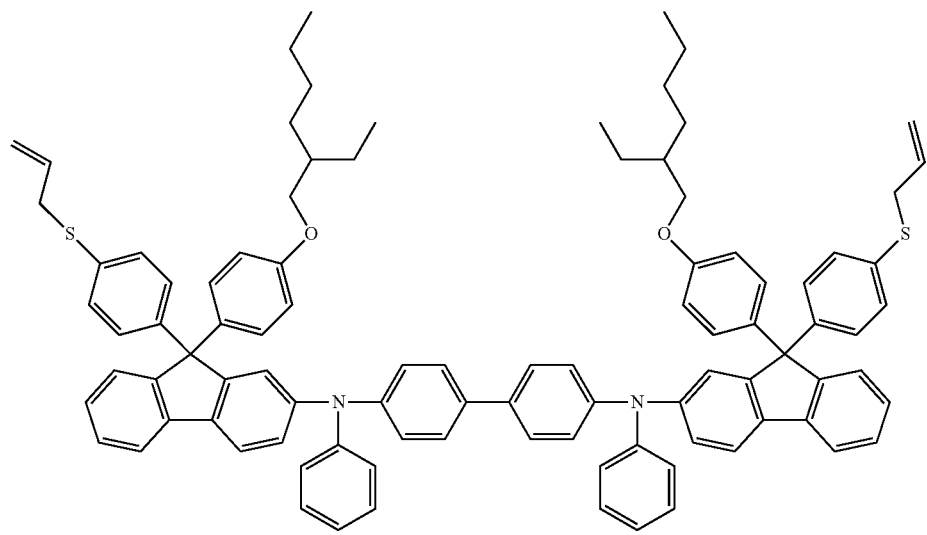
Compound 123
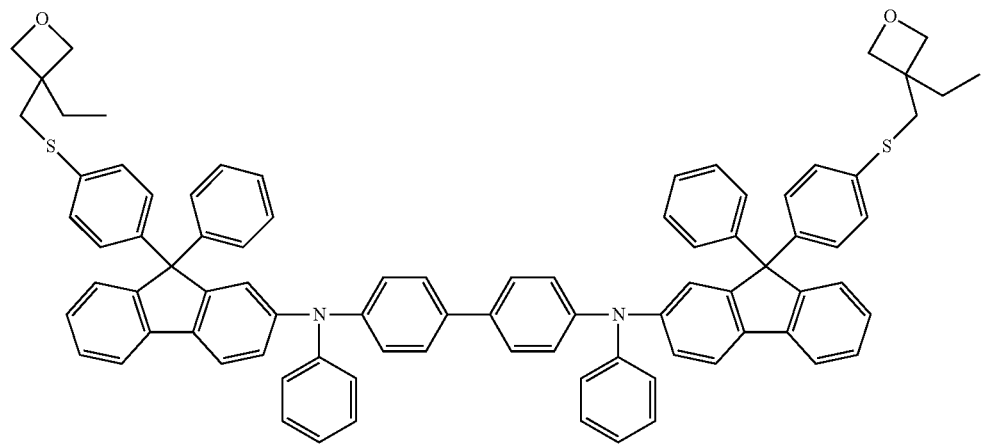

-continued
Compound 124
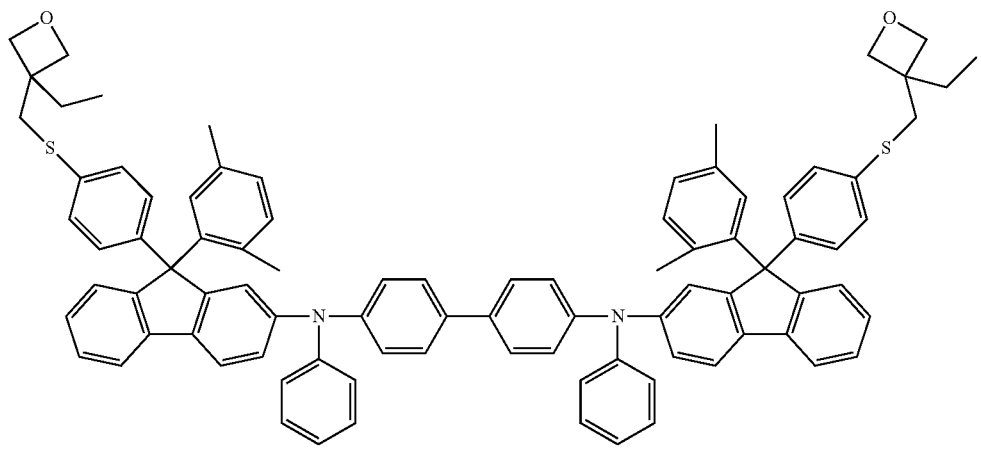
Compound 125
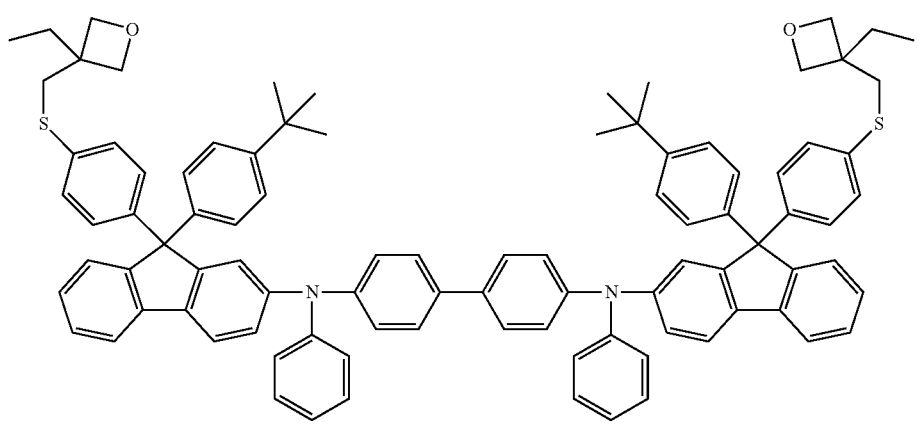
Compound 126
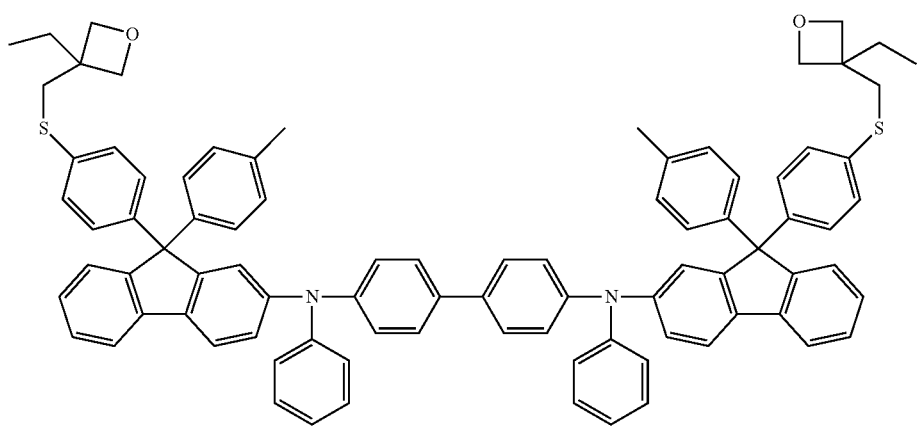

-continued
Compound 127
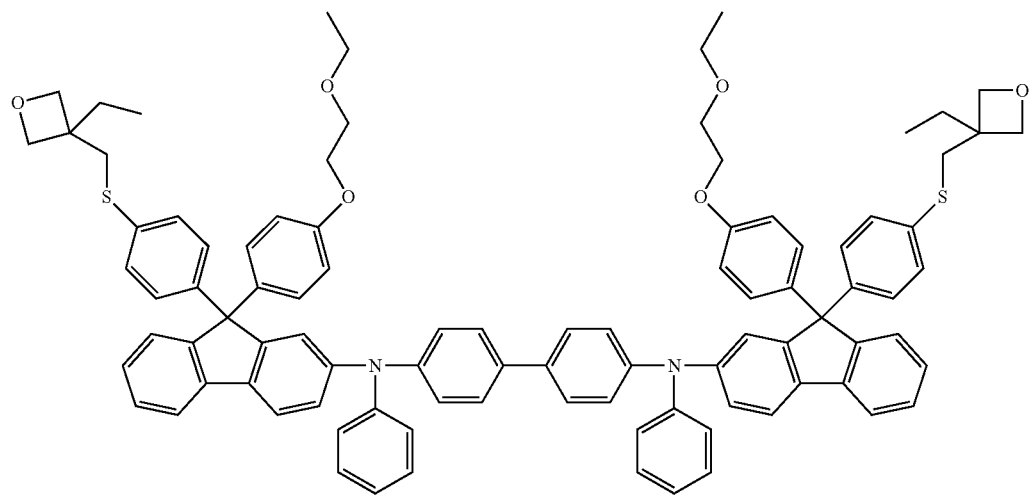
Compound 128
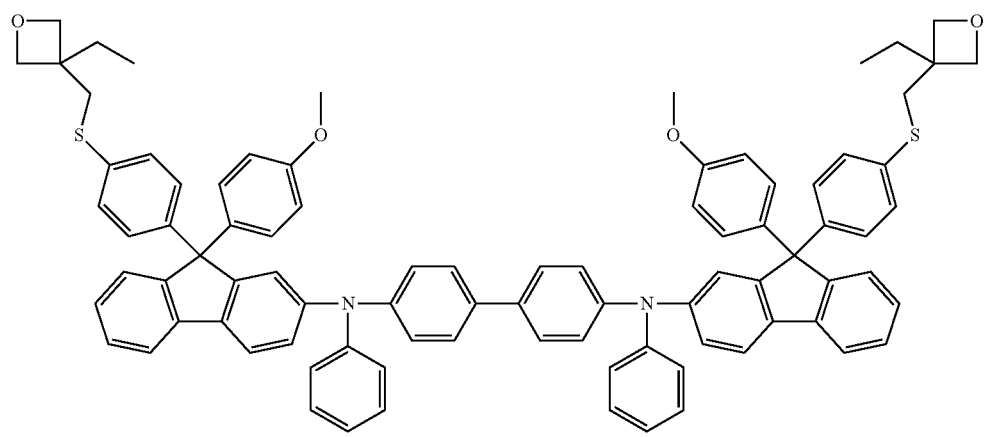
Compound 129
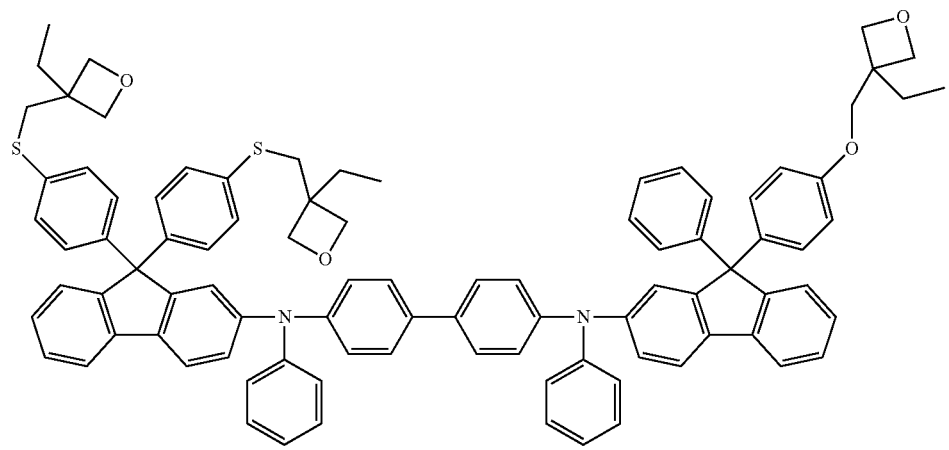

Compound 130
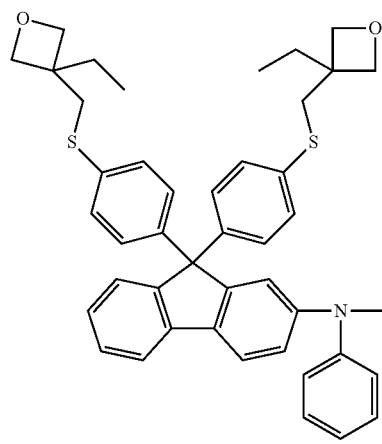
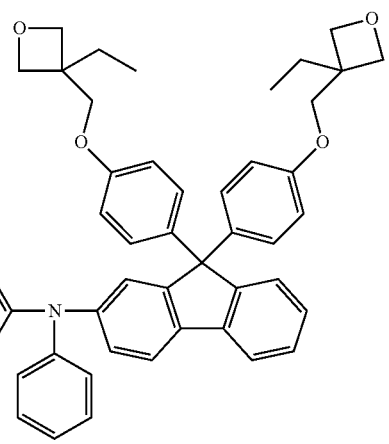
Compound 131
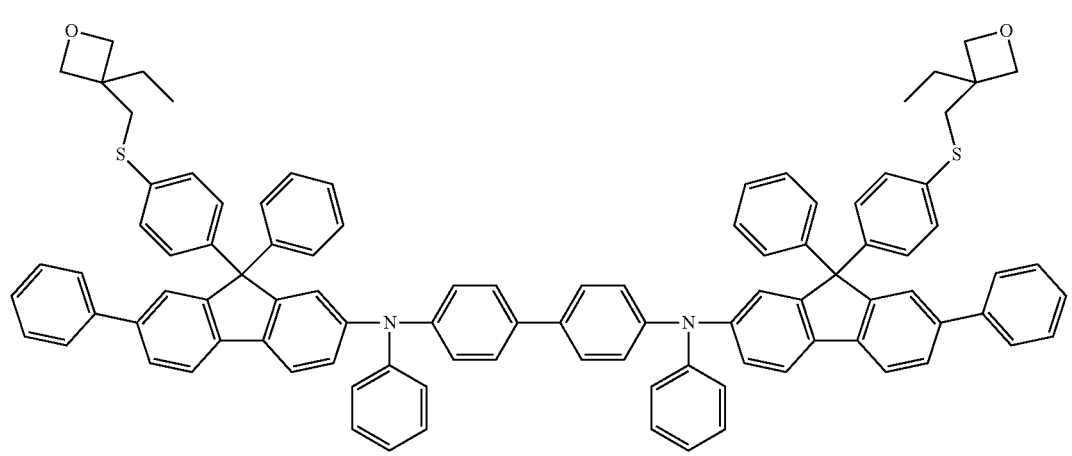
Compound 132
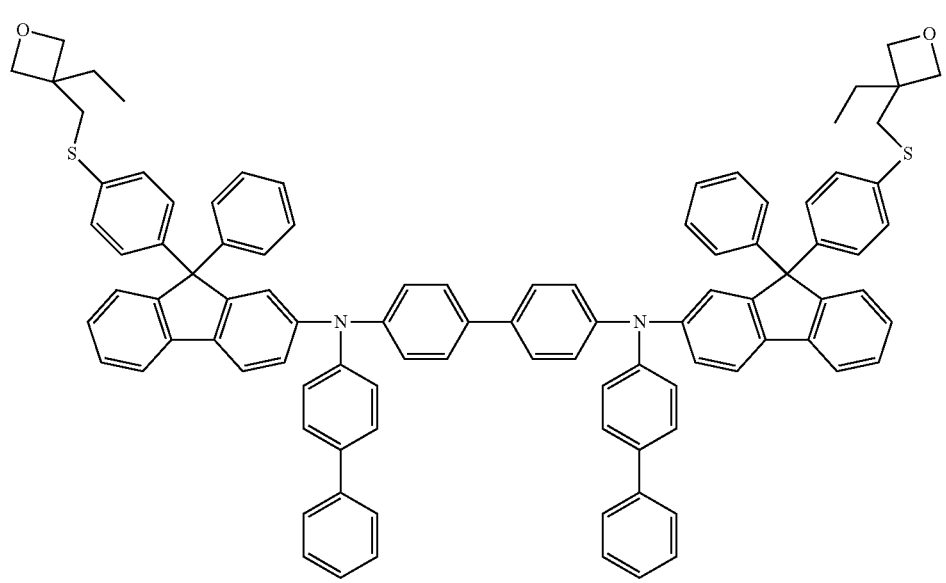

-continued
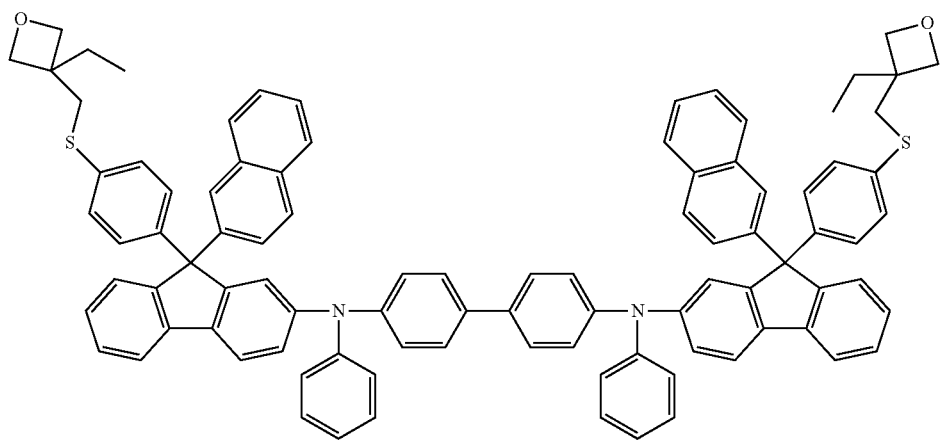
Compound 133
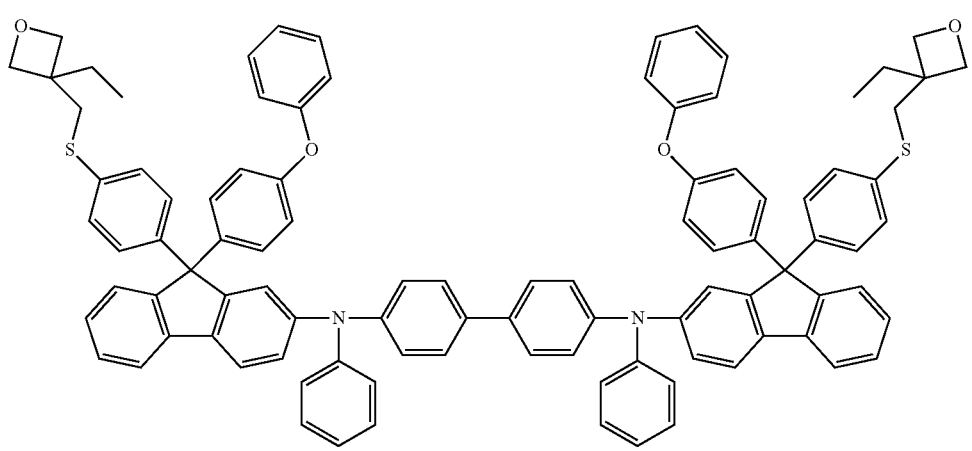
Compound 134
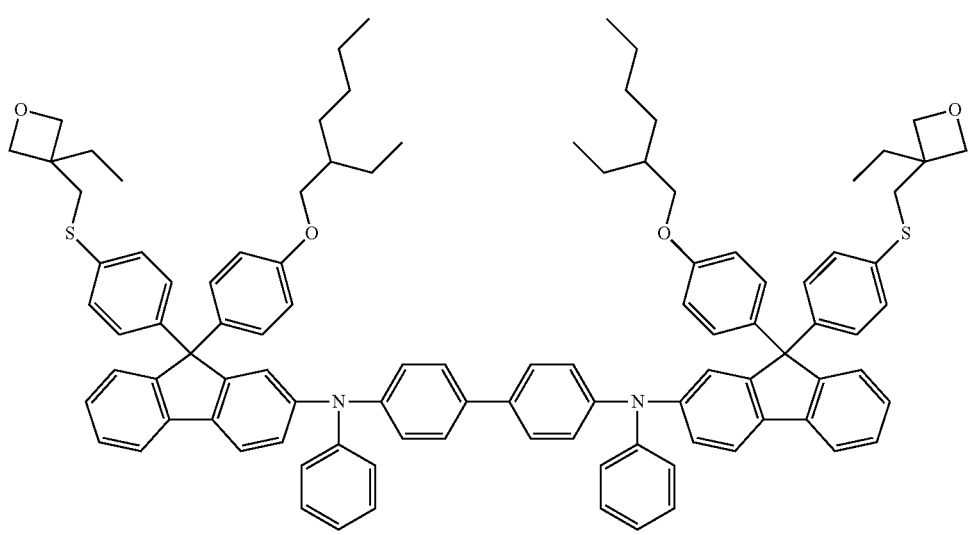
Compound 135

-continued
Compound 136
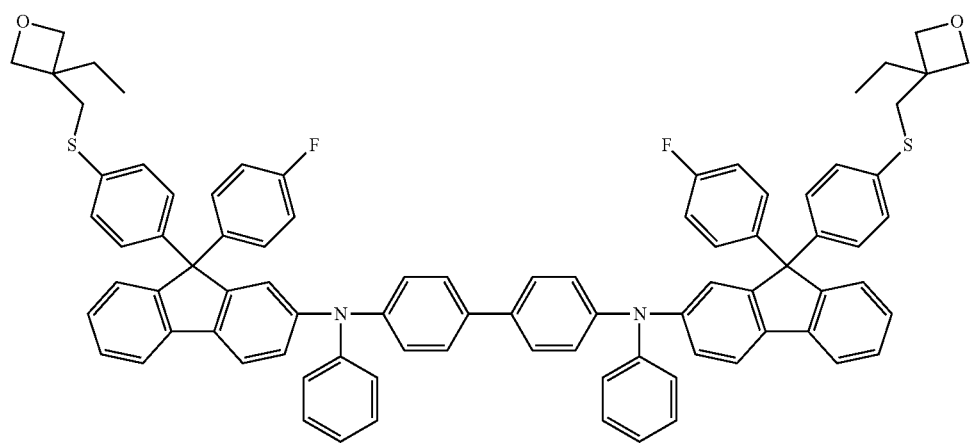
Compound 137
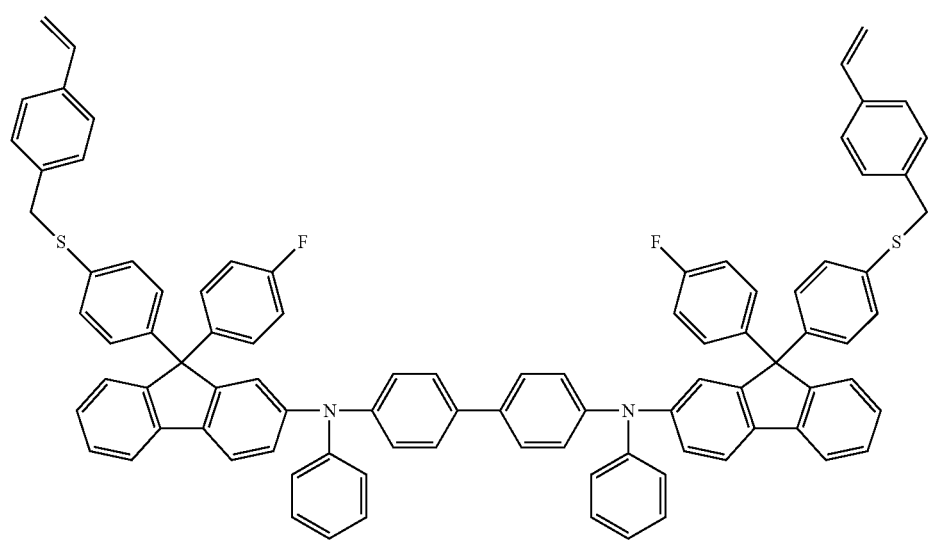
Compound 138
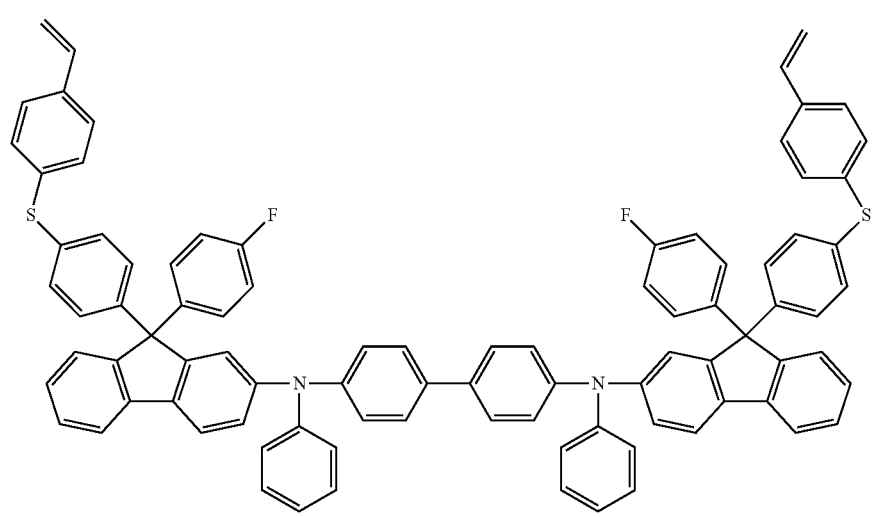

-continued

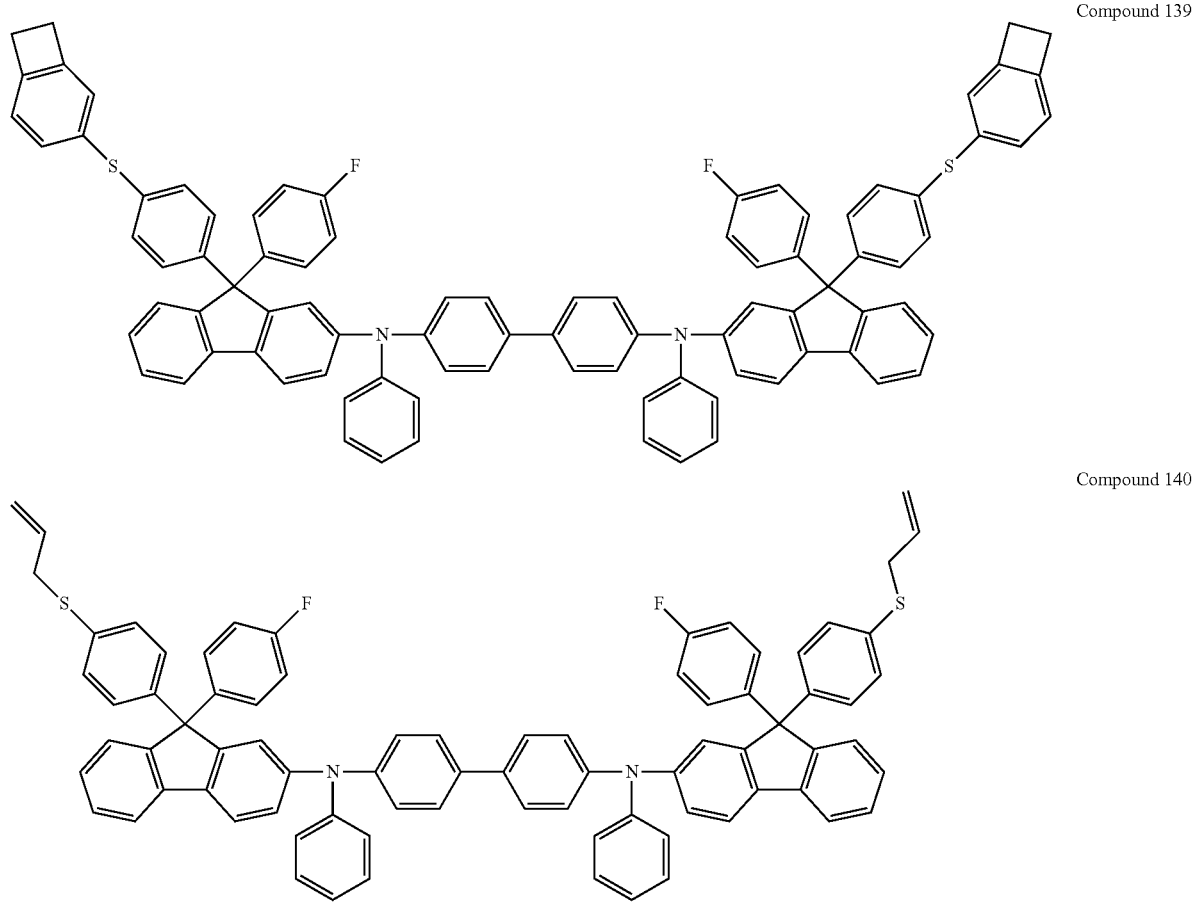

Compound 139

Compound 140

The compound represented by Chemical Formula 1 according to one embodiment of the present specification may be prepared using a preparation method to describe below.

For example, the compound represented by Chemical Formula 1 may have its core structure prepared as in the following Reaction Formula 1. Substituents may bond using methods known in the art, and types, positions or the number of the substituents may vary depending on technologies known in the art.

<Reaction Formula 1>

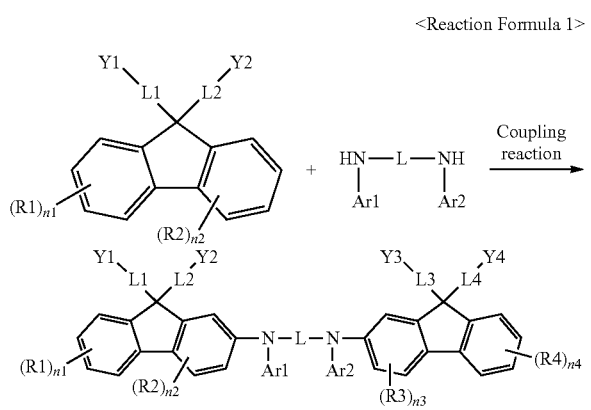

In Reaction Formula 1, substituents have the same definitions as the substituents in Chemical Formula 1.

According to one embodiment of the present specification, the number of the functional group crosslinkable by heat or light of the anion group represented by Chemical Formula 10 is from 1 to 4. When the anion group represented by Chemical Formula 10 does not comprise a curing group, curing does not occur, and device properties decline due to migration of the cation group and the anion group of the present specification between electrode layers. In addition, as the number of the curing groups increases, a curing rate of the coating composition increases and a film retention rate is enhanced.

According to one embodiment of the present specification, the number of the F, the cyano group, or the substituted or unsubstituted fluoroalkyl group in the anion group represented by Chemical Formula 10 is from 8 to 36.

In one embodiment of the present specification, the content of the F in the anion group represented by Chemical Formula 10 is from 10 parts by weight to 50 parts by weight, and preferably from 10 parts by weight to 45 parts by weight with respect to 100 parts by weight of the anion group.

In one embodiment of the present specification, the ionic compound comprising the anion group represented by Chemical Formula 10 may be used in a hole injection layer of an organic light emitting device, and, when used in the hole injection layer, may be used as a dopant. Herein, when the content of the F in the anion group represented by Chemical Formula 10 increases, an electron attracting force from other compounds (host compound) increases, and holes are more favorably produced in the host compound resulting in performance enhancement in the hole injection layer.

According to one embodiment of the present specification, the content of the F in the anion group represented by Chemical Formula 10 may be analyzed using a COSA AQF-100 combustion furnace coupled to a Dionex ICS 2000 ion-chromatograph, or may be identified through 19F NMR, a method generally used for F analysis.

According to one embodiment of the present specification, in Chemical Formula 10, at least one benzene ring among the Rc1 to Rc5-bonding benzene ring, the Rc6 to Rc10-bonding benzene ring, the Rc11 to Rc15-bonding benzene ring and the Rc16 to Rc20-bonding benzene ring is selected from among the following structural formulae.

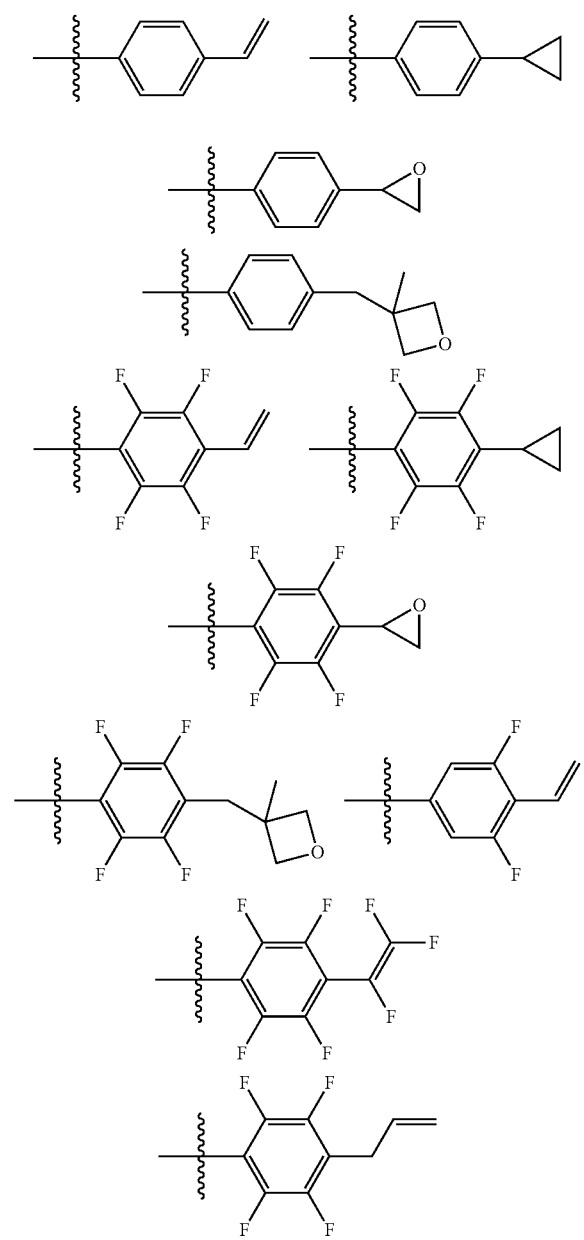

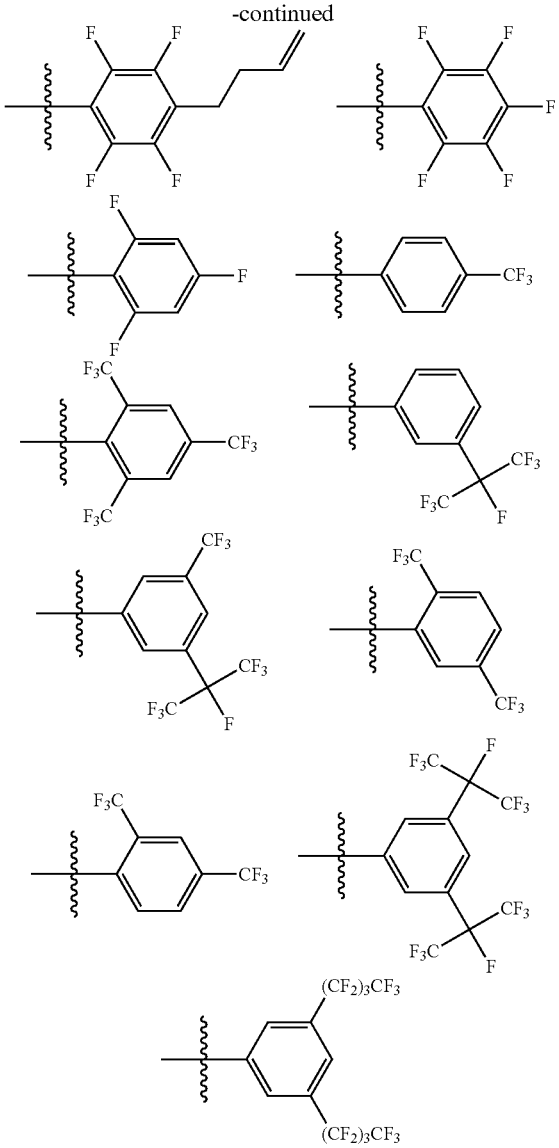

In one embodiment of the present specification, the anion group represented by Chemical Formula 10 is selected from among the following structural formulae.

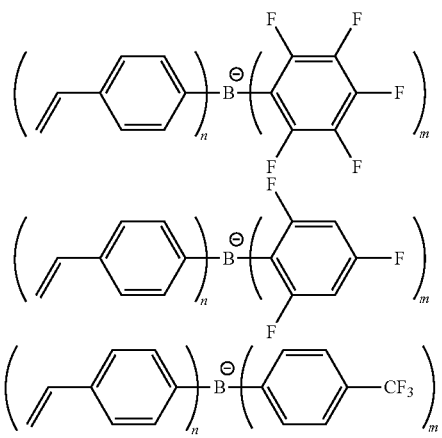

115
-continued
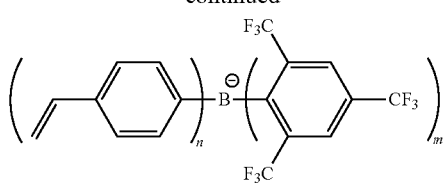
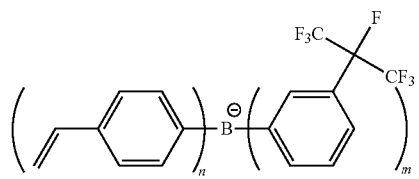
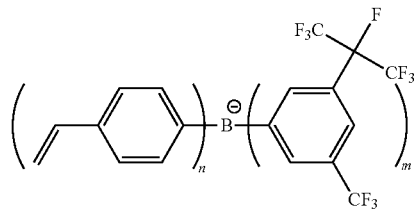
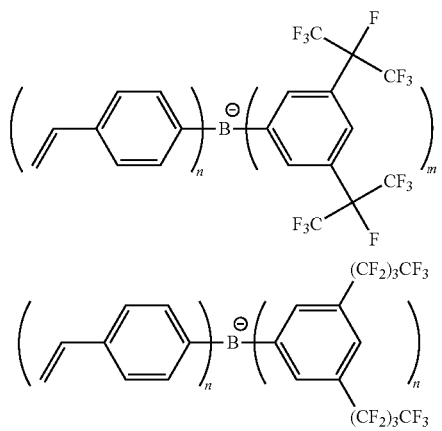
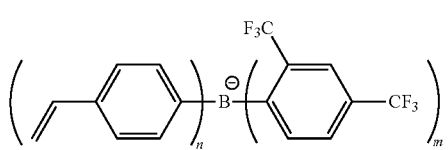
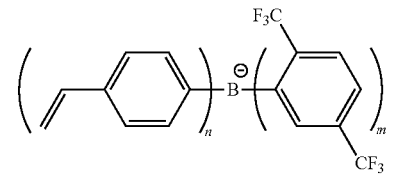
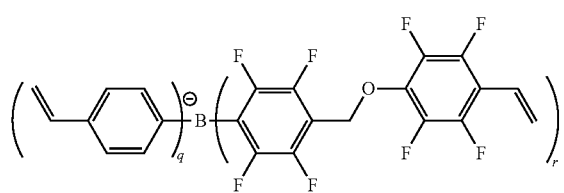
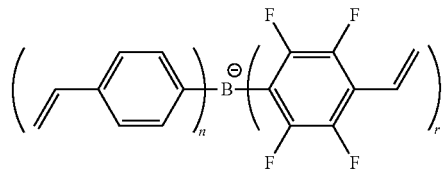
116
-continued
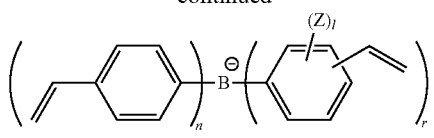
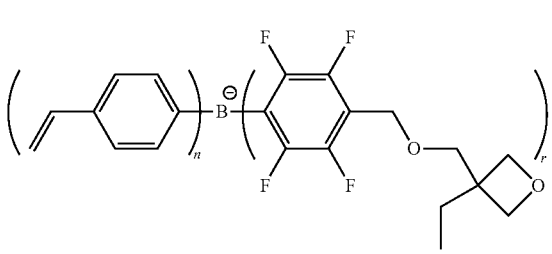
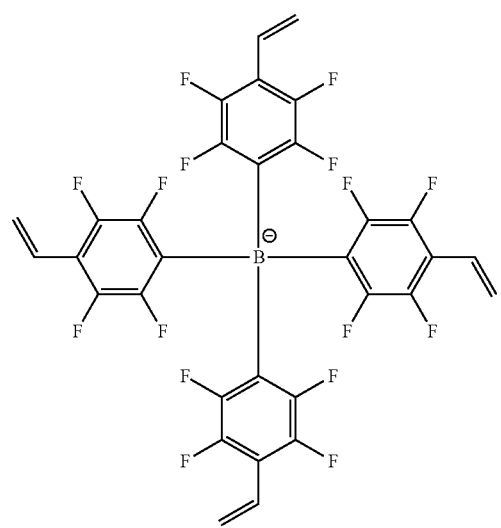
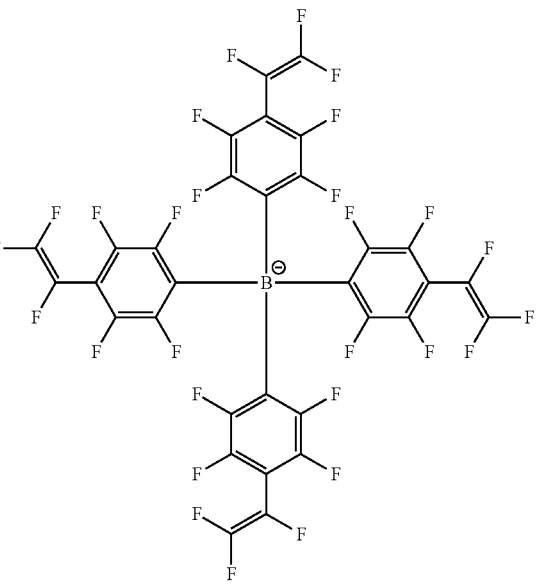

117
-continued
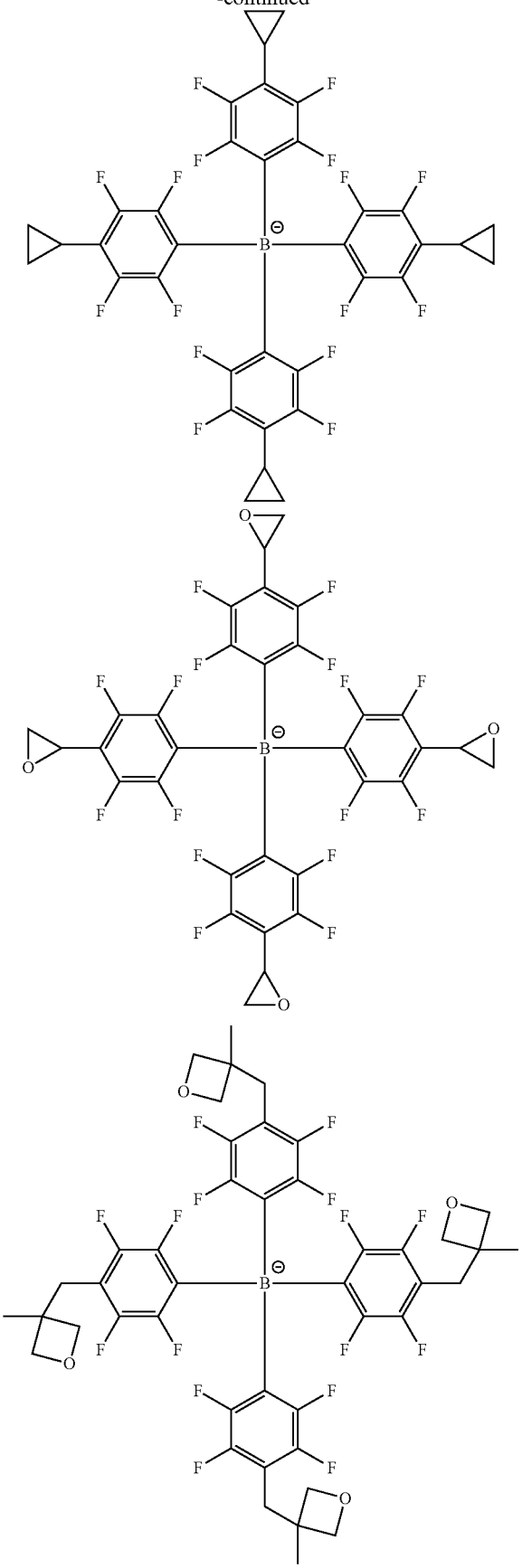
118
-continued
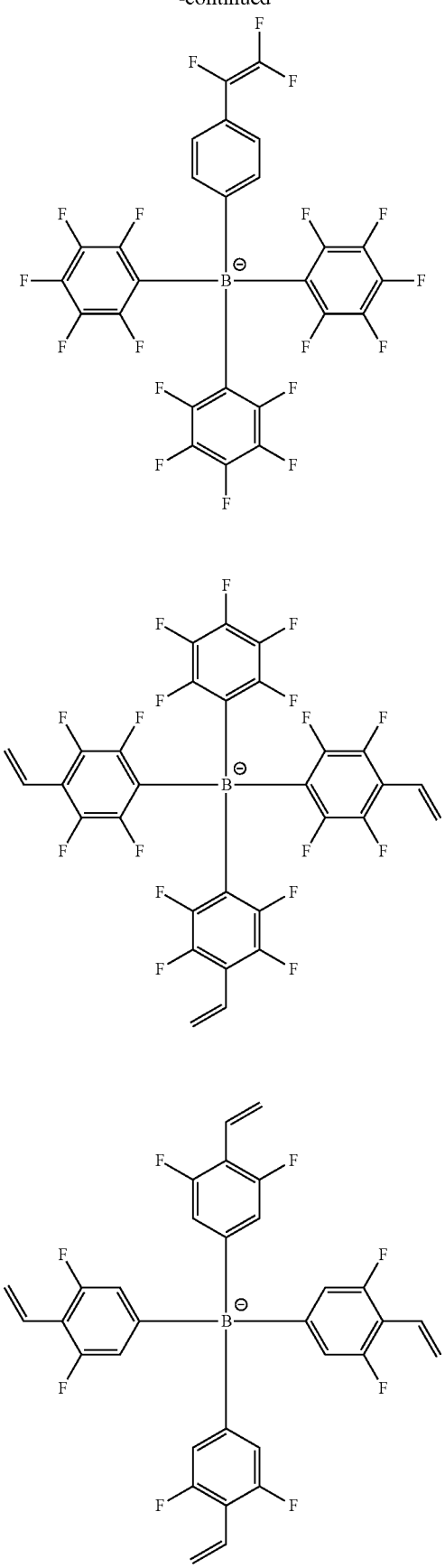

119
-continued

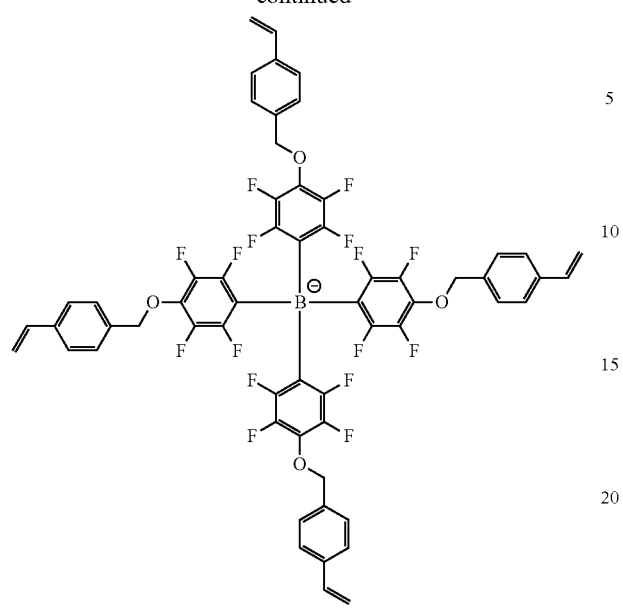

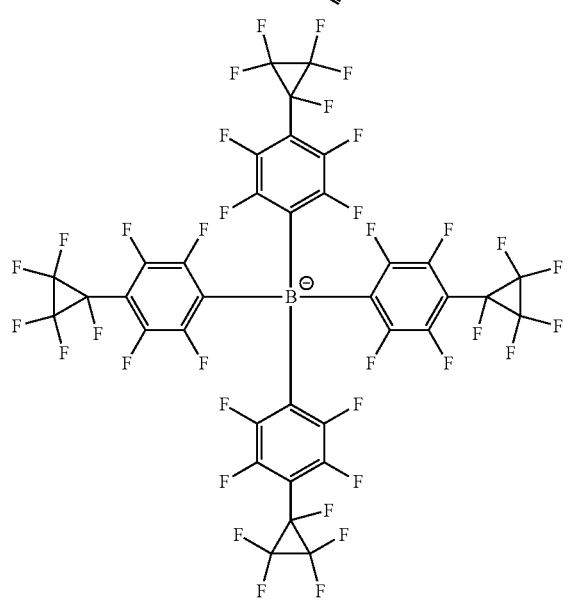

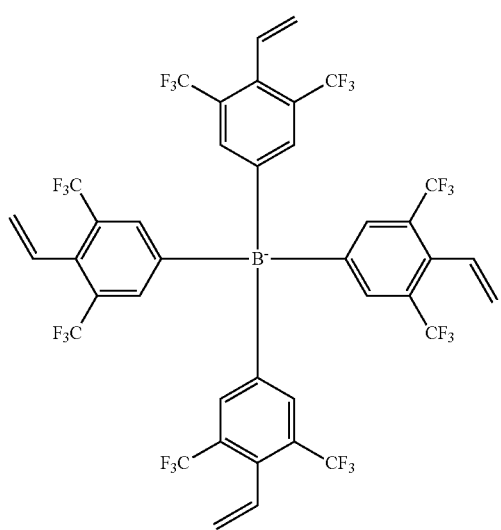

120
-continued

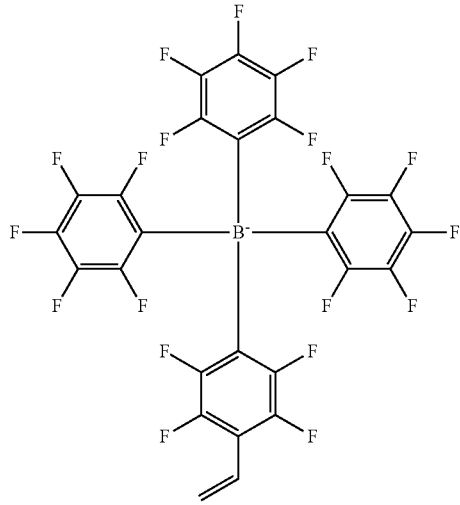

In the structural formulae, n is an integer of 1 to 3, m is an integer of 1 to 3, and m+n=4, q is an integer of 0 to 3, r is an integer of 1 to 4, and q+r=4, Z is deuterium; a halogen group; a nitro group; a cyano group; an amino group; —C(O)$R_{100}$; —O$R_{101}$; —S$R_{102}$; —S$O_3R_{103}$; —COO$R_{104}$; —OC(O)$R_{105}$; —C(O)N$R_{106}R_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, l is an integer of 1 to 4, and when l is 2 or greater, Zs are the same as or different from each other, and $R_{100}$ to $R_{107}$ are the same as or different from each other, and each independently hydrogen; deuterium; or a substituted or unsubstituted alkyl group.

In the present specification, the ionic compound further comprises a cation group, and the cation group is selected from among monovalent cation groups, onium compounds or the following structural formulae.

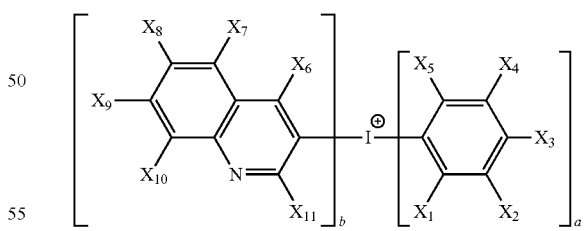

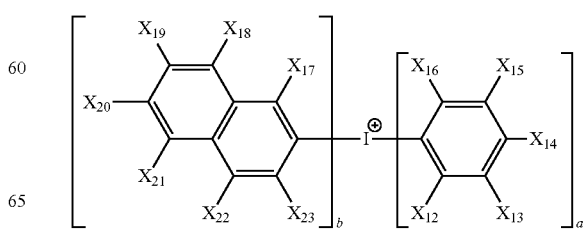

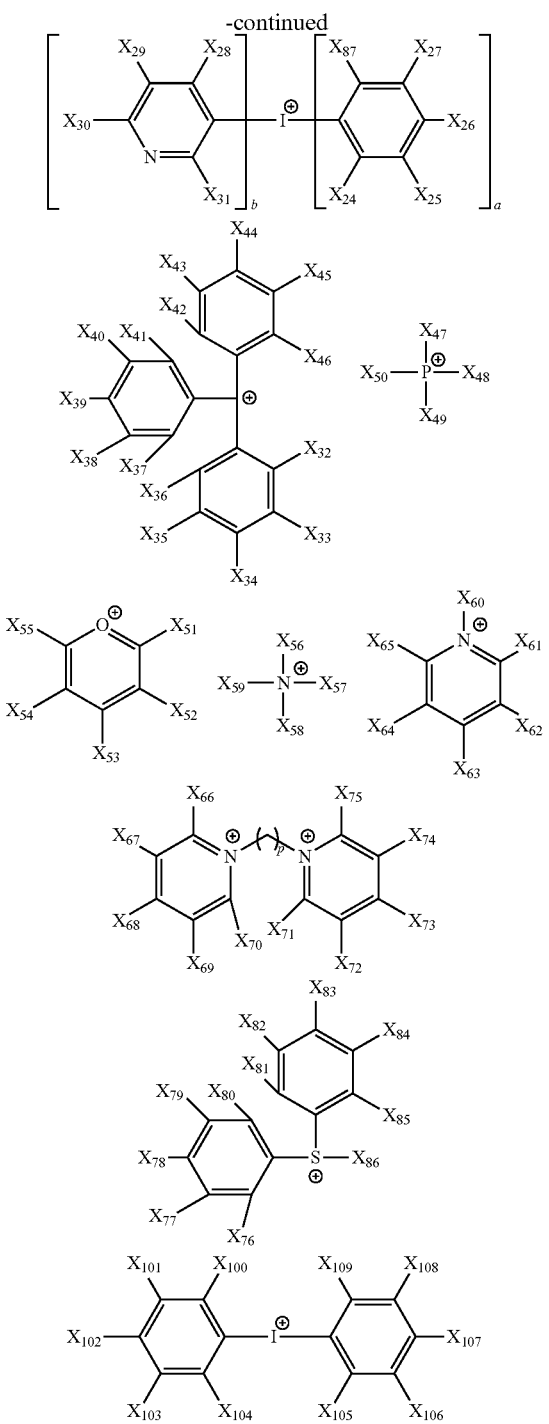

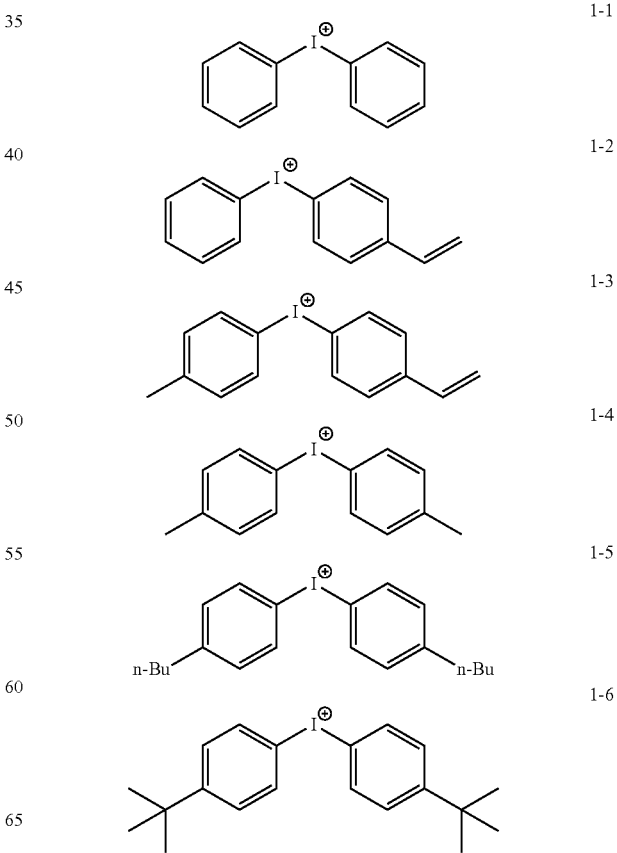

In the structural formulae, $X_1$ to $X_{87}$ and $X_{100}$ to $X_{109}$ are the same as or different from each other, and each independently hydrogen; a cyano group; a nitro group; a hydroxyl group; a halogen group; —COOR$_{104}$; a substituted or unsubstituted alkyl group; a substituted or unsubstituted alkoxy group; a substituted or unsubstituted aryloxy group; a substituted or unsubstituted cycloalkyl group; a substituted or unsubstituted fluoroalkyl group; a substituted or unsubstituted aryl group; or a functional group crosslinkable by heat or light, R$_{104}$ is hydrogen; deuterium; or a substituted or unsubstituted alkyl group, p is an integer of 0 to 10, and a is 1 or 2, b is 0 or 1, and a+b=2.

In one embodiment of the present specification, $X_1$ to $X_{87}$ and $X_{100}$ to $X_{109}$ are the same as or different from each other, and each independently hydrogen; a cyano group; a nitro group; a hydroxyl group; a halogen group; —COOR$_{104}$; an alkyl group having 1 to 20 carbon atoms unsubstituted or substituted with an alkyl group having 1 to 20 carbon atoms substituted with an aryl group having 6 to 30 carbon atoms; an alkoxy group having 1 to 20 carbon atoms unsubstituted or substituted with an aryl group having 6 to 30 carbon atoms or an alkoxy group having 1 to 20 carbon atoms; an aryloxy group having 6 to 30 carbon atoms; a cycloalkyl group having 3 to 30 carbon atoms; an aryl group having 6 to 30 carbon atoms; or a functional group crosslinkable by heat or light.

In one embodiment of the present specification, $X_1$ to $X_{87}$ and $X_{100}$ to $X_{109}$ are the same as or different from each other, and each independently hydrogen; a cyano group; F; Cl; —COOR$_{104}$; a nitro group; a hydroxyl group; a methyl group; an ethyl group; a propyl group; a butyl group; a pentyl group; a hexyl group; a methoxy group; a phenylmethoxy group; a cyclopropyl group; an ethoxyethoxy group; a phenoxy group; a phenylmethoxymethyl group; a phenyl group; a naphthyl group; or a functional group crosslinkable by heat or light, and R$_{104}$ is a methyl group.

According to one embodiment of the present specification, the monovalent cation group may comprise Na$^+$, Li$^+$, K$^+$ and the like, but is not limited thereto.

In one embodiment of the present specification, the cation group is selected from among the following structural formulae.

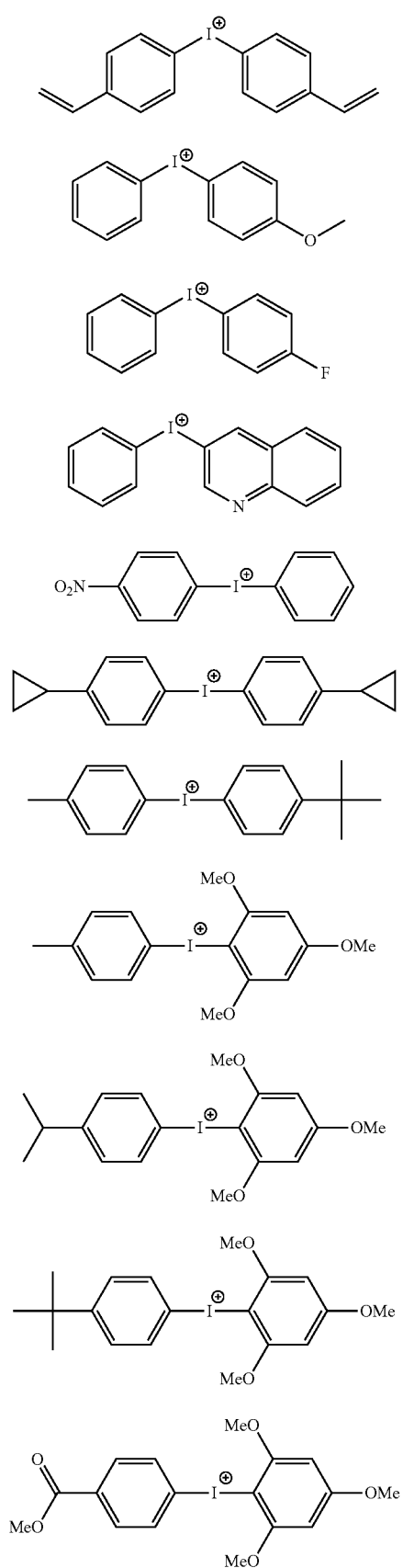
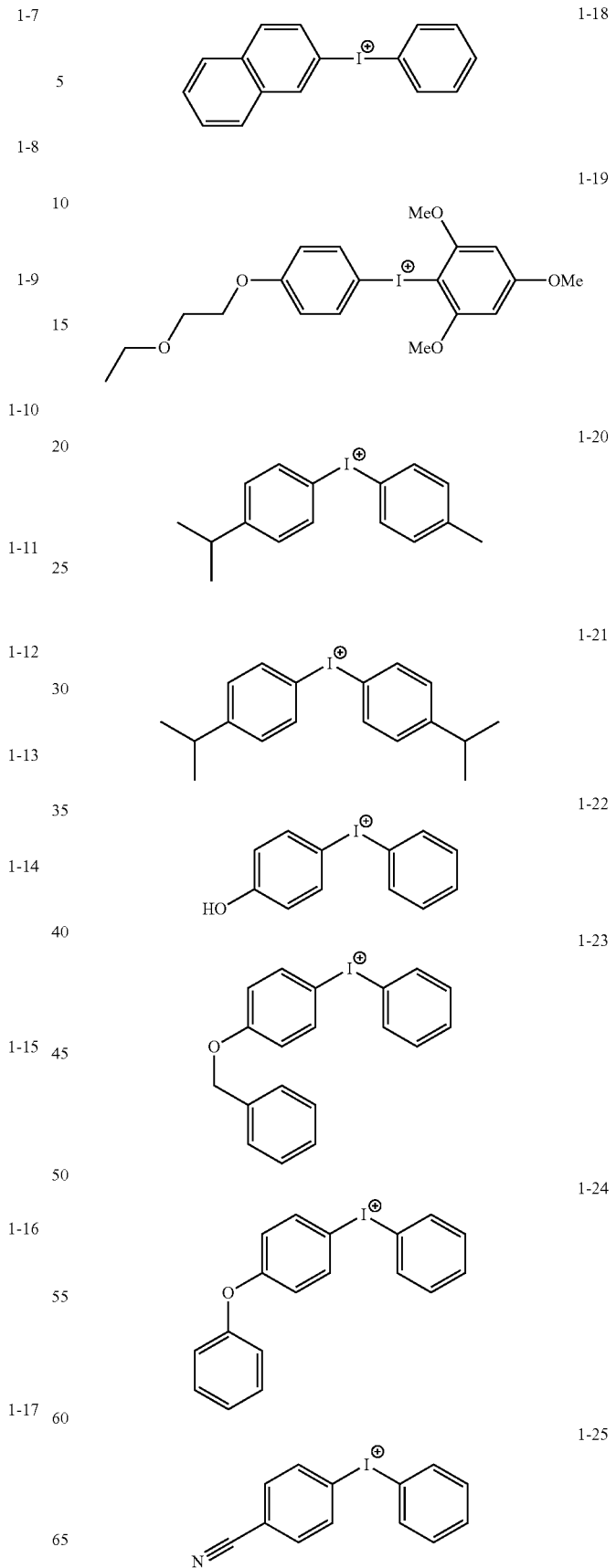

125
-continued
1-26
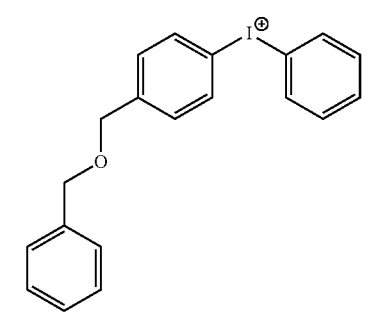
1-27
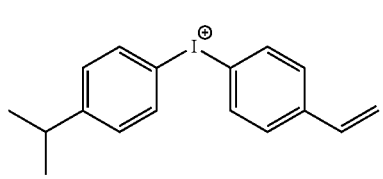
2-1
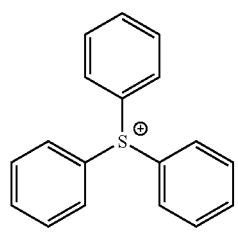
2-2
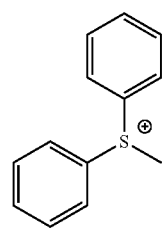
2-3
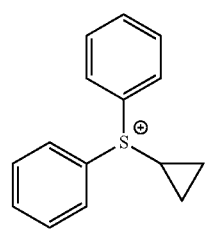
2-4
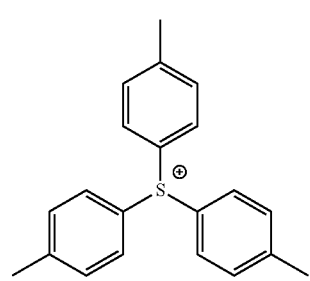
126
-continued
3-1
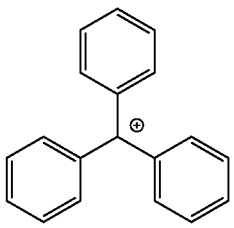
3-2
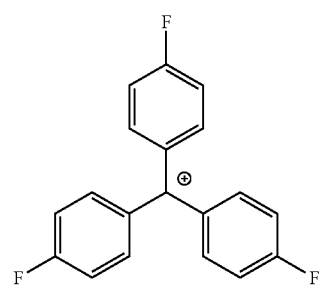
3-3
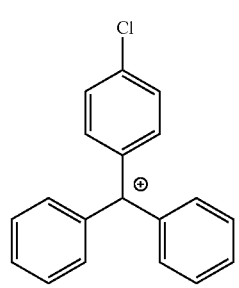
4-1
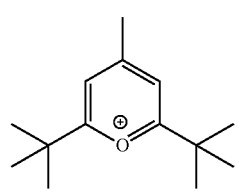
4-2
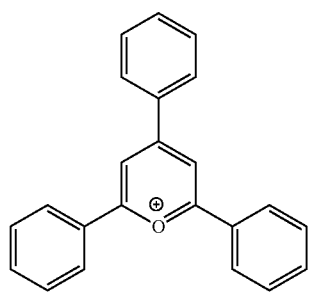
4-3
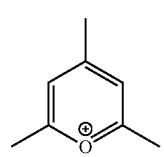

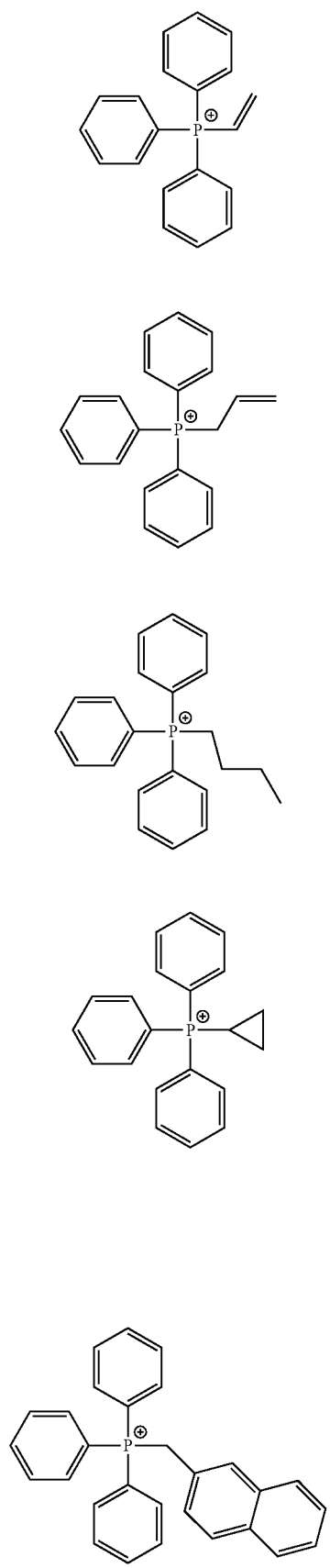
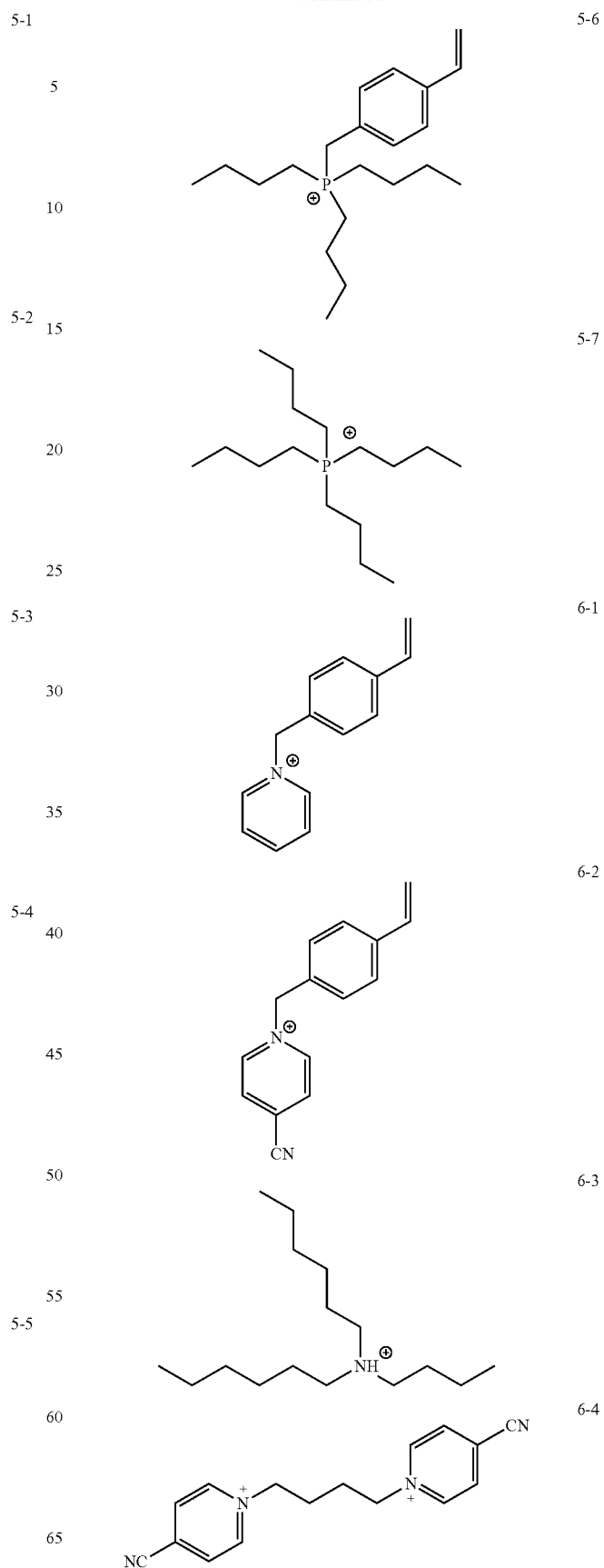

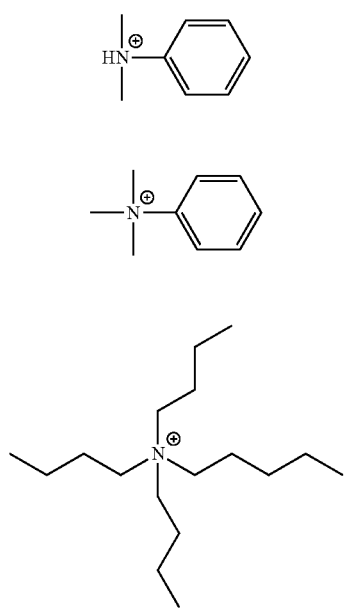
In one embodiment of the present specification, the ionic compound is selected from among the following structural formulae.
[Chemical Formula 1-1-1]
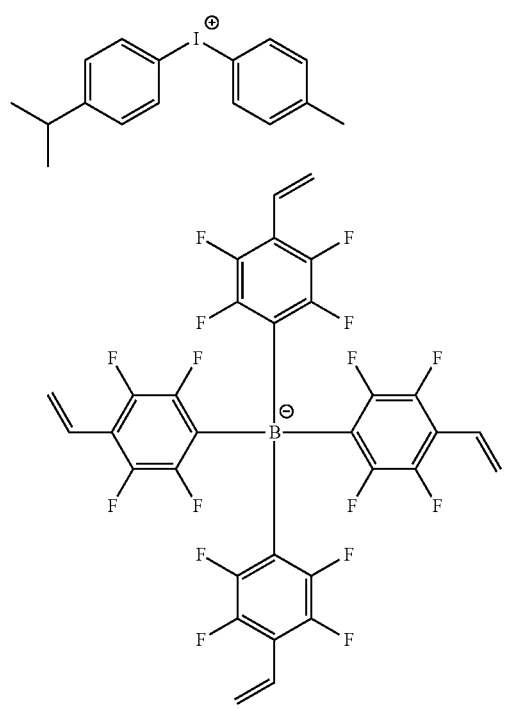
[Chemical Formula 1-1-2]
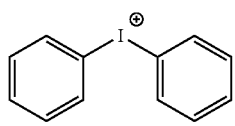
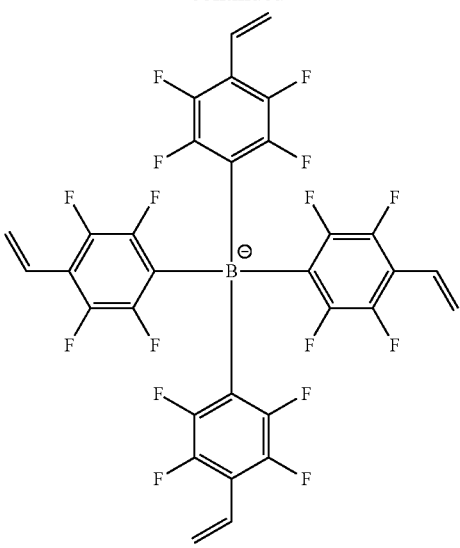
[Chemical Formula 1-1-3]
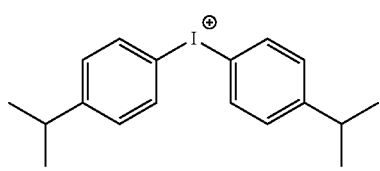
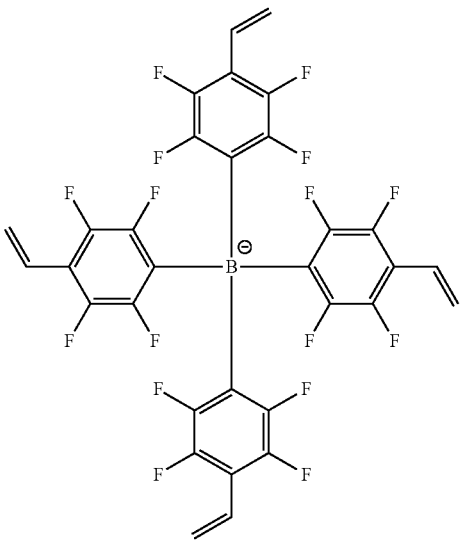
[Chemical Formula 1-1-4]
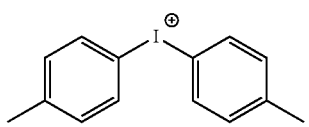

-continued
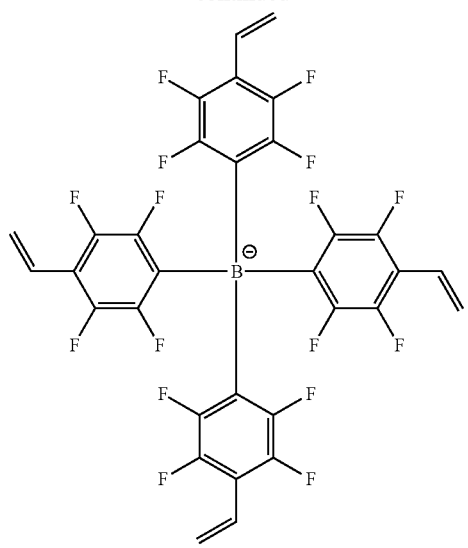
[Chemical Formula 1-1-5]
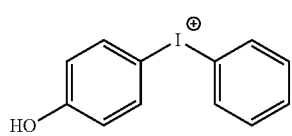
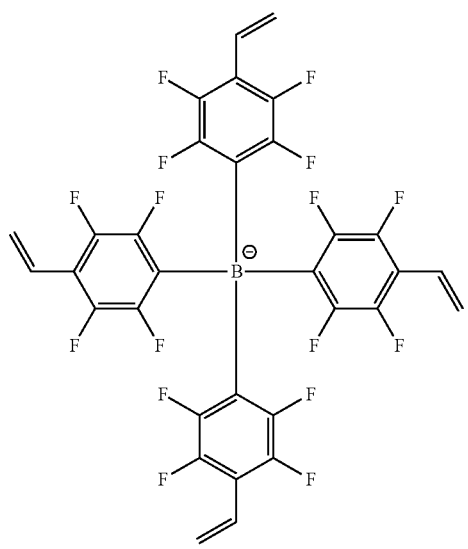
[Chemical Formula 1-1-6]
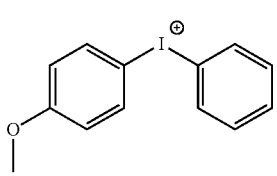
-continued
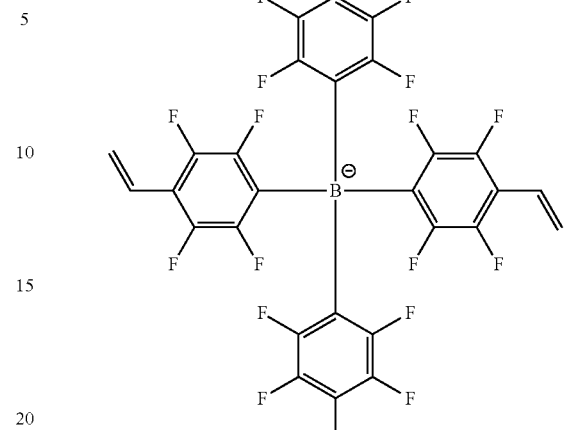
[Chemical Formula 1-1-7]
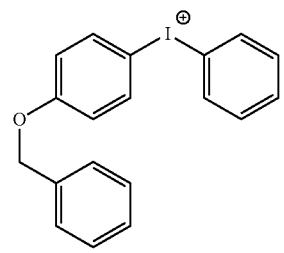
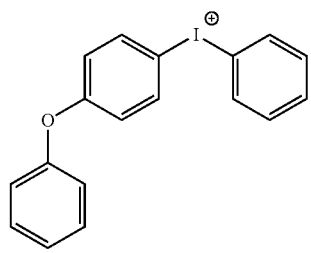
[Chemical Formula 1-1-8]

-continued
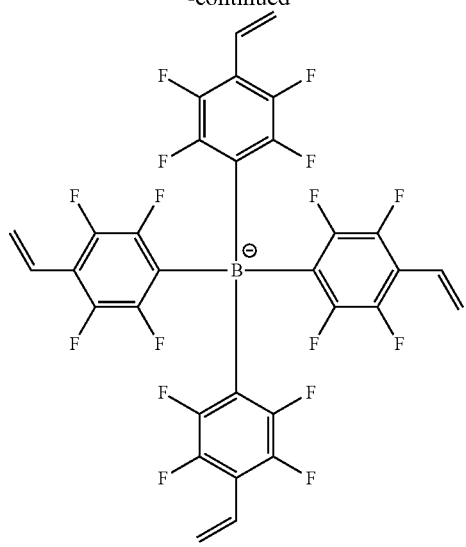
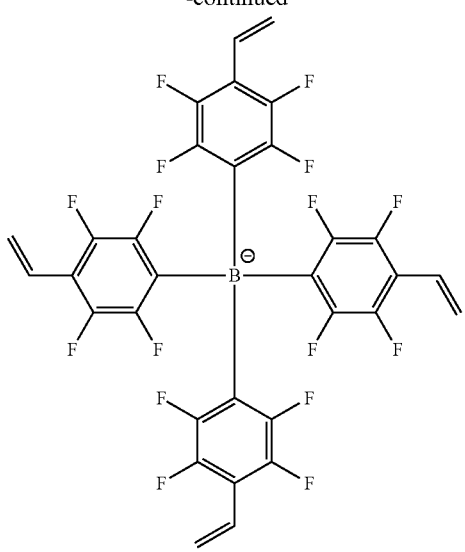
[Chemical Formula 1-1-9]
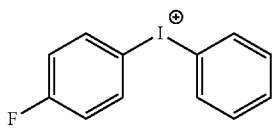
[Chemical Formula 1-1-11]
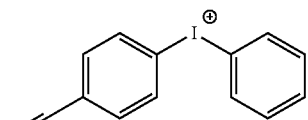
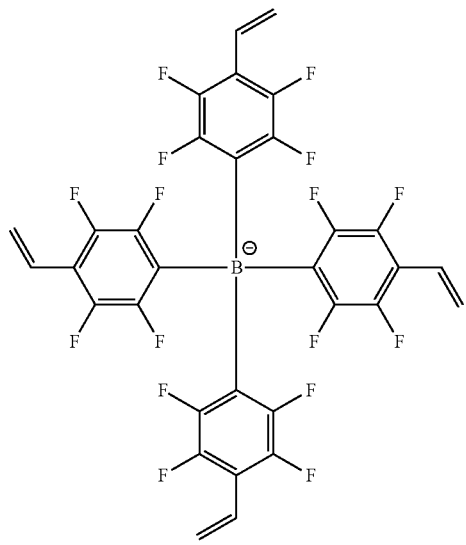
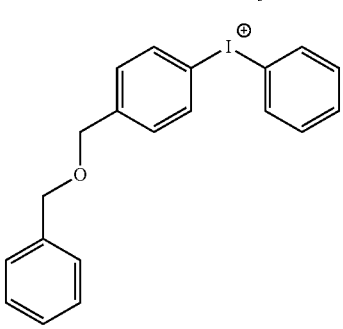
[Chemical Formula 1-1-12]
[Chemical Formula 1-1-10]
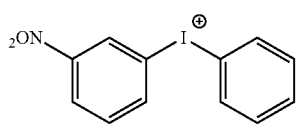

-continued
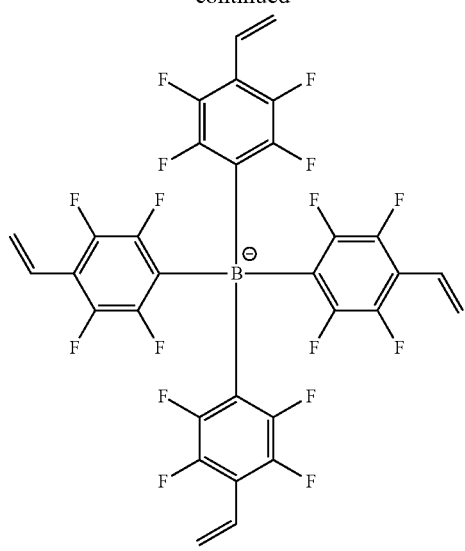
[Chemical Formula 1-1-14]
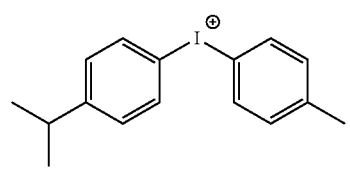
-continued
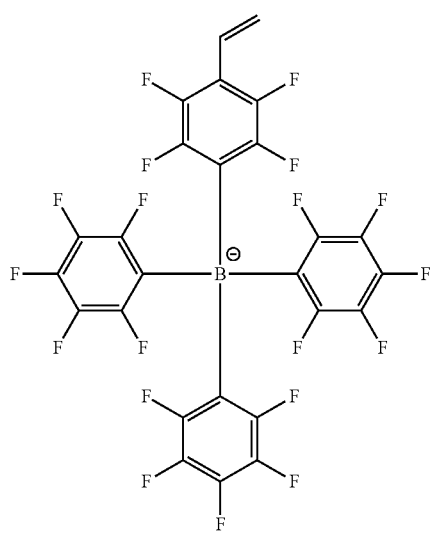
[Chemical Formula 1-1-16]
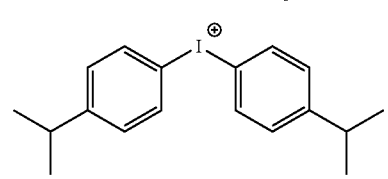
[Chemical Formula 1-1-15]
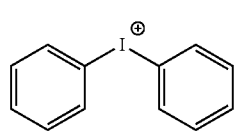
[Chemical Formula 1-1-17]
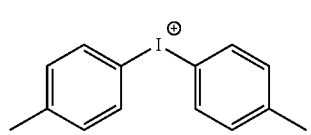

137
-continued
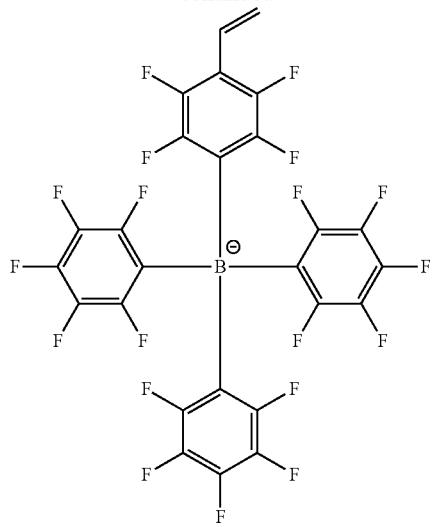
[Chemical Formula 1-1-18]
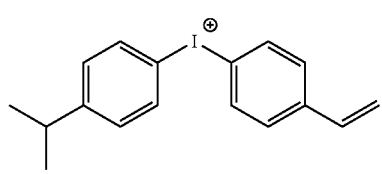
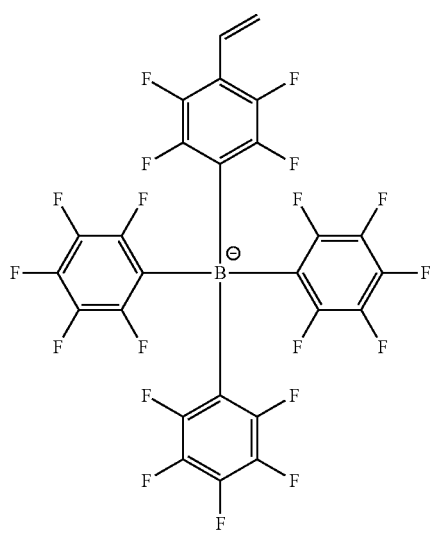
[Chemical Formula 1-1-19]
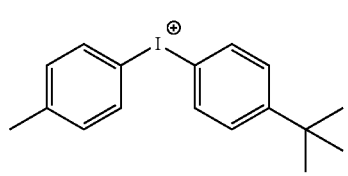
138
-continued
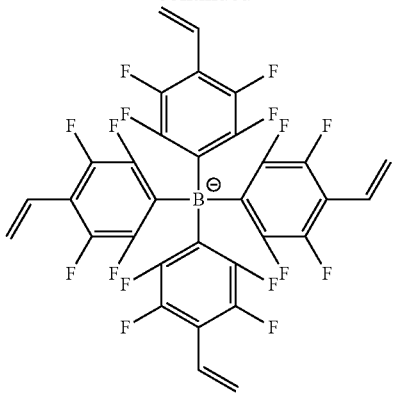
[Chemical Formula 1-1-20]
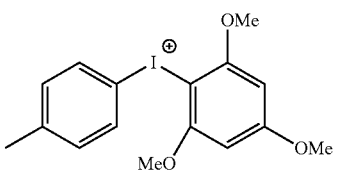
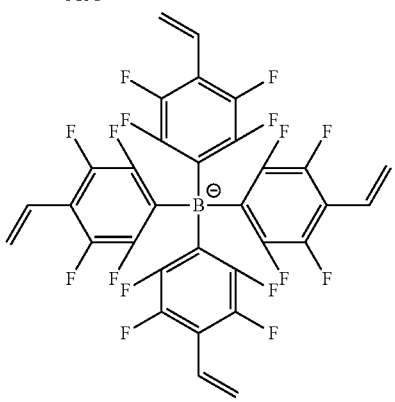
[Chemical Formula 1-1-21]
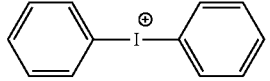
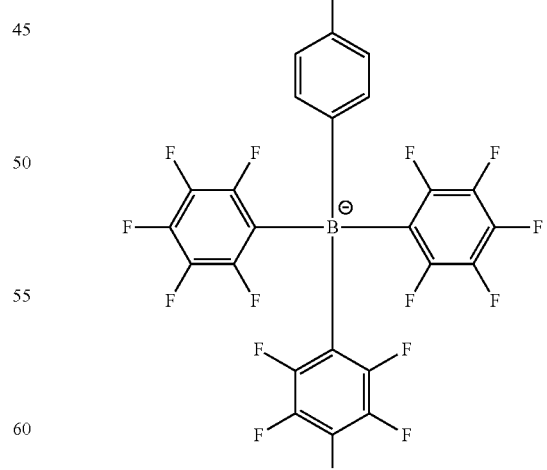
[Chemical Formula 1-1-21]
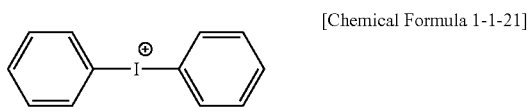

139
-continued
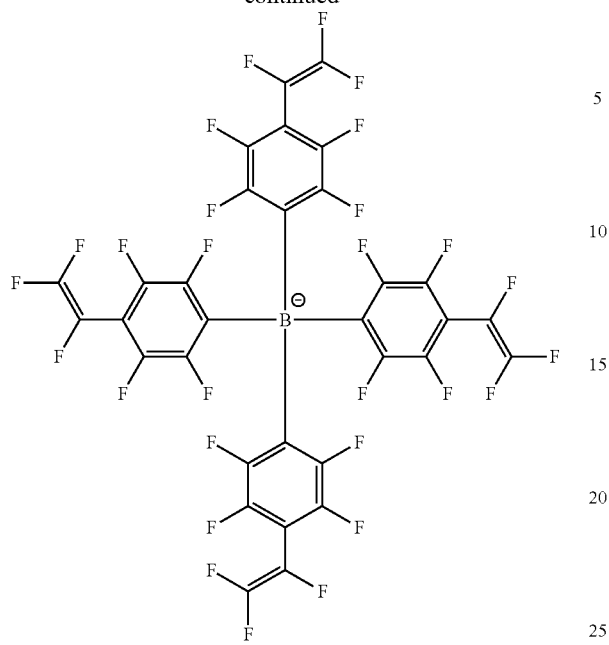
[Chemical Formula 1-1-22]
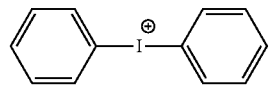
[Chemical Formula 1-1-23]
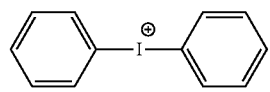
140
-continued
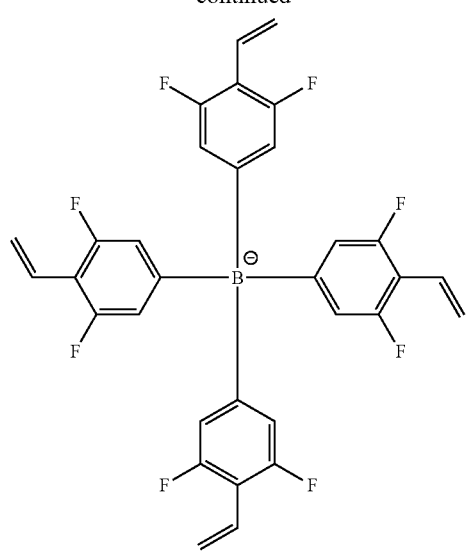
[Chemical Formula 1-1-24]
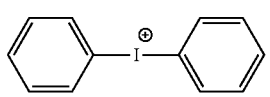
[Chemical Formula 1-1-25]
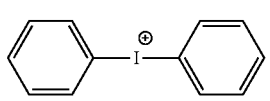

-continued
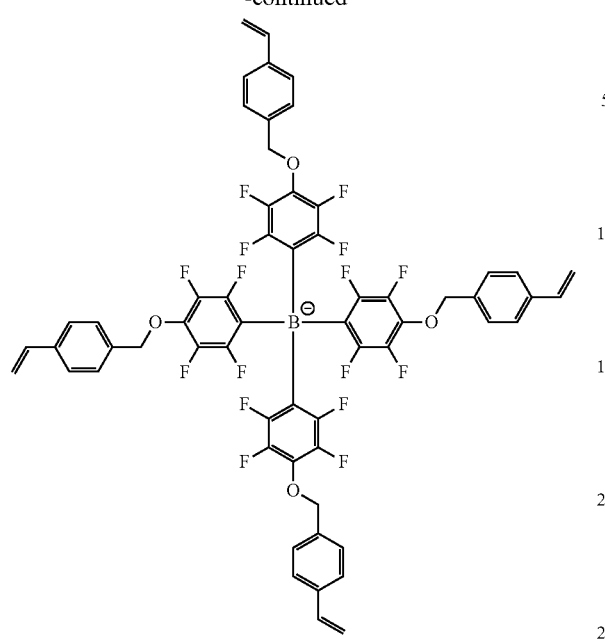
[Chemical Formula 1-1-26]
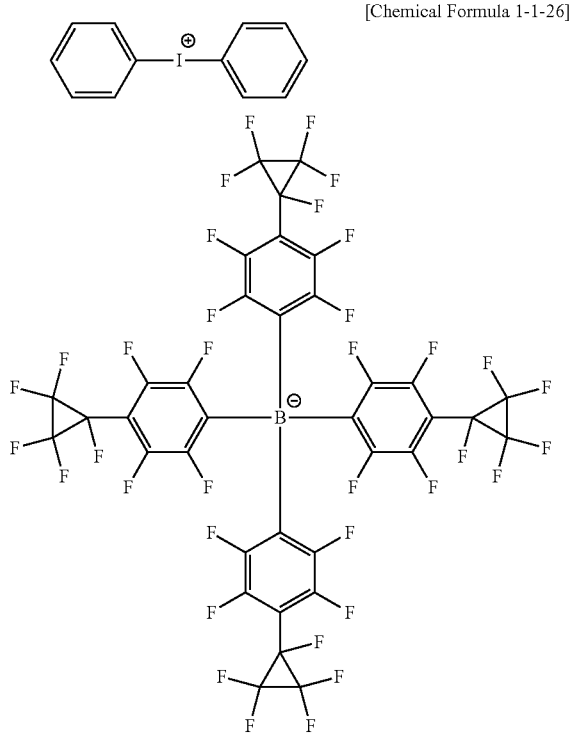
[Chemical Formula 1-2-1]
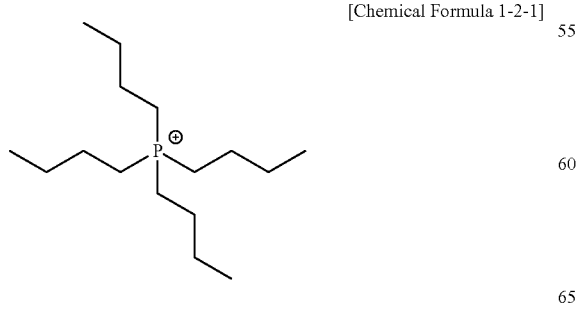
-continued
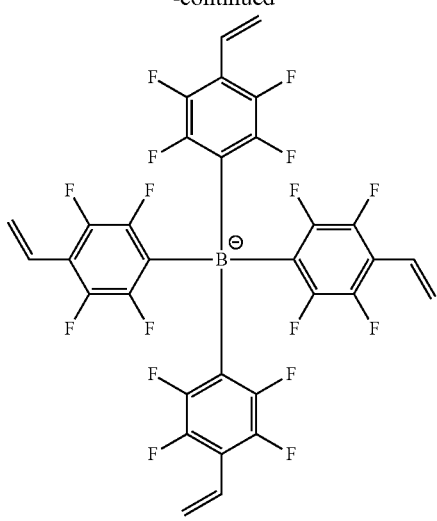
[Chemical Formula 1-2-3]
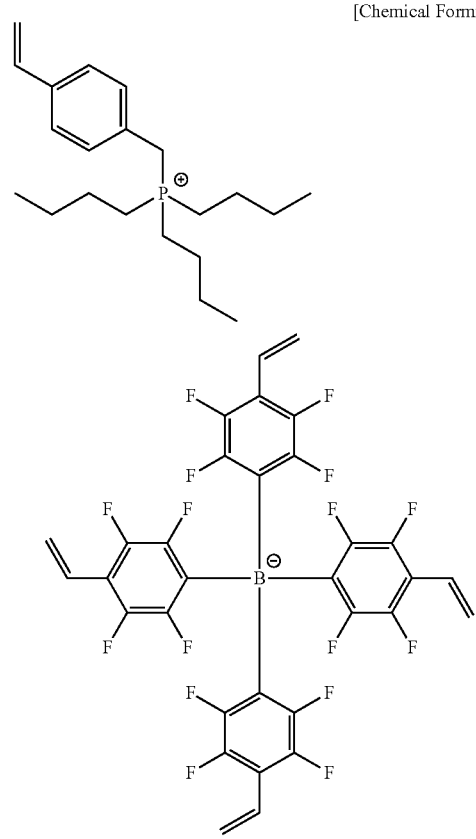
[Chemical Formula 1-2-4]
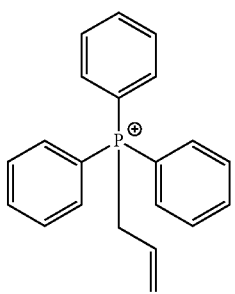

143
-continued
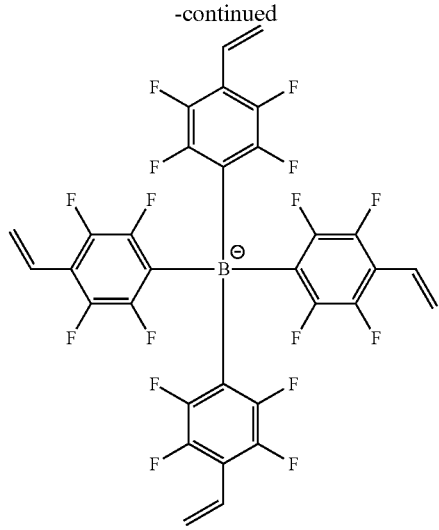
[Chemical Formula 1-2-5]
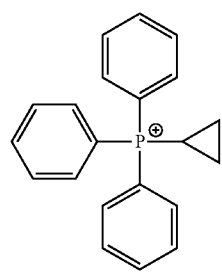
144
-continued
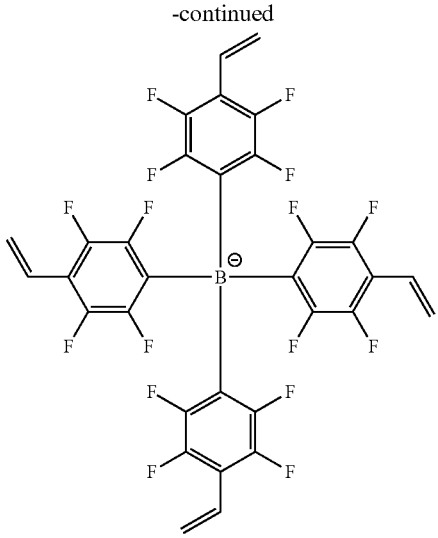
[Chemical Formula 1-3-2]
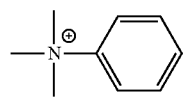
[Chemical Formula 1-3-3]
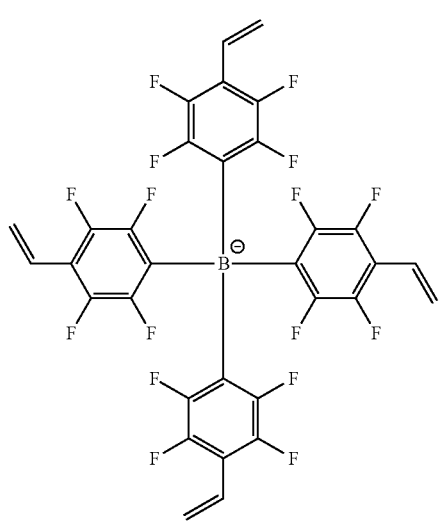
[Chemical Formula 1-3-1]
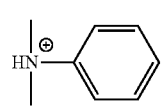
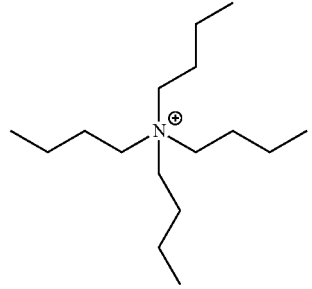

145
-continued
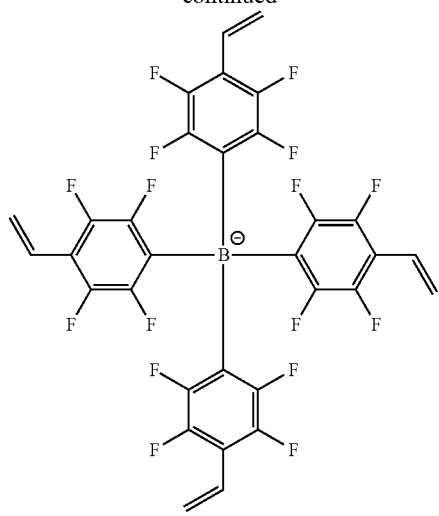
[Chemical Formula 1-3-4]
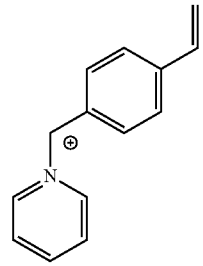
[Chemical Formula 1-4-1]
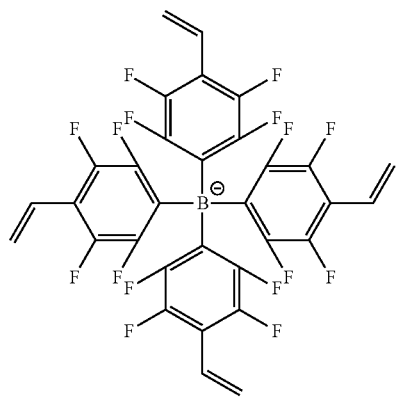
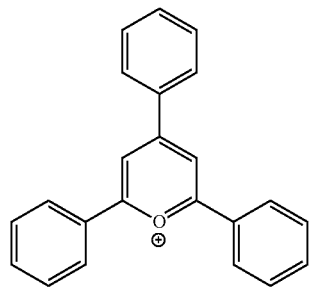
146
-continued
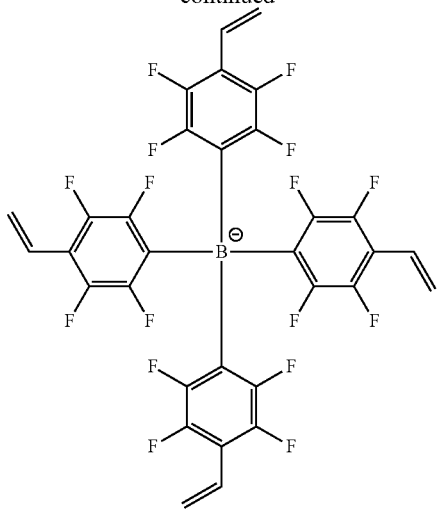
[Chemical Formula 1-5-1]
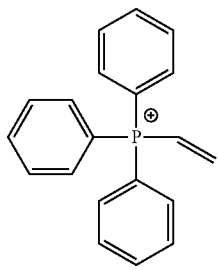
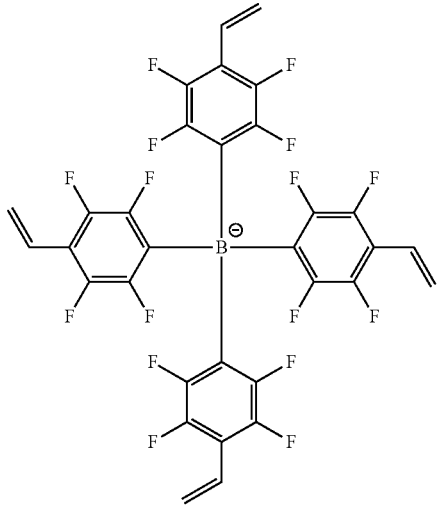
[Chemical Formula 1-5-2]
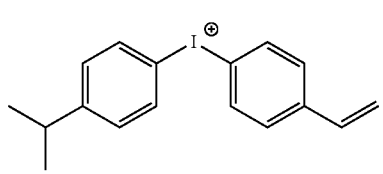

147
-continued
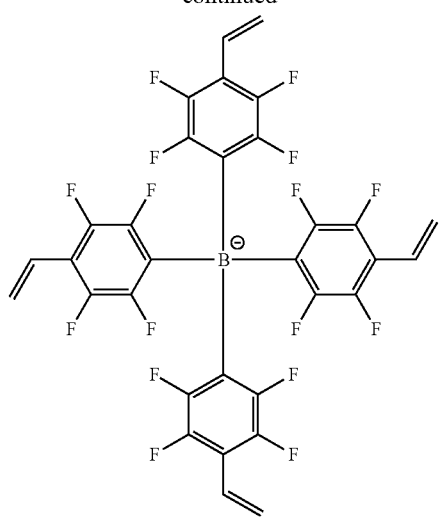
148
-continued
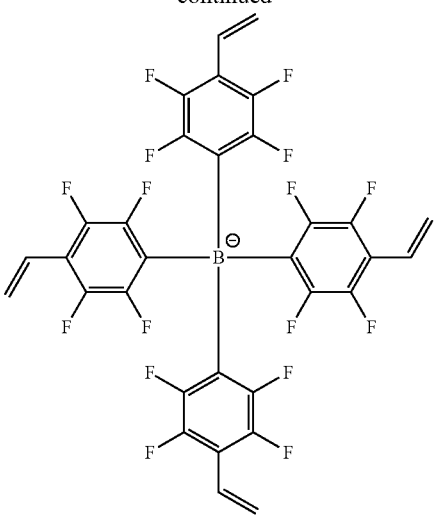
[Chemical Formula 1-5-3]
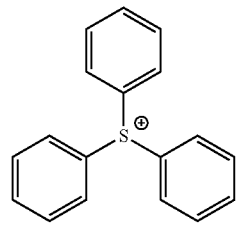
[Chemical Formula 1-5-5]
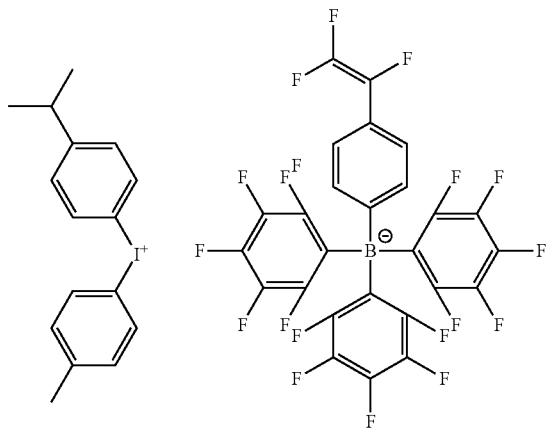
[Chemical Formula 1-5-4]
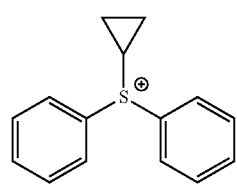
[Chemical Formula 1-5-6]
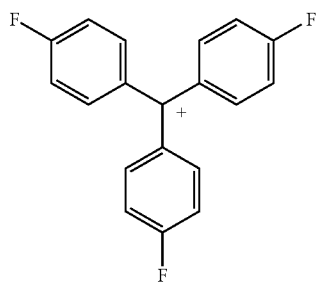

-continued

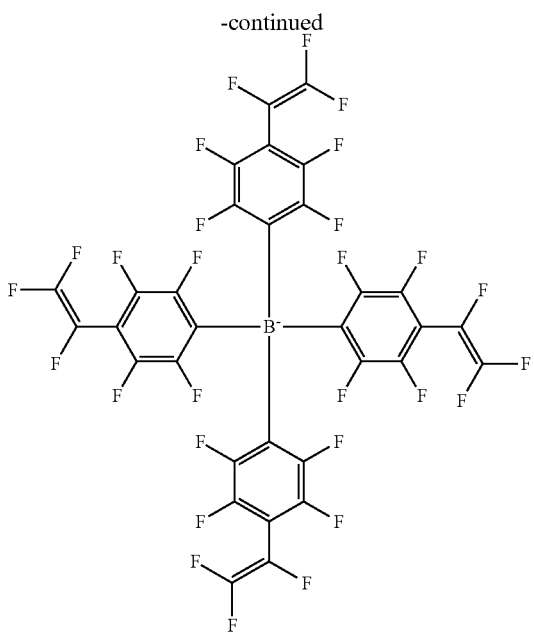

According to one embodiment of the present specification, in the ionic compound comprising the anion group represented by Chemical Formula 10, a content ratio of the anion group represented by Chemical Formula 10 and the cation group (anion group:cation group) is from 1:5 to 5:1 in an equivalent ratio.

According to another embodiment, in the ionic compound comprising the anion group represented by Chemical Formula 10, a content ratio of the anion group represented by Chemical Formula 10 and the cation group (anion group:cation group) is 1:1 in an equivalent ratio.

In one embodiment of the present specification, the coating composition comprises the compound represented by Chemical Formula 1, the ionic compound comprising the anion group represented by Chemical Formula 10, and a solvent.

In one embodiment of the present specification, the coating composition may be a liquid phase. The "liquid phase" means in a liquid state at room temperature and atmospheric pressure.

In one embodiment of the present specification, examples of the solvent may comprise chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone, cyclohexanone, isophorone, tetralone, decalone or acetylacetone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; tetraline, and the like, however, the solvent is not limited thereto as long as it is a solvent capable of dissolving or dispersing the compound of Chemical Formula 1 according to one embodiment of the present disclosure.

In another embodiment, the solvent may be used either alone as one type, or as a mixture mixing two or more solvent types.

In the present specification, the ionic compound is not limited as long as it has a p semiconductor property, and one, two or more types thereof may be used, and types thereof are not limited.

In one embodiment of the present specification, a content of the ionic compound is from 1% by weight to 50% by weight, preferably from 5% by weight to 30% by weight, and more preferably from 8% by weight to 20% by weight based on the compound represented by Chemical Formula 1, however, the content is not limited thereto. When the ionic compound content satisfies the above-mentioned content range, the ionic compound helps the compound to be favorably cured without declining device performance, and the fluorine (F) included in the ionic compound helps with hole formation of a host material (the compound of Chemical Formula 1) enhancing device performance.

In addition, the ionic compound content being greater than the above-mentioned range causes interlayer diffusion, and causes a problem of declining device performance by the ionic compound performing a role of an insulator.

In another embodiment, the coating composition may further comprise a monomer comprising a functional group crosslinkable by heat or light; or a monomer comprising an end group capable of forming a polymer by heat. The monomer comprising a functional group crosslinkable by heat or light;

or the monomer comprising an end group capable of forming a polymer by heat as above may be a compound having a molecular weight of 3,000 g/mol or less.

In one embodiment of the present specification, the coating composition has a molecular weight of 2,000 g/mol or less, and further comprises a monomer comprising a functional group crosslinkable by heat or light; or a monomer comprising an end group capable of forming a polymer by heat.

The monomer comprising a functional group crosslinkable by heat or light; or the monomer comprising an end group capable of forming a polymer by heat may mean a monomer in which aryl such as phenyl, biphenyl, fluorene or naphthalene; arylamine; or fluorene is substituted with a functional group crosslinkable by heat or light or an end group capable of forming a polymer by heat.

In one embodiment of the present specification, the coating composition may further comprise one, two or more types of additives selected from the group consisting of thermal polymerization initiators and photopolymerization initiators.

Examples of the thermal polymerization initiator may comprise peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5,5-trimethyl hexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxy-isopropyl)benzene, t-butyl cumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may comprise acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl) propan-1-one or 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether or benzoin isopropyl ether;

benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; and, as other photopolymerization initiators, ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds, imidazole-based compounds, and the like. In addition, those having a photopolymerization facilitating effect may be used either alone or together with the photopolymerization initiator. Examples thereof may comprise triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

In another embodiment, the coating composition has viscosity of 2 cP to 15 cP. Satisfying the above-mentioned viscosity is advantageous in manufacturing a device.

The coating composition preferably has a concentration of 0.1 wt/v % to 30 wt/v %, and more preferably 0.3 wt/v % to 15 wt/v %, however, the concentration is not limited thereto.

Another embodiment of the present specification provides an organic light emitting device formed using the coating composition.

In one embodiment of the present specification, the organic light emitting device includes a first electrode; a second electrode; and one or more organic material layers provided between the first electrode and the second electrode, wherein one or more layers of the organic material layers comprise the coating composition or a cured material thereof, and the cured material of the coating composition is in a cured state by heat treating or light treating the coating composition.

In one embodiment of the present specification, the organic material layer comprising the coating composition or a cured material thereof is a hole transfer layer or a hole injection layer.

In one embodiment of the present specification, the organic material layer comprising the coating composition or a cured material thereof is an electron transfer layer or an electron injection layer.

In another embodiment, the organic material layer comprising the coating composition or a cured material thereof is a light emitting layer.

In another embodiment, the organic material layer comprising the coating composition or a cured material thereof is a light emitting layer, and the light emitting layer comprises the compound of Chemical Formula 1 as a host of the light emitting layer.

In another embodiment, the organic material layer comprising the coating composition or a cured material thereof is a light emitting layer, and the light emitting layer comprises the compound of Chemical Formula 1 as a dopant of the light emitting layer.

In one embodiment of the present specification, the organic light emitting device further comprises one, two or more layers selected from the group consisting of a hole injection layer, a hole transfer layer, an electron transfer layer, an electron injection layer, an electron blocking layer and a hole blocking layer.

In one embodiment of the present specification, the first electrode is an anode, and the second electrode is a cathode.

According to another embodiment, the first electrode is a cathode, and the second electrode is an anode.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

For example, a structure of the organic light emitting device according to one embodiment of the present specification is illustrated in the FIGURE.

The FIGURE illustrates a structure of the organic light emitting device in which an anode (201), a hole injection layer (301), a hole transfer layer (401), a light emitting layer (501), an electron transfer layer (601) and a cathode (701) are consecutively laminated on a substrate (101).

The FIGURE illustrates the organic light emitting device, however, the organic light emitting device is not limited thereto.

When the organic light emitting device comprises a plurality of organic material layers, the organic material layers may be formed with materials that are the same as or different from each other.

The organic light emitting device of the present specification may be manufactured using materials and methods known in the art, except that one or more layers of the organic material layers are formed using the coating composition comprising the compound of Chemical Formula 1.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD)

method such as sputtering or e-beam evaporation, and forming an organic material layer comprising a hole injection layer, a hole transfer layer, a light emitting layer and an electron transfer layer thereon through a solution process, a deposition process or the like, and then depositing a material capable of being used as a cathode thereon. In addition to such a method, the organic light emitting device may also be manufactured by consecutively depositing a cathode material, an organic material layer and an anode material on a substrate.

In addition, one embodiment of the present specification provides a method for manufacturing an organic light emitting device formed using the coating composition.

Specifically, in one embodiment of the present specification, the method for manufacturing an organic light emitting device comprises preparing a substrate; forming a first electrode on the substrate; forming one or more organic material layers on the first electrode; and forming a second electrode on the organic material layer, wherein the forming of organic material layers comprises forming one or more organic material layers using the coating composition.

In one embodiment of the present specification, the forming of one or more organic material layers using the coating composition uses a spin coating method.

In another embodiment, the forming of one or more organic material layers using the coating composition uses a printing method.

In an embodiment of the present specification, examples of the printing method comprise inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of one or more organic material layers using the coating composition comprises coating the coating composition on the first electrode; and heat treating or light treating the coated coating composition.

In one embodiment of the present specification, the heat treating may be performed through heat treatment, and a heat treatment temperature in the heat treating is from 85° C. to 250° C. According to one embodiment, the temperature may be from 100° C. to 250° C., and in another embodiment, the temperature may be from 150° C. to 250° C.

In another embodiment, a heat treatment time in the heat treating is from 1 minute to 2 hours. According to one embodiment, the time may be from 1 minute to 1 hours, and in another embodiment, the time may be from 30 minutes to 1 hour.

When the heat treatment or the light treatment is included in the forming of an organic material layer formed using the coating composition, an organic material layer comprising a thin-filmed structure by a plurality of the compounds included in the coating composition forming crosslinkage may be provided. In this case, being dissolved by a solvent or being morphologically affected or decomposed may be prevented when other layers are laminated on a surface of the organic material layer formed using the coating composition.

Accordingly, when the organic material layer formed using the coating composition is formed comprising the heat treatment or the light treatment, resistance for the solvent increases, and multiple layers may be formed by repeatedly performing solution deposition and crosslinking methods, and as a result, lifetime properties of a device may be enhanced by increasing stability.

As the anode material, materials having large work function are normally preferred so that hole injection to an organic material layer is smooth. Specific examples of the anode material capable of being used in the present disclosure comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material comprise metals such as barium, magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof comprise arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof comprise 8-hydroxy-quinoline aluminum complexes (Alq$_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, or the like, but are not limited thereto.

The light emitting layer may include a host material and a dopant material.

The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq$_3$; organic radical compounds; hydroxyflavon-metal complexes, or the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato) aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

Preparation Example

Preparation Example 1. Preparation of Compound 1

1) Preparation of Intermediate 1-1

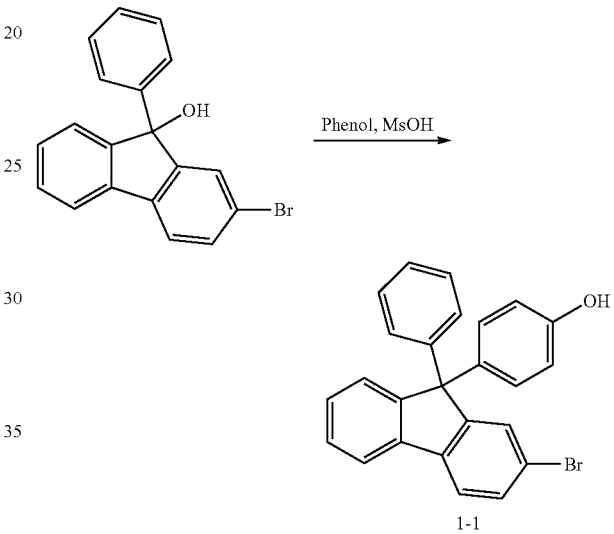

To a 500 ml round bottom flask [RBF], 2-bromo-9-phenyl-9H-fluoren-9-ol (50 g, 148.3 mmol, 1.0 eq.) and phenol (41.8 g, 444.9 mmol, 3.0 eq.) were introduced, and dissolved in methanesulfonic acid (200 ml, 0.74 M). The result was stirred overnight under reflux after installing a dean-stark apparatus. After that, the reaction was stopped using a saturated aqueous NaHCO$_3$ solution, and the organic layer was extracted using ethyl acetate [EA]. The organic layer was dried with magnesium sulfate, and after removing the solvent, the result was purified using column chromatography to obtain Intermediate Compound 1-1.

2) Preparation of Intermediate 1-2

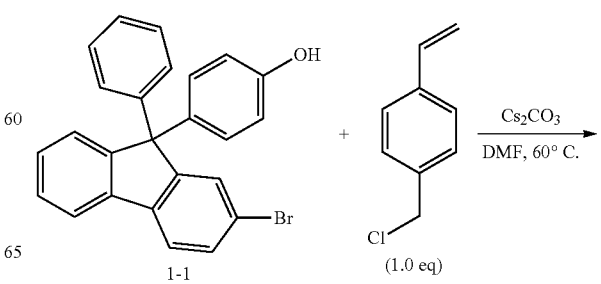

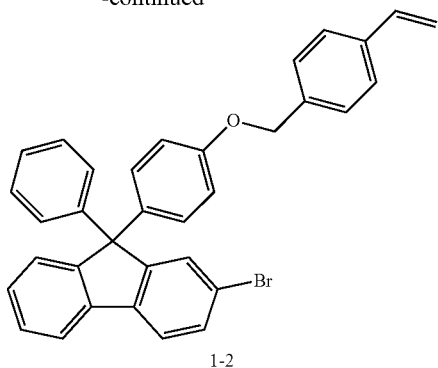

1-2

In a 500 ml round bottom flask, Intermediate 1-1 (30 g, 63.9 mmol, 1.0 eq.) and cesium carbonate (41.6 g, 127.8 mmol, 2.0 eq.) were dissolved in DMF (120 ml, 0.5 M), and then the result was stirred after raising the temperature to 50° C. After that, 4-vinylbenzyl chloride (9.15 ml, 9.75 g, 1.0 eq.) was introduced thereto, and the result was stirred at 60° C. After cooling the result to room temperature [RT], water was introduced thereto to stop the reaction, and then the organic layer was extracted using ethyl acetate [EA]. The organic layer was separated, dried with magnesium sulfate, and after removing the solvent, the result was purified using column chromatography to obtain Intermediate Compound 1-2.

3) Preparation of Compound 1

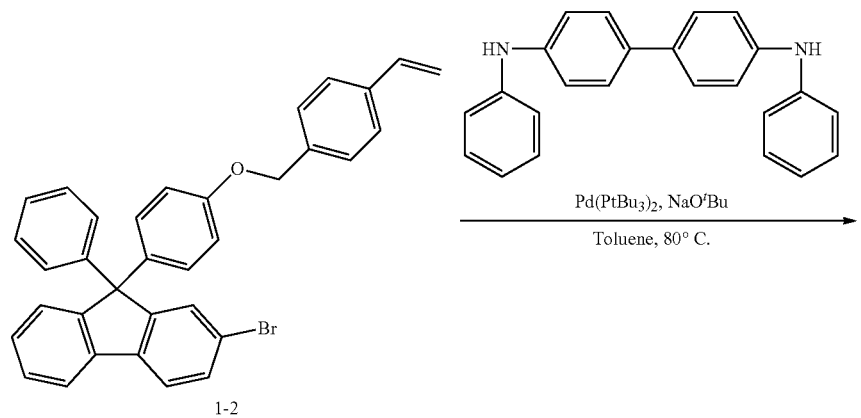

1-2

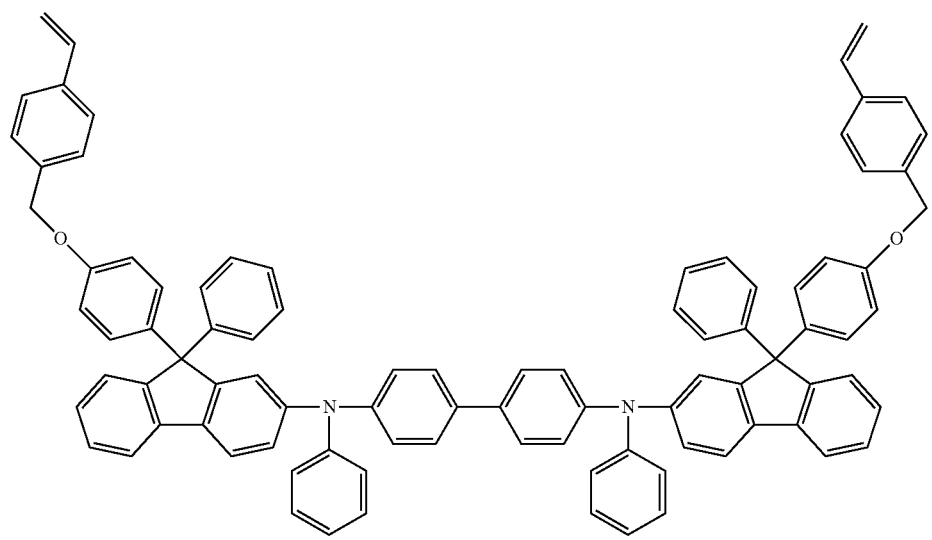

1

In a 250 ml round bottom flask, Intermediate 1-2 (12.0 g, 20.49 mmol, 2.05 eq.), N4,N4'-diphenyl-[1,1'-biphenyl]-4,4'-diamine (3.36 g, 10.0 mmol, 1.0 eq.), NaOtBu (3.36 g, 34.99 mmol, 3.5 eq.) and Pd(PtBu₃)₂ (255 mg, 0.5 mmol, 0.05 eq.) were dissolved in toluene (100 ml), and the result was stirred and reacted under N₂ charge. When the reaction was finished, the result was worked up with H₂O and ethyl acetate [EA], and the organic layer was separated, dried and then filtered. After that, the solvent was removed using a rotary evaporator. The obtained crude material was purified using column chromatography, and after removing the solvent, Compound 1 in a white solid form was obtained, and NMR data values of Compound 1 are as follows.

1H NMR (500 MHz): δ=8.00-7.82 (m, 4H), 7.70-7.68 (d, 4H), 7.62-7.55 (m, 6H), 7.35-7.15 (m, 38H), 7.05-7.03 (t, 2H), 6.92-9.85 (d, 4H), 6.73-6.70 (m, 2H), 5.76-5.73 (d, 2H), 5.39-5.37 (d, 2H), 5.17 (s, 4H)

Preparation Example 2. Preparation of Compound 15

1) Preparation of Intermediate 15-1

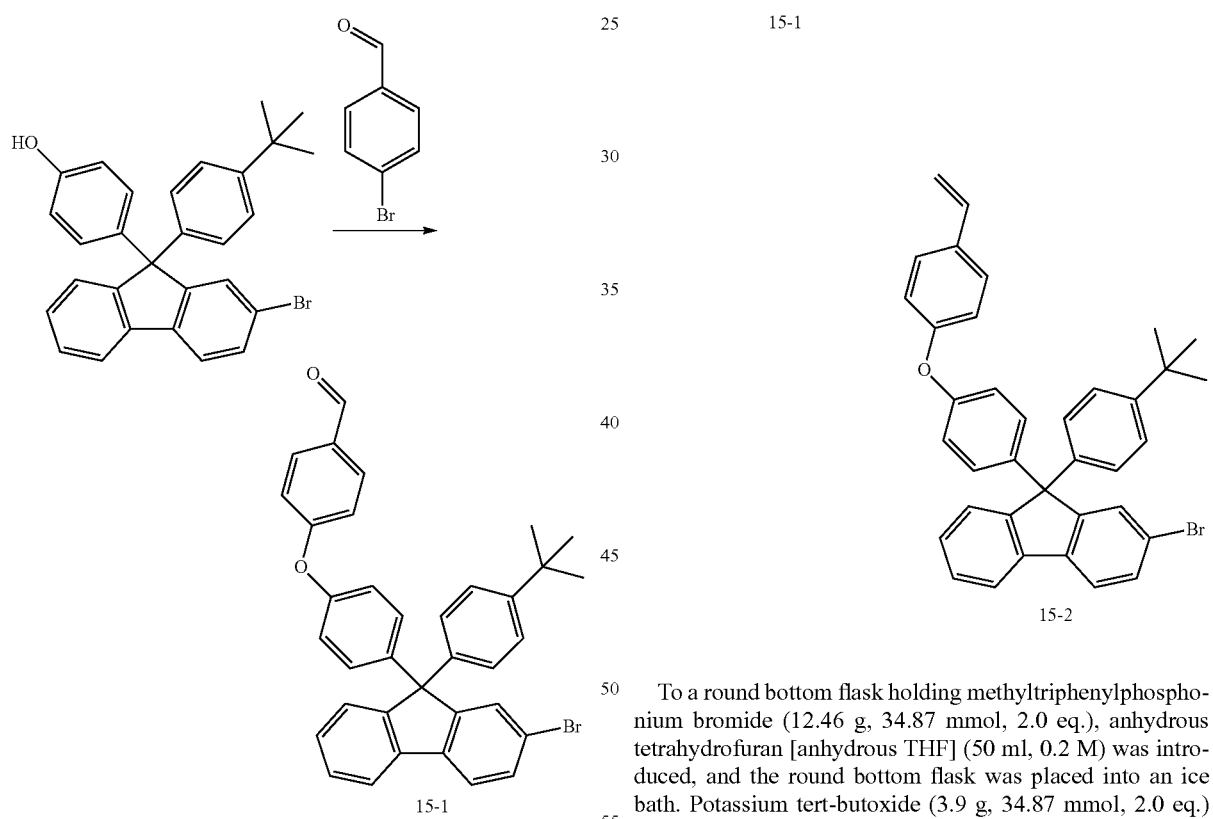

To a 500 ml round bottom flask, 4-(2-bromo-9-(4-(tert-butyl)phenyl)-9H-fluoren-9-yl)phenol (50 g, 106.50 mmol, 1.0 eq.), 4-bromobenzaldehyde (23.6 g, 127.8 mmol, 1.2 eq.) and potassium carbonate (44.2 g, 319.50 mmol, 3.0 eq.) were introduced, and dissolved in dry pyridine (200 ml, 0.5 M). After that, copper(II) oxide (17.0 g, 213.0 mmol, 2 eq.) was slowly added thereto, and the reaction was progressed under reflux after raising the temperature to 120° C. When the reaction was finished, the reaction was stopped using a saturated aqueous NaHCO₃ solution, and the organic layer was extracted using ethyl acetate [EA]. The organic layer was dried with magnesium sulfate, then a crude obtained by removing the solvent was dissolved in dichloromethane, and by collecting precipitates in ethanol, Intermediate Compound 15-1 in a solid form was obtained.

2) Preparation of Intermediate 15-2

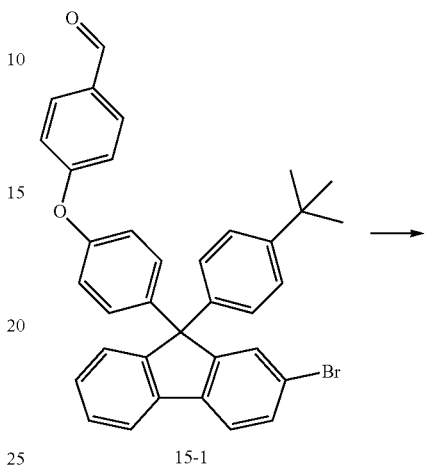

To a round bottom flask holding methyltriphenylphosphonium bromide (12.46 g, 34.87 mmol, 2.0 eq.), anhydrous tetrahydrofuran [anhydrous THF] (50 ml, 0.2 M) was introduced, and the round bottom flask was placed into an ice bath. Potassium tert-butoxide (3.9 g, 34.87 mmol, 2.0 eq.) was introduced thereto at once, and the result was stirred for 20 minutes in an ice bath. Intermediate Compound 15-1 (10.0 g, 17.44 mmol, 1.0 eq.) dissolved in tetrahydrofuran [THF] (30 ml) was gradually added to the mixture using a dropping funnel. After that, while washing the round bottom flask and the funnel with tetrahydrofuran [THF] (10 ml), the rest was added. Water (50 ml) was introduced thereto to terminate the reaction, and the organic layer was extracted using ethyl acetate [EA]. The organic layer was dried with magnesium sulfate, and after removing the solvent, the result was purified using column chromatography to obtain Intermediate Compound 15-2.

3) Preparation of Compound 15

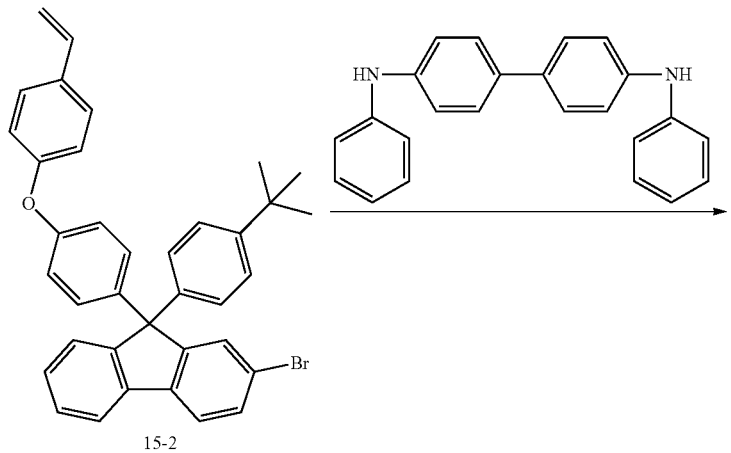

15-2

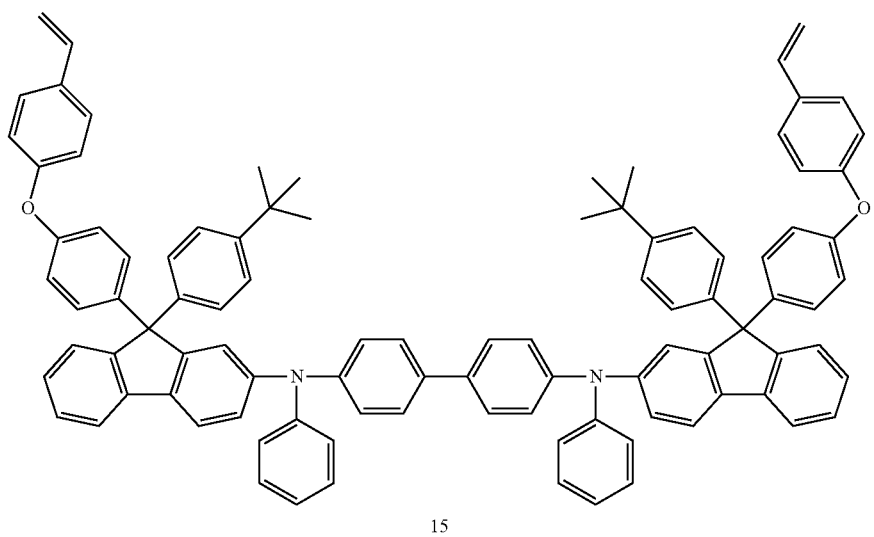

15

In a 250 ml round bottom flask, Intermediate Compound 15-(10.0 g, 17.50 mmol, 2.05 eq.), N4,N4'-diphenyl-[1,1'-biphenyl]-4,4'-diamine (2.87 g, 8.53 mmol, 1.0 eq.), NaOtBu (2.87 g, 29.86 mmol, 3.5 eq.) and Pd(PtBu$_3$)$_2$ (218.0 mg, 0.43 mmol, 0.05 eq.) were dissolved in toluene (90 ml), and the result was stirred and reacted under N$_2$ charge. When the reaction was finished, the result was worked up with H$_2$O and ethyl acetate [EA], and the organic layer was separated, dried and then filtered. After that, the solvent was removed using a rotary evaporator. The obtained crude material was purified using column chromatography, and after removing the solvent, Compound 15 in a white solid form was obtained, and NMR data values of Compound 15 are as follows.

1H NMR (500 MHz): δ=7.95-7.83 (m, 4H), 7.65-7.58 (m, 10H), 7.54-7.26 (m, 22H), 7.24-7.05 (m, 12H), 6.95-6.93 (d, 4H), 6.86-6.84 (d, 4H), 6.80-6.76 (m, 2H), 5.65-5.61 (d, 2H), 5.16-5.13 (d, 2H), 1.35 (s, 18H)

Preparation Example 3. Preparation of Compound 28

1) Preparation of Intermediate 28-1

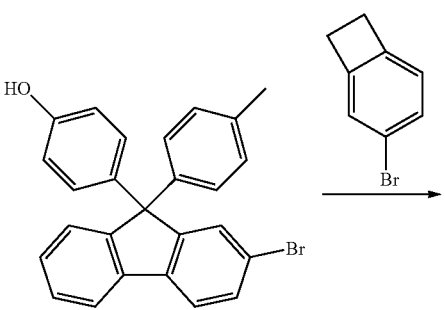

-continued

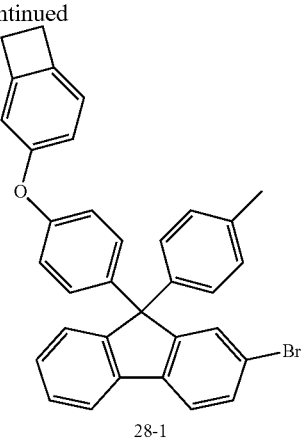
28-1

To a 250 ml round bottom flask, 4-(2-bromo-9-(p-tolyl)-9H-fluoren-9-yl)phenol (15 g, 35.1 mmol, 1.0 eq.), potassium carbonate (14.6 g, 105.3 mmol, 3 eq.), copper(I) iodide (334.3 mg, 1.76 mmol, 0.05 eq.) and 1-butylimidazole (4.4 g, 35.1 mmol, 1.0 eq.) were introduced, and dissolved in toluene (175 ml). After installing a reflux apparatus, the temperature was raised to 120° C., and the reaction was progressed while stirring the result. When the reaction was finished, the reaction was stopped using a saturated aqueous NaHCO$_3$ solution, and the result was worked up with water [H$_2$O] and ethyl acetate [EA]. The organic layer was separated, dried through MgSO$_4$, and then filtered. After that, the solvent was removed using a rotary evaporator. The obtained crude material was purified using column chromatography to obtain Intermediate Compound 28-1.

2) Preparation of Compound 28

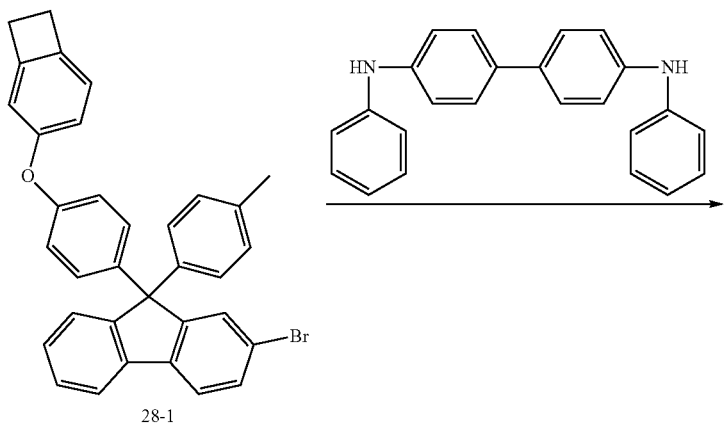
28-1

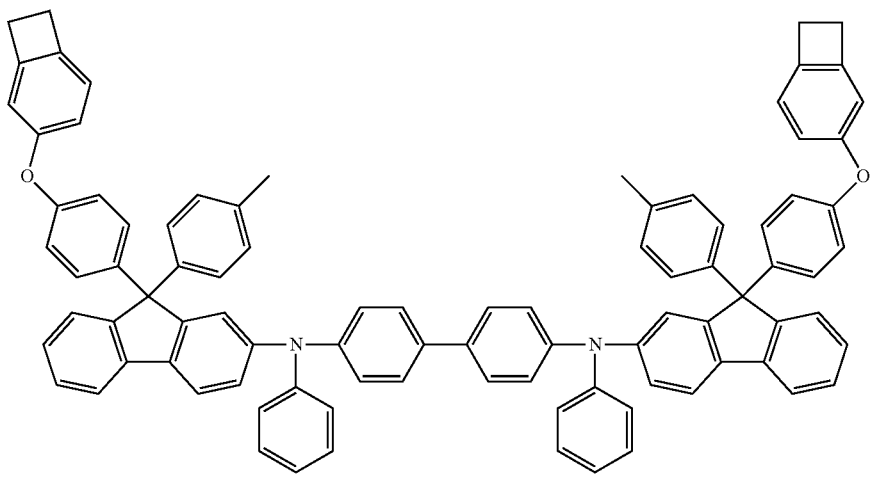
28

In a 250 ml round bottom flask, Intermediate Compound 28-(10.0 g, 18.89 mmol, 2.05 eq.), N4,N4'-diphenyl-[1,1'-biphenyl]-4,4'-diamine (3.10 g, 9.21 mmol, 1.0 eq.), NaOtBu (3.10 g, 32.24 mmol, 3.5 eq.) and Pd(PtBu$_3$)$_2$ (235.1 mg, 0.46 mmol, 0.05 eq.) were dissolved in toluene (120 ml), and the result was stirred and reacted under N$_2$ charge. When the reaction was finished, the result was worked up with H$_2$O and ethyl acetate [EA], and the organic layer was separated, dried and then filtered. After that, the solvent was removed using a rotary evaporator. The obtained crude material was purified using column chromatography, and after removing the solvent, Compound 28 in a white solid form was obtained, and NMR data values of Compound 28 are as follows.

1H NMR (500 MHz): δ=7.90-7.87 (m, 4H), 7.56-7.53 (m, 6H), 7.48-7.30 (m, 16H), 7.27 (s, 2H), 7.25-7.22 (d, 4H), 7.20-7.15 (m, 18H), 7.14-7.12 (d, 4H), 2.88 (s, 8H), 2.19 (s, 6H)

Preparation Example 4. Preparation of Compound 36

1) Preparation of Intermediate 36-1

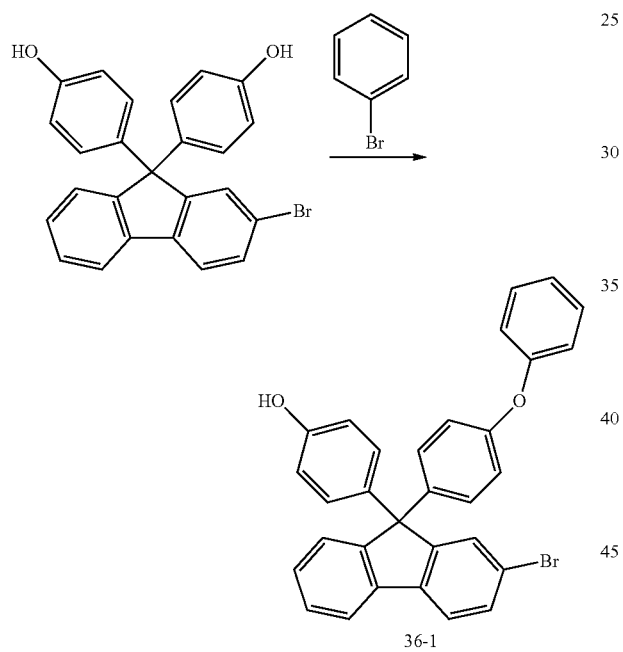

36-1

To a 250 ml round bottom flask, Intermediate 4,4'-(2-bromo-9H-fluorene-9,9-diyl)diphenol (10 g, 23.3 mmol, 1.0 eq.), potassium carbonate (9.7 g, 69.9 mmol, 3 eq.), copper (I) iodide (220.4 mg, 1.17 mmol, 0.05 eq.) and 1-butylimidazole (2.9 g, 23.3 mmol, 1.0 eq.) were introduced, and dissolved in toluene (100 ml). After adding 3-bromobenzene (3.66 g, 23.3 mmol, 1.0 eq.) thereto, a reflux apparatus was installed, the temperature was raised to 120° C., and the reaction was progressed while stirring the result. When the reaction was finished, the reaction was stopped using a saturated aqueous NaHCO$_3$ solution, and the result was worked up with water [H$_2$O] and ethyl acetate [EA]. The organic layer was separated, dried through MgSO$_4$, and then filtered. After that, the solvent was removed using a rotary evaporator. The obtained crude material was purified using column chromatography to obtain Intermediate Compound 36-1.

2) Preparation of Intermediate 36-2

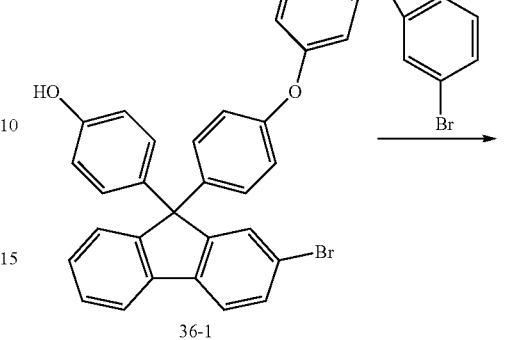

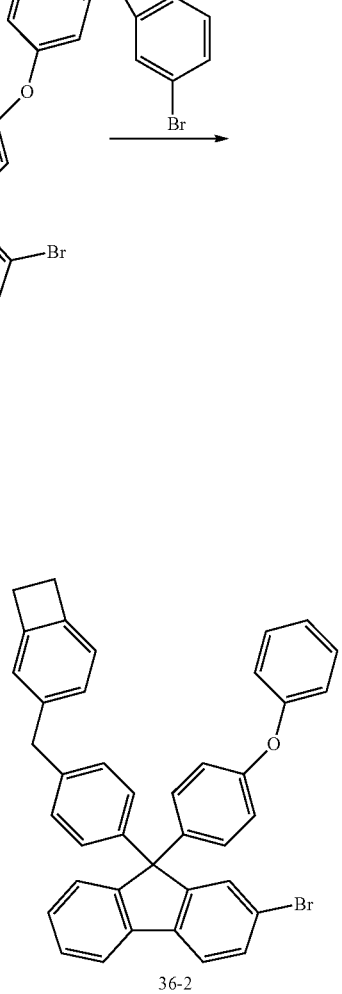

36-2

To a 250 ml round bottom flask, Intermediate 36-1 (10 g, 19.78 mmol, 1.0 eq.), potassium carbonate (8.20 g, 59.36 mmol, 3 eq.), copper(I) iodide (187.1 mg, 0.99 mmol, 0.05 eq.) and 1-butylimidazole (2.42 g, 19.78 mmol, 1.0 eq.) were introduced, and dissolved in toluene (100 ml). After adding 3-bromobicyclo[4.2.0]octa-1(6),2,4-triene (3.98 g, 21.75 mmol, 1.1 eq.) thereto, a reflux apparatus was installed, the temperature was raised to 120° C., and the reaction was progressed while stirring the result. When the reaction was finished, the reaction was stopped using a saturated aqueous NaHCO$_3$ solution, and the result was worked up with water [H$_2$O] and ethyl acetate [EA]. The organic layer was separated, dried through MgSO$_4$, and then filtered. After that, the solvent was removed using a rotary evaporator. The obtained crude material was purified using column chromatography to obtain Intermediate Compound 36-2.

3) Preparation of Compound 36

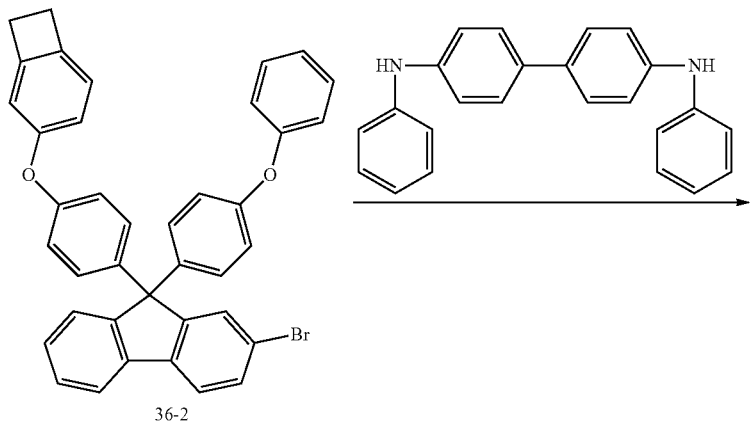

36-2

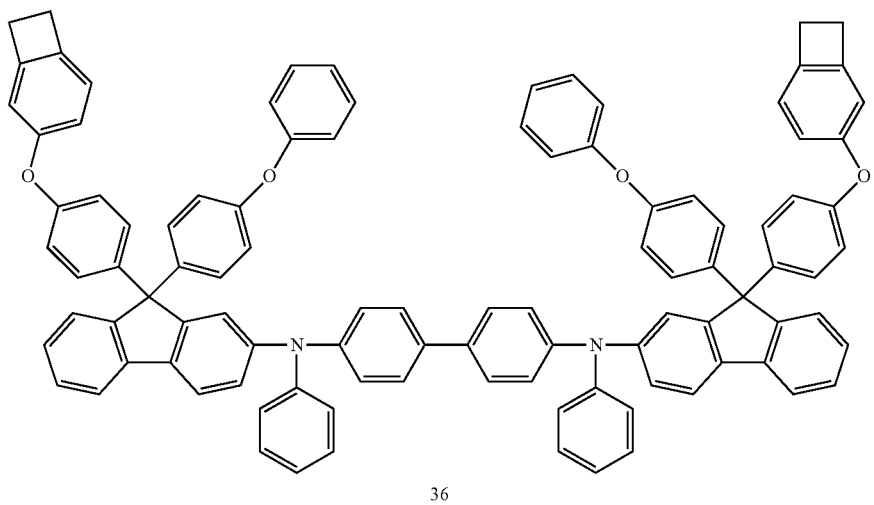

36

In a 250 ml round bottom flask, Intermediate Compound 36-(10.0 g, 16.46 mmol, 2.05 eq.), N4,N4'-diphenyl-[1,1'-biphenyl]-4,4'-diamine (2.70 g, 8.03 mmol, 1.0 eq.), NaOtBu (2.70 g, 28.10 mmol, 3.5 eq.) and Pd(PtBu$_3$)$_2$ (205.2 mg, 0.40 mmol, 0.05 eq.) were dissolved in toluene (90 ml), and the result was stirred and reacted under N$_2$ charge. When the reaction was finished, the result was worked up with H$_2$O and ethyl acetate [EA], and the organic layer was separated, dried and then filtered. After that, the solvent was removed using a rotary evaporator. The obtained crude material was purified using column chromatography, and after removing the solvent, Compound 36 in a white solid form was obtained, and NMR data values of Compound 36 are as follows.

1H NMR (500 MHz): δ=7.88-7.85 (m, 4H), 7.57-7.55 (m, 6H), 7.52-7.30 (m, 20H), 7.27-7.15 (m, 18H), 7.07-6.90 (m, 16H), 2.85 (s, 8H)

Preparation Example 5. Preparation of Compound 51

1) Preparation of Intermediate 51-1

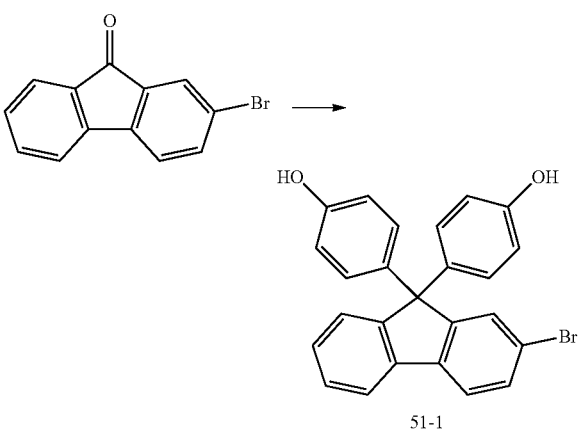

51-1

To a 250 ml round bottom flask, 2-bromo-9H-fluoren-9-one (15 g, 57.9 mmol, 1.0 eq.) and phenol (54.5 g, 579 mmol, 10.0 eq.) were introduced, and dissolved in methanesulfonic acid (70 ml, 0.8 M). The result was stirred overnight under 60° C. After that, water was poured thereto to terminate the reaction, and then produced precipitates were filtered while washing with water. A precipitation process was progressed while dropping the obtained filtered material dissolved in a small amount of ethyl acetate into hexane. The result was filtered to obtain Intermediate Compound 51-1 in a white solid form.

2) Preparation of Intermediate 51-2

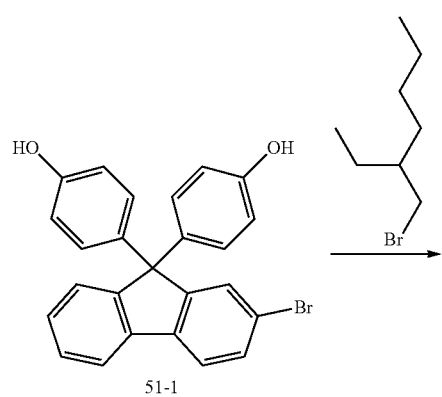

51-1

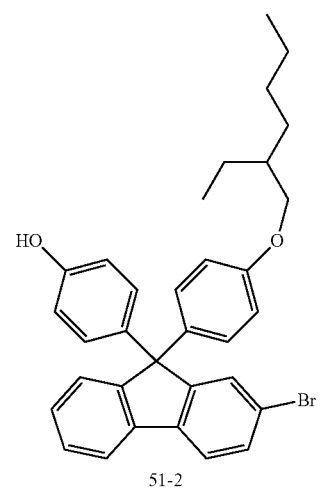

51-2

In a 250 ml round bottom flask, Intermediate 51-1 (10 g, 23.29 mmol, 1.0 eq.) and cesium carbonate (9.1 g, 27.95 mmol, 1.2 eq.) were dissolved in dimethylformamide [DMF] (50 ml, 0.47 M), and the result was stirred after raising the temperature to 100° C. After that, 4-ethylhexyl bromide (3.71 ml, 20.96 mmol, 0.9 eq.) was slowly introduced thereto, and the result was stirred. When the reaction was finished, the result was cooled to room temperature [RT], water was poured thereto to stop the reaction, and then the organic layer was extracted using EA. The organic layer was separated, dried with magnesium sulfate, and after removing the solvent, the result was purified using column chromatography to obtain Intermediate Compound 51-2.

3) Preparation of Intermediate 51-3

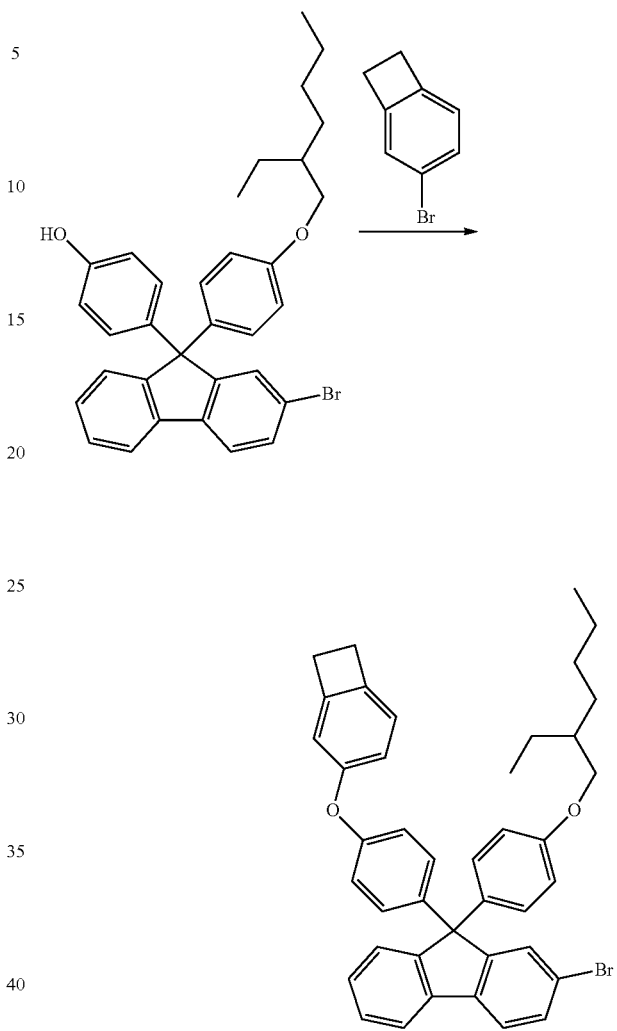

51-3

To a 250 ml round bottom flask, Intermediate 51-2 (10 g, 15.5 mmol, 1.0 eq.), potassium carbonate (6.4 g, 46.6 mmol, 3 eq.), copper(I) iodide (147.6 mg, 0.78 mmol, 0.05 eq.) and 1-butylimidazole (1.9 g, 15.5 mmol, 1.0 eq.) were introduced, and dissolved in toluene (77 ml). After installing a reflux apparatus, the temperature was raised to 120° C., and the reaction was progressed while stirring the result. When the reaction was finished, the reaction was stopped using a saturated aqueous NaHCO$_3$ solution, and the result was worked up with water [H$_2$O] and ethyl acetate [EA]. The organic layer was separated, dried through MgSO$_4$, and then filtered. After that, the solvent was removed using a rotary evaporator. The obtained crude material was purified using column chromatography to obtain Intermediate Compound 51-3.

4) Preparation of Compound 51

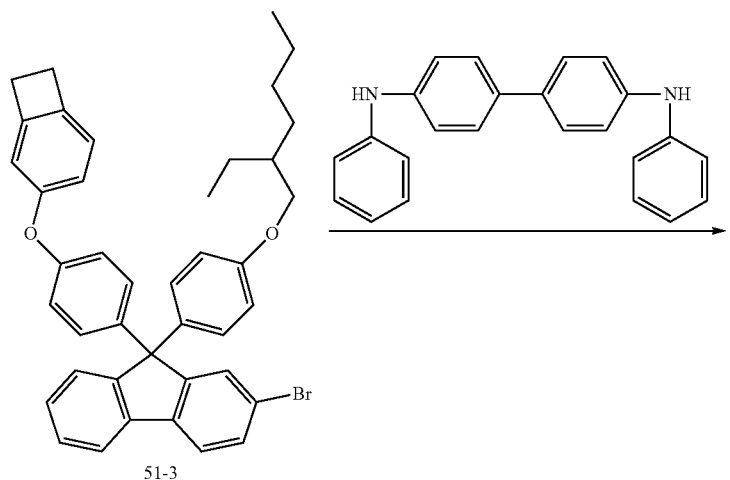

51-3

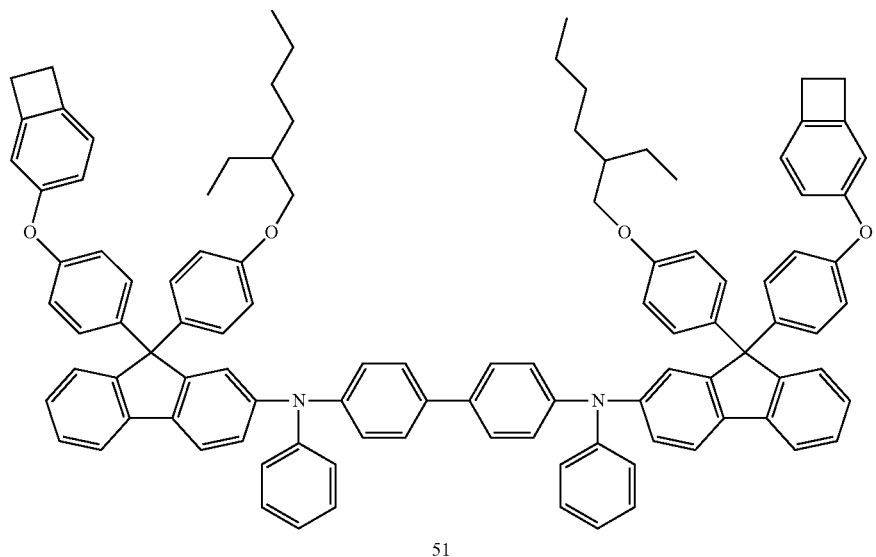

51

In a 250 ml round bottom flask, Intermediate Compound 51-(10.0 g, 15.54 mmol, 2.05 eq.), N4,N4'-diphenyl-[1,1'-biphenyl]-4,4'-diamine (2.55 g, 7.58 mmol, 1.0 eq.), NaOtBu (2.55 g, 26.53 mmol, 3.5 eq.) and Pd(PtBu$_3$)$_2$ (194 mg, 0.38 mmol, 0.05 eq.) were dissolved in toluene (90 ml), and the result was stirred and reacted under N$_2$ charge. When the reaction was finished, the result was worked up with H$_2$O and ethyl acetate [EA], and the organic layer was separated, dried and then filtered. After that, the solvent was removed using a rotary evaporator. The obtained crude material was purified using column chromatography, and after removing the solvent, Compound 51 in a white solid form was obtained, and NMR data values of Compound 51 are as follows.

1H NMR (500 MHz): δ=7.90-7.85 (m, 4H), 7.55-7.52 (m, 6H), 7.48-7.26 (m, 22H), 7.24-7.05 (m, 10H), 6.95-6.93 (d, 4H), 6.86-6.84 (d, 4H), 3.98-3.97 (m, 2H), 3.73-3.70 (m, 2H), 2.90 (s, 8H), 1.70-1.67 (m, 2H), 1.55-1.52 (m, 4H), 1.32-1.25 (m, 12H), 0.95-0.92 (t, 6H), 0.90-0.88 (t, 6H)

Preparation Example 6. Preparation of Compound 65

1) Preparation of Intermediate 65-1

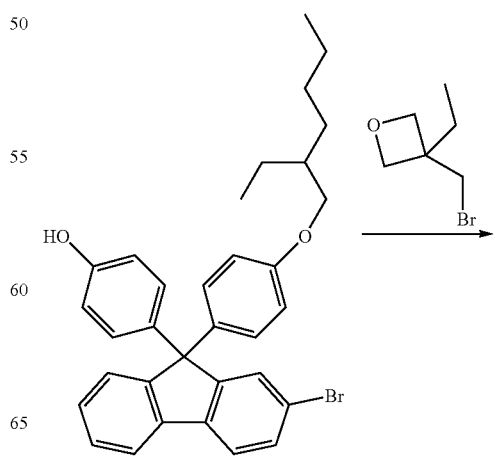

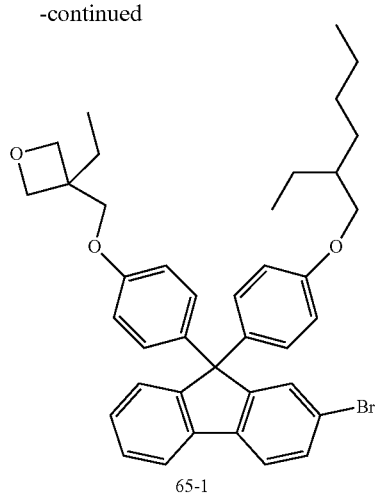

65-1

To a 250 ml round bottom flask, 4-(2-bromo-9-(4-((2-ethylhexyl)oxy)phenyl)-9H-fluoren-9-yl)phenol (15 g, 27.7 mmol, 1.0 eq.) and potassium carbonate (11.5 g, 83.1 mmol, 3 eq.) were introduced, and dissolved in DMF (150 ml). After adding 3-(bromomethyl)-3-ethyloxetane (5.5 g, 30.5 mmol, 1.1 eq.) thereto, the reaction was progressed while heating and stirring the result at 70° C. When the reaction was finished, the result was worked up with $H_2O$ and EA. The organic layer was separated, dried through $MgSO_4$, and then filtered. After that, the solvent was removed using a rotary evaporator. The obtained crude material was purified using column chromatography to obtain Intermediate Compound 65-1.

2) Preparation of Compound 65

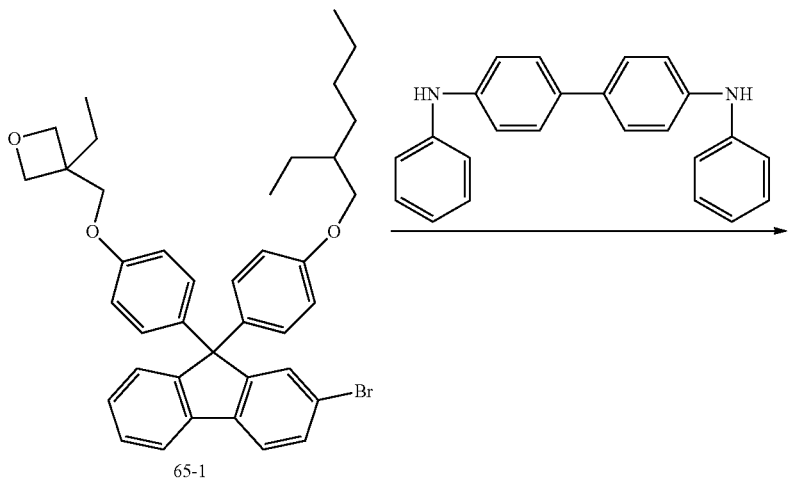

65-1

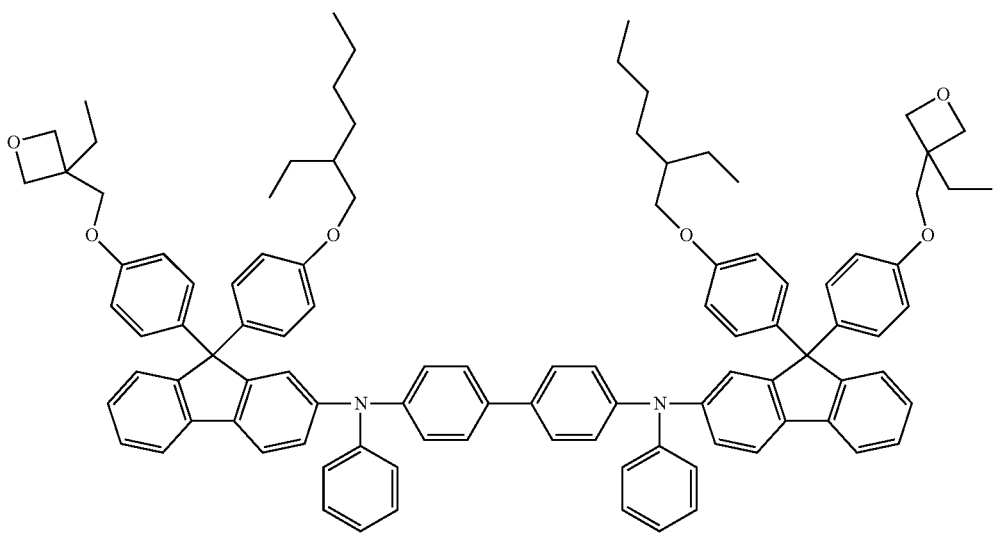

65

In a 250 ml round bottom flask, Intermediate Compound 65-(10.0 g, 15.63 mmol, 2.05 eq.), N4,N4'-diphenyl-[1,1'-biphenyl]-4,4'-diamine (2.56 g, 7.62 mmol, 1.0 eq.), NaOtBu (2.56 g, 26.67 mmol, 3.5 eq.) and Pd(PtBu$_3$)$_2$ (194.7 mg, 0.38 mmol, 0.05 eq.) were dissolved in toluene (100 ml), and the result was stirred and reacted under N$_2$ charge. When the reaction was finished, the result was worked up with H$_2$O and EA, and the organic layer was separated, dried and then filtered. After that, the solvent was removed using a rotary evaporator. The obtained crude material was purified using column chromatography, and after removing the solvent, Compound 65 in a white solid form was obtained, and NMR data values of Compound 65 are as follows.

1H NMR (500 MHz): δ=7.91-7.95 (m, 4H), 7.56-7.53 (m, 6H), 7.45-7.20 (m, 30H), 6.87-6.83 (m, 8H), 4.37-4.35 (d, 4H), 4.13-4.10 (d, 4H), 3.94-3.90 (m, 2H), 3.80 (s, 2H), 3.75-3.71 (m, 2H), 1.80-1.78 (m, 2H), 1.70-1.68 (q, 4H), 1.55-1.53 (m, 4H), 1.30-1.18 (m, 12H), 0.99-0.96 (t, 6H), 0.88-0.84 (m, 12H)

Example

Example 1

A glass substrate on which indium tin oxide (ITO) was coated as a thin film to a thickness of 1,500 Å was placed in detergent-dissolved distilled water and ultrasonic cleaned. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone for 30 minutes each, then dried, and then transferred to a glove box.

On the transparent ITO electrode prepared as above, a hole injection layer having a thickness of 300 Å was formed by spin coating a coating composition mixing the following Compound 1 (20 mg), Chemical Formula D (1 mg) and toluene (1 mg), and the coating composition was cured for 1 hour on a hot plate in the air. After that, the result was transferred to a vacuum depositor, and a hole transfer layer was formed by vacuum depositing the following a-NPD on the hole injection layer.

After depositing the a-NPD to a thickness of 40 nm, the following Alq$_3$ was vacuum deposited to 50 nm on the hole transfer layer to form a light emitting layer. On the electron transfer layer, LiF and aluminum were deposited to thicknesses of 0.5 nm and 100 nm, respectively, to form a cathode.

In the above-mentioned process, the deposition rates of the organic materials were maintained at 0.4 Å/sec to 0.7 Å/sec, the deposition rates of the LiF and the aluminum of the cathode were maintained at 0.3 Å/sec and 2 Å/sec, respectively, and the degree of vacuum during the deposition was maintained at 2×10$^{-7}$ to 3×10$^{-5}$ torr.

[Compound 1]

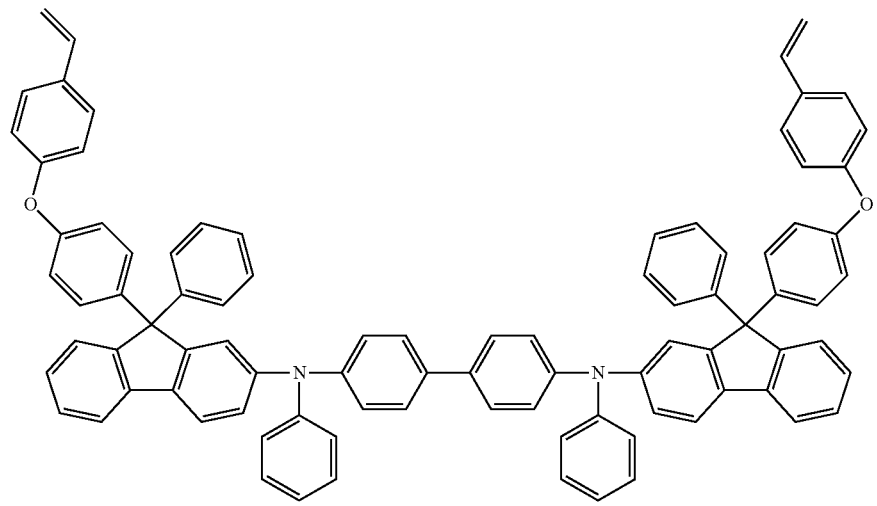

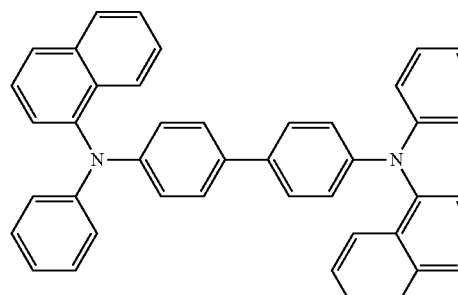

[a-NPD]

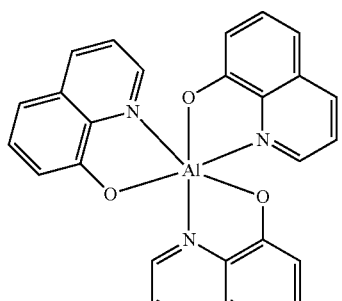

[Alq$_3$]

-continued
[Chemical Formula C]
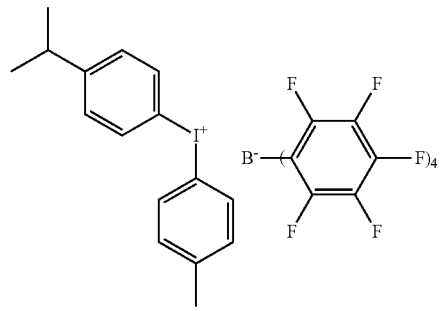
[Chemical Formula D]
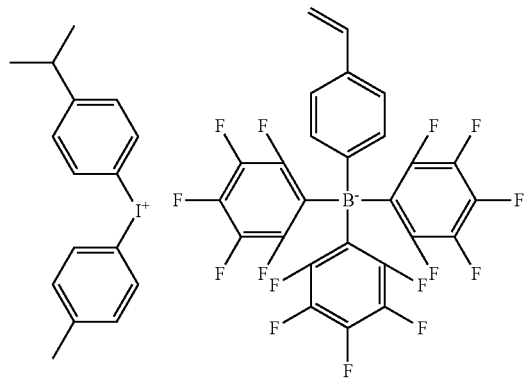
[Chemical Formula F]
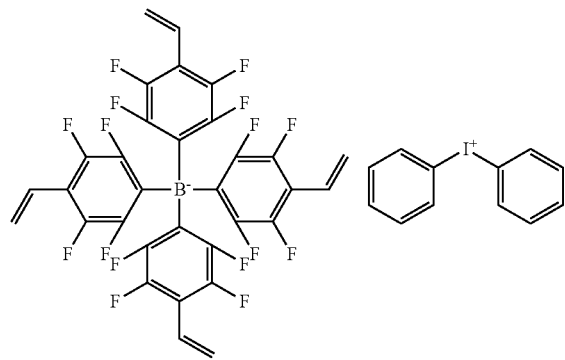
[Chemical Formula G]
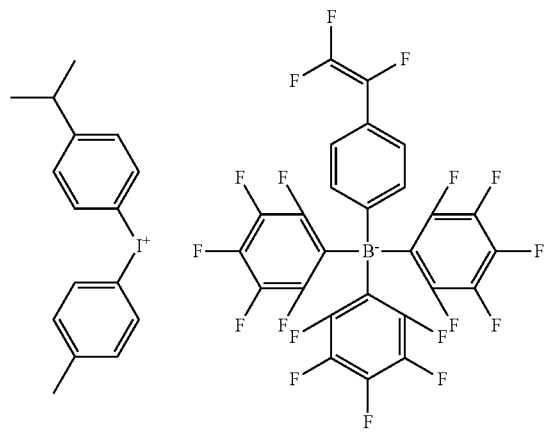
[Chemical Formula H]
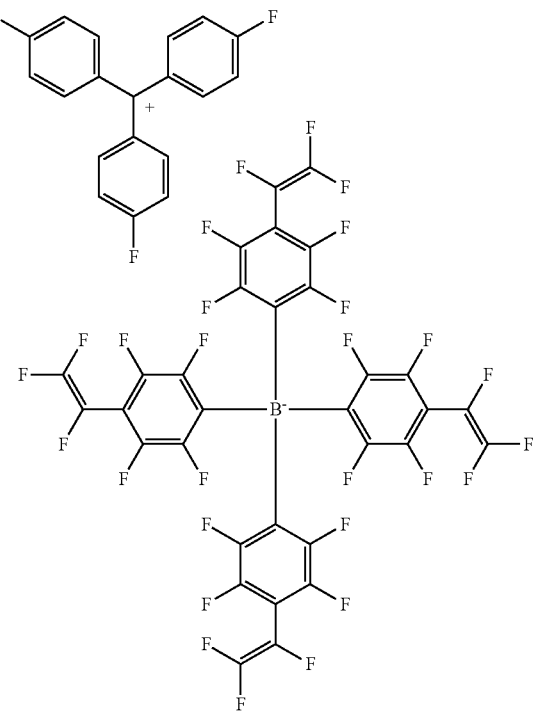

Example 2

An organic light emitting device was manufactured in the same manner as in Example 1 except that Compound 15 was used instead of Compound 1.

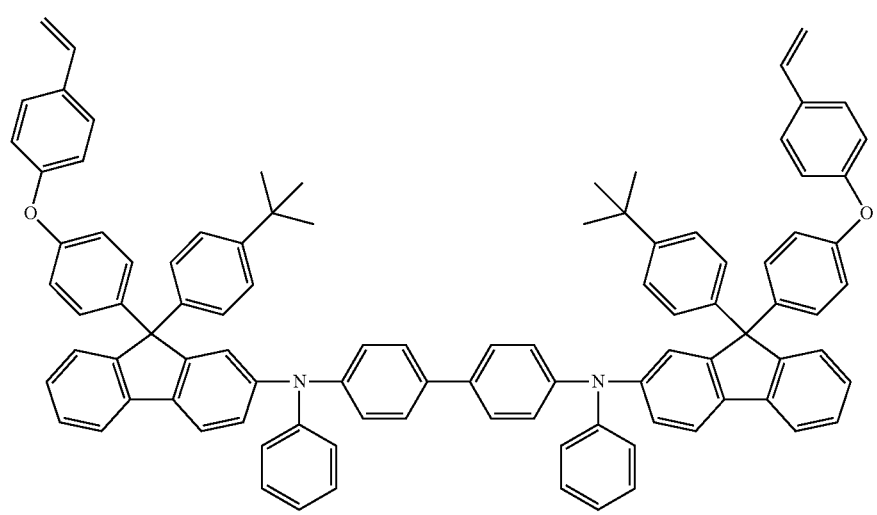

[Compound 15]

Example 3

An organic light emitting device was manufactured in the same manner as in Example 1 except that Compound 28 was used instead of Compound 1.

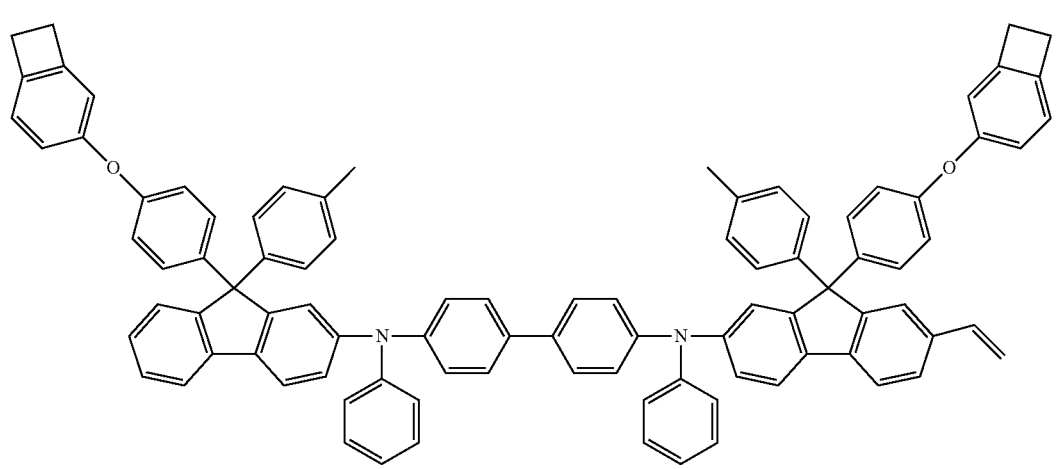

[Compound 28]

Example 4

An organic light emitting device was manufactured in the same manner as in Example 1 except that Chemical Formula F was used instead of Chemical Formula D.

Example 5

An organic light emitting device was manufactured in the same manner as in Example 1 except that Compound 15 was used instead of Compound 1, and Chemical Formula F was used instead of Chemical Formula D.

Example 6

An organic light emitting device was manufactured in the same manner as in Example 1 except that Compound 28 was used instead of Compound 1, and Chemical Formula F was used instead of Chemical Formula D.

Example 7

An organic light emitting device was manufactured in the same manner as in Example 1 except that Compound 36 was used instead of Compound 1, and Chemical Formula G was used instead of Chemical Formula D.

Example 8

An organic light emitting device was manufactured in the same manner as in Example 1 except that Compound 51 was used instead of Compound 1, and Chemical Formula G was used instead of Chemical Formula D.

Example 9

An organic light emitting device was manufactured in the same manner as in Example 1 except that Compound 65 was used instead of Compound 1, and Chemical Formula G was used instead of Chemical Formula D.

Example 10

An organic light emitting device was manufactured in the same manner as in Example 1 except that Chemical Formula H was used instead of Chemical Formula D.

Example 11

An organic light emitting device was manufactured in the same manner as in Example 1 except that Compound 15 was used instead of Compound 1, and Chemical Formula H was used instead of Chemical Formula D.

Example 12

An organic light emitting device was manufactured in the same manner as in Example 1 except that Compound 28 was used instead of Compound 1, and Chemical Formula H was used instead of Chemical Formula D.

Example 13

An organic light emitting device was manufactured in the same manner as in Example 1 except that Compound 36 was used instead of Compound 1, and Chemical Formula H was used instead of Chemical Formula D.

Example 14

An organic light emitting device was manufactured in the same manner as in Example 1 except that Compound 51 was used instead of Compound 1, and Chemical Formula H was used instead of Chemical Formula D.

Example 15

An organic light emitting device was manufactured in the same manner as in Example 1 except that Compound 65 was used instead of Compound 1, and Chemical Formula H was used instead of Chemical Formula D.

Comparative Example 1

An organic light emitting device was manufactured in the same manner as in Example 1 except that the following Compound V-1 was used instead of Compound 1, and Chemical Formula C was used instead of Chemical Formula D.

[Compound V-1]

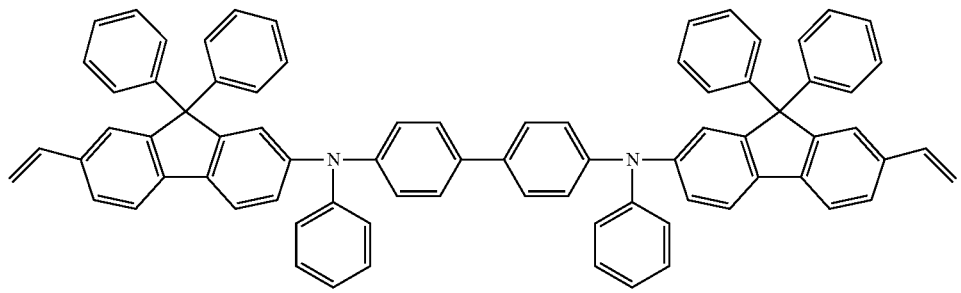

Comparative Example 2

An organic light emitting device was manufactured in the same manner as in Example 1 except that the following Compound V-2 was used instead of Compound 1.

[Compound V-2]

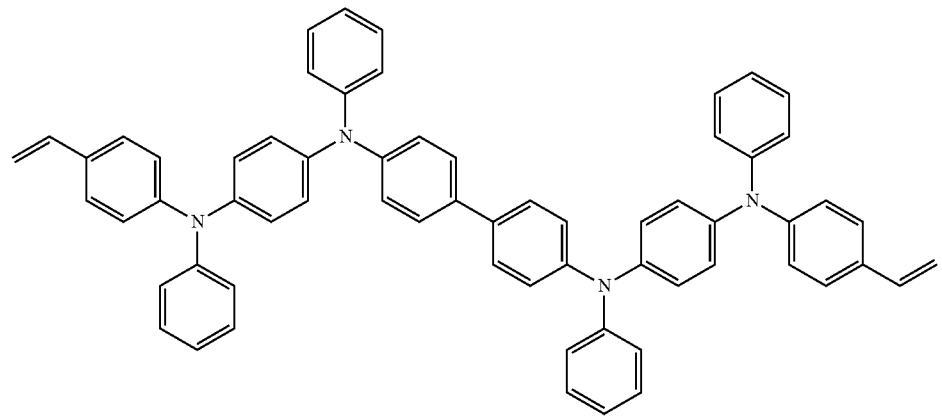

Comparative Example 3

An organic light emitting device was manufactured in the same manner as in Example 1 except that Chemical Formula C was used instead of Chemical Formula D.

Comparative Example 4

An organic light emitting device was manufactured in the same manner as in Example 1 except that Compound 28 was used instead of Compound 1, and Chemical Formula C was used instead of Chemical Formula D.

For the organic light emitting devices manufactured in Examples 1 to 15 and Comparative Examples 1 to 4, driving voltage, current efficiency, quantum efficiency (QE) and luminance values were measured at current density of 10 mA/cm$^2$, and time taken for the luminance decreasing to 90% compared to its initial luminance (T90) was measured at current density of 10 mA/cm$^2$. The results are shown in the following Table 1.

TABLE 1

| Device | Driving Voltage (V) | Current Efficiency (cd/A) | QE (%) | Luminance (Cd/m$^2$) | Lifetime T90 (10 mA/cm$^2$) |
|---|---|---|---|---|---|
| Example 1 | 3.81 | 5.00 | 5.47 | 499.7 | 67.2 |
| Example 2 | 3.85 | 5.15 | 5.43 | 515.6 | 65.1 |
| Example 3 | 3.83 | 5.10 | 5.49 | 509.9 | 66.7 |
| Example 4 | 3.90 | 4.80 | 5.23 | 466.4 | 59.1 |
| Example 5 | 3.87 | 5.00 | 5.41 | 505.5 | 65.0 |
| Example 6 | 3.81 | 5.20 | 5.54 | 511.2 | 67.0 |
| Example 7 | 3.90 | 4.75 | 4.92 | 455.1 | 55.7 |
| Example 8 | 3.92 | 4.54 | 5.12 | 447.0 | 48.5 |
| Example 9 | 3.98 | 4.60 | 5.01 | 464.1 | 57.9 |
| Example 10 | 3.88 | 5.10 | 5.56 | 511.1 | 66.0 |
| Example 11 | 3.90 | 4.88 | 5.31 | 470.3 | 65.9 |
| Example 12 | 3.91 | 4.99 | 5.38 | 460.5 | 68.9 |
| Example 13 | 3.93 | 5.21 | 5.60 | 513.4 | 71.1 |
| Example 14 | 3.81 | 5.12 | 5.61 | 515.0 | 68.7 |
| Example 15 | 3.85 | 5.10 | 5.50 | 510.3 | 65.0 |
| Comparative Example 1 | 4.04 | 4.25 | 4.60 | 424.7 | 36.3 |
| Comparative Example 2 | 4.01 | 4.34 | 4.70 | 433.3 | 32.7 |
| Comparative Example 3 | 3.98 | 4.10 | 4.51 | 450.1 | 39.4 |
| Comparative Example 4 | 4.01 | 4.45 | 4.78 | 422.7 | 38.8 |

From the results of Table 1, it was identified that Examples 1 to 15 manufacturing an organic light emitting device using the compound of the present application had a lower driving voltage, had excellent current efficiency and quantum efficiency, and also had excellent lifetime properties compared to the organic light emitting devices manufactured in Comparative Examples 1 to 4.

The invention claimed is:

1. A coating composition comprising:
   a compound represented by the following Chemical Formula 1; and
   an ionic compound comprising an anion group represented by the following Chemical Formula 10:

[Chemical Formula 1]

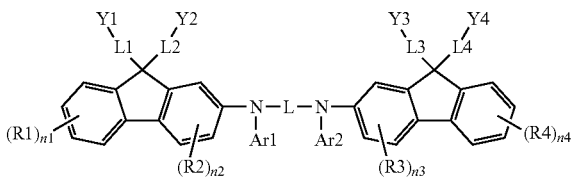

wherein, in Chemical Formula 1,
L and L1 to L4 are the same as or different from each other, and each independently a substituted or unsubstituted arylene group;
Ar1 and Ar2 are the same as or different from each other, and each independently a substituted or unsubstituted aryl group; or a substituted or unsubstituted heteroaryl group;
R1 to R4 are the same as or different from each other, and each independently hydrogen; deuterium; a substituted or unsubstituted alkyl group; a substituted or unsubstituted alkoxy group; a substituted or unsubstituted aryl group; or a substituted or unsubstituted heteroaryl group;
Y1 to Y4 are the same as or different from each other, and each independently —(R201)s; or
—X-A, and two or more of Y1 to Y4 are —X-A;
R201 is hydrogen; deuterium; a halogen group; a substituted or unsubstituted alkyl group; a substituted or unsubstituted alkoxy group; a substituted or unsubstituted aryl group; or a substituted or unsubstituted aryloxy group;
s is an integer of 0 to 5, and when s is 2 or greater, two or more R201s are the same as or different from each other;
X is O or S;
A is a functional group crosslinkable by heat or light;
n1 and n4 are each independently an integer of 0 to 4;
n2 and n3 are each independently an integer of 0 to 3; and
when n1 to n4 are each 2 or greater, R2s, R3s and R4s are each the same as or different from each other,

[Chemical Formula 10]

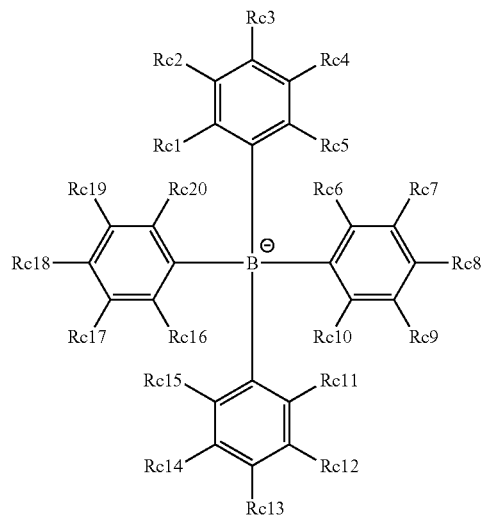

in Chemical Formula 10, at least one of Rc1 to Rc20 is F, a cyano group, or a substituted or unsubstituted fluoroalkyl group;

at least one of the remaining Rc1 to Rc20 is a functional group crosslinkable by heat or light;

the remaining Rc1 to Rc20 if available are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group; and R$_{100}$ to R$_{107}$ are the same as or different from each other, and each independently hydrogen; deuterium; or a substituted or unsubstituted alkyl group;

and wherein the functional group crosslinkable by heat or light is any one of the following structures:

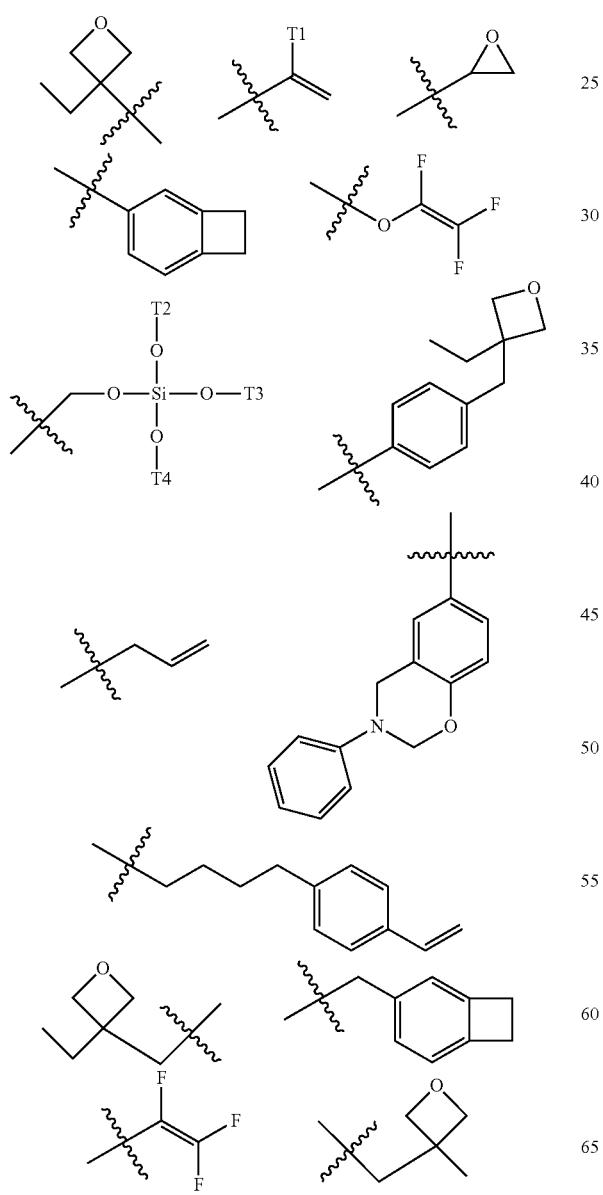

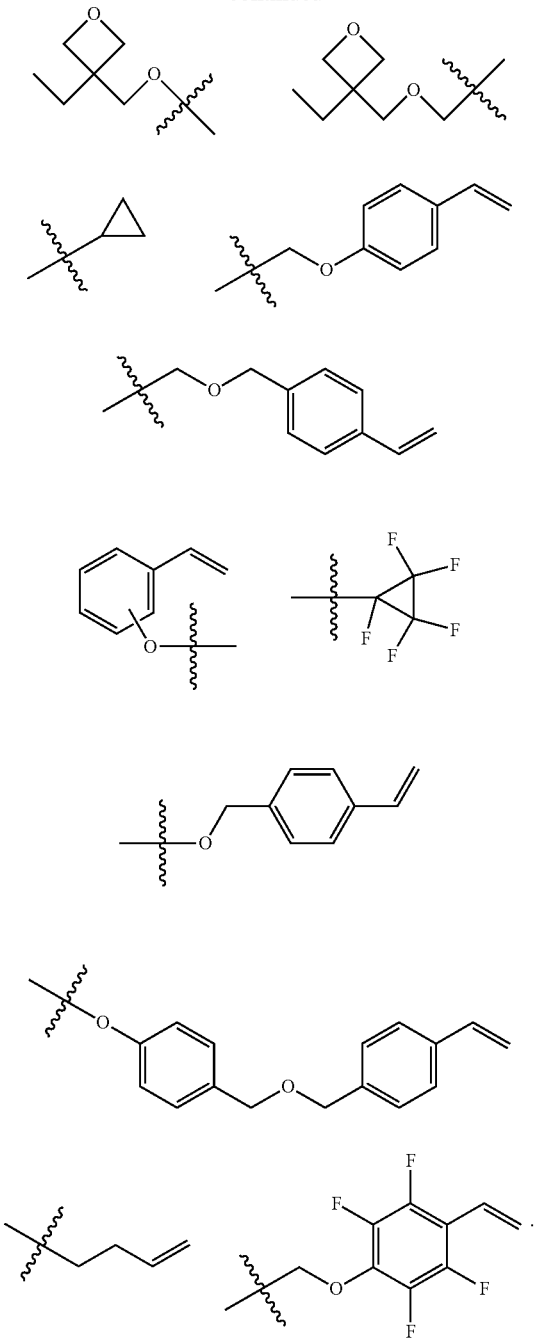

in the structures,

T1 is hydrogen; or a substituted or unsubstituted alkyl group having 1 to 6 carbon atoms; and T2 to T4 are the same as or different from each other, and each independently a substituted or unsubstituted alkyl group having 1 to 6 carbon atoms."

2. The coating composition of claim 1, which is for coating an organic material layer of an organic light emitting device.

3. The Coating composition of claim 1, wherein Chemical Formula 1 is represented by any one of the following Chemical Formulae 2 to 5:

[Chemical Formula 2]

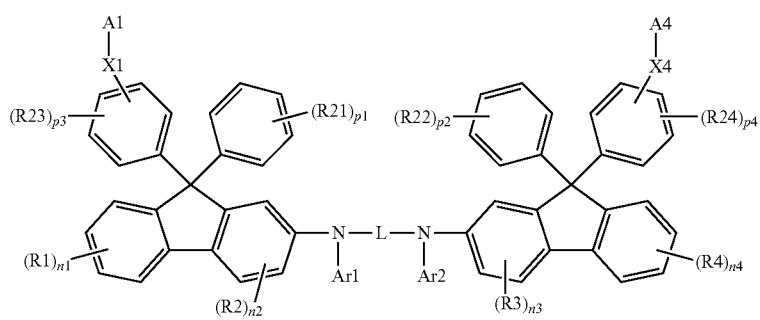

[Chemical Formula 3]

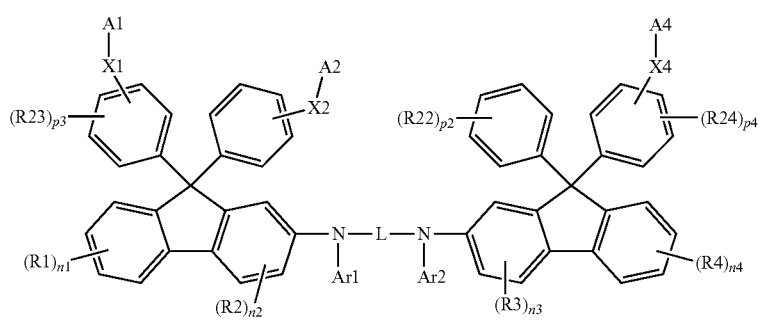

[Chemical Formula 4]

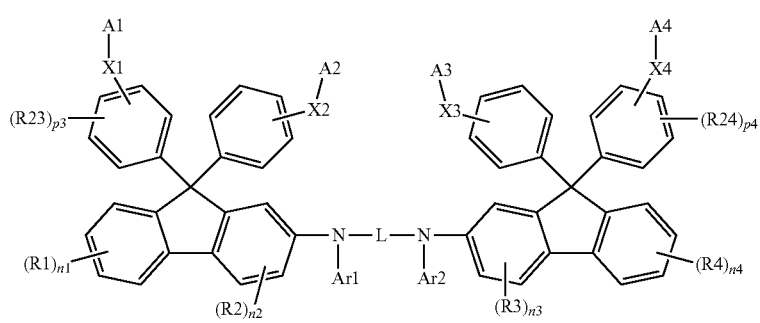

[Chemical Formula 5]

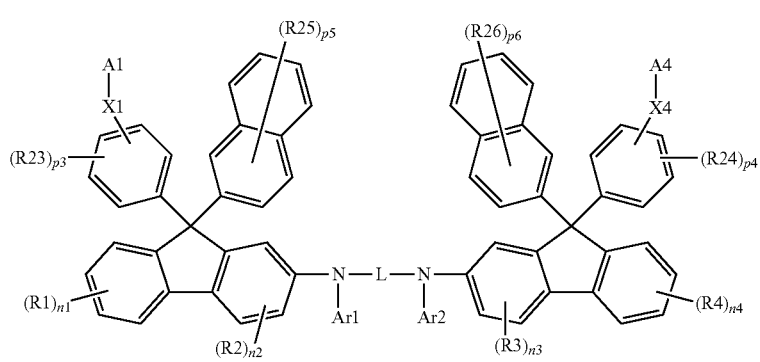

in Chemical Formulae 2 to 5,

R1 to R4, n1 to n4, Ar1, Ar2 and L have the same definitions as in Chemical Formula 1;

X1 to X4 are the same as or different from each other, and each independently O or S;

A1 to A4 are the same as or different from each other, and each independently a functional group crosslinkable by heat or light;

R21 to R26 are the same as or different from each other, and each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group;

p1 and p2 are each independently an integer of 0 to 5;

p3 and p4 are each independently an integer of 0 to 4;

p5 and p6 are each independently an integer of 0 to 7; and when p1 to p6 are each 2 or greater, R21s to R26s are each the same as or different from each other.

4. The coating composition of claim 1, wherein L is the following Chemical Formula 1-A or 1-B:

[Chemical Formula 1-A]

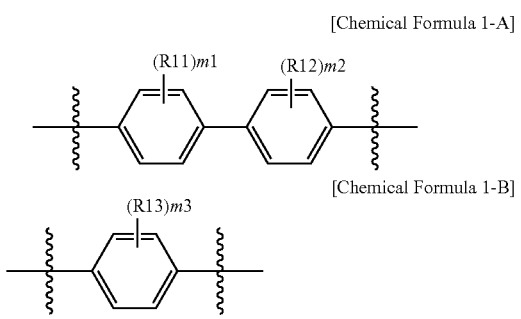

[Chemical Formula 1-B]

in Chemical Formulae 1-A and 1-B,

R11 to R13 are the same as or different from each other, and each independently hydrogen; deuterium; a substituted or unsubstituted alkyl group; a substituted or unsubstituted alkoxy group; a substituted or unsubstituted aryl group; or a substituted or unsubstituted heteroaryl group;

m1 to m3 are each independently an integer of 0 to 4; and when m1 to m3 are 2 or greater, R11s to R13s are each the same as or different from each other.

5. The coating composition of claim 1, wherein Chemical Formula 1 is represented by any one of the following Compounds 1 to 140:

Compound 1

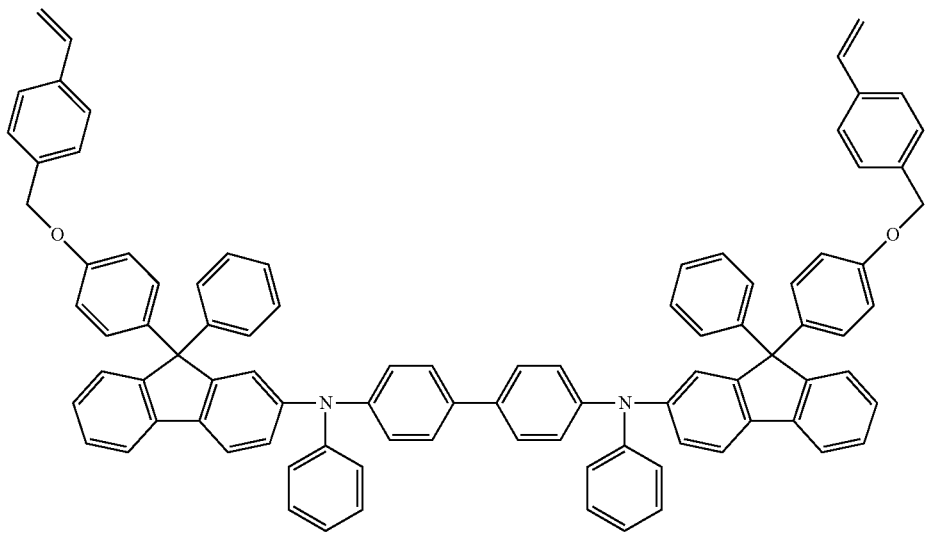

Compound 2

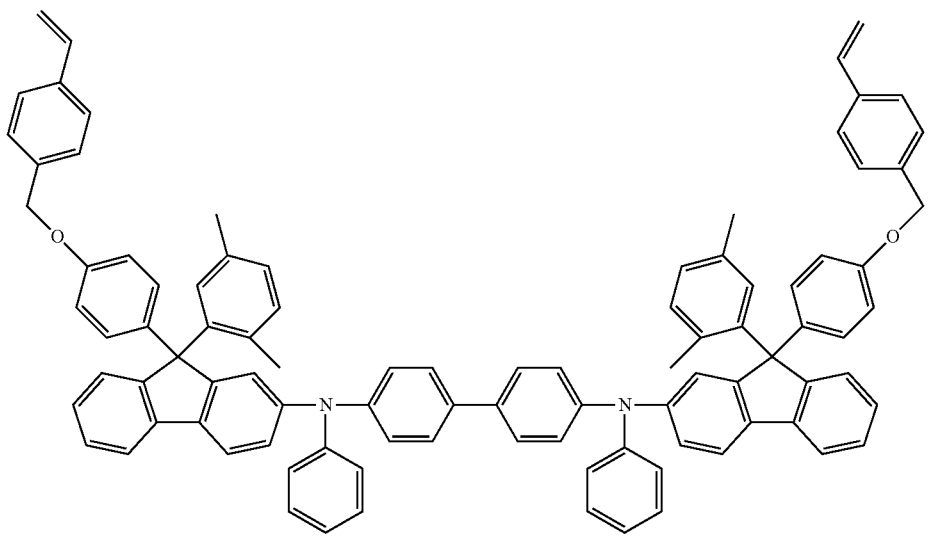

-continued
Compound 3
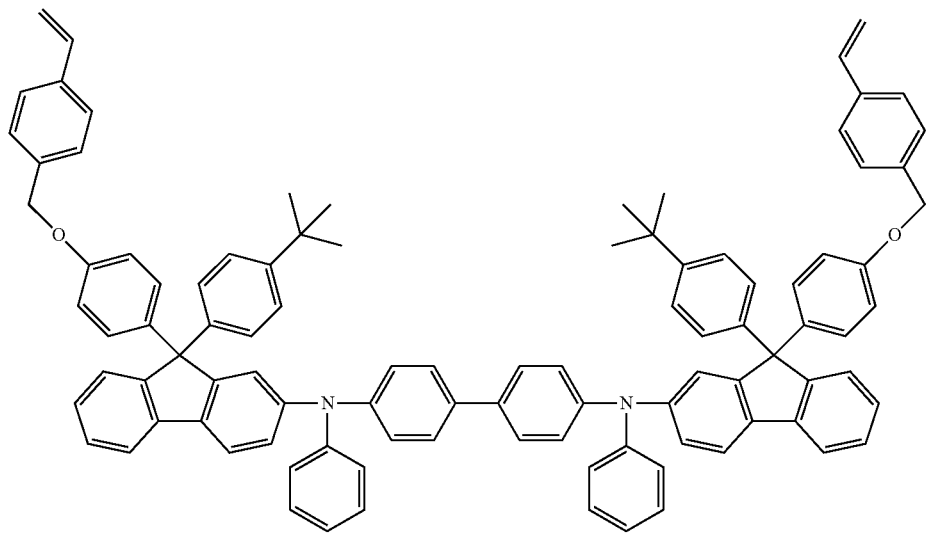
Compound 4
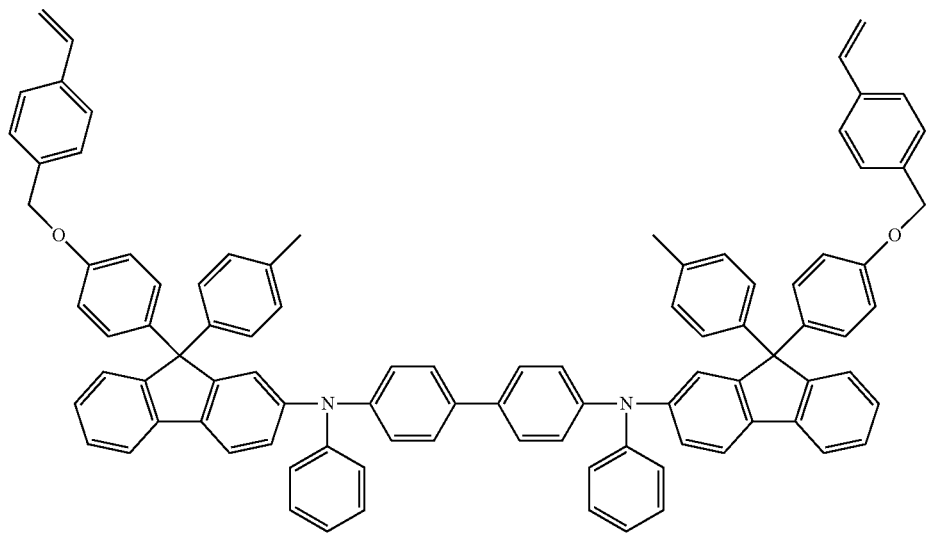
Compound 5
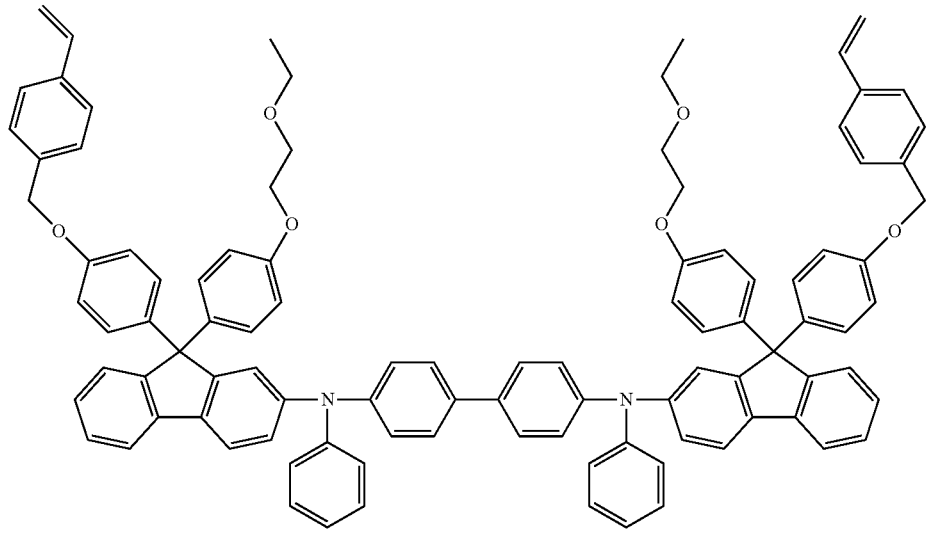

Compound 6
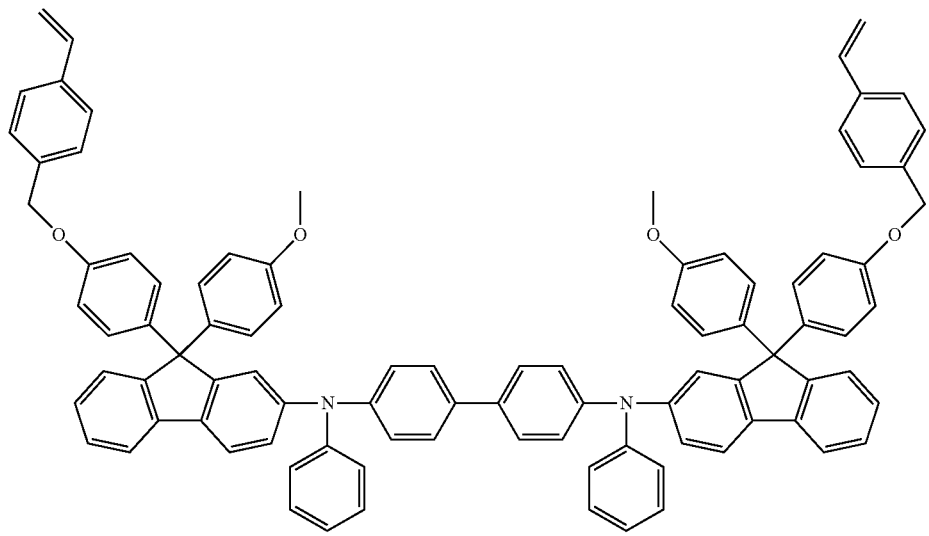
Compound 7
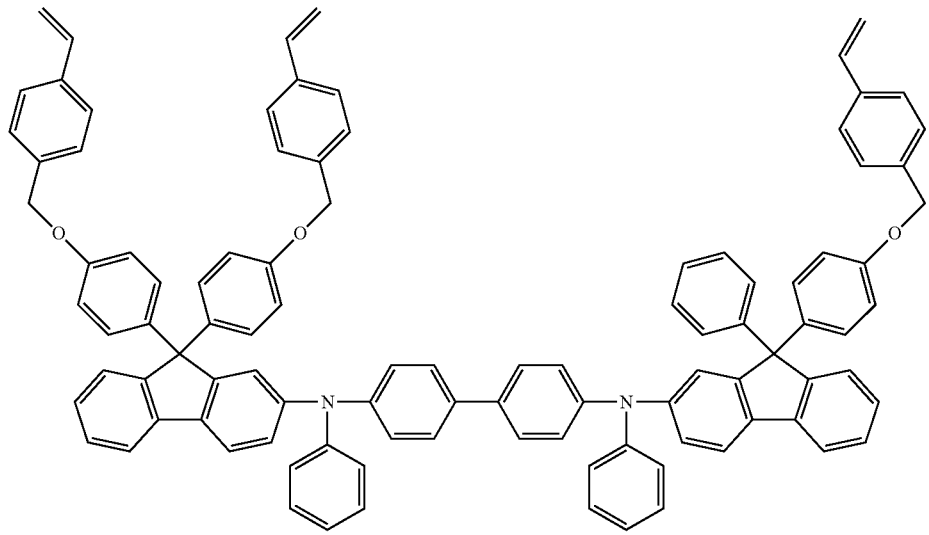
Compound 8
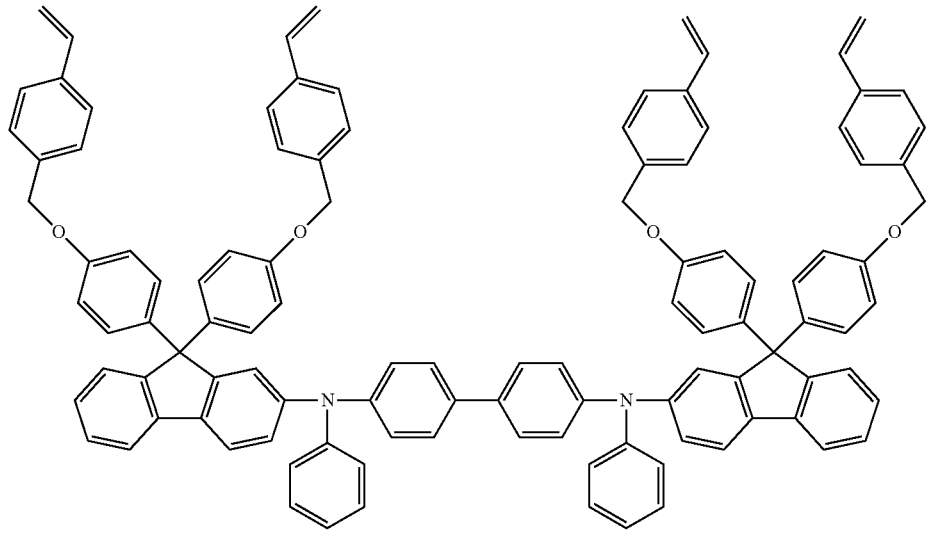

Compound 9
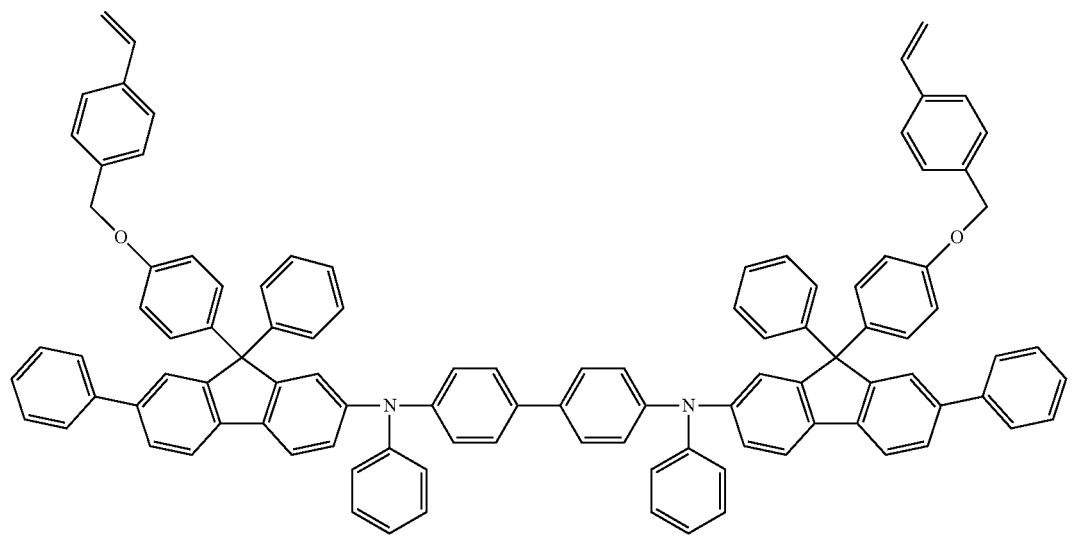
Compound 10
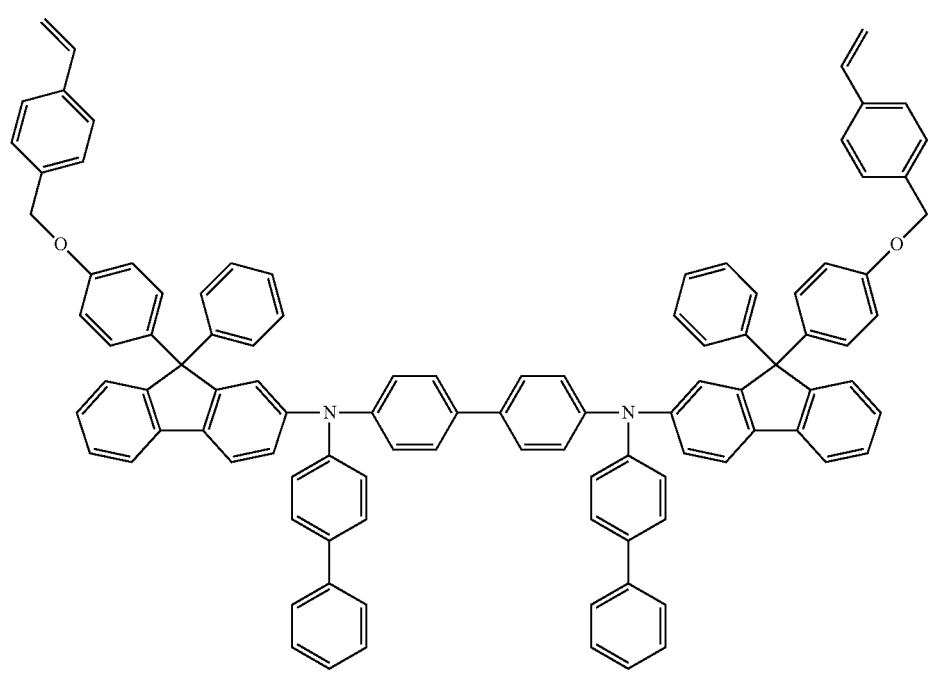

Compound 11
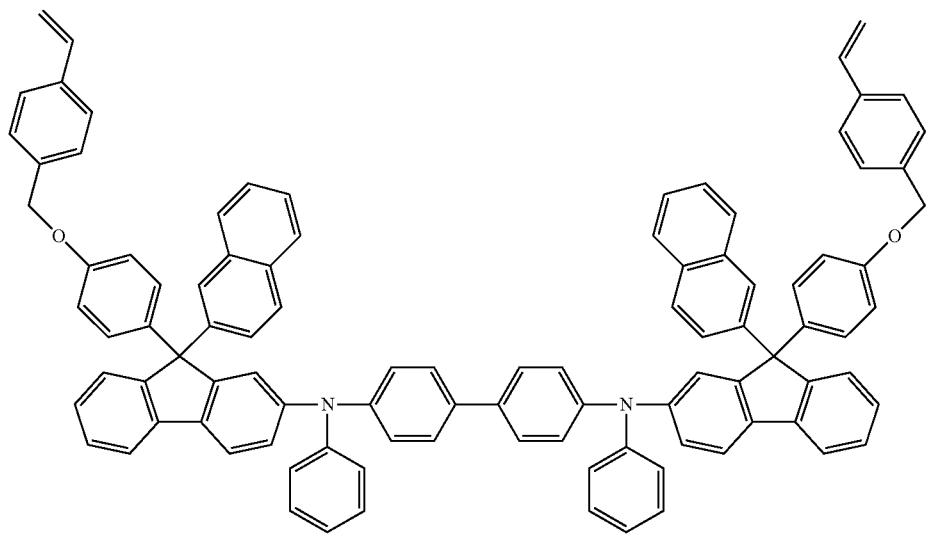
Compound 12
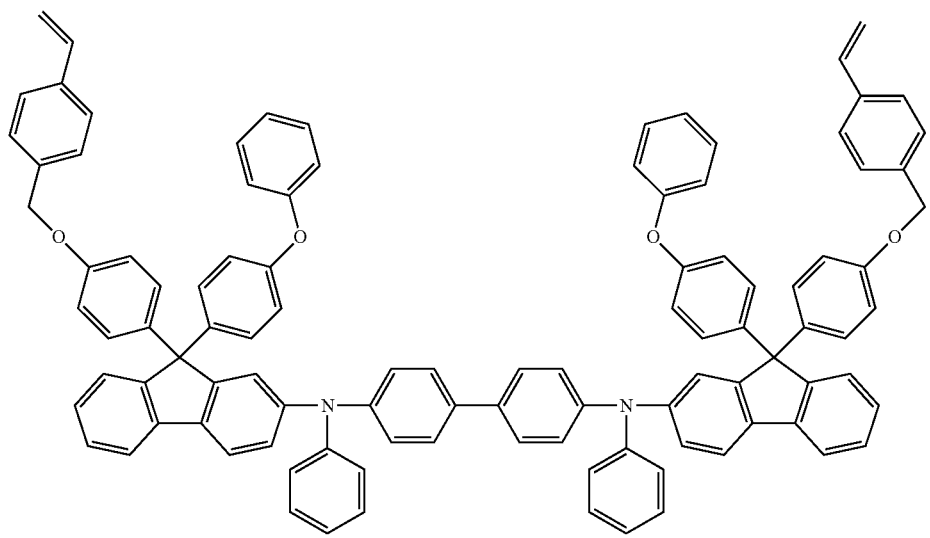
Compound 13
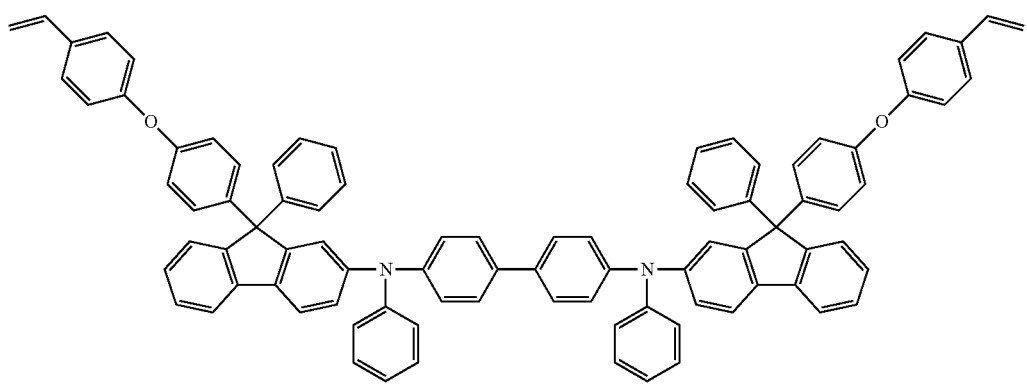

-continued
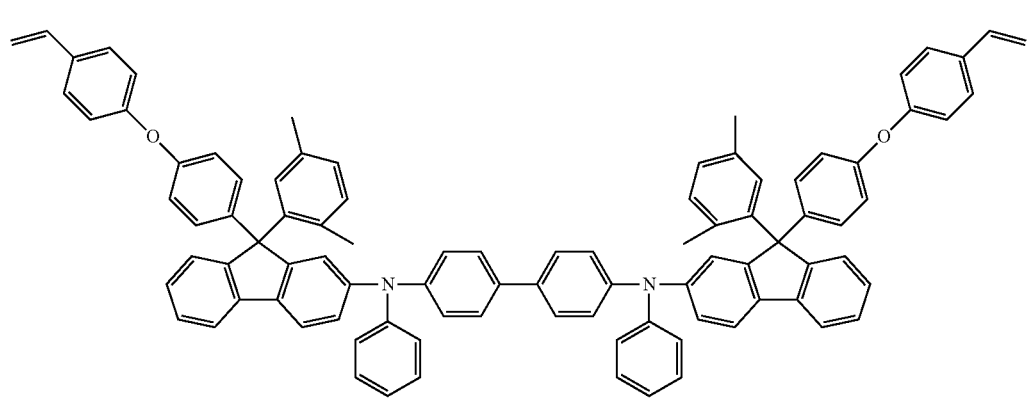
Compound 14
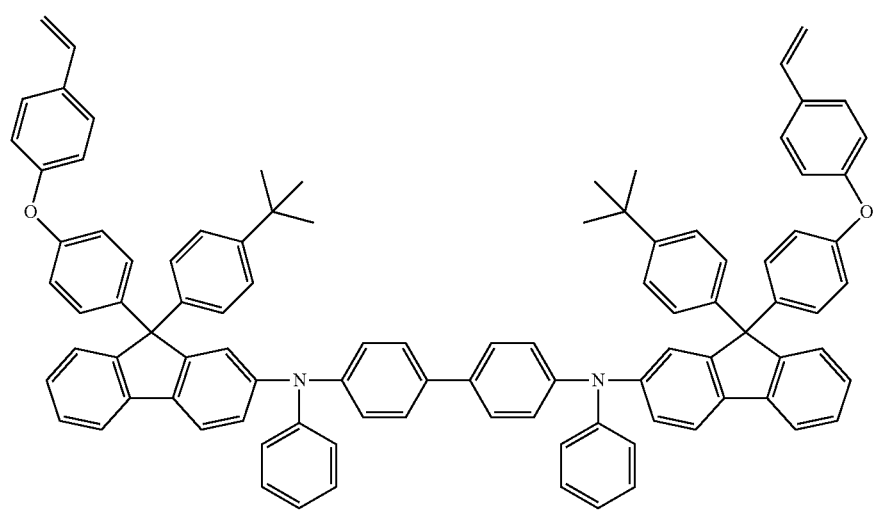
Compound 15
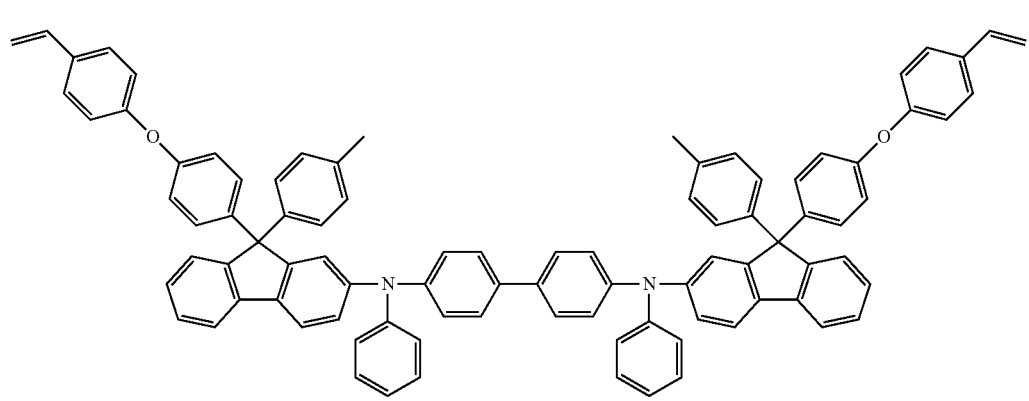
Compound 16

Compound 17
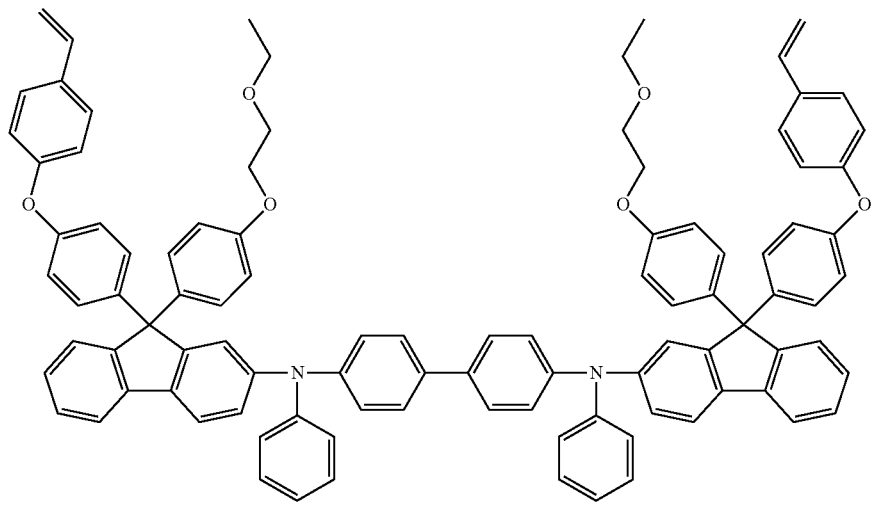
Compound 18
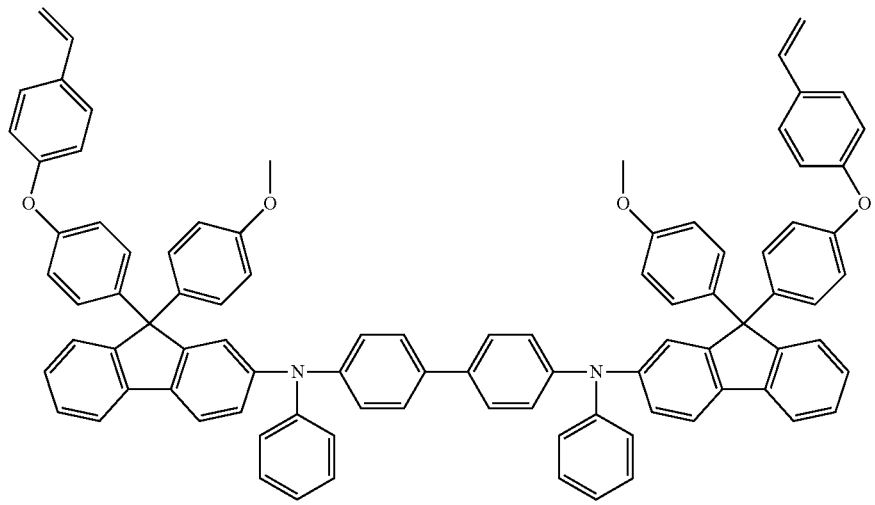
Compound 19
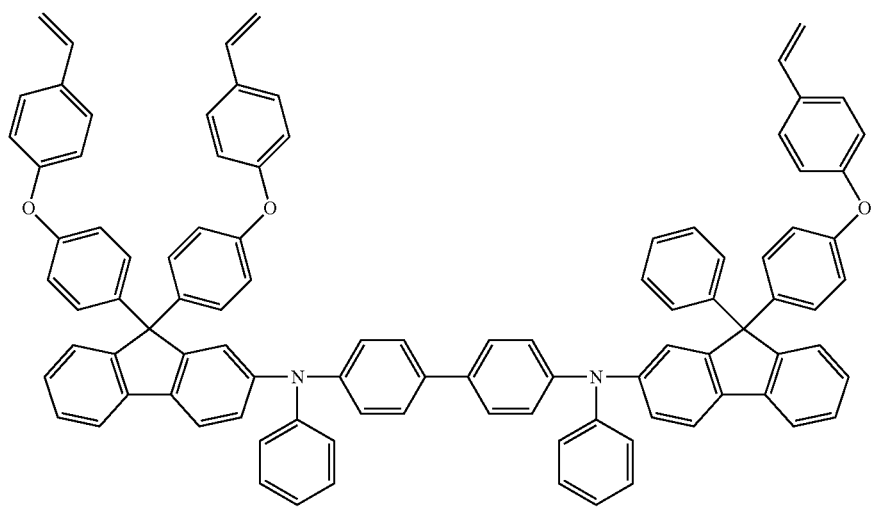

Compound 20
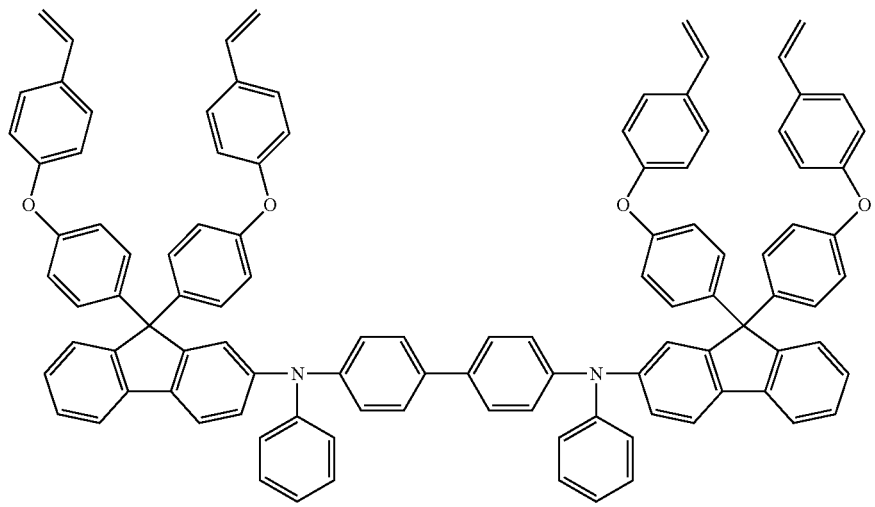
Compound 21
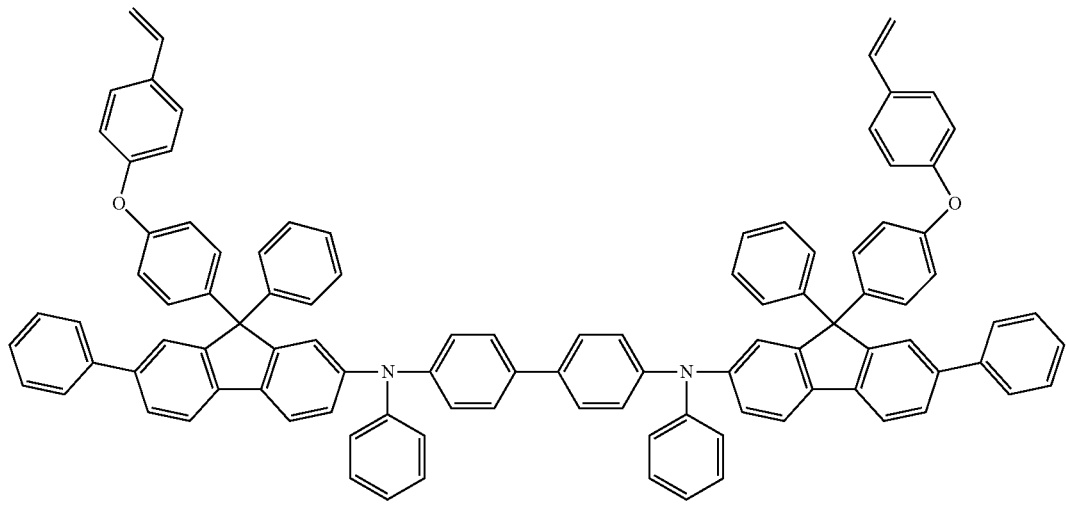
Compound 22
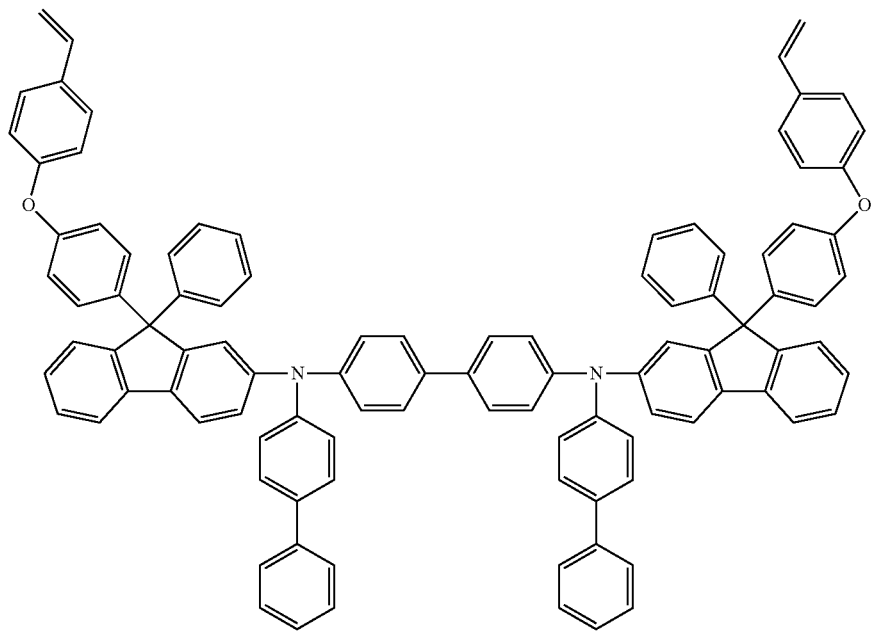

Compound 23
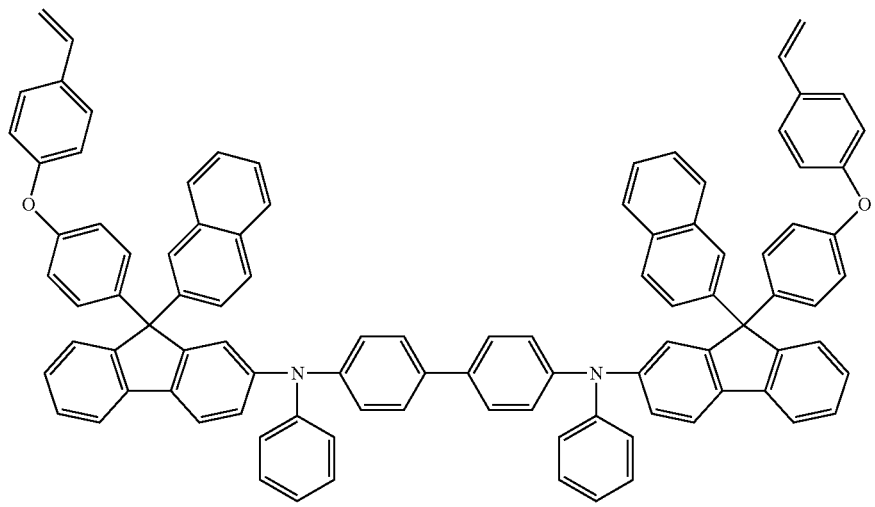
Compound 24
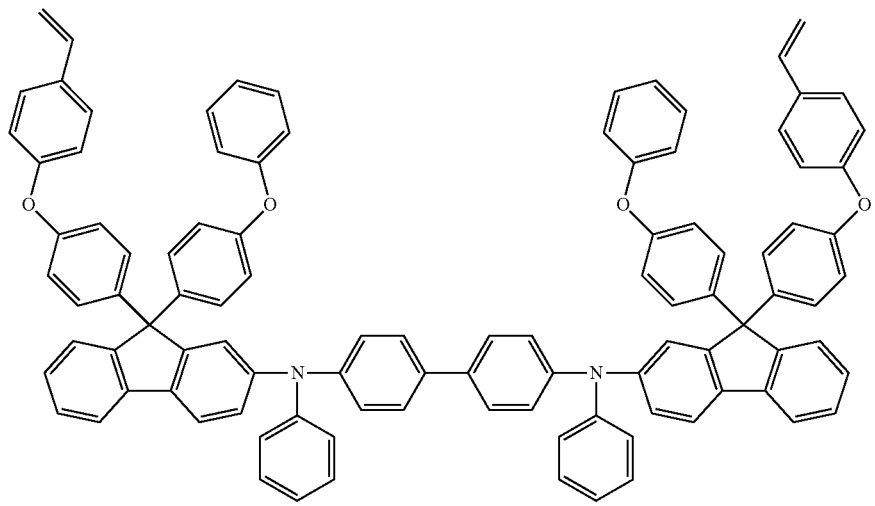
Compound 25
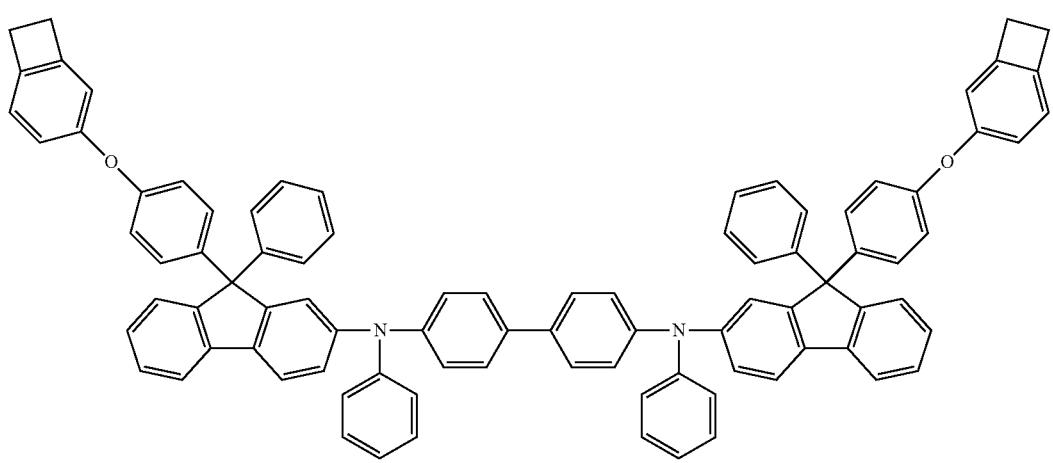

-continued
Compound 26
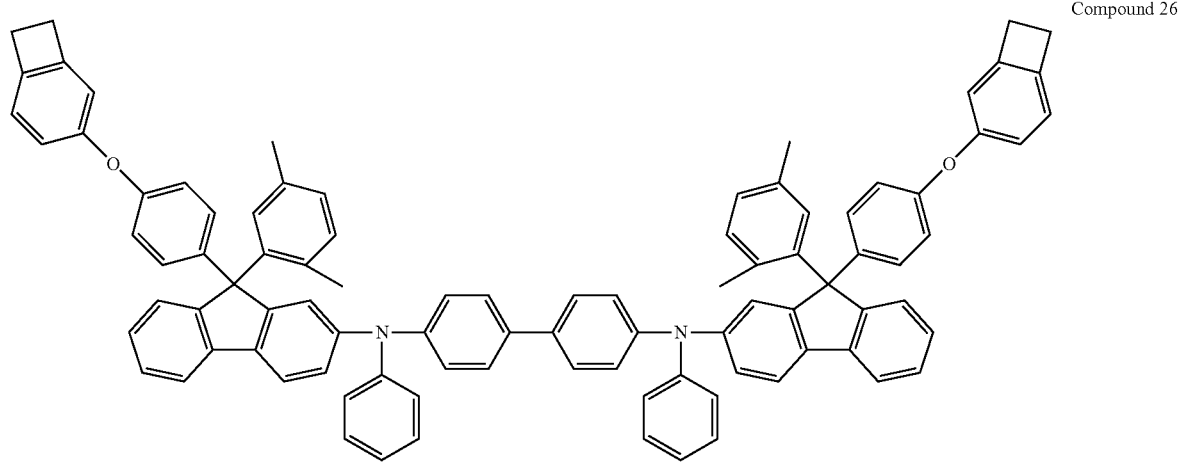
Compound 27
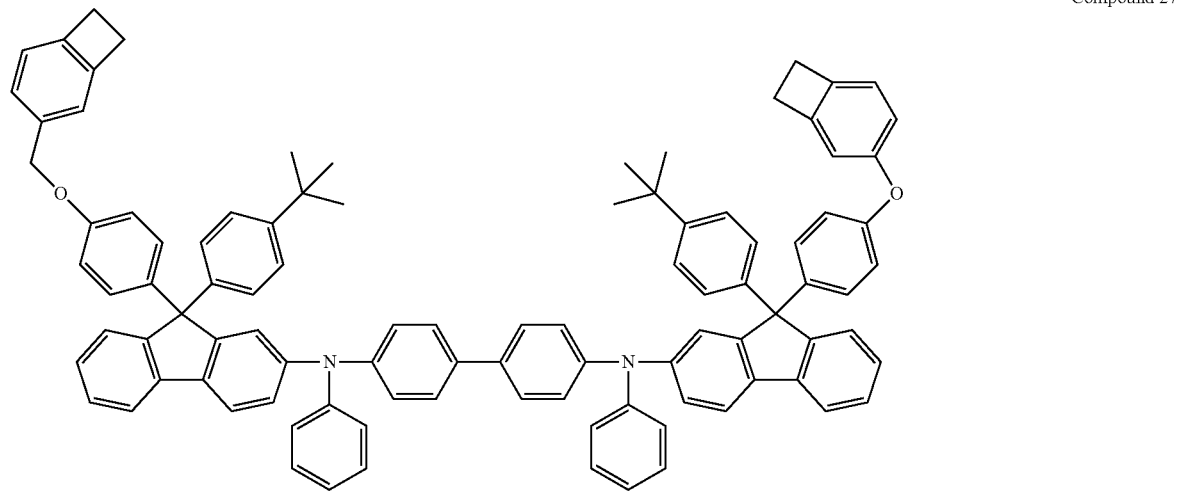
Compound 28
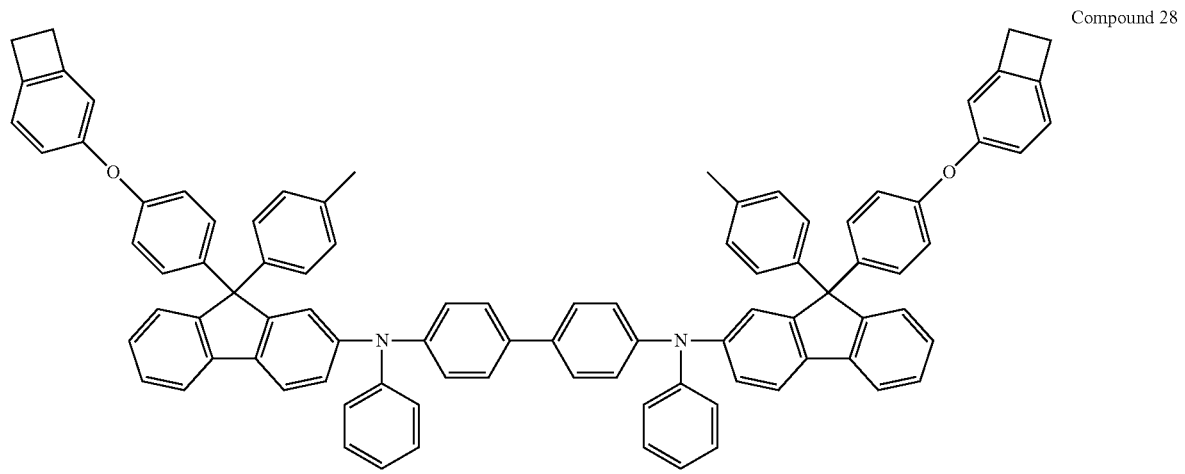

Compound 29
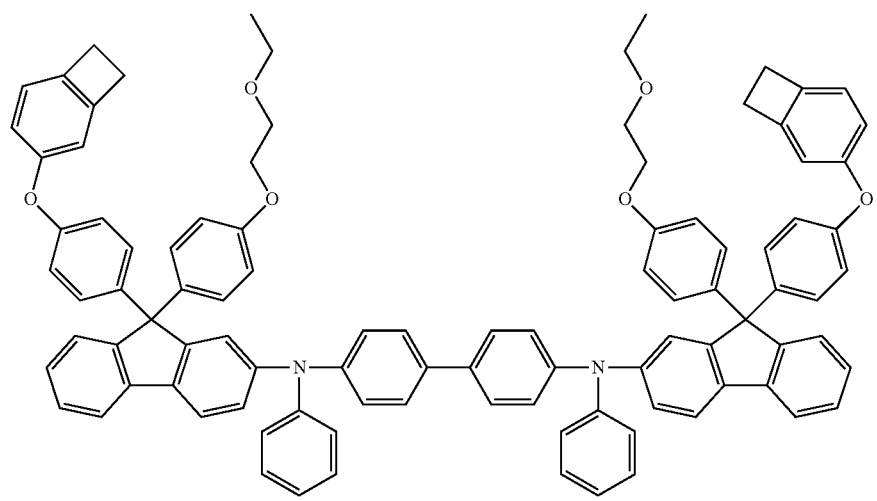
Compound 30
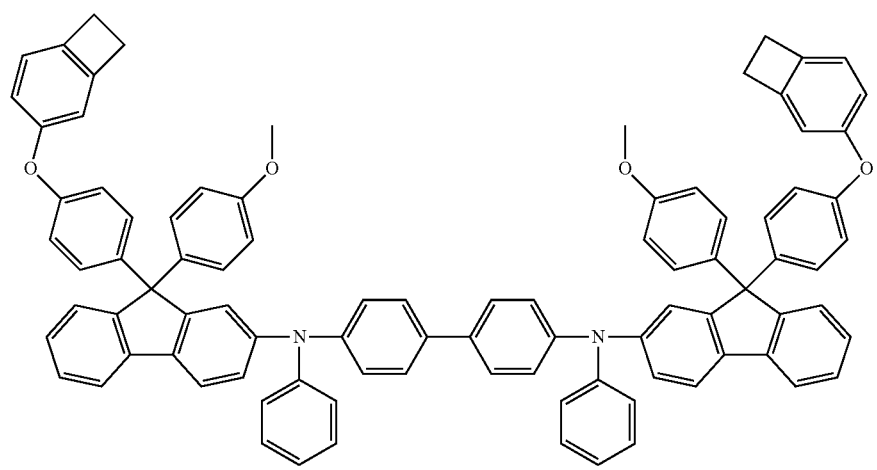
Compound 31
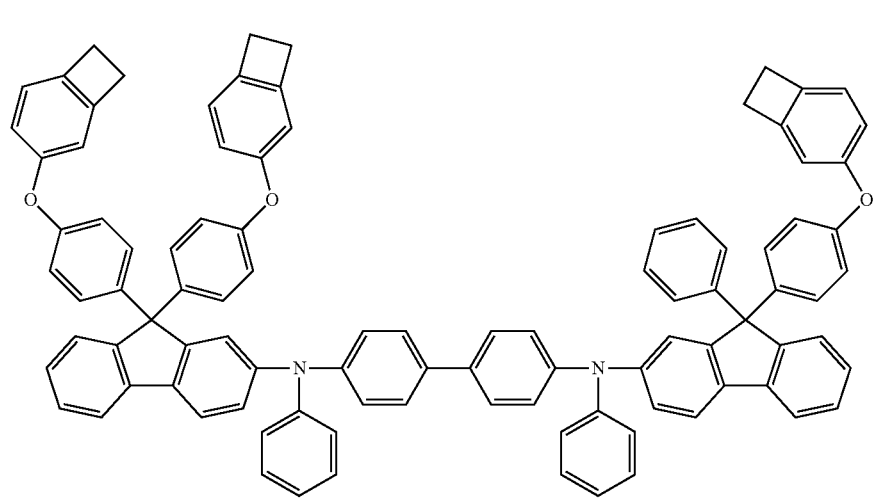

-continued
Compound 32
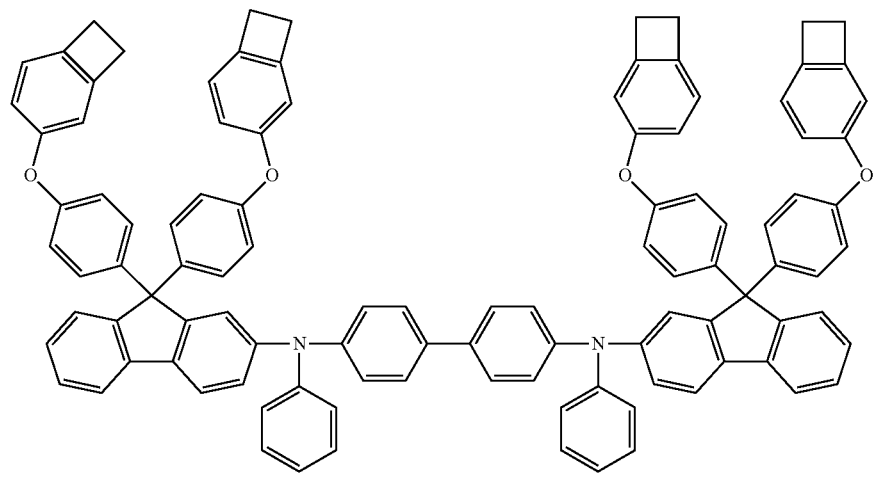
Compound 33
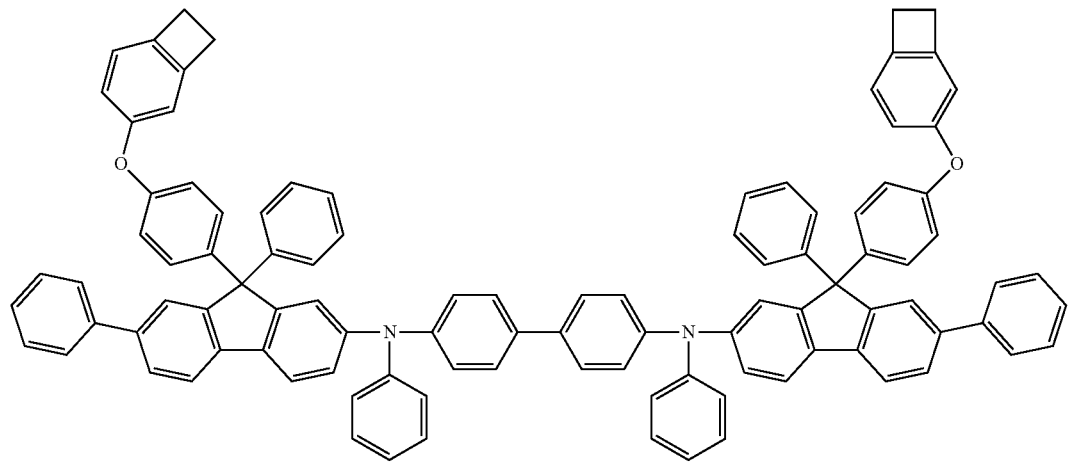
Compound 34
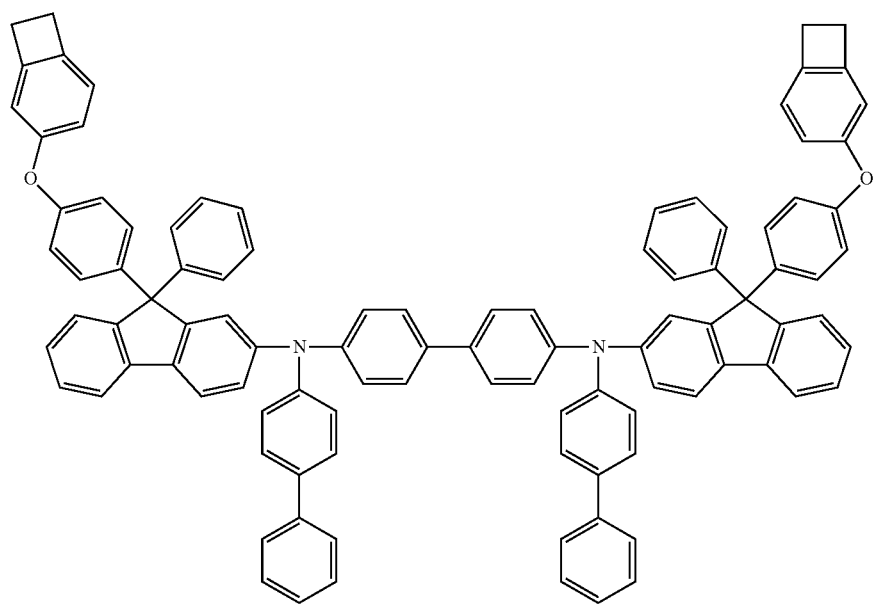

Compound 35
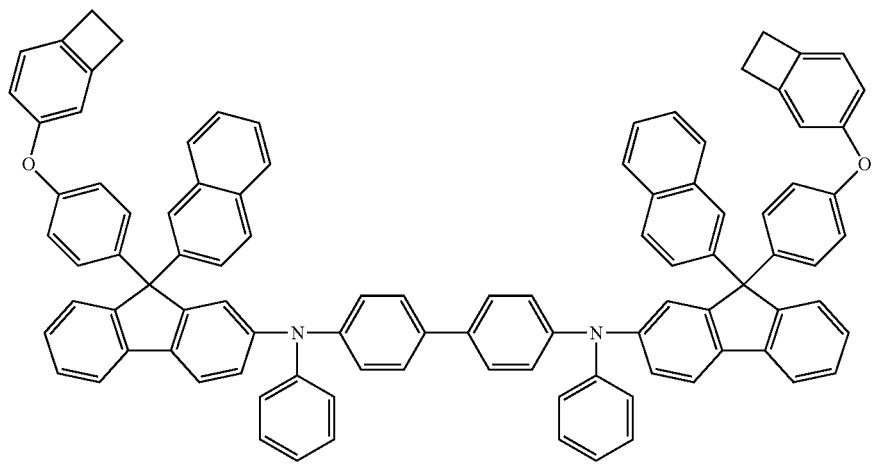
Compound 36
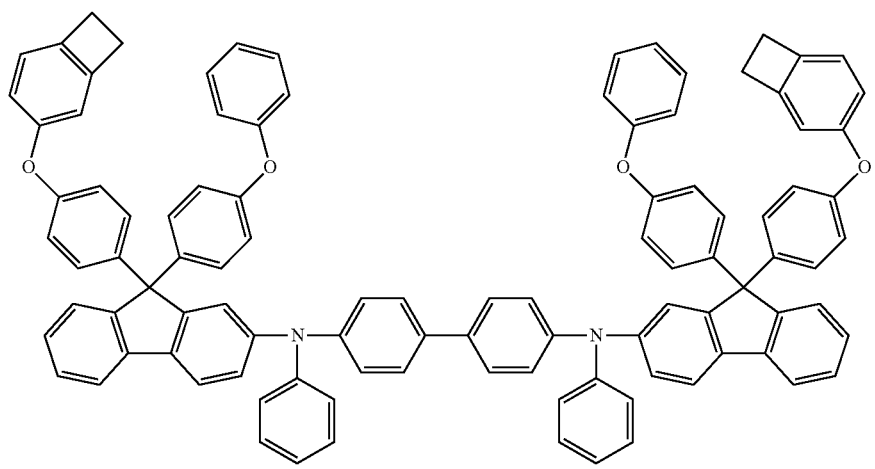
Compound 37
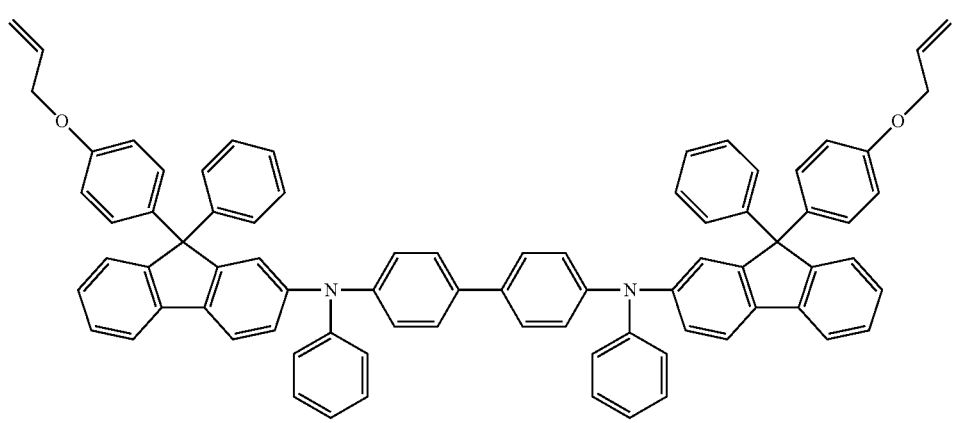

Compound 38
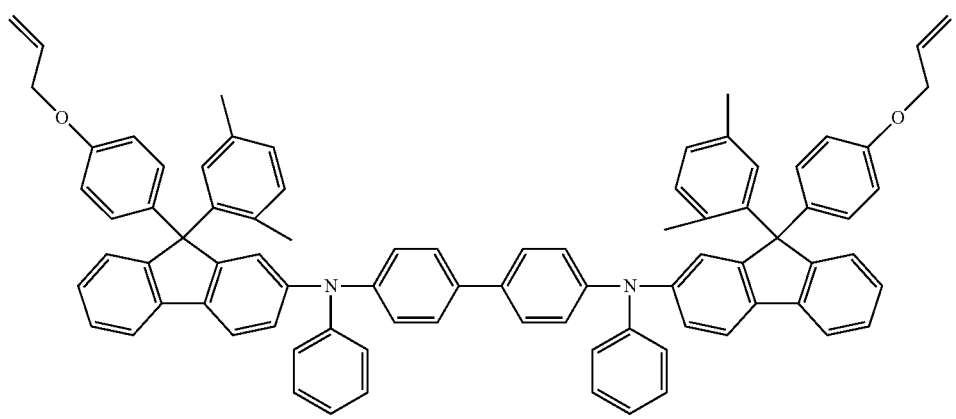
Compound 39
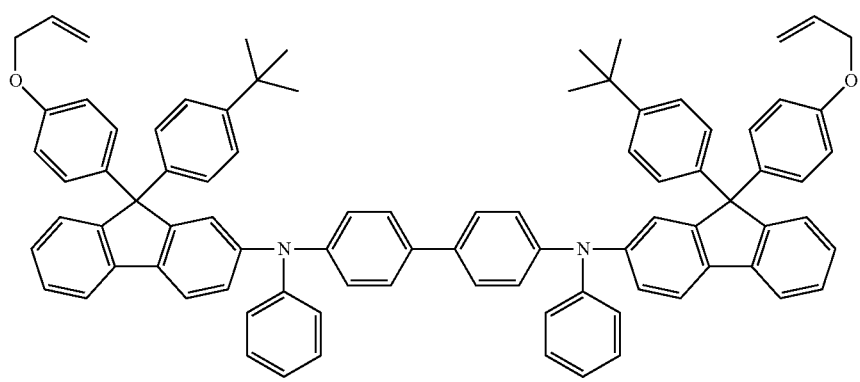
Compound 40
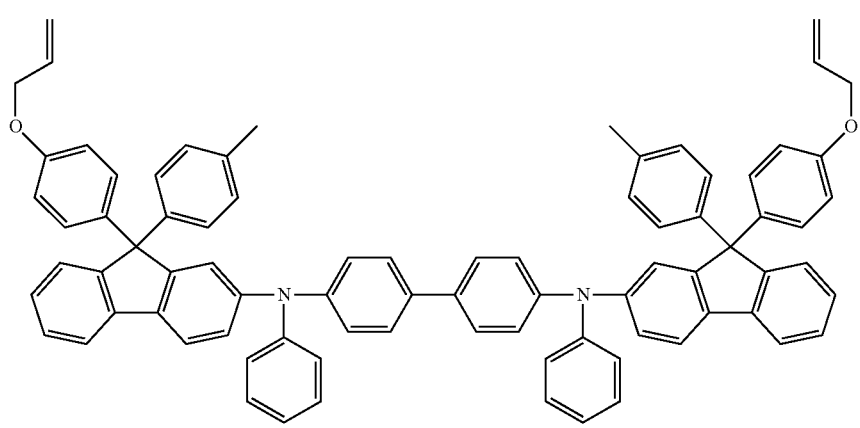

Compound 41
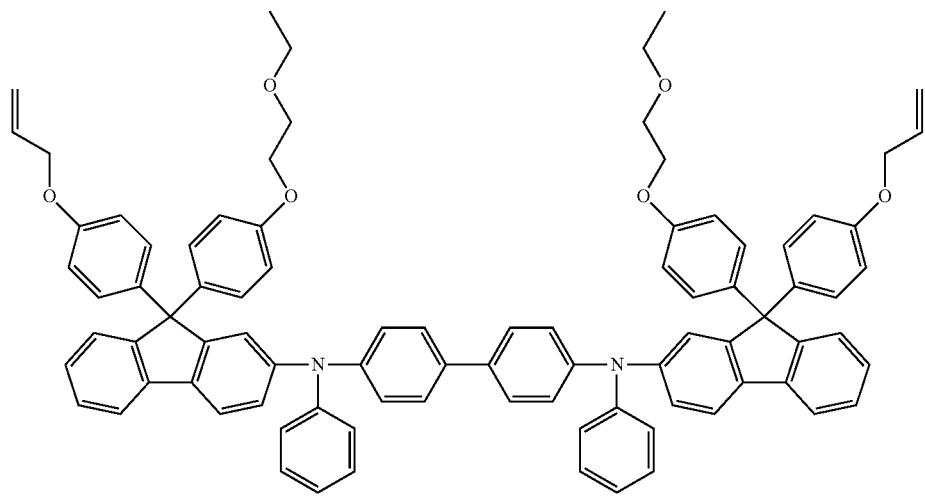
Compound 42
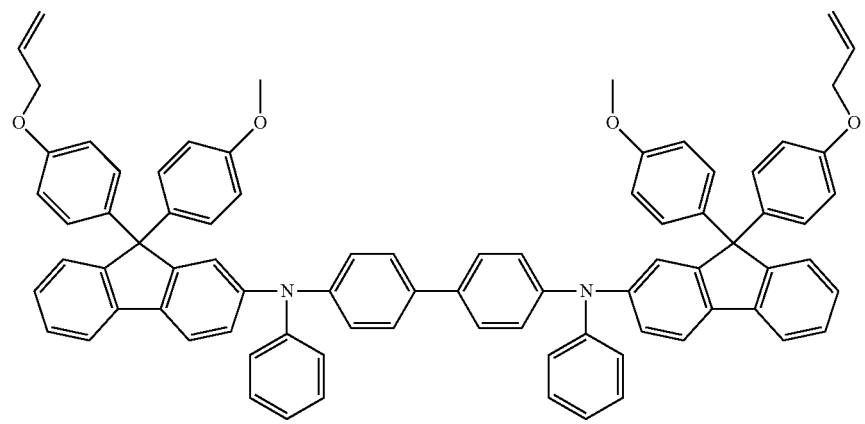
Compound 43
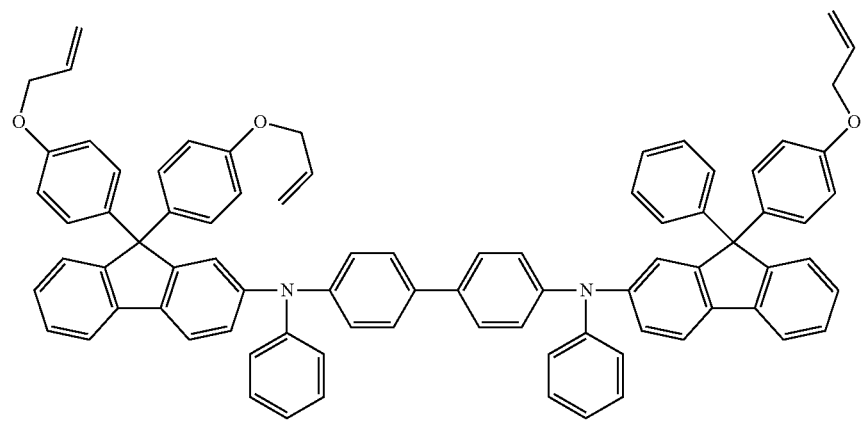

-continued
Compound 44
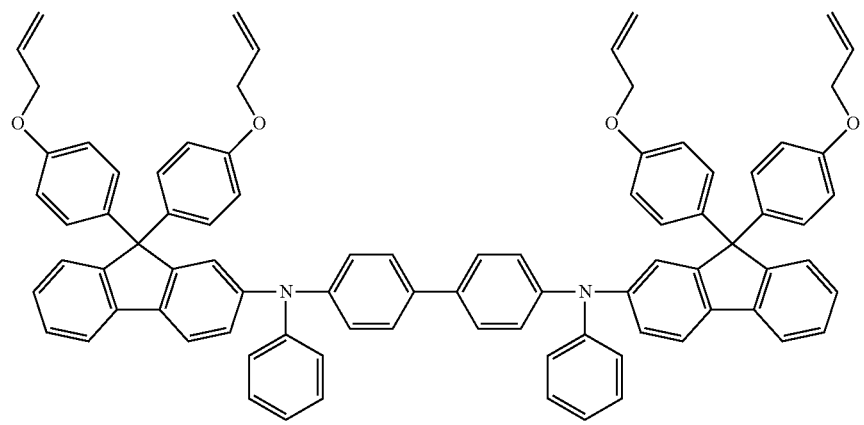
Compound 45
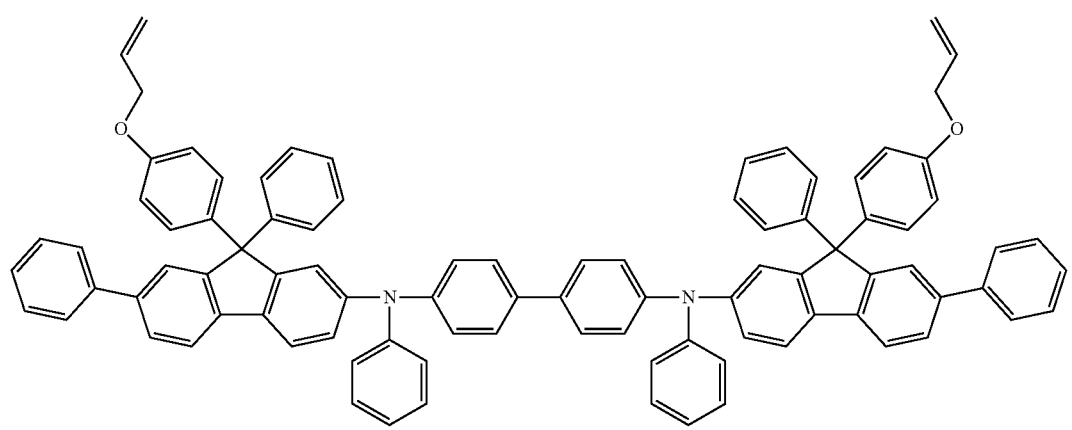
Compound 46
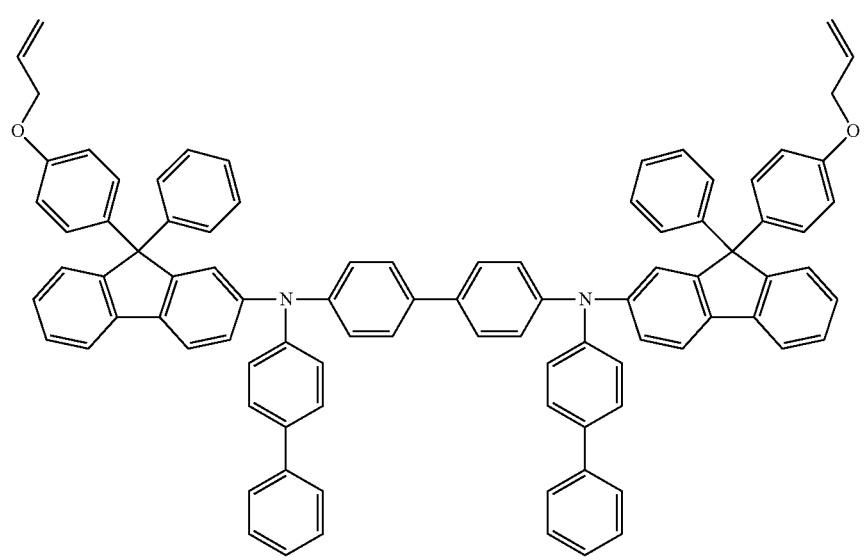

Compound 47
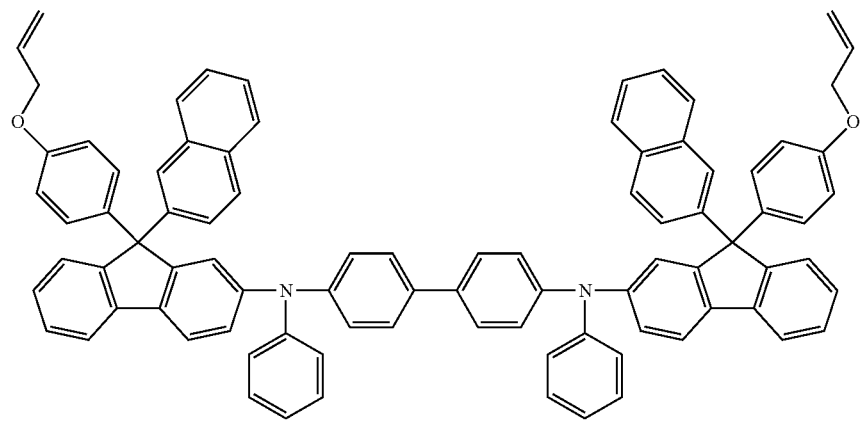
Compound 48
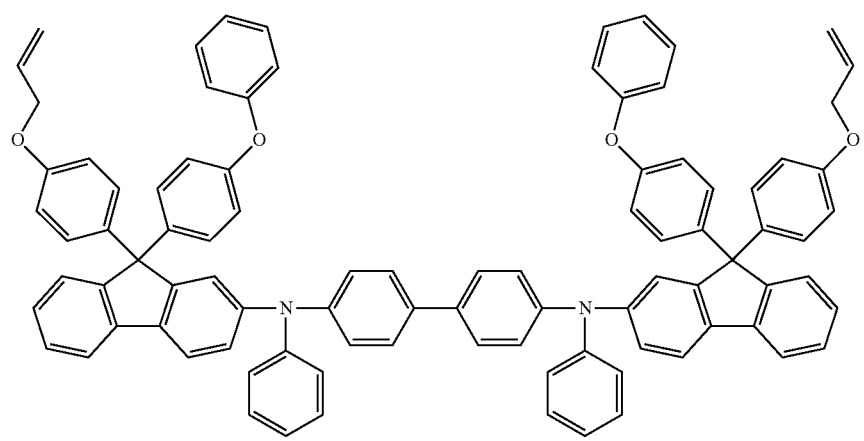
Compound 49
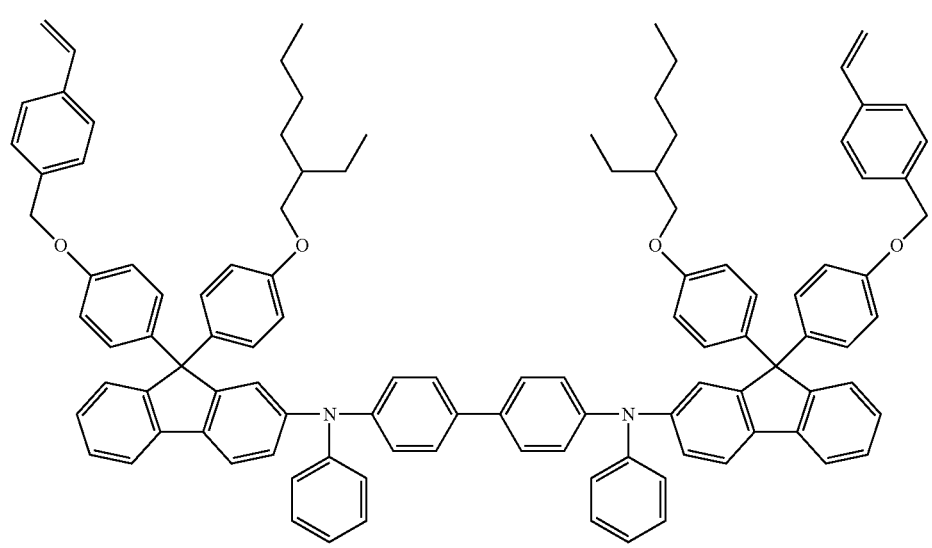

Compound 50
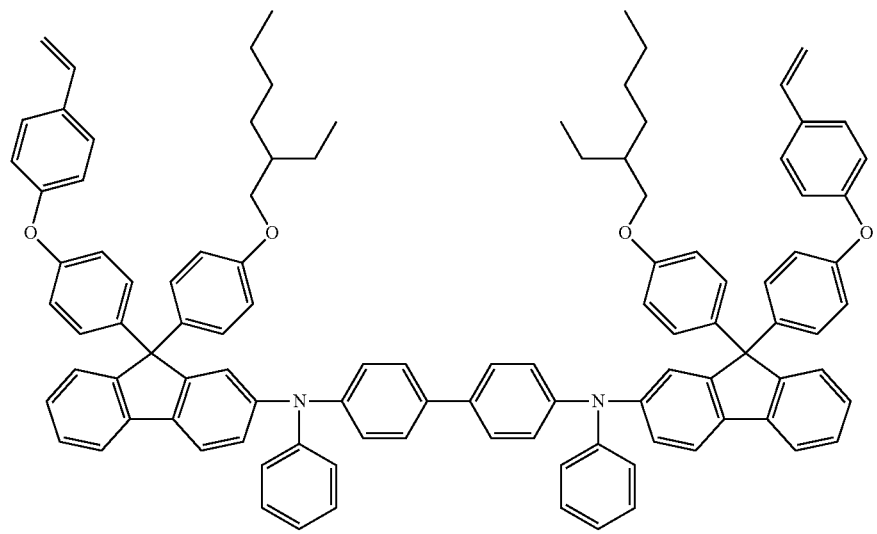
Compound 51
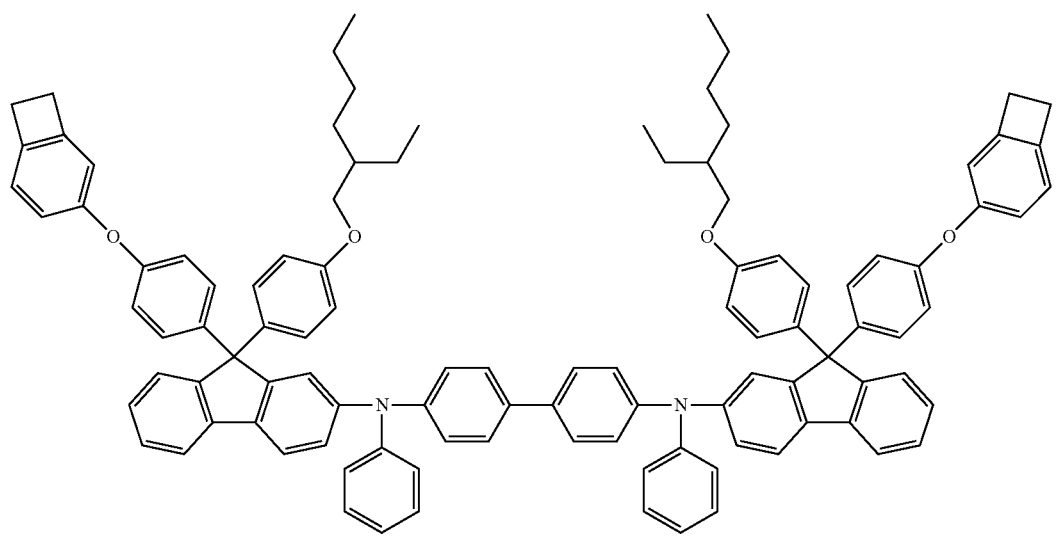
Compound 52
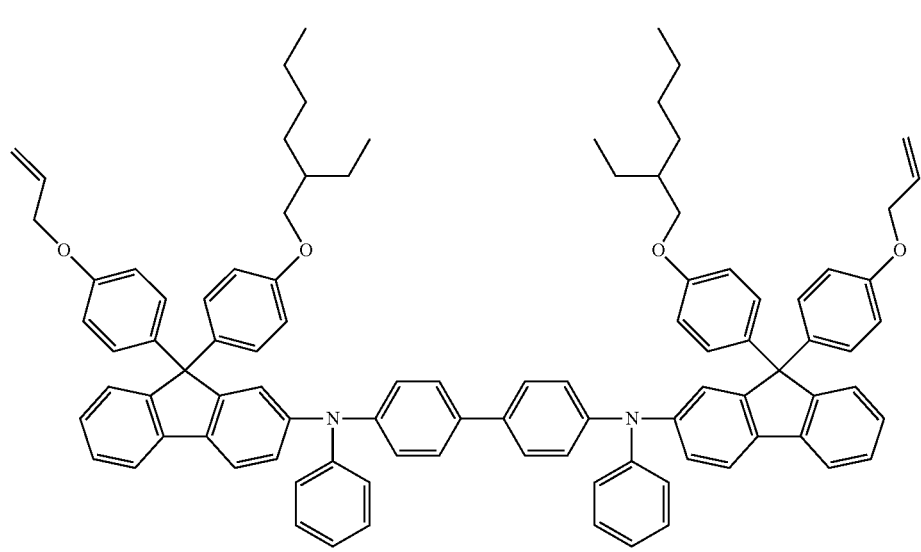

-continued
Compound 53
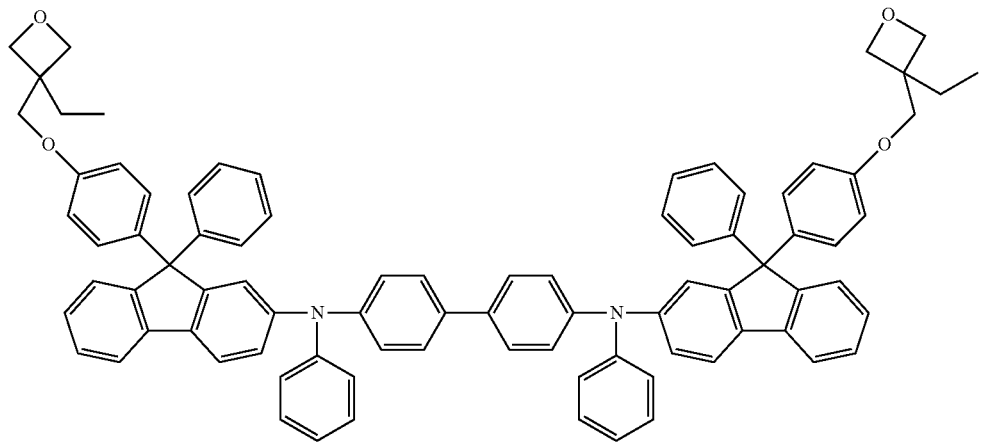
Compound 54
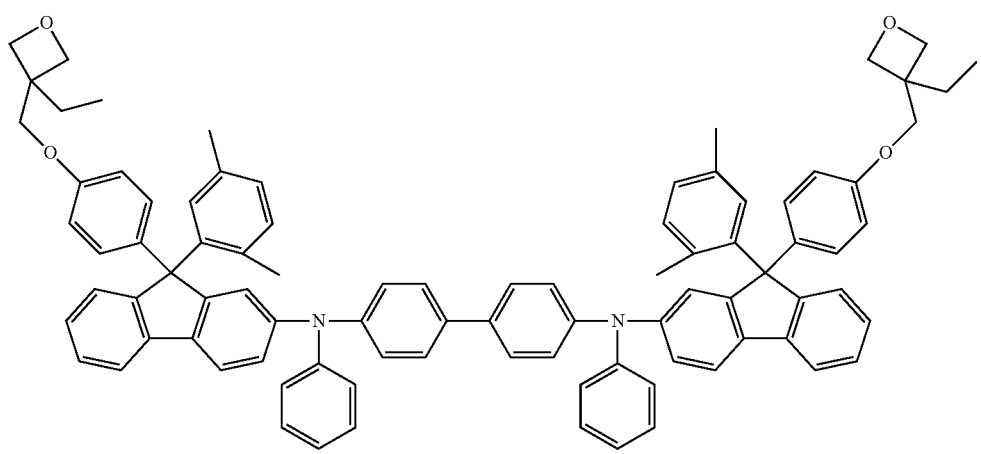
Compound 55
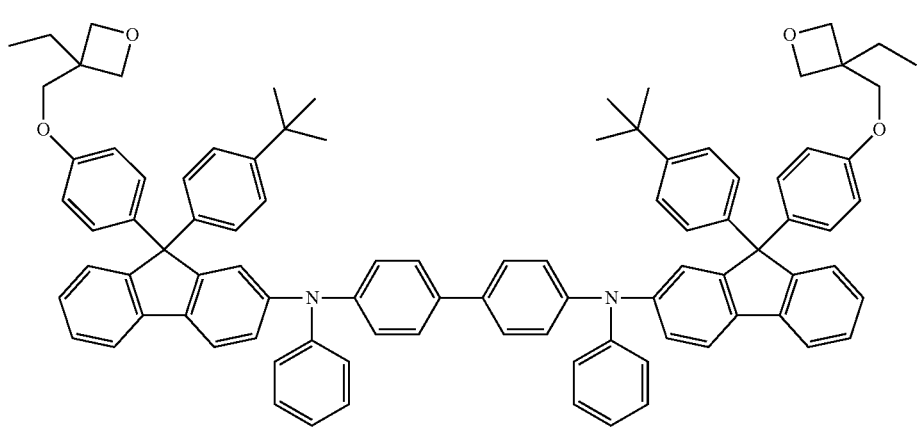

-continued
Compound 56
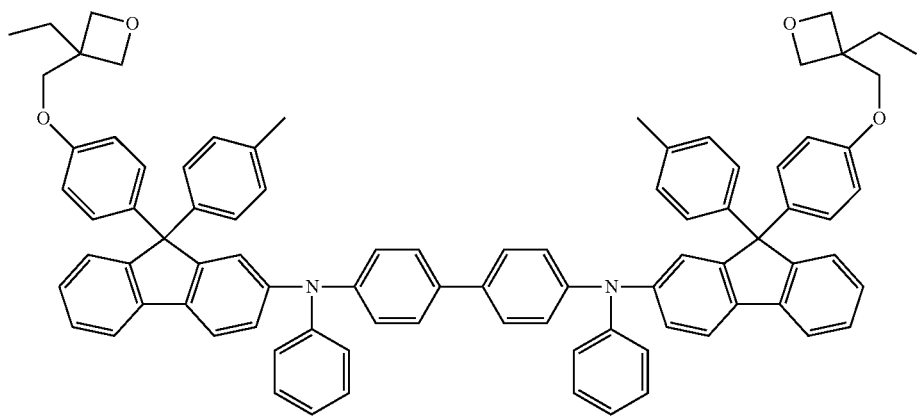
Compound 57
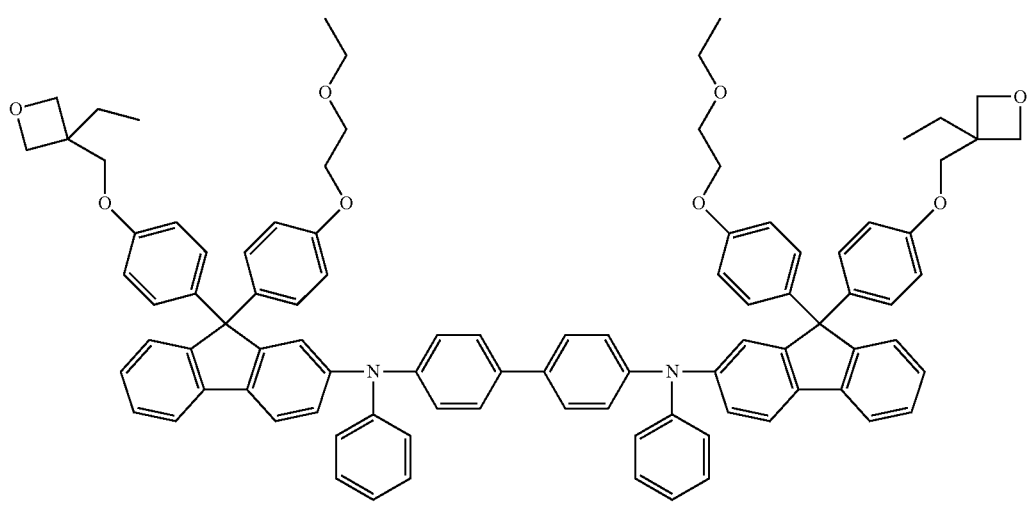
Compound 58
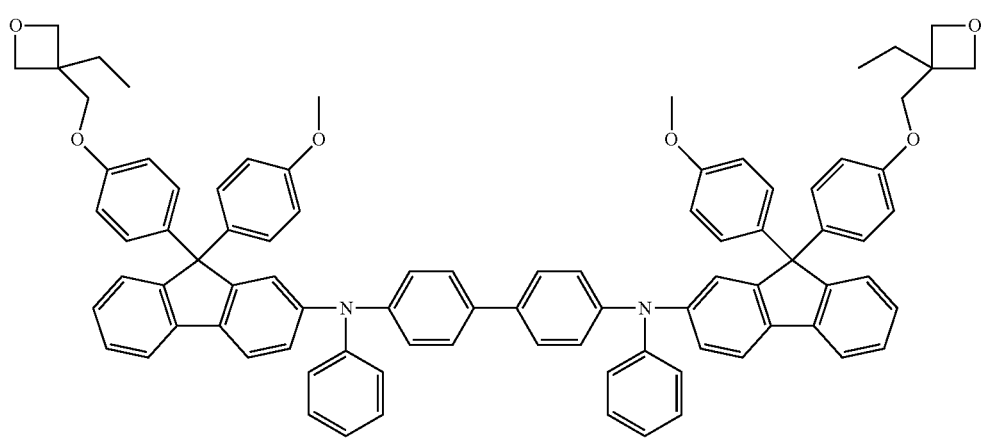

Compound 59
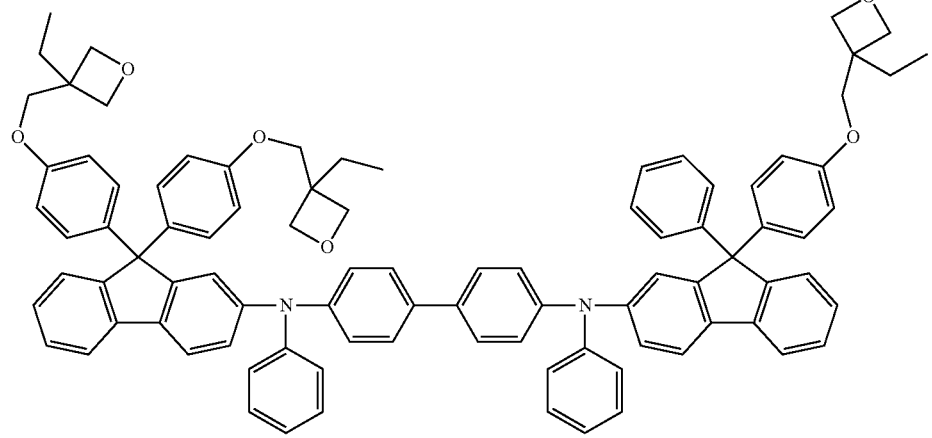
Compound 60
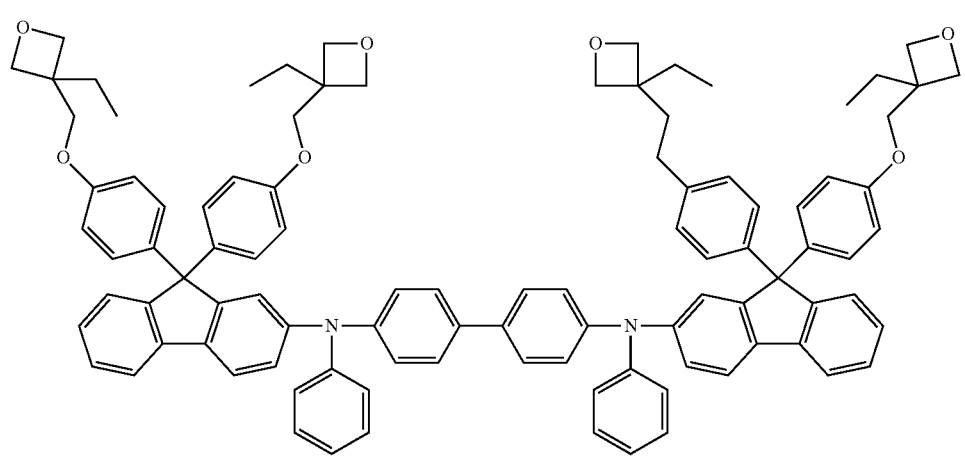
Compound 61
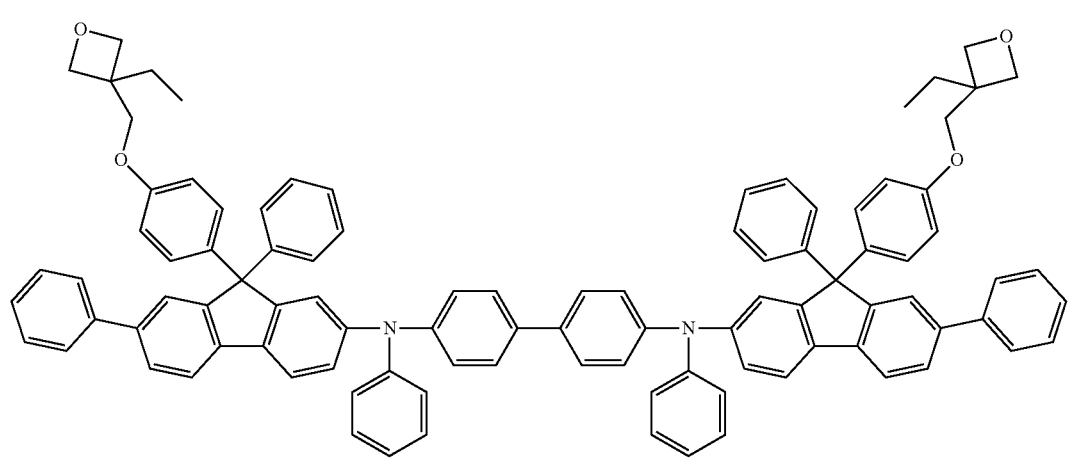

Compound 62
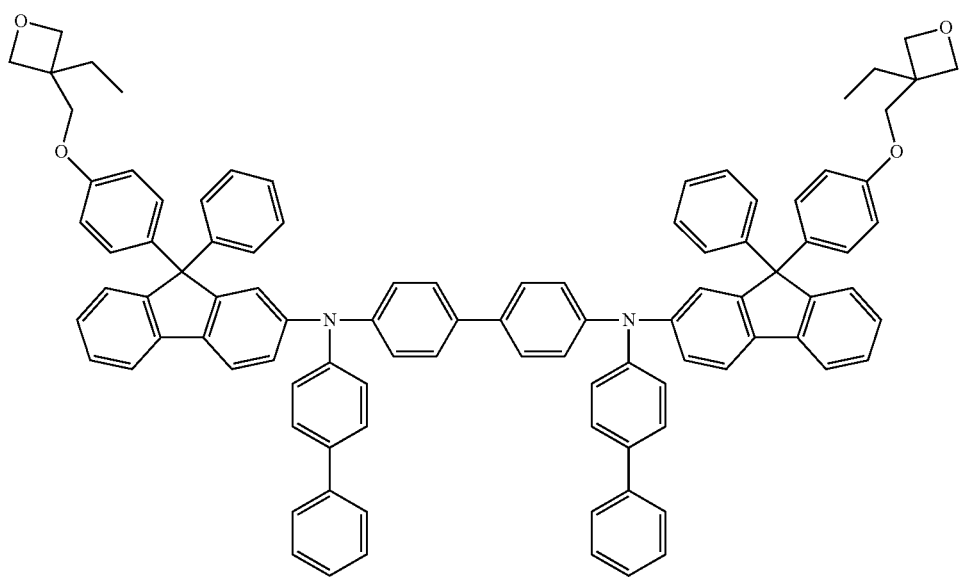
Compound 63
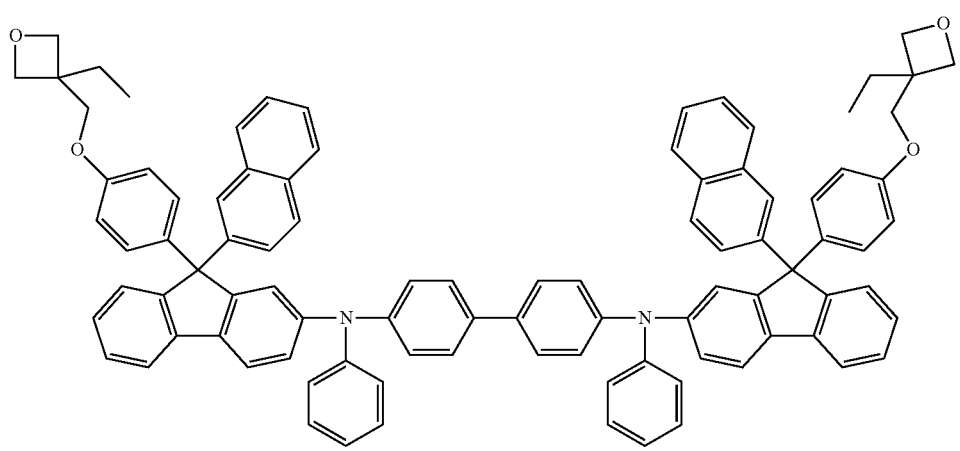
Compound 64
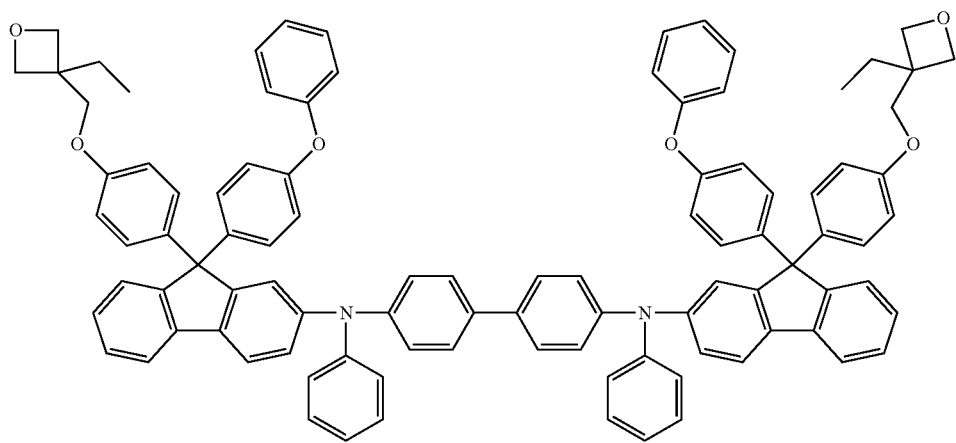

-continued
Compound 65
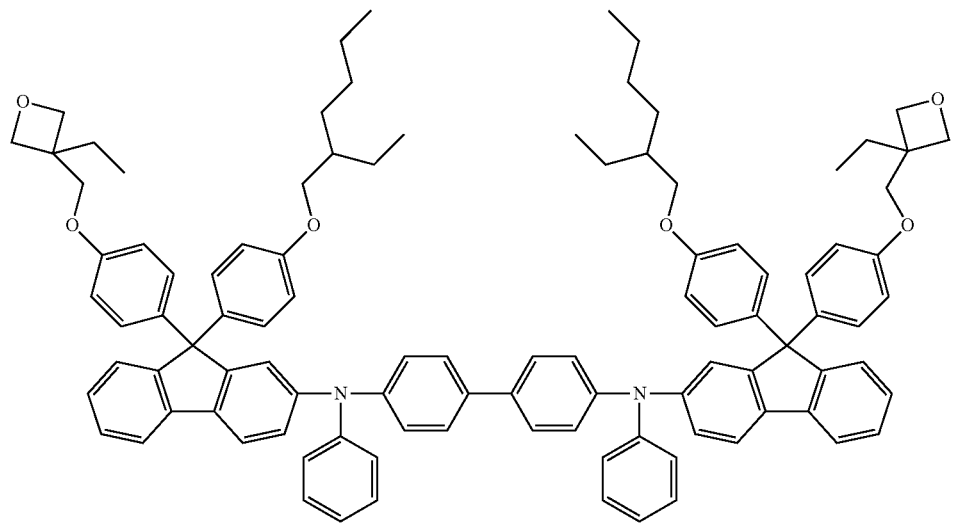
Compound 66
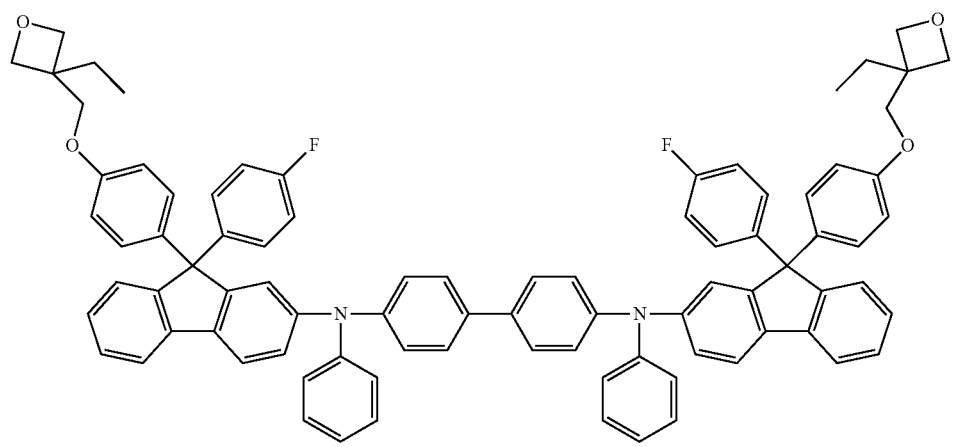
Compound 67
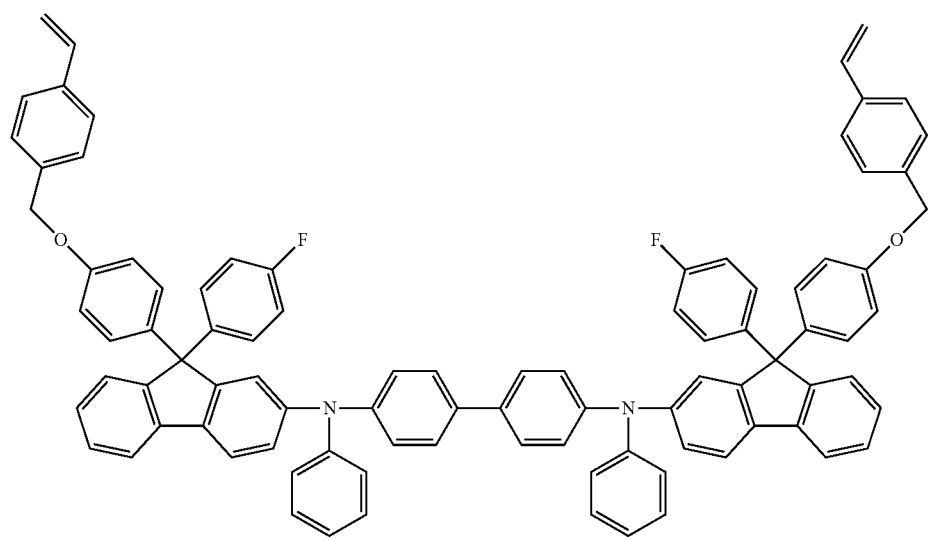

Compound 68
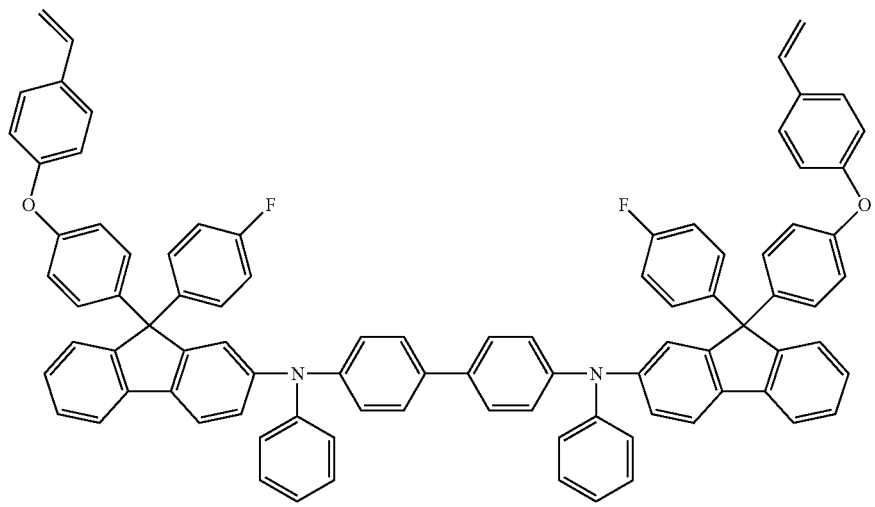
Compound 69
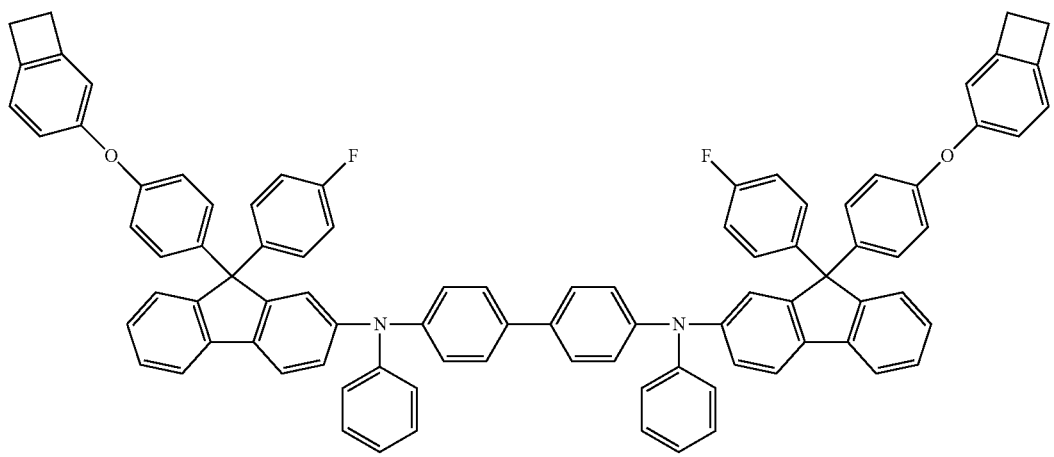
Compound 70
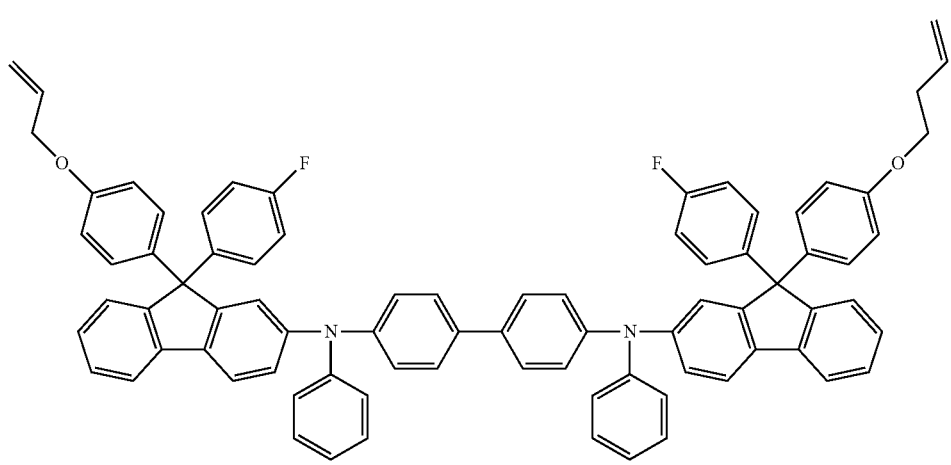

Compound 71
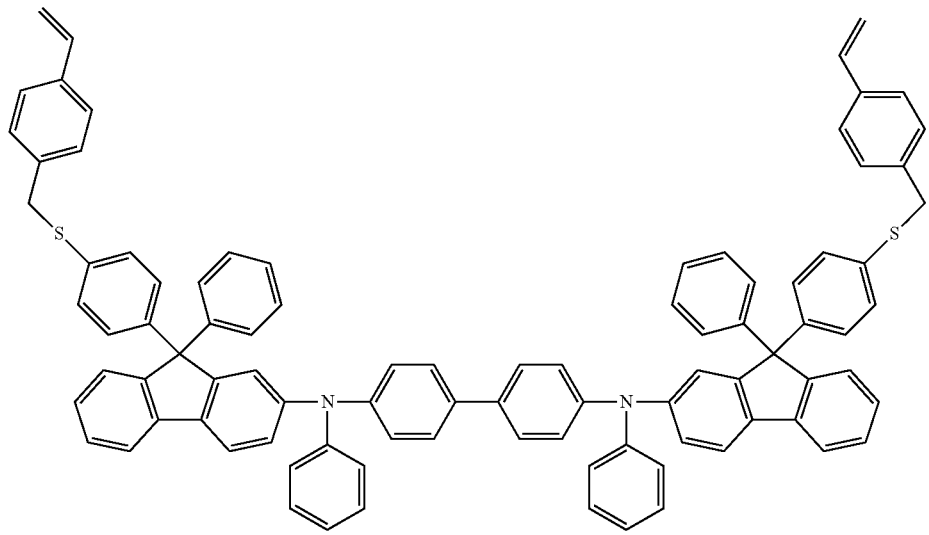
Compound 72
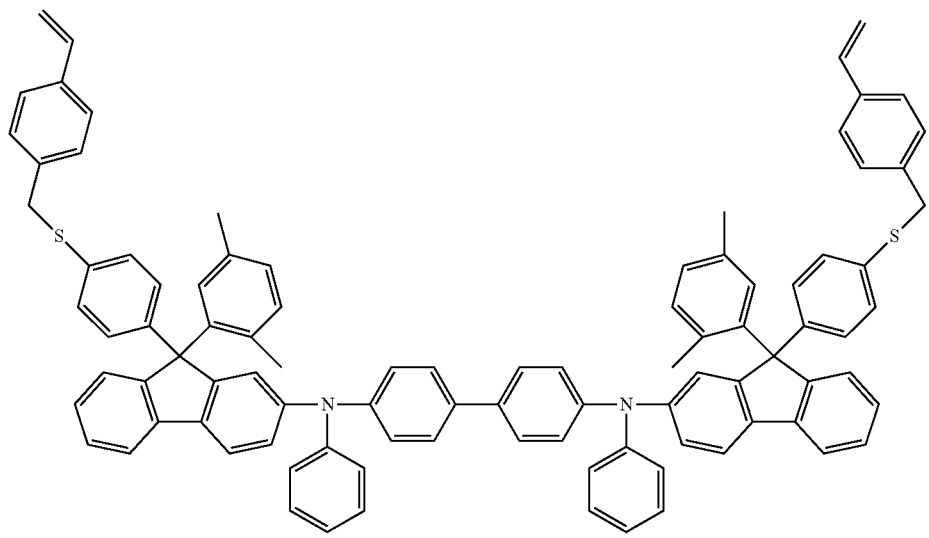
Compound 73
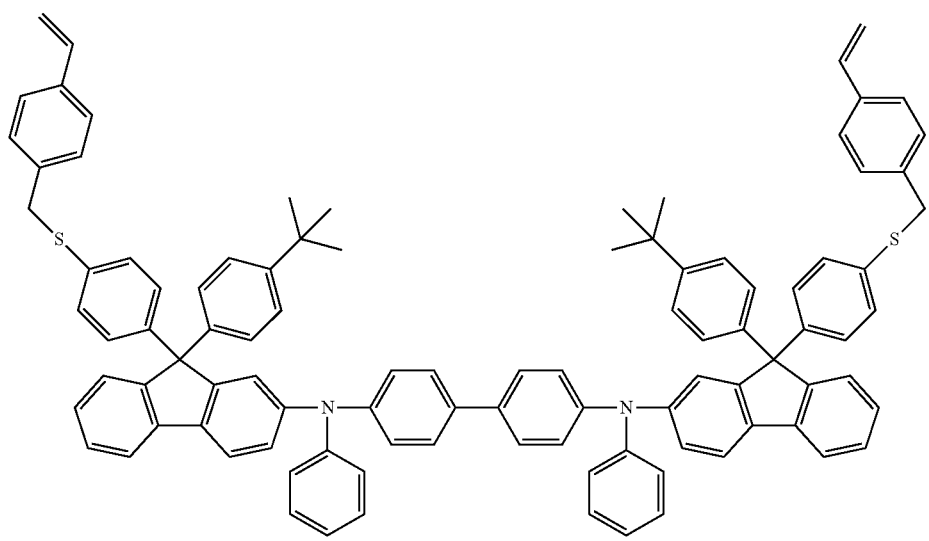

Compound 74
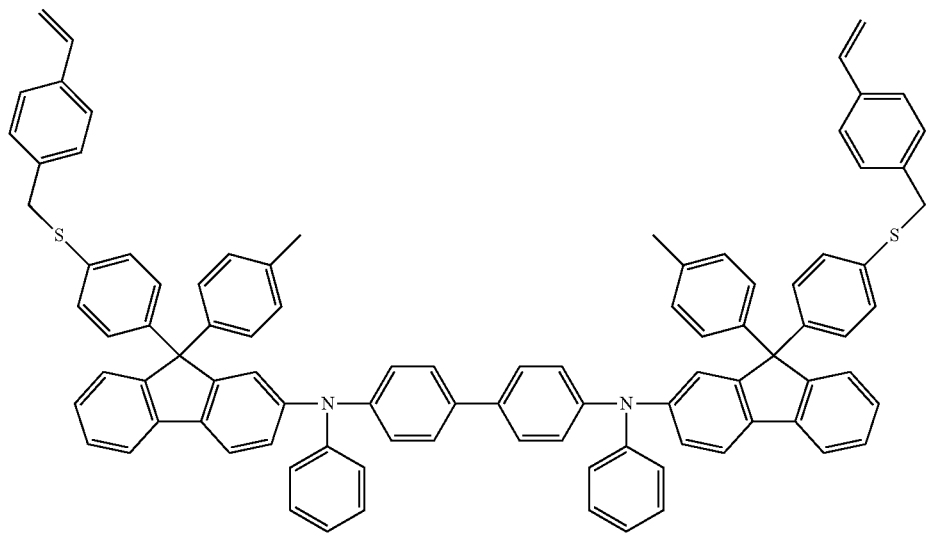
Compound 75
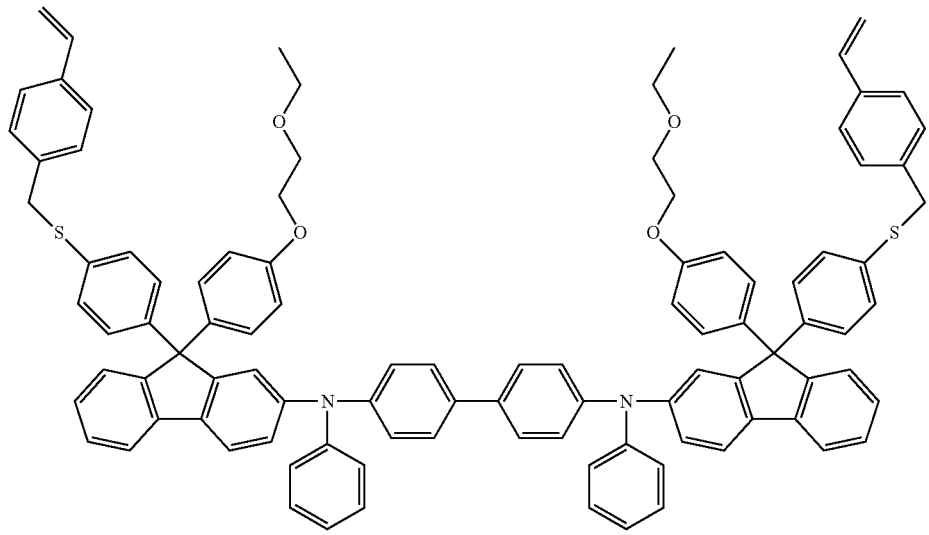
Compound 76
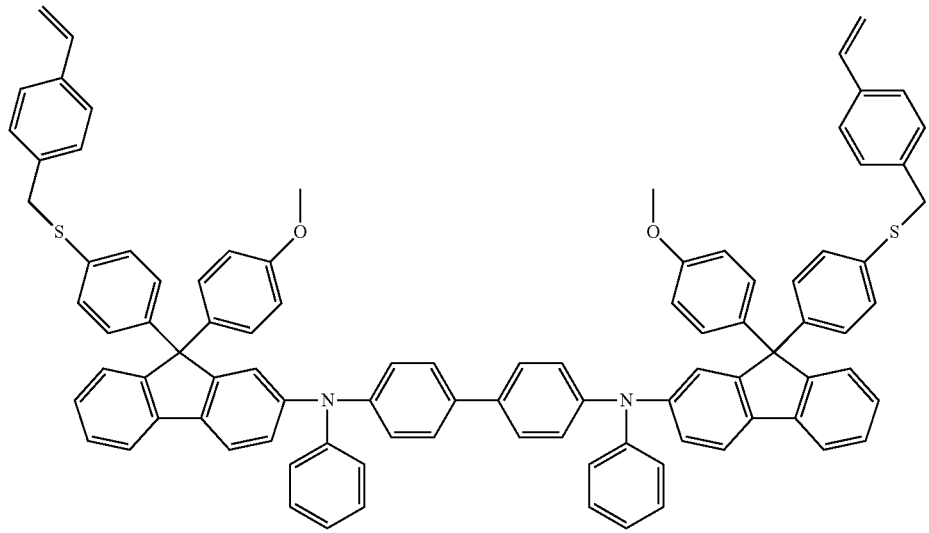

Compound 77
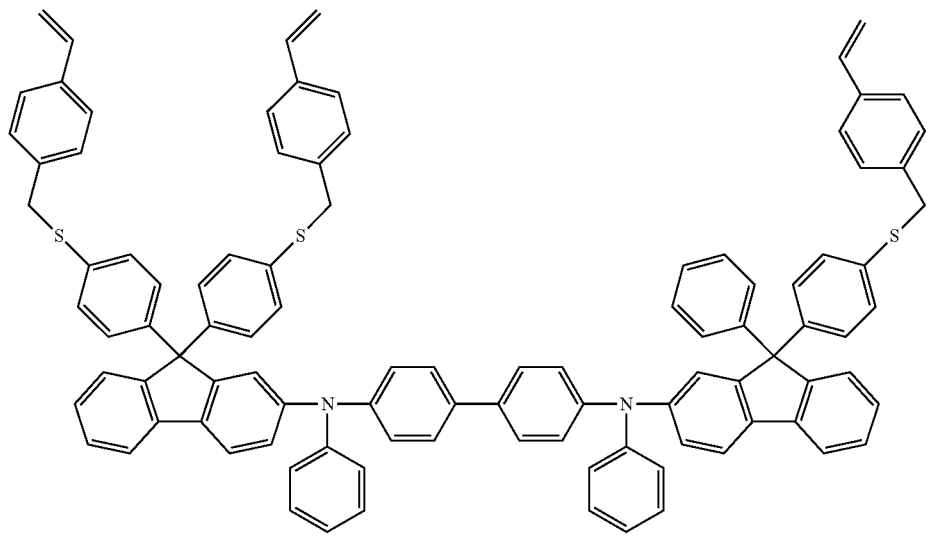
Compound 78
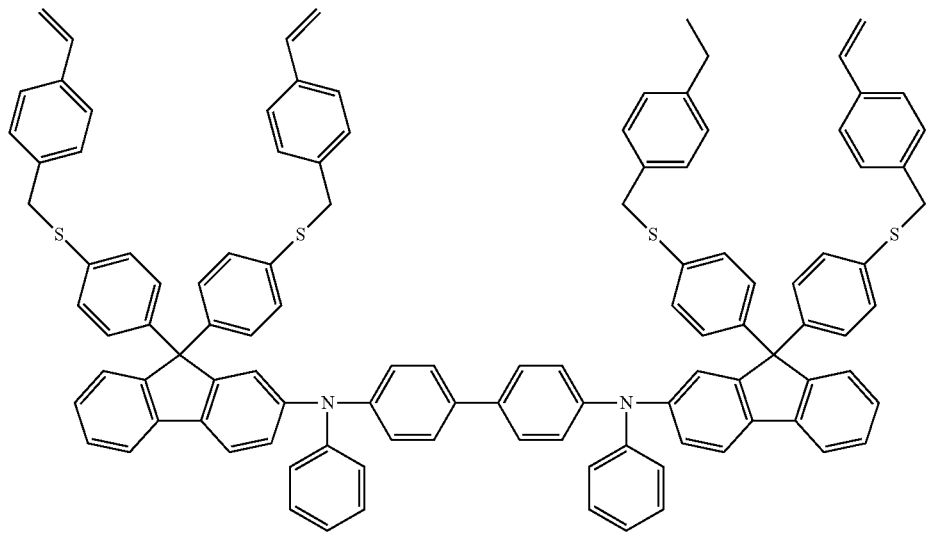
Compound 79
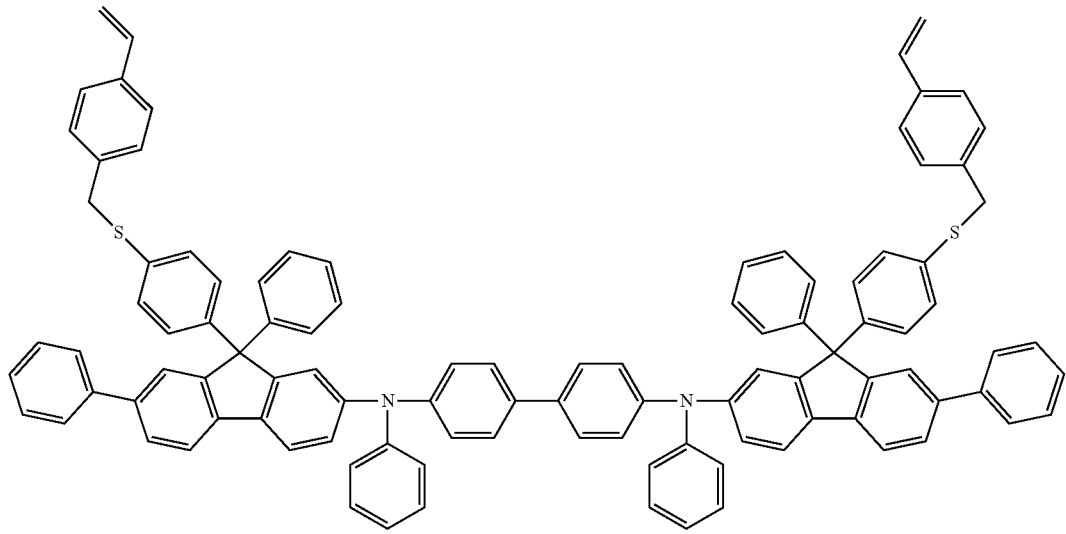

Compound 80
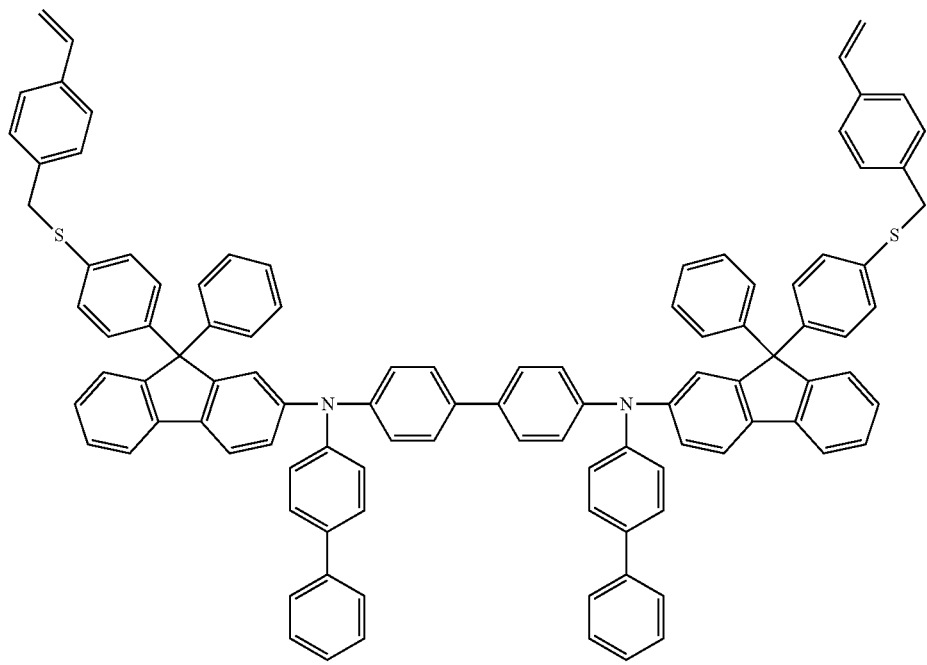
Compound 81
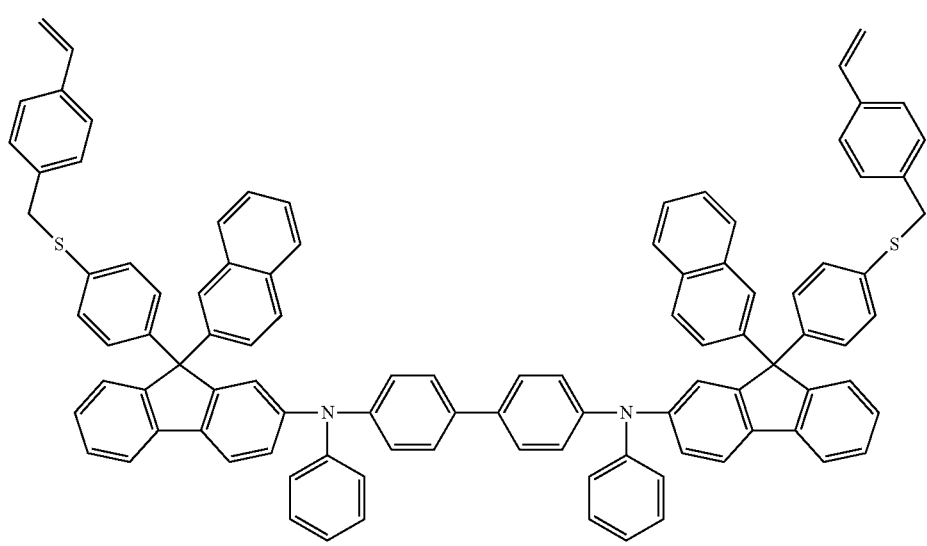

Compound 82
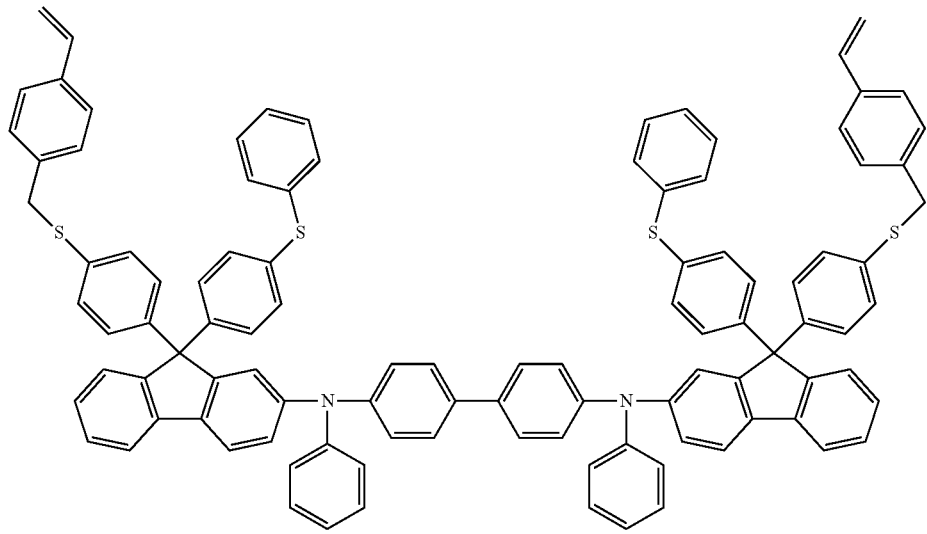
Compound 83
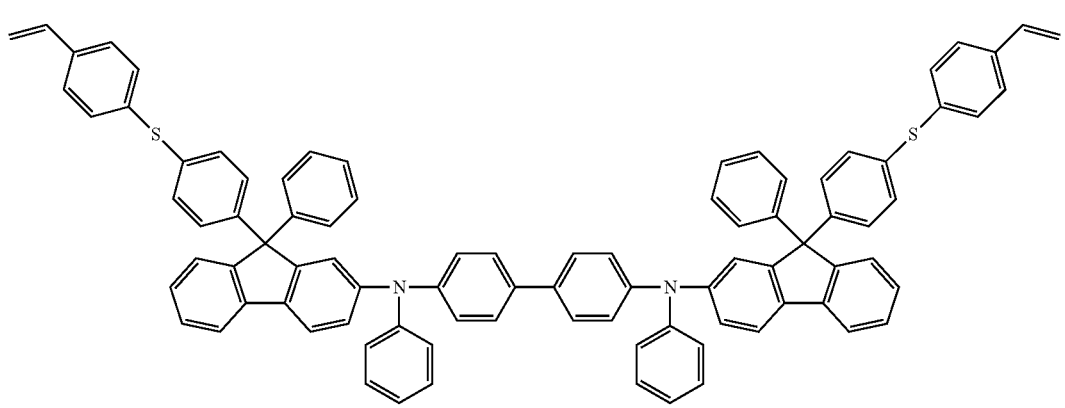
Compound 84
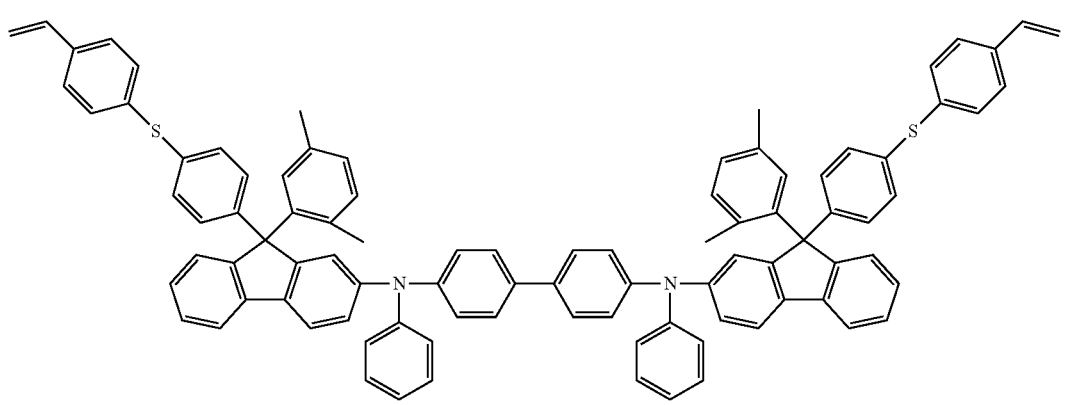

-continued
Compound 85
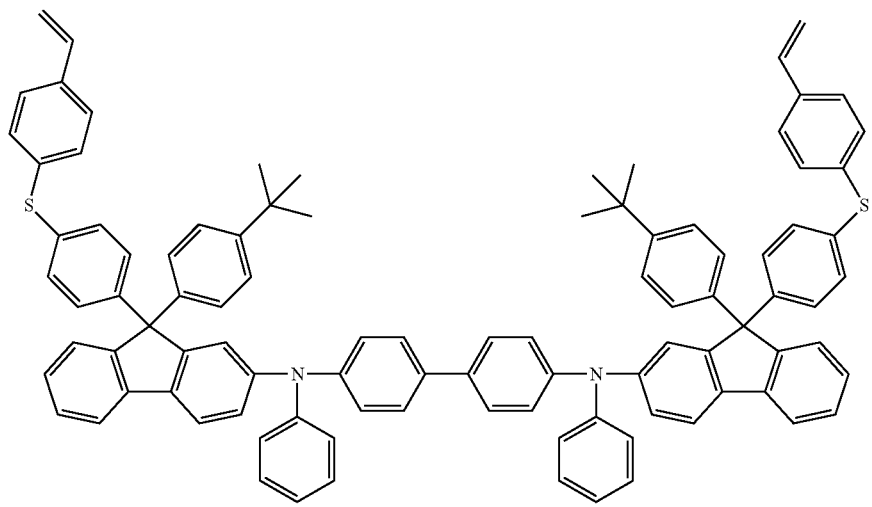
Compound 86
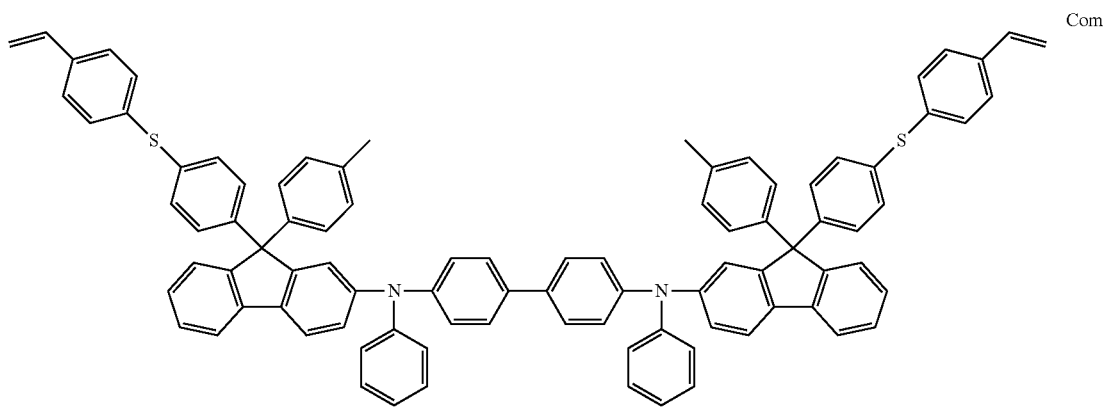
Compound 87
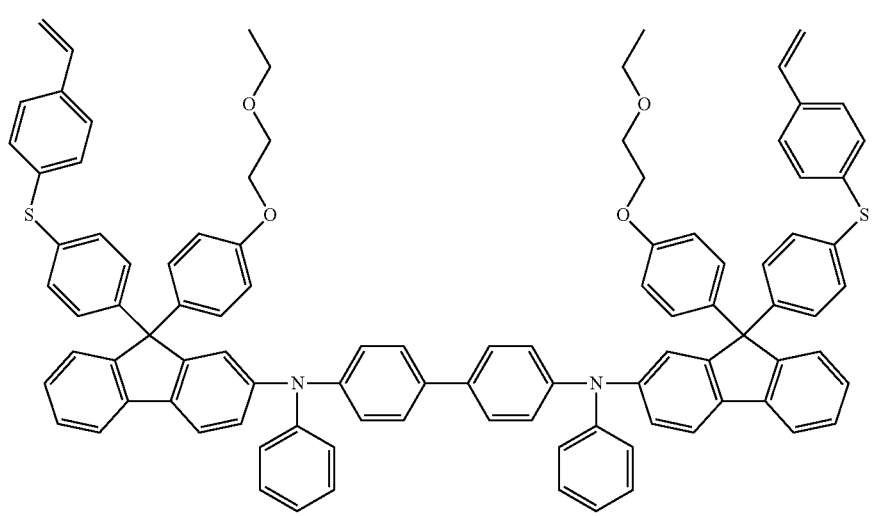

Compound 88
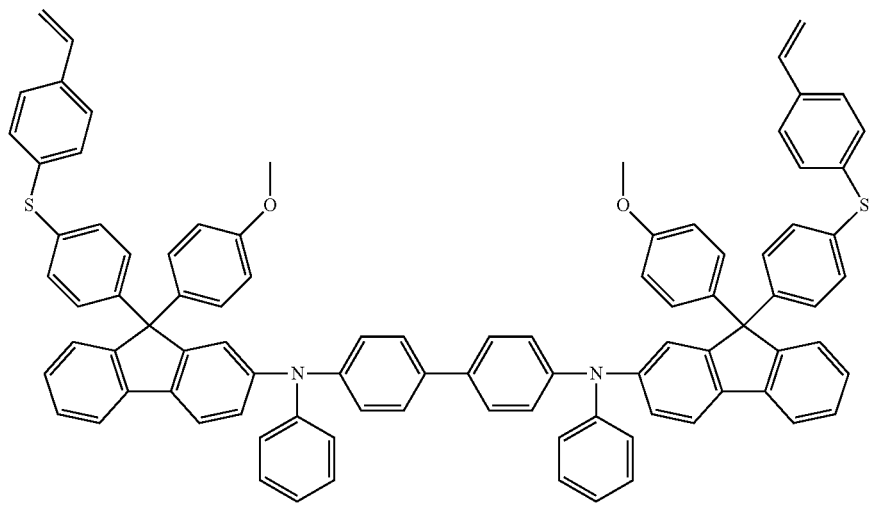
Compound 89
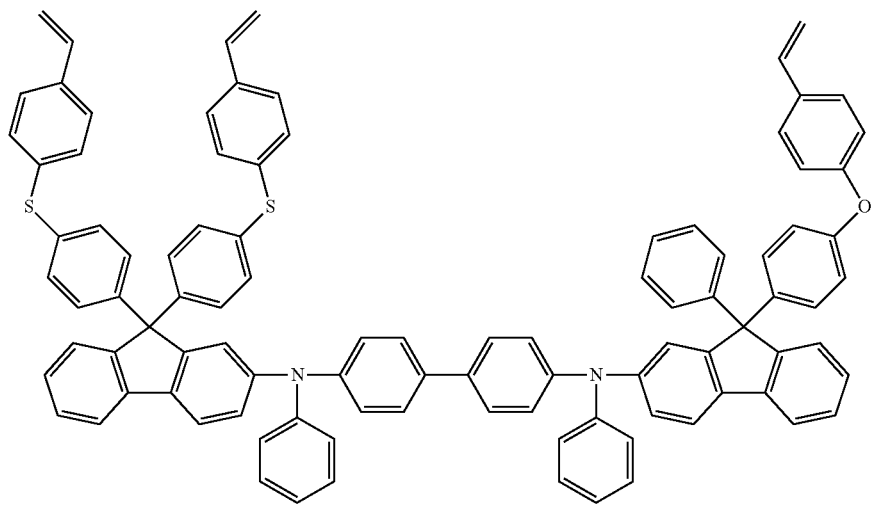
Compound 90
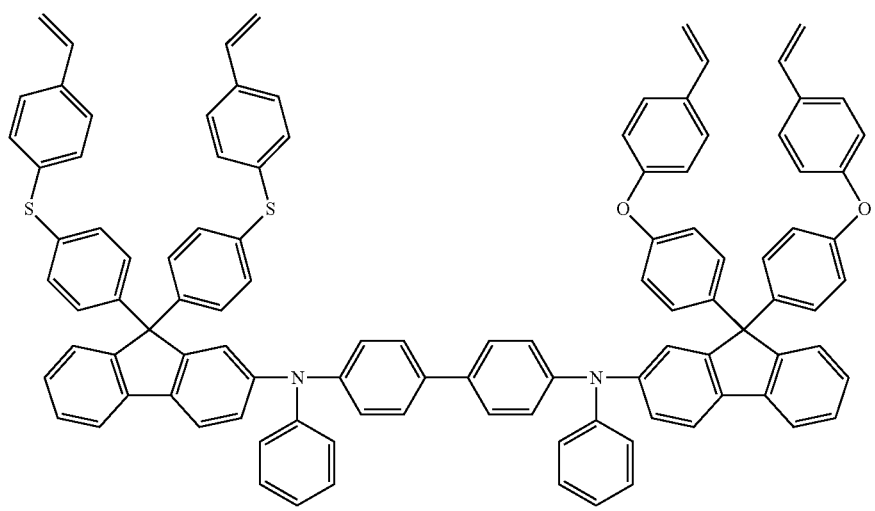

Compound 91
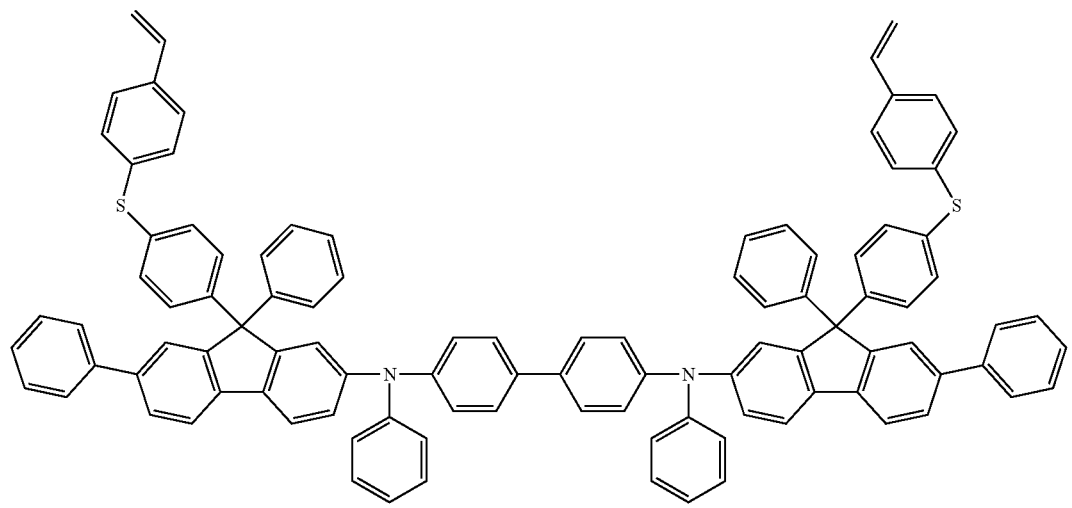
Compound 92
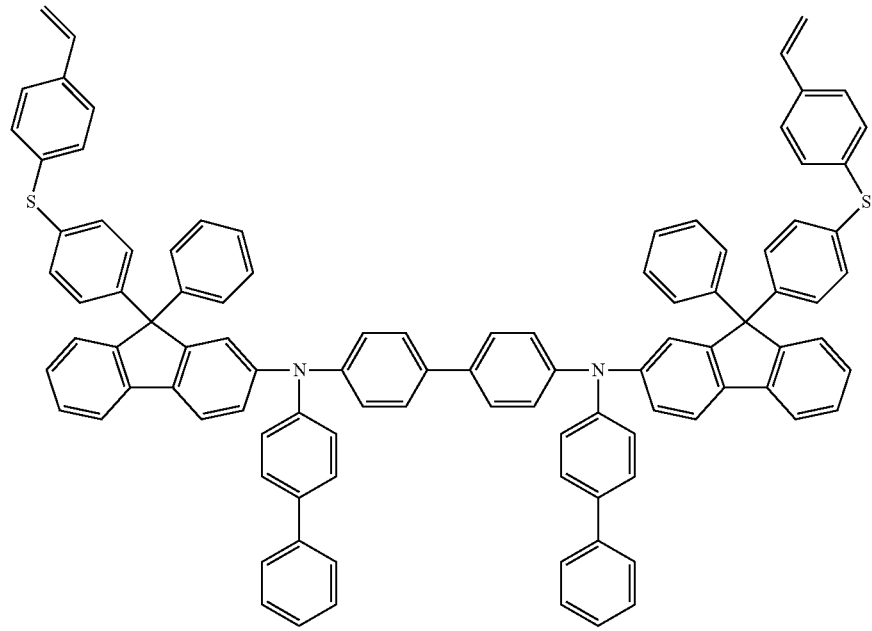
Compound 93
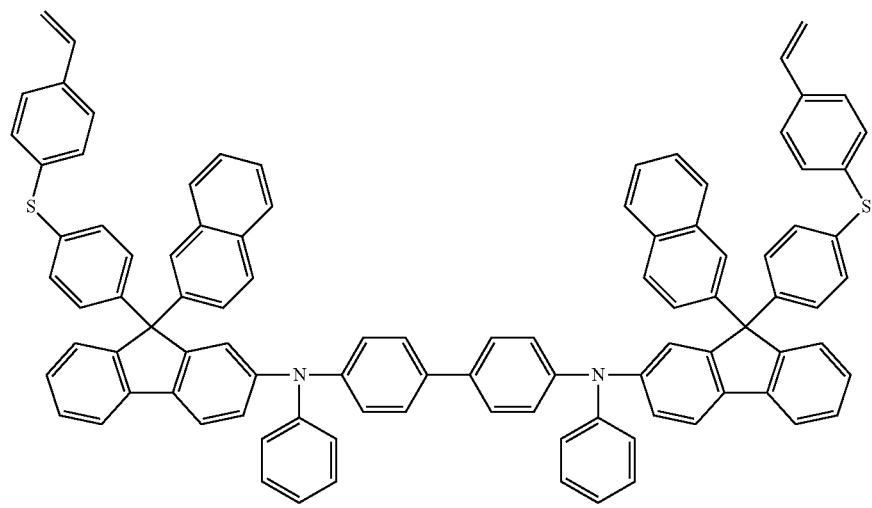

-continued
Compound 94
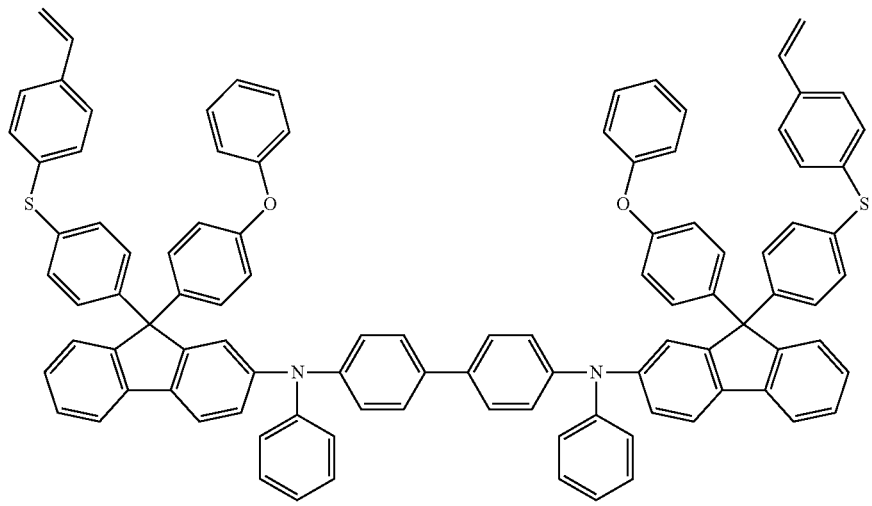
Compound 95
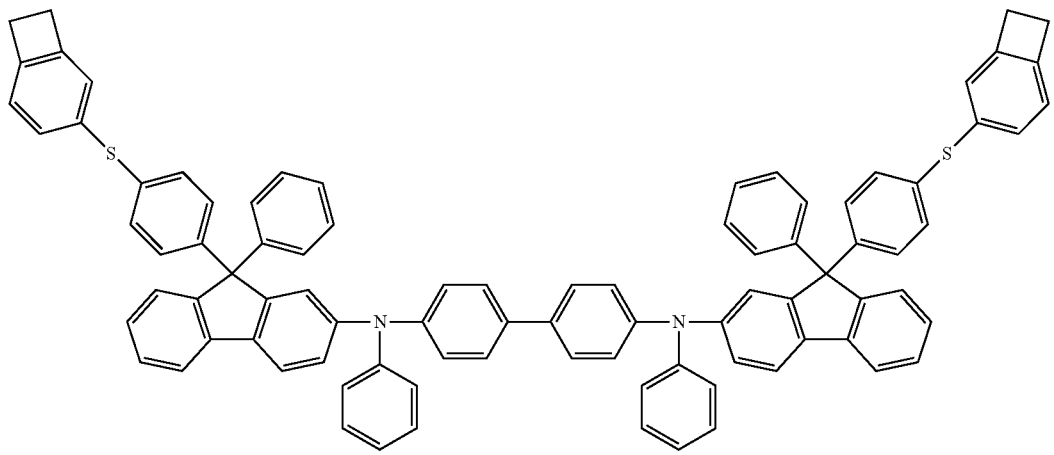
Compound 96
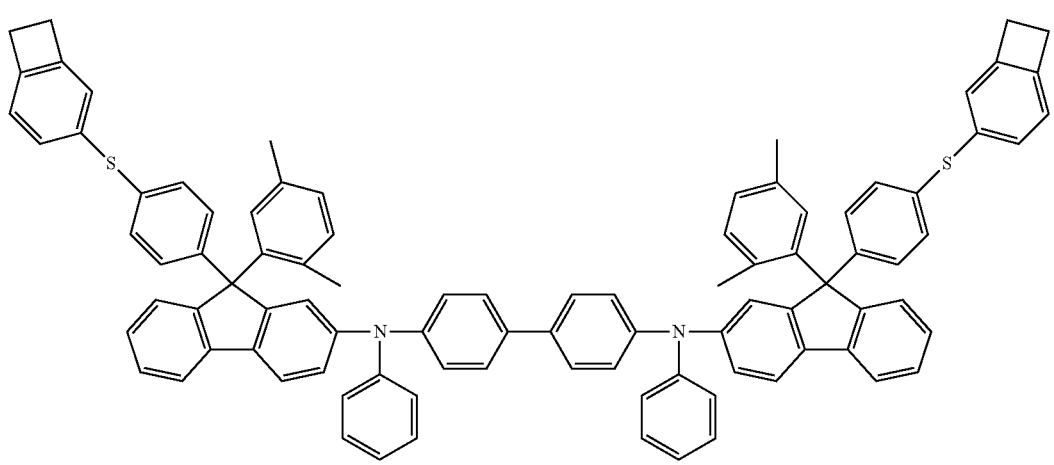

Compound 97
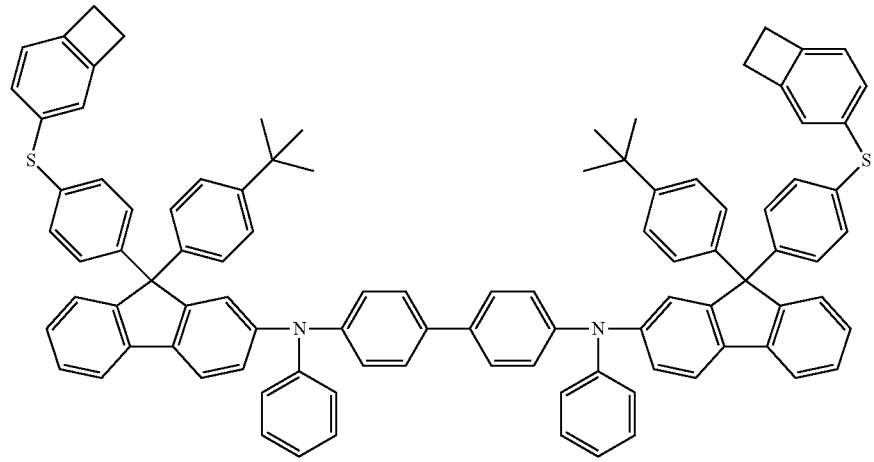
Compound 98
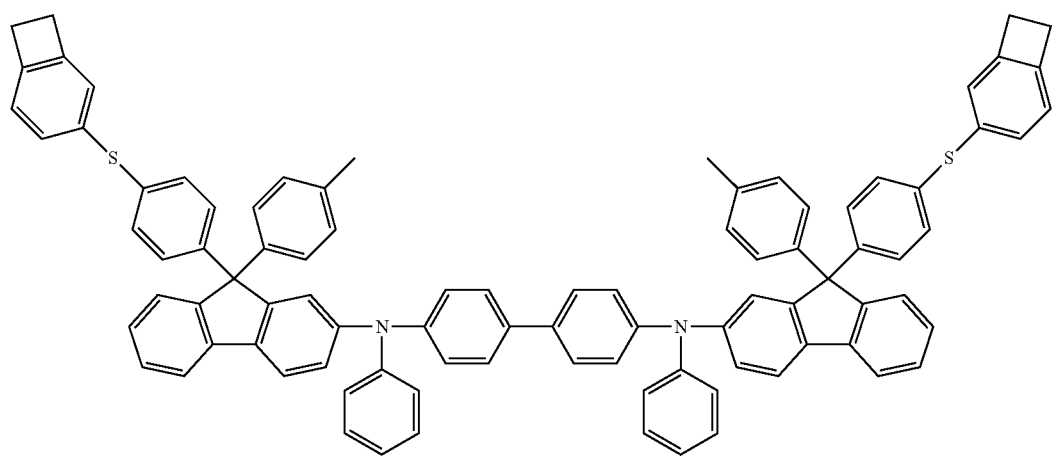
Compound 99
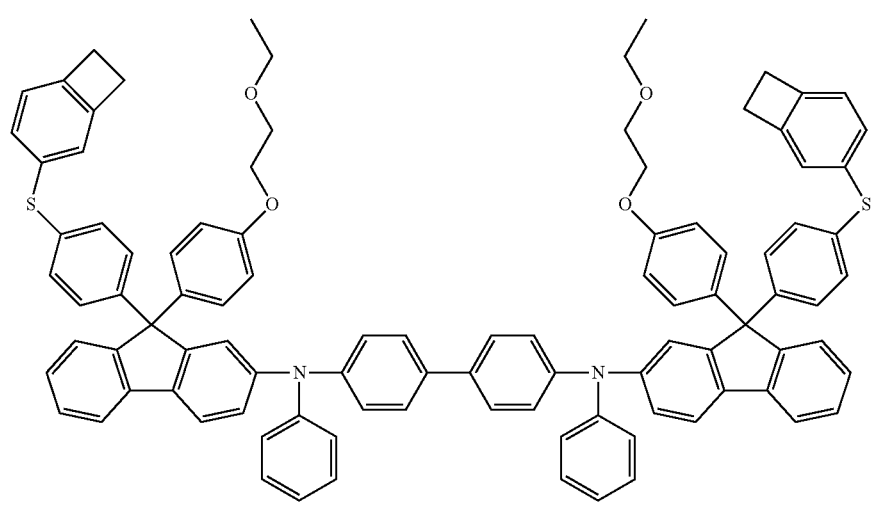

-continued
Compound 100
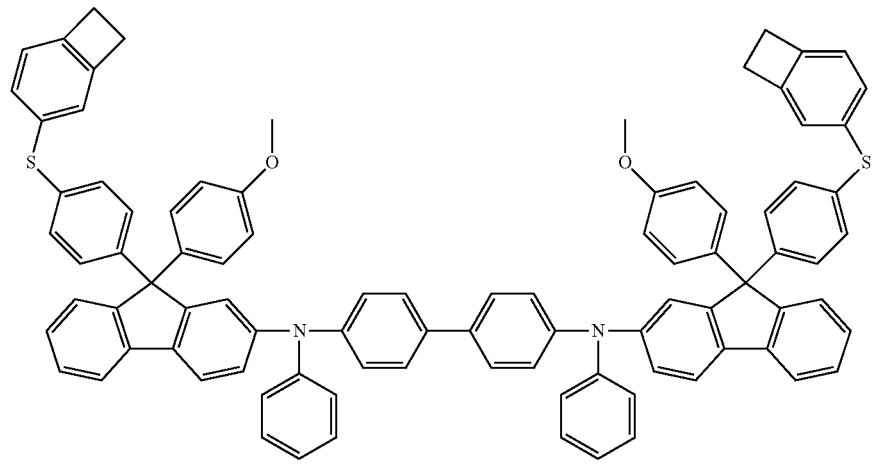
Compound 101
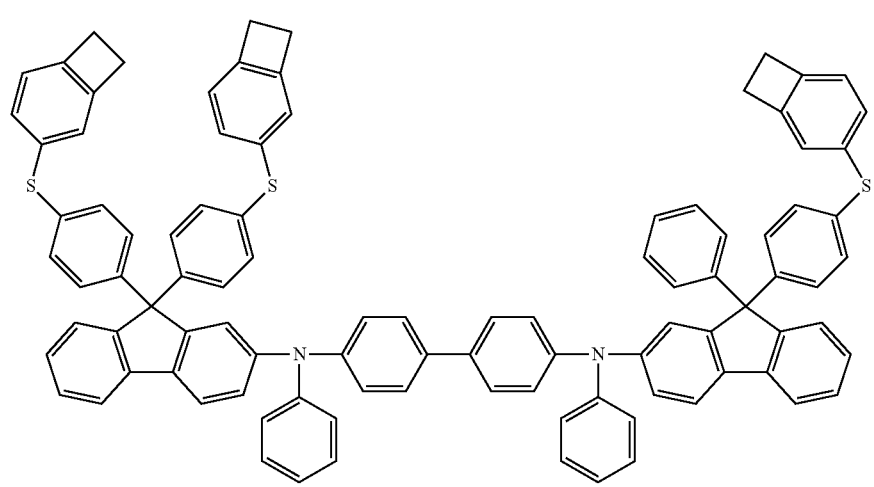
Compound 102
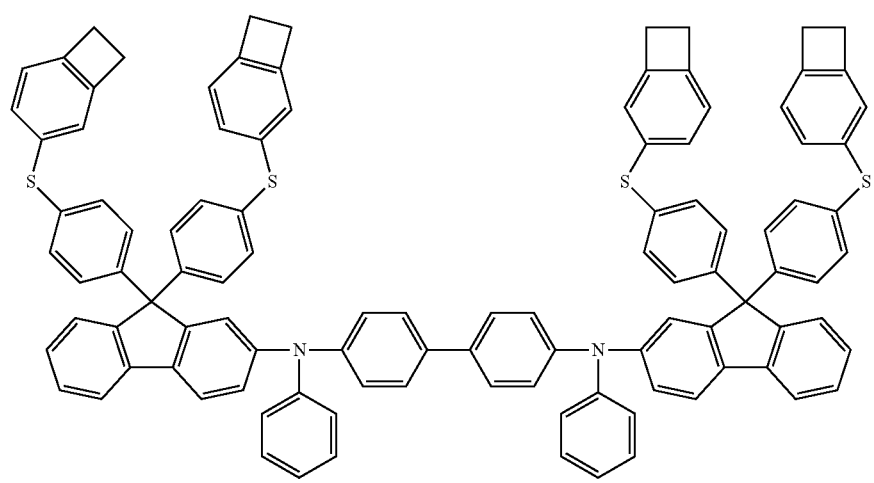

Compound 103
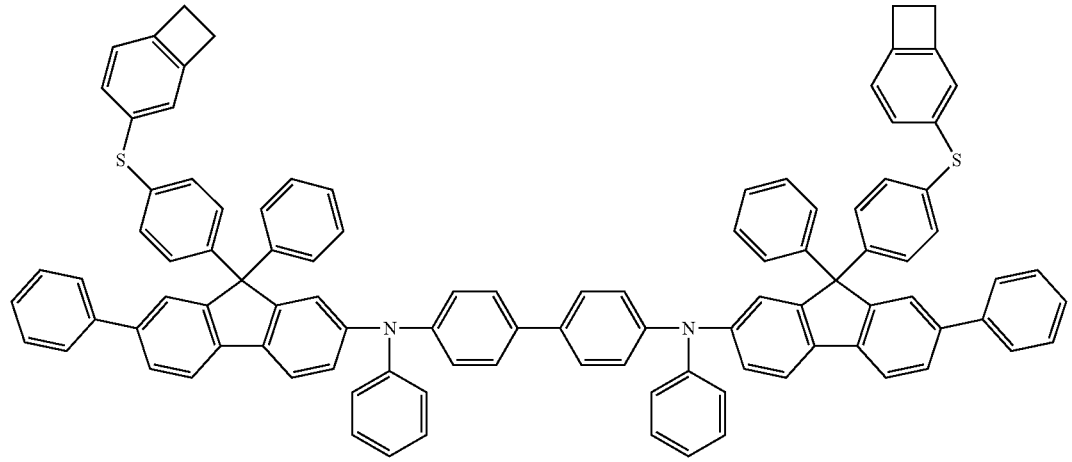
Compound 104
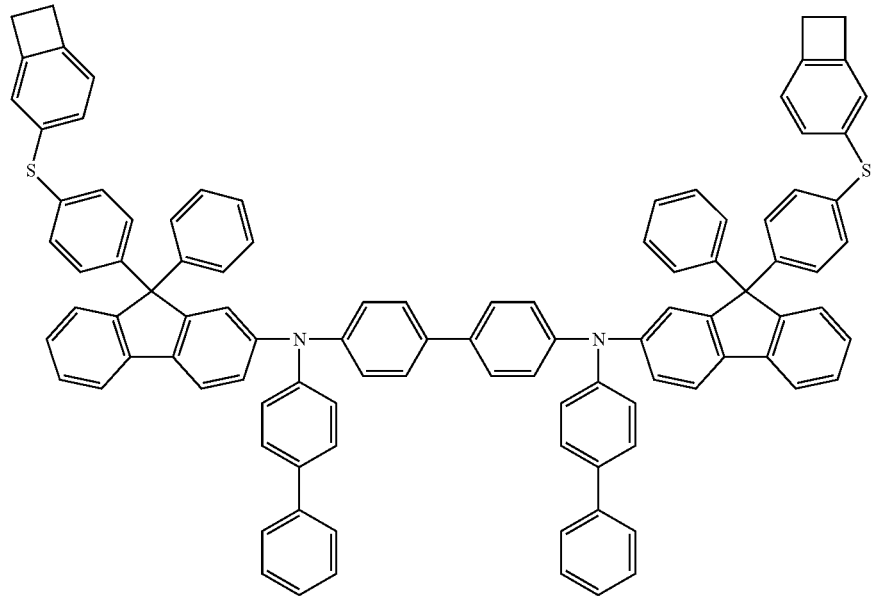
Compound 105
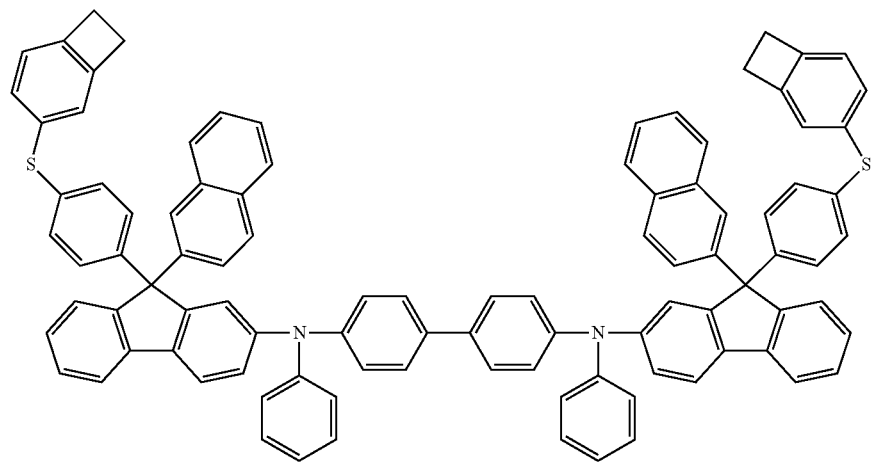

-continued
Compound 106
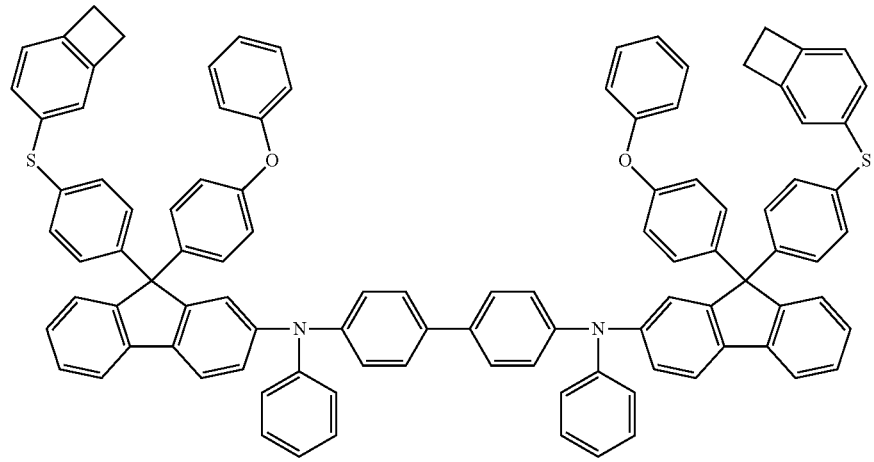
Compound 107
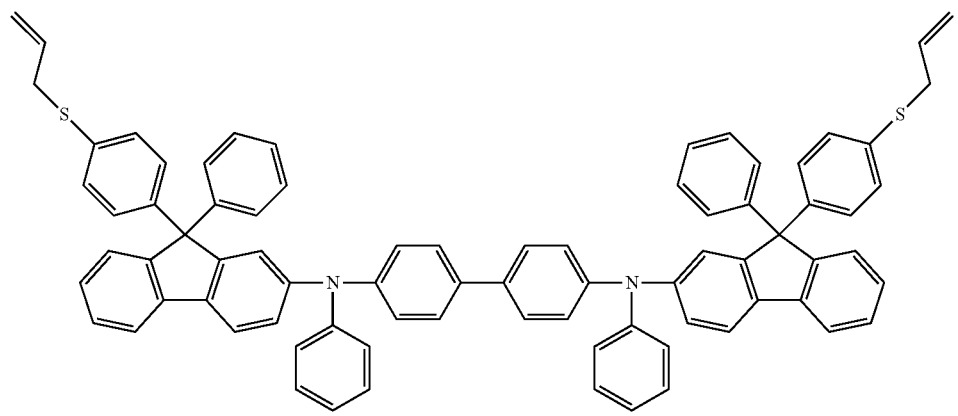
Compound 108
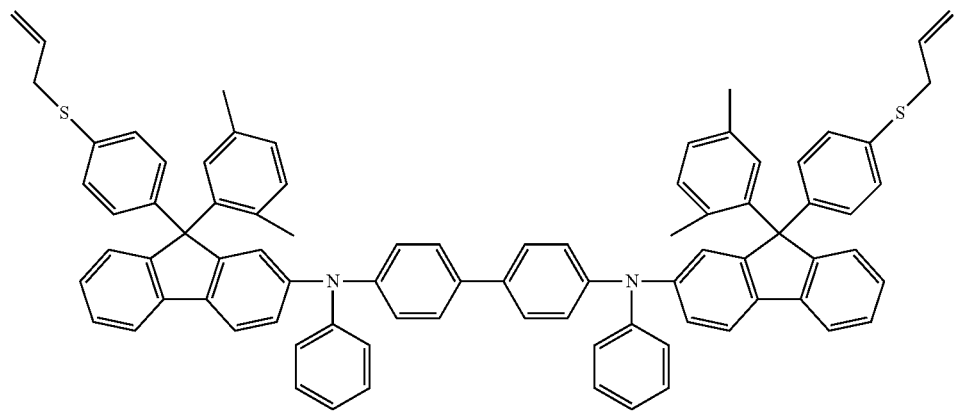
Compound 109
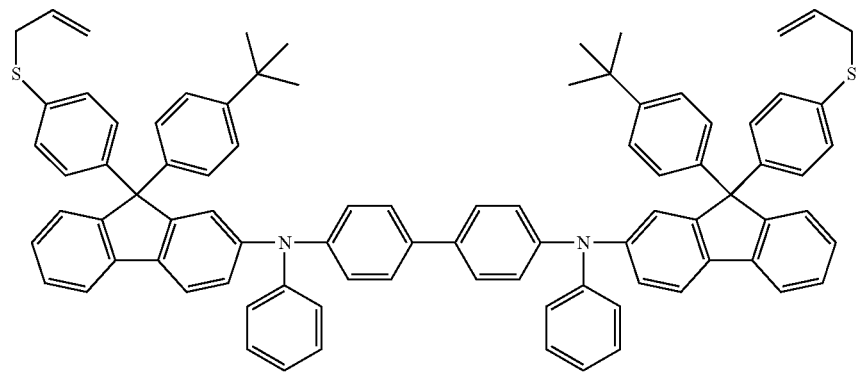

-continued
Compound 110
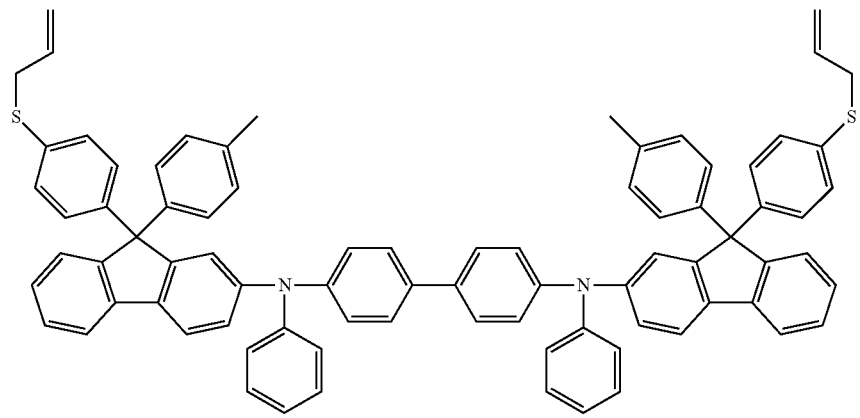
Compound 111
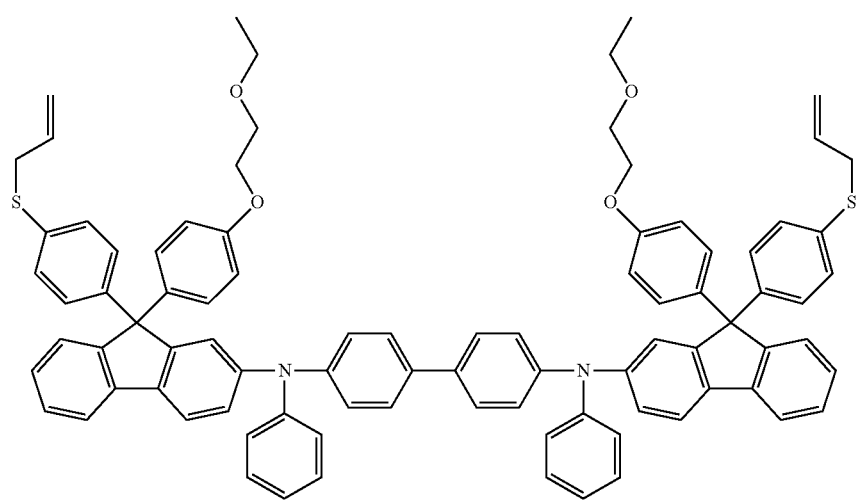
Compound 112
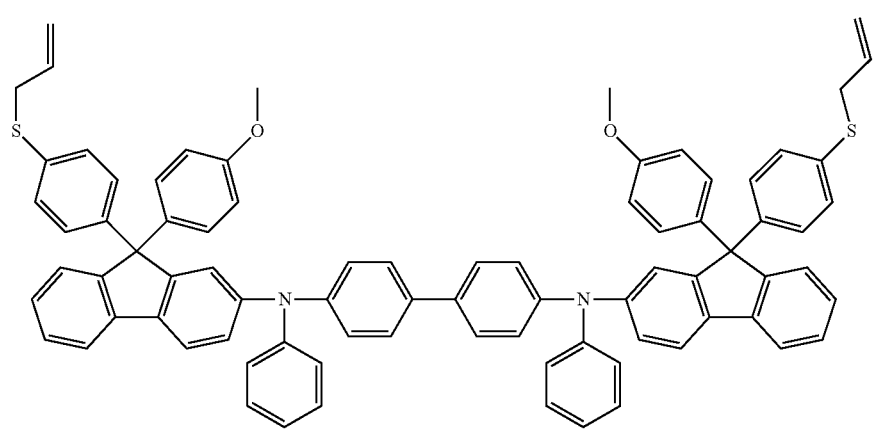

Compound 113
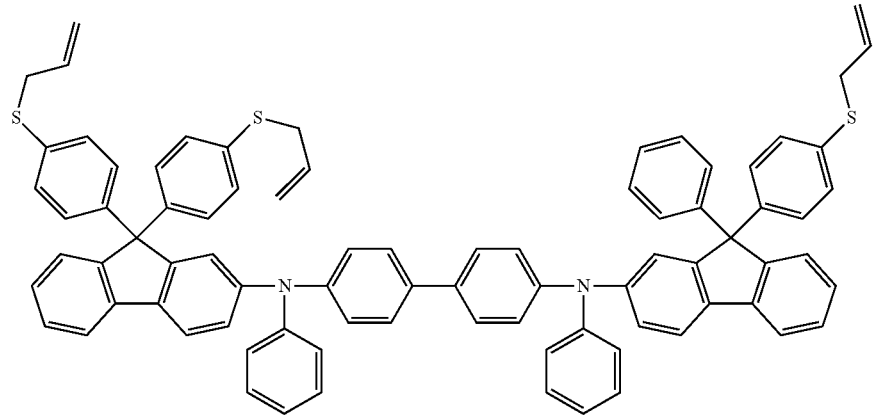
Compound 114
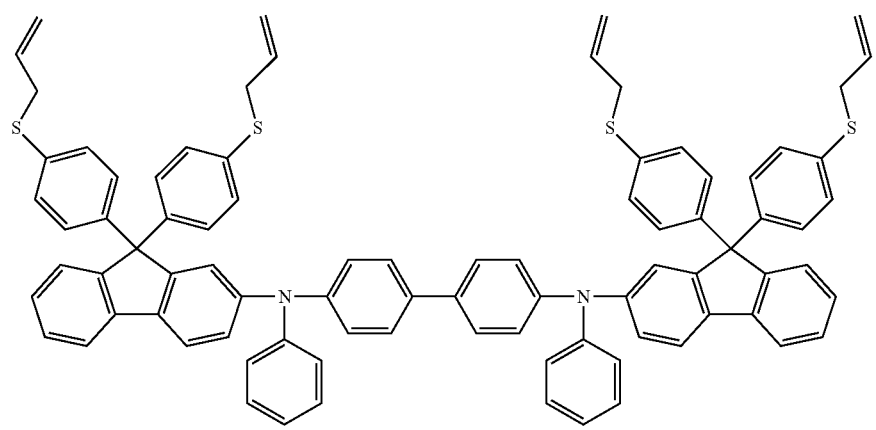
Compound 115
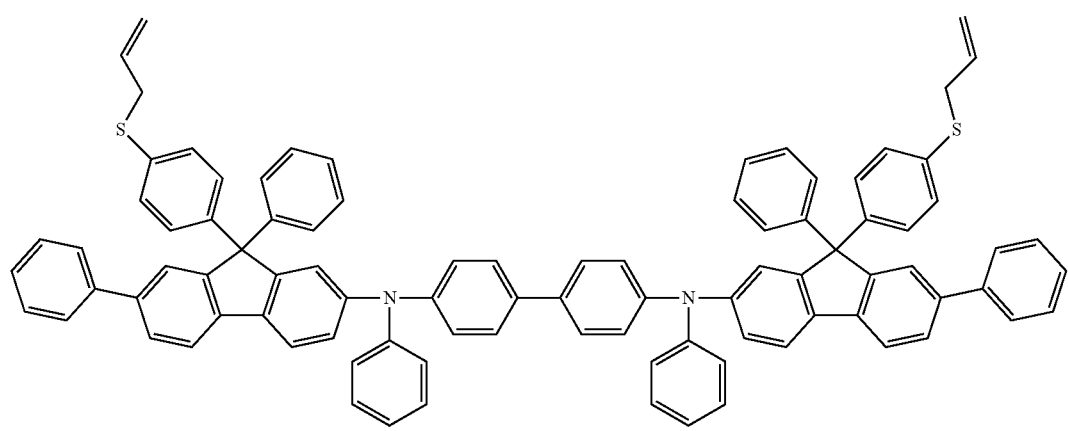

Compound 116
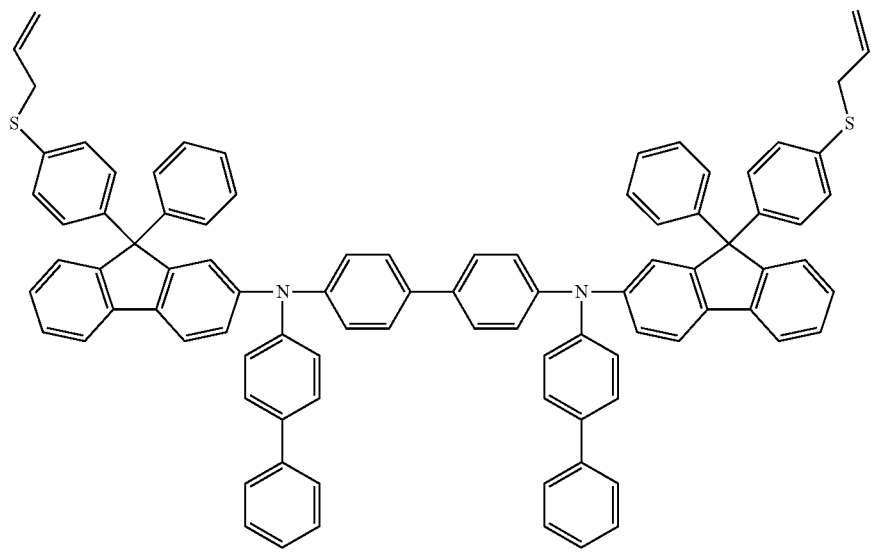
Compound 117
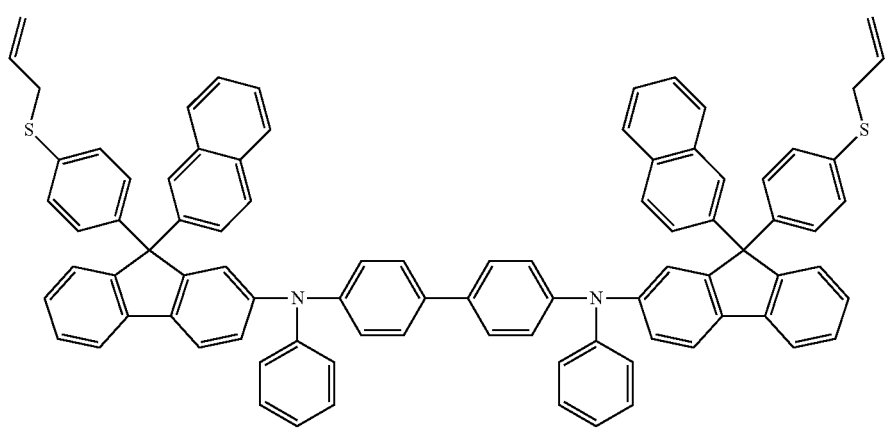
Compound 118
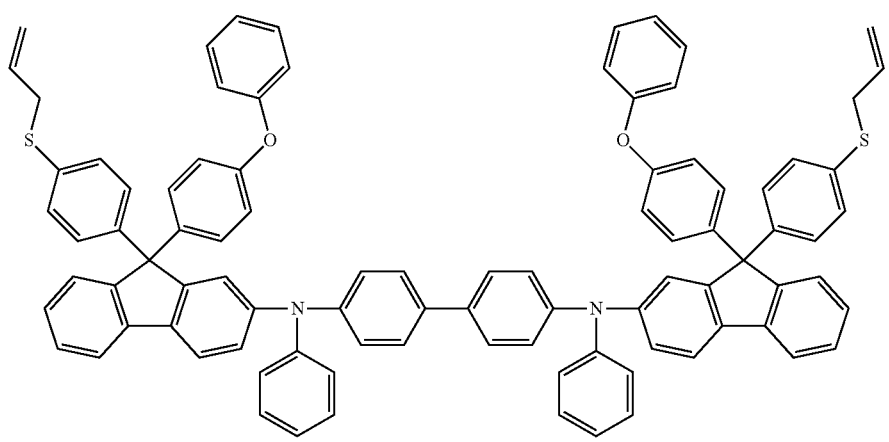

Compound 119
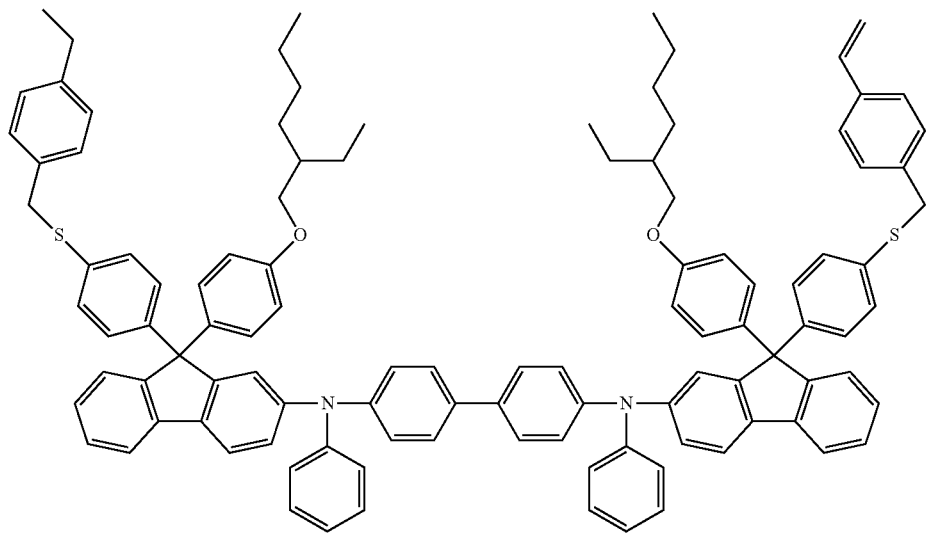
Compound 120
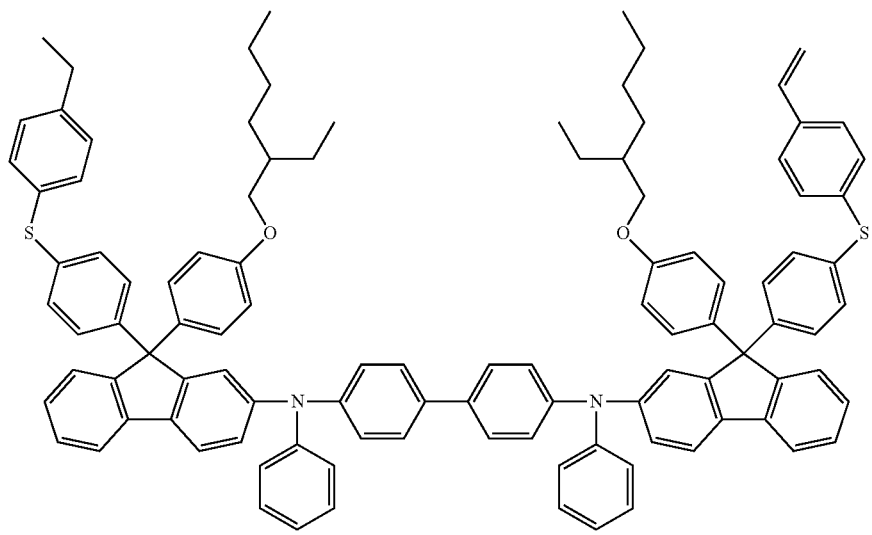
Compound 121
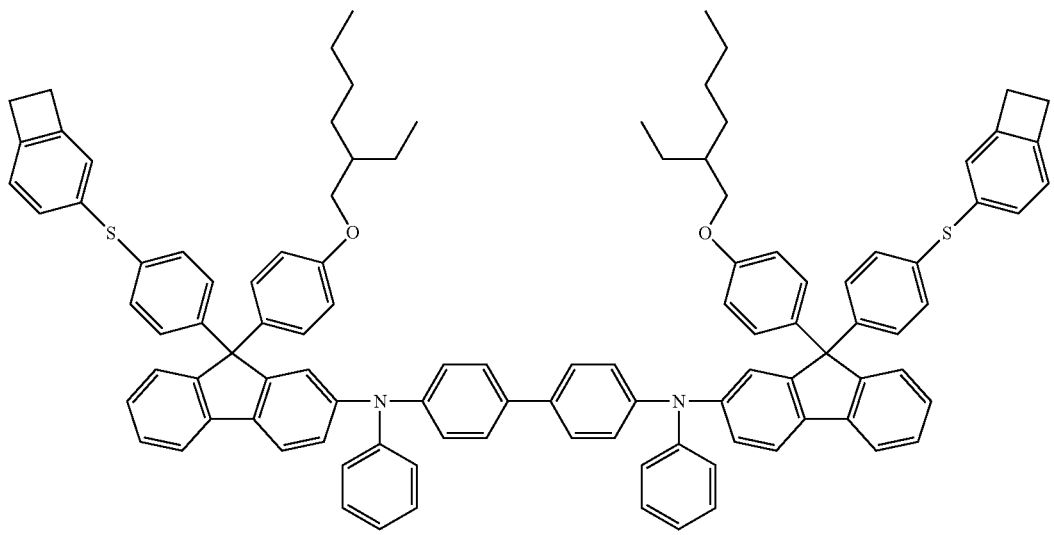

Compound 122
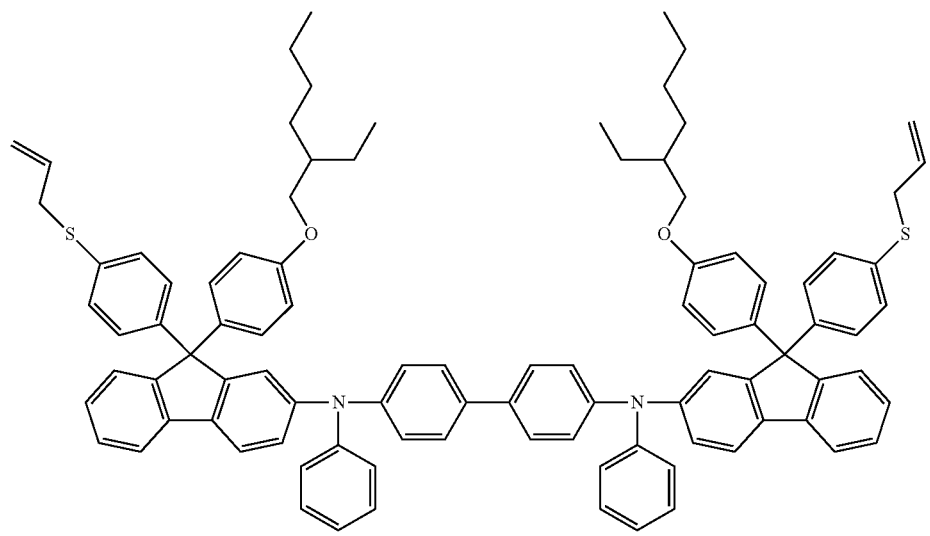
Compound 123
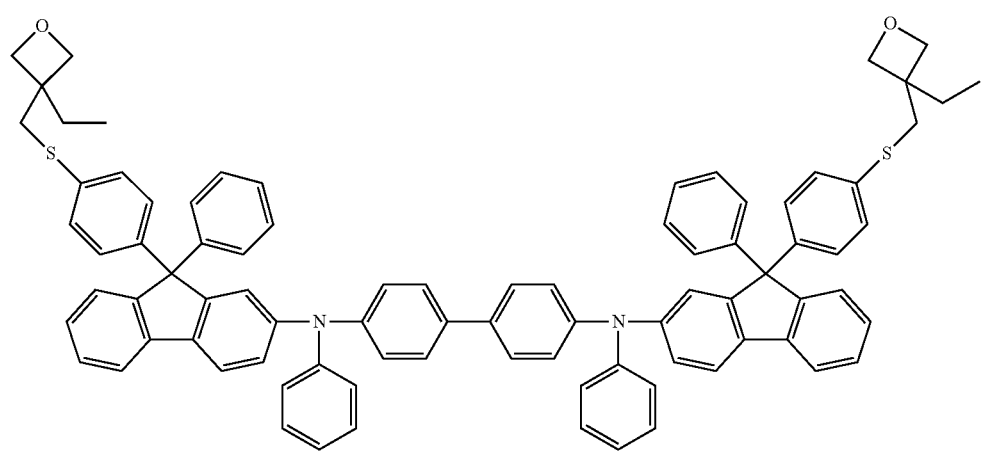
Compound 124
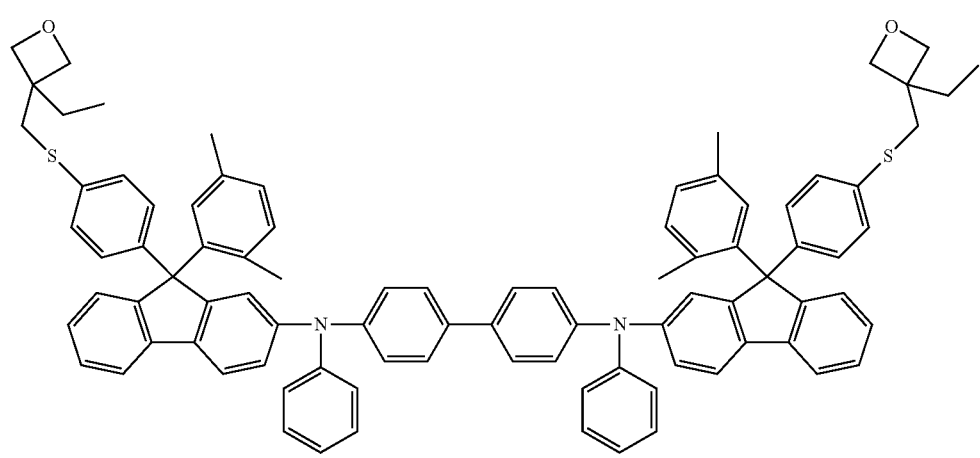

-continued
Compound 125
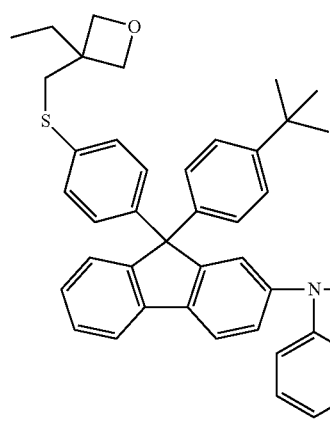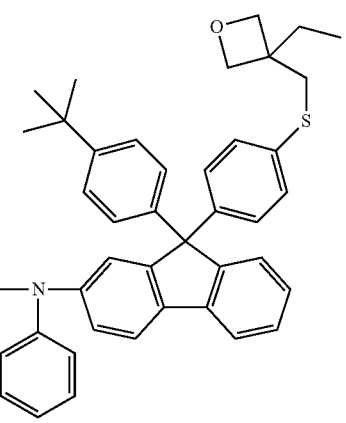
Compound 126
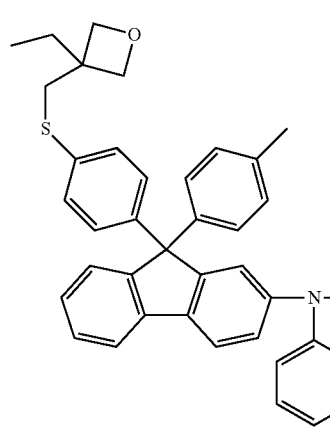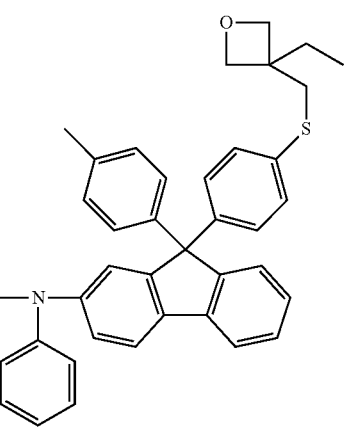
Compound 127
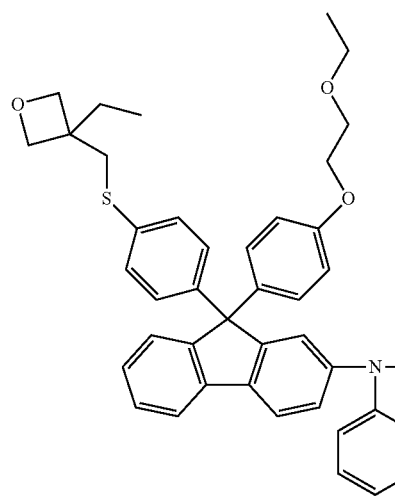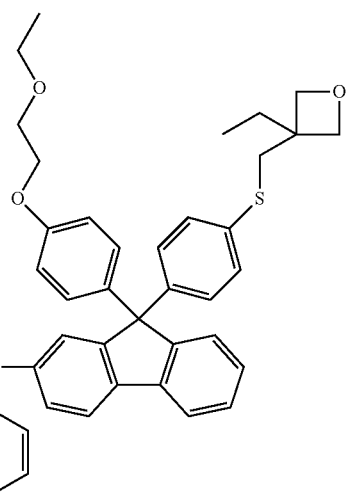

-continued
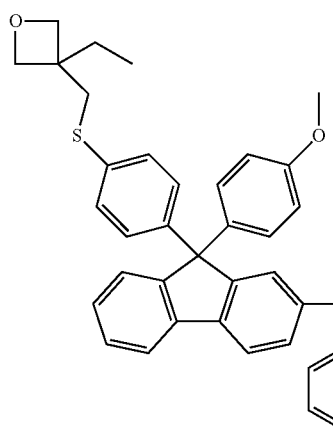
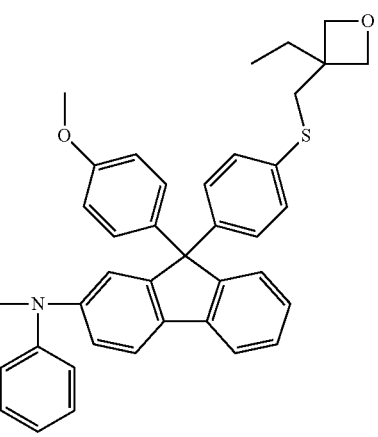
Compound 128
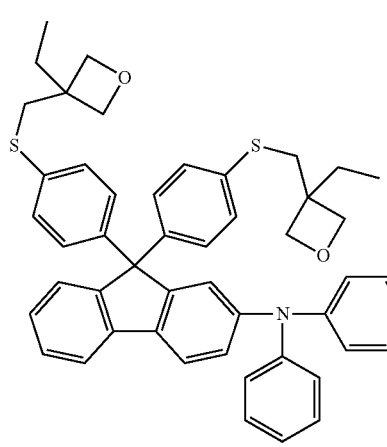
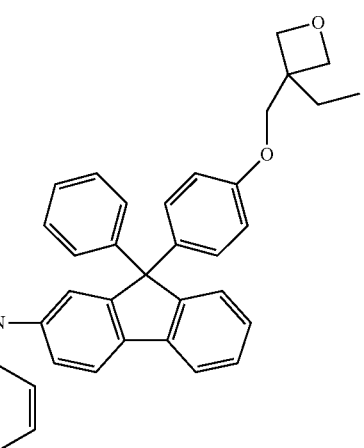
Compound 129
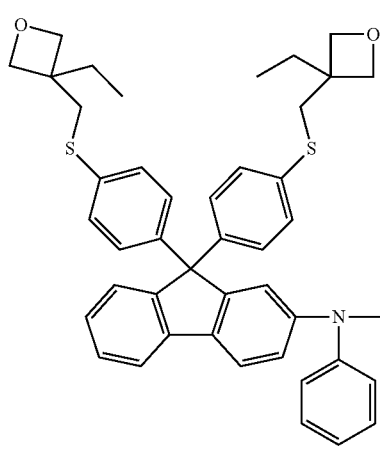
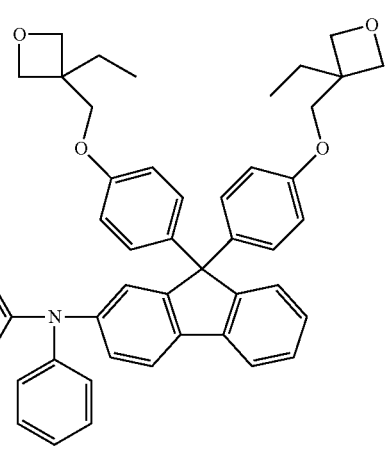
Compound 130

-continued
Compound 131
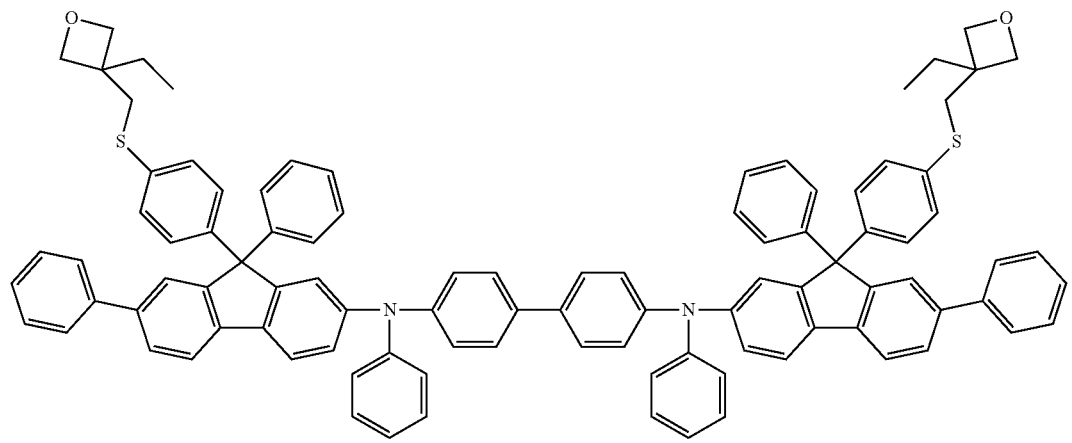
Compound 132
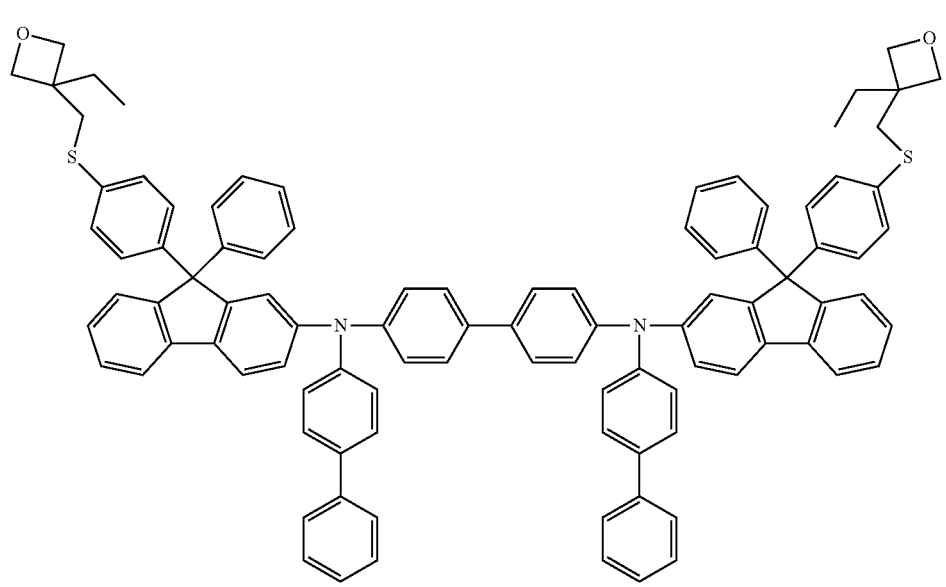
Compound 133
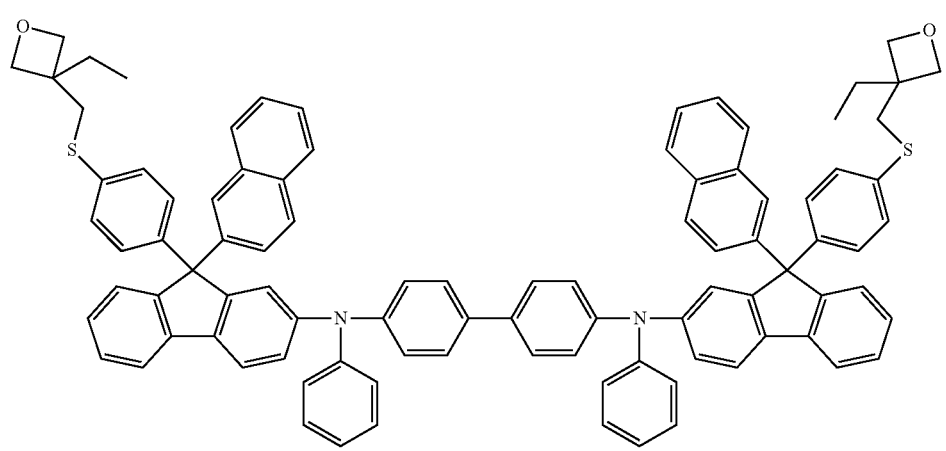

-continued
Compound 134
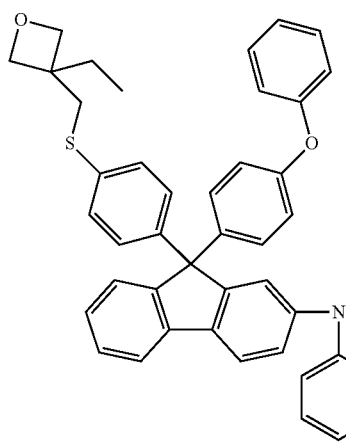 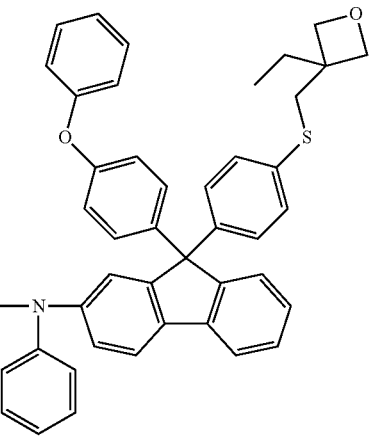
Compound 135
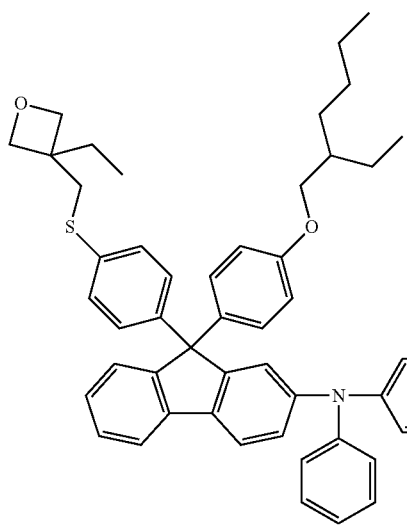 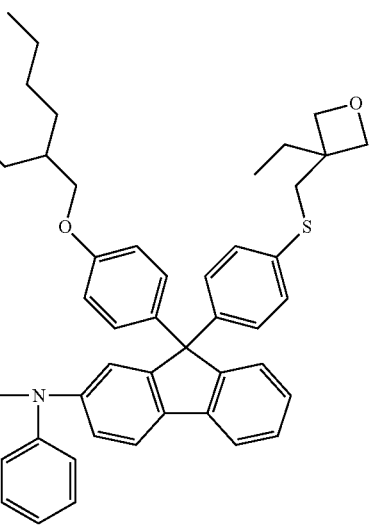
Compound 136
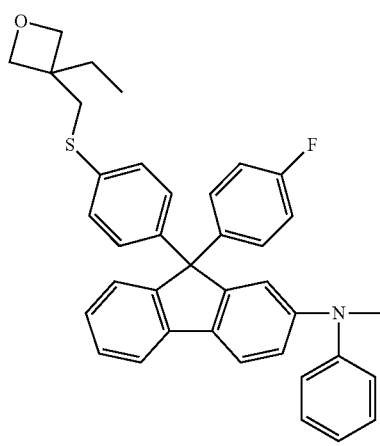 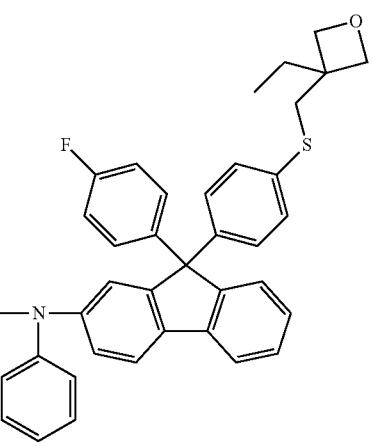

-continued
Compound 137
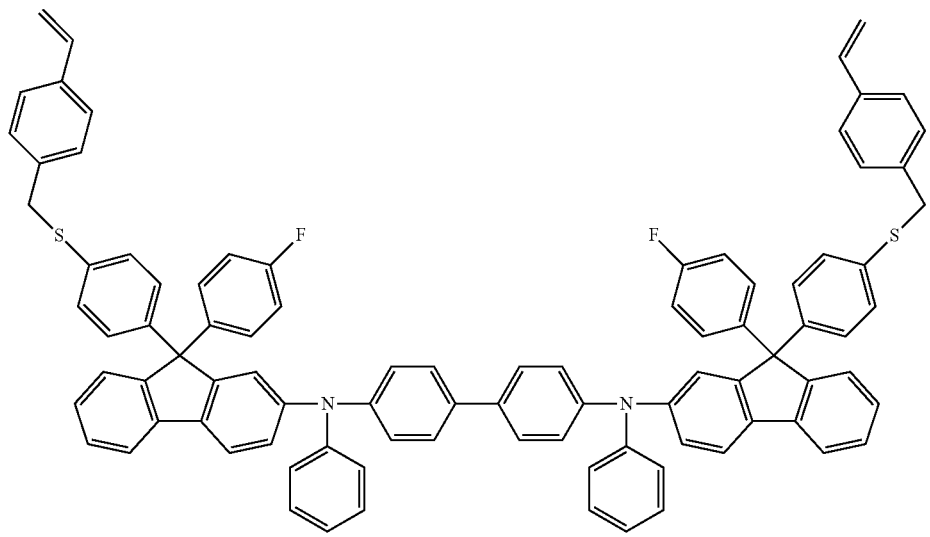
Compound 138
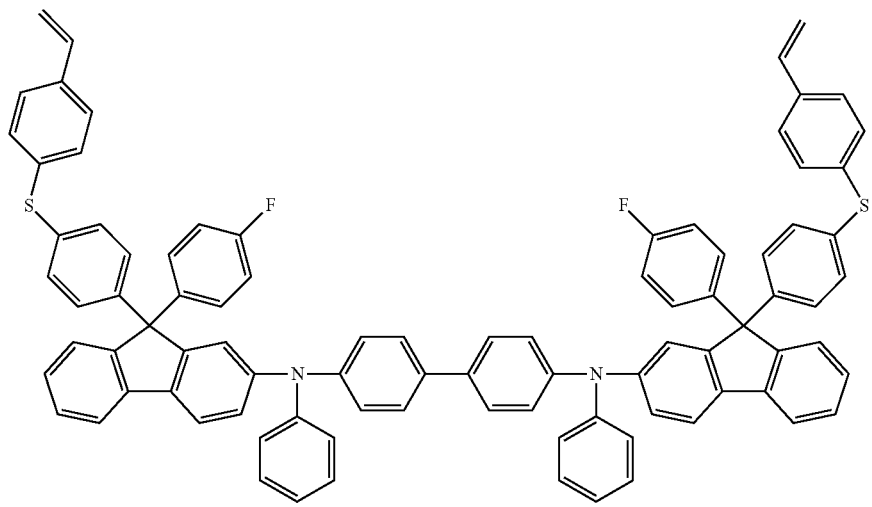
Compound 139
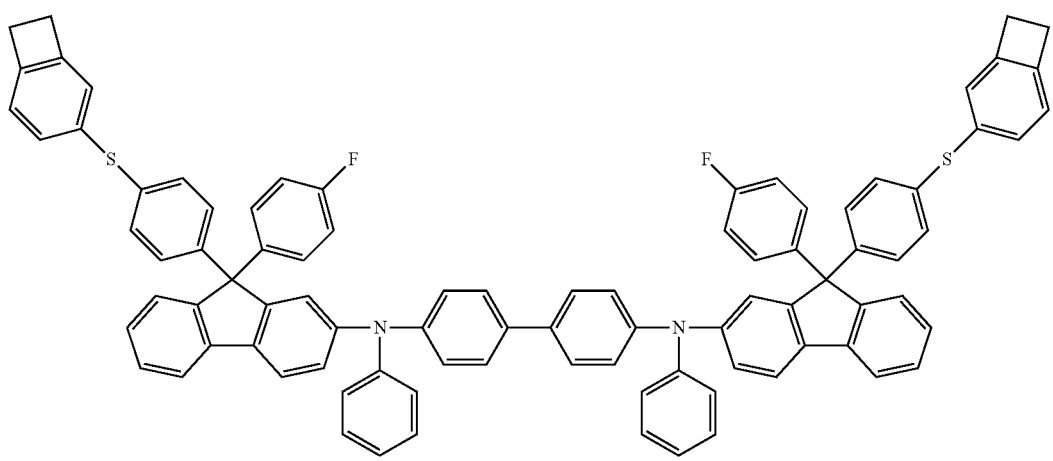

Compound 140

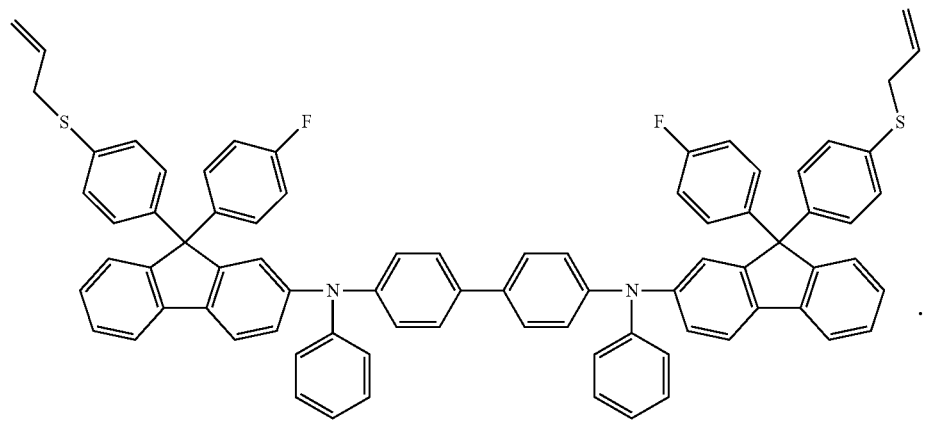

6. The coating composition of claim 1, wherein a number of the functional group crosslinkable by heat or light of the anion group represented by Chemical Formula 10 is from 1 to 4.

7. The coating composition of claim 1, wherein a content of the F in the anion group is from 10 parts by weight to 50 parts by weight with respect to 100 parts by weight of the anion group.

8. The coating composition of claim 1, wherein, in Chemical Formula 10, at least one benzene ring among the Rc1 to Rc5-bonding benzene ring, the Rc6 to Rc10-bonding benzene ring, the Rc11 to Rc15-bonding benzene ring and the Rc16 to Rc20-bonding benzene ring in Chemical Formula 10 is selected from among the following structural formulae:

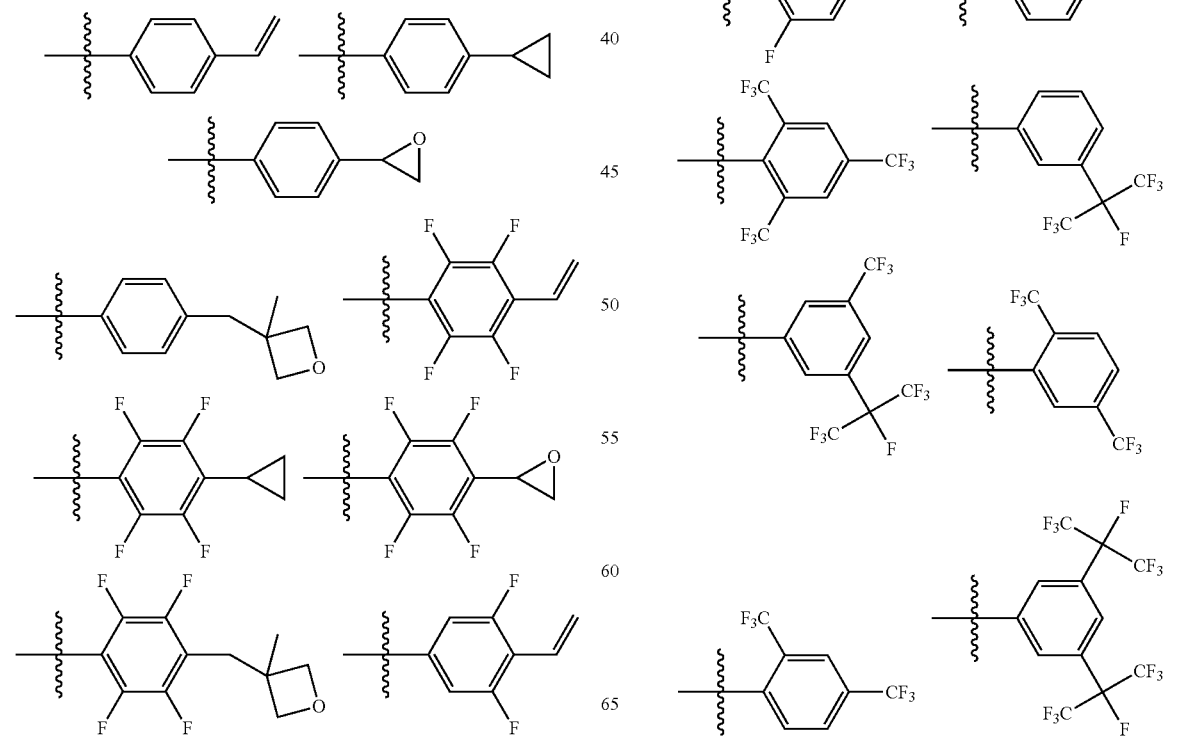

-continued
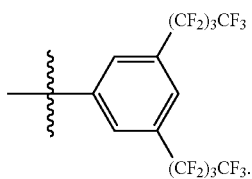
9. The coating composition of claim 1, wherein the anion group represented by Chemical Formula 10 is selected from among the following structural formulae:
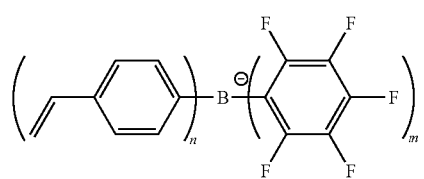
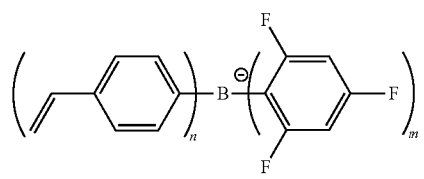
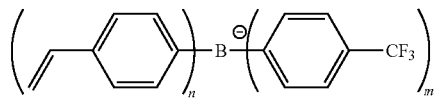
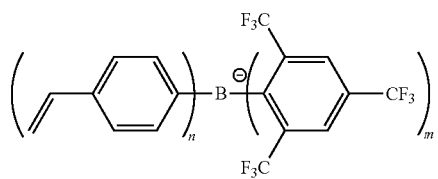
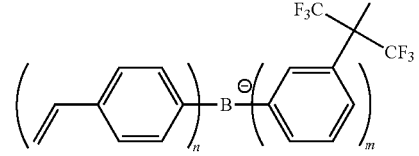
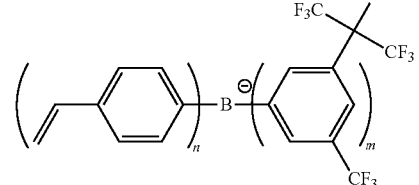
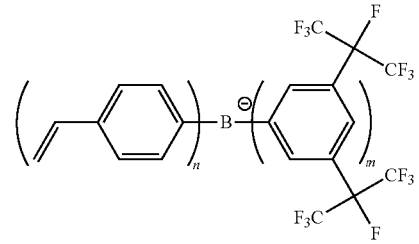
-continued
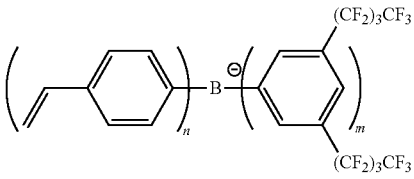
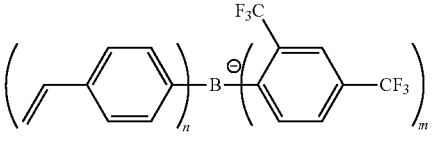
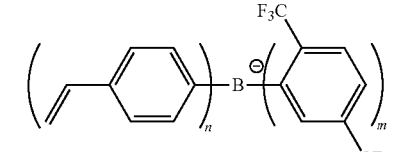
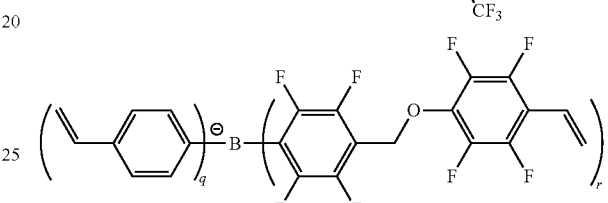
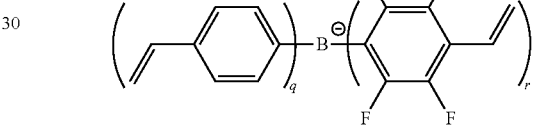
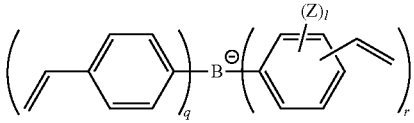
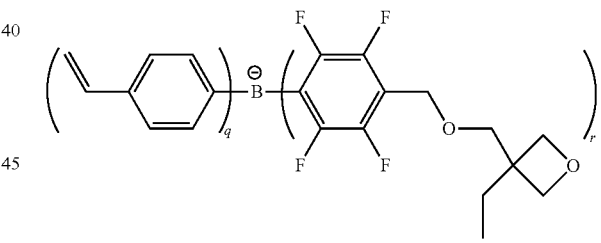
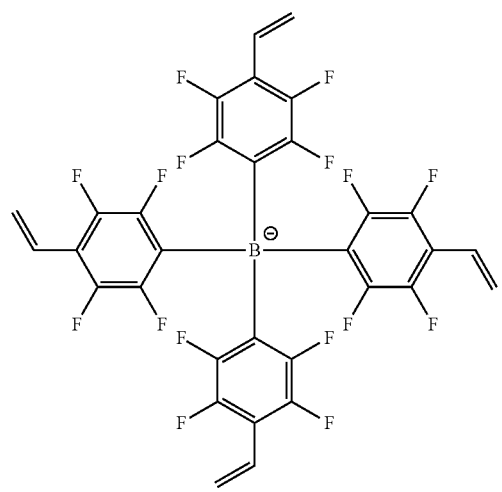

287
-continued
288
-continued
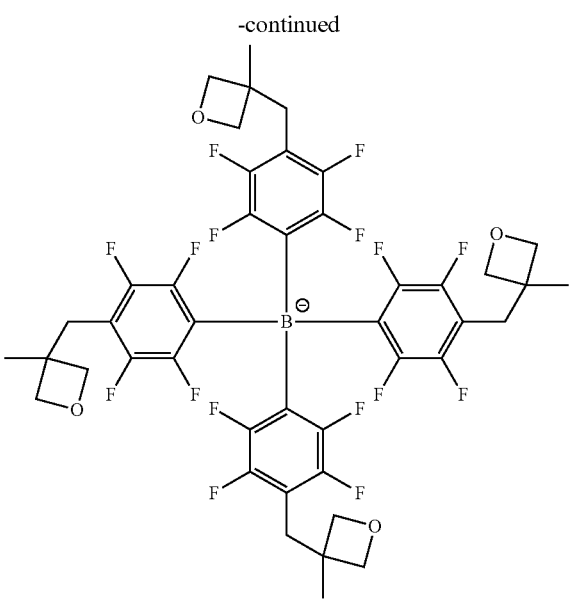
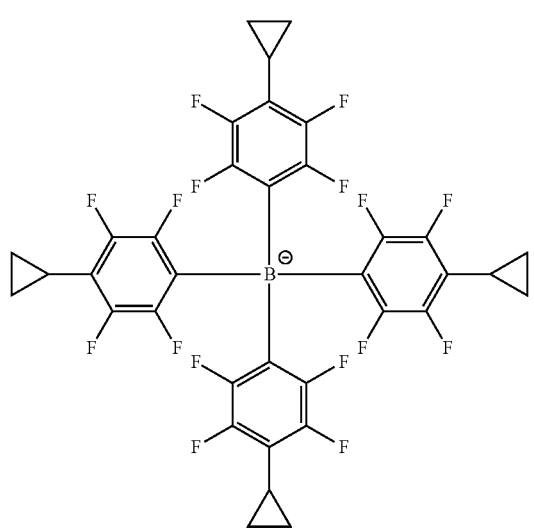
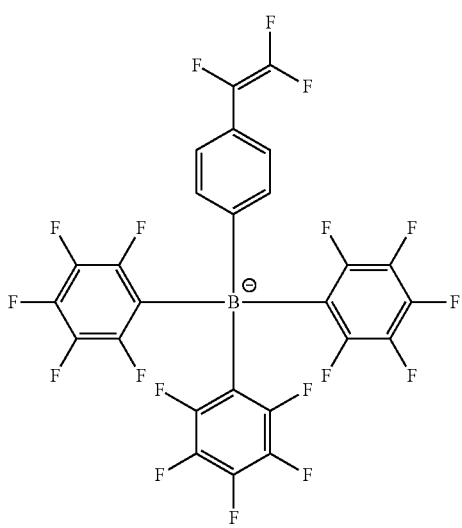
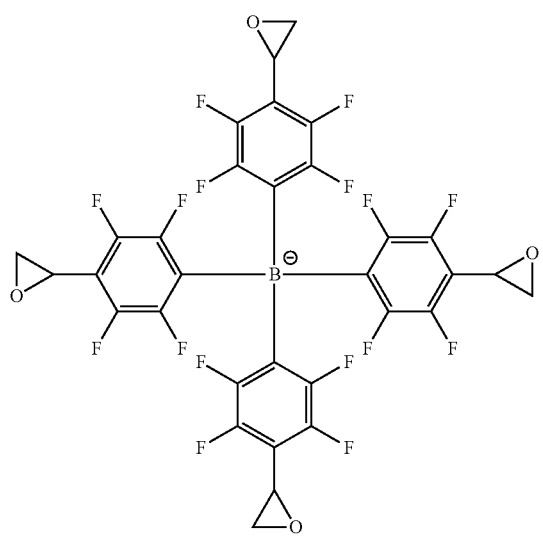
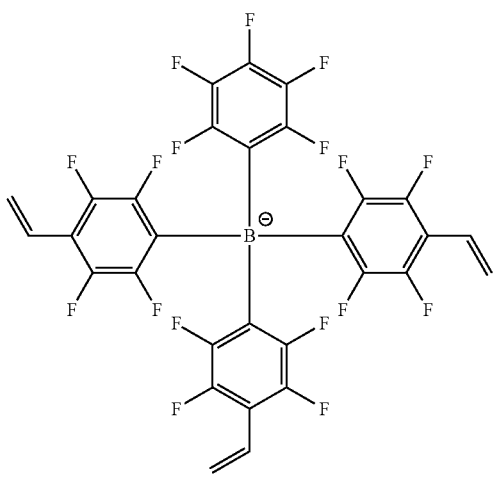

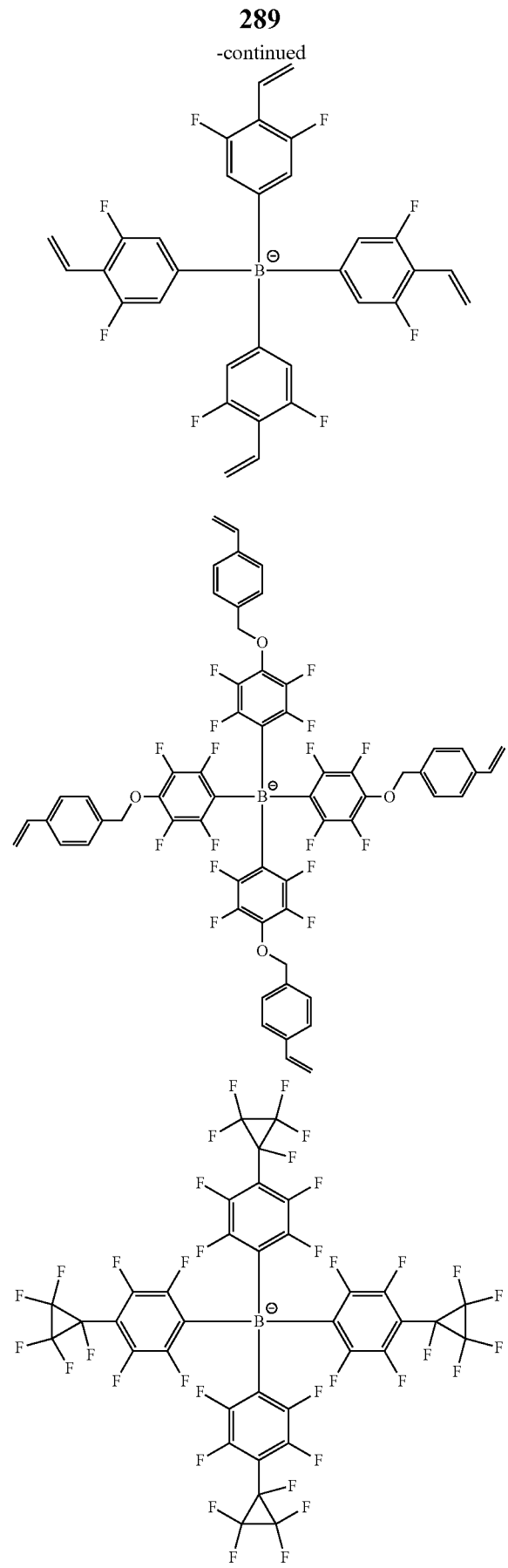

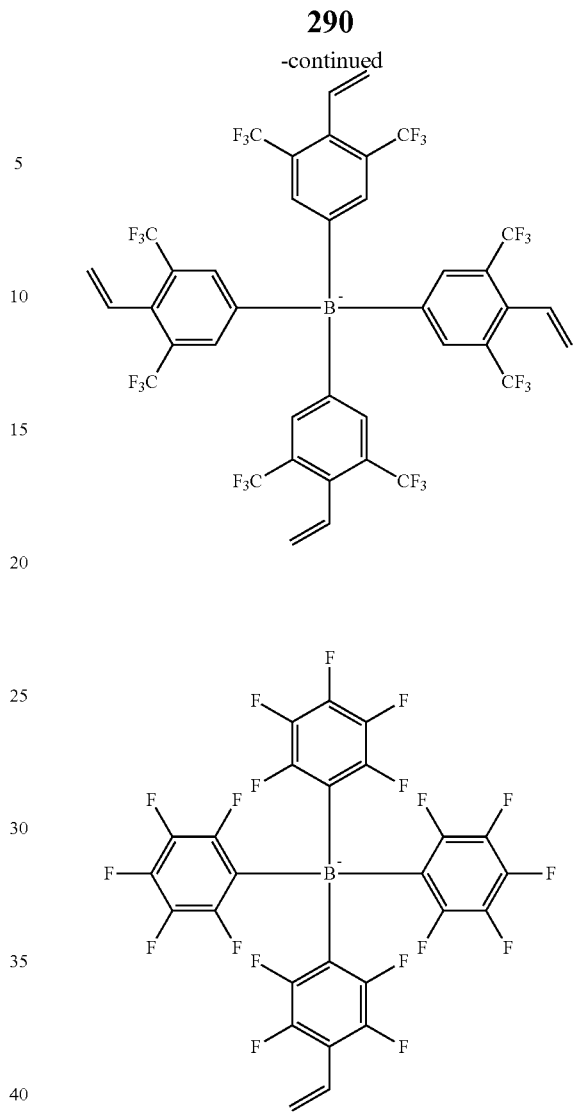

in the structural formulae, n is an integer of 1 to 3, m is an integer of 1 to 3, and m+n=4;

q is an integer of 0 to 3, r is an integer of 1 to 4, and q+r=4;

Z is deuterium; a halogen group; a nitro group; a cyano group; an amino group; —C(O)$R_{100}$; —$OR_{101}$; —$SR_{102}$; —$SO_3R_{103}$; —$COOR_{104}$; —$OC(O)R_{105}$; —C(O)$NR_{106}R_{107}$; a substituted or unsubstituted alkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group;

l is an integer of 1 to 4, and when l is 2 or greater, Zs are the same as or different from each other; and $R_{100}$ to $R_{107}$ are the same as or different from each other, and each independently hydrogen; deuterium; or a substituted or unsubstituted alkyl group.

10. The coating composition of claim 1, wherein the ionic compound further comprises a cation group, and the cation group is selected from among monovalent cation groups, onium compounds or the following structural formulae:

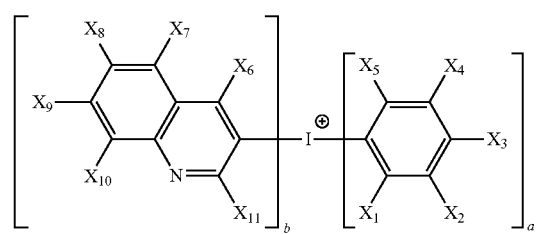

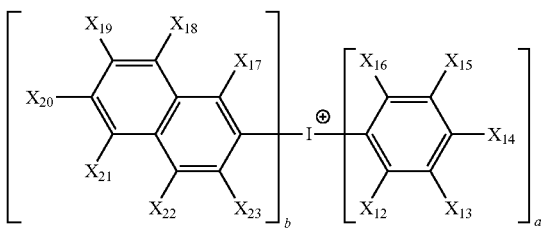

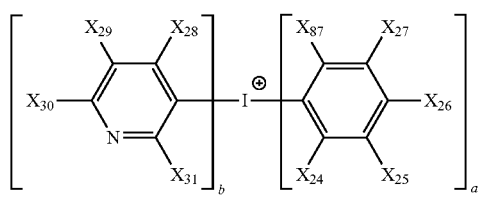

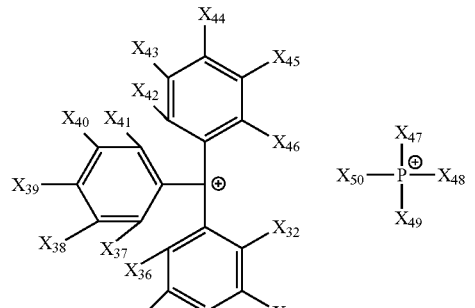

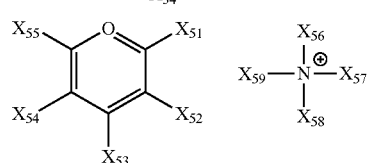

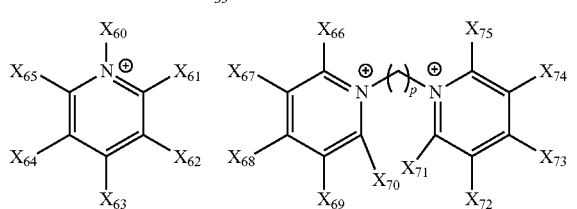

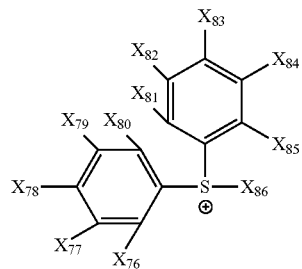

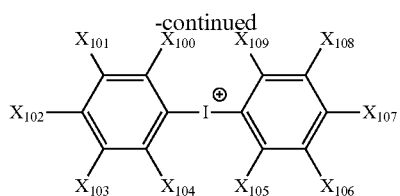

-continued in the structural formulae, $X_1$ to $X_{87}$ and $X_{100}$ to $X_{109}$ are the same as or different from each other, and each independently hydrogen; a cyano group; a nitro group; a hydroxyl group; a halogen group; —$COOR_{104}$; a substituted or unsubstituted alkyl group; a substituted or unsubstituted alkoxy group; a substituted or unsubstituted aryloxy group; a substituted or unsubstituted cycloalkyl group; a substituted or unsubstituted fluoroalkyl group; a substituted or unsubstituted aryl group; or a functional group crosslinkable by heat or light;

$R_{104}$ is hydrogen; deuterium; or a substituted or unsubstituted alkyl group;

p is an integer of 0 to 10; and a is 1 or 2, b is 0 or 1, and a+b=2.

11. The coating composition of claim 10, wherein the cation group is any one selected from among the following structural formulae:

1-1

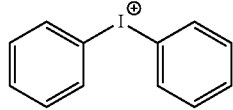

1-2

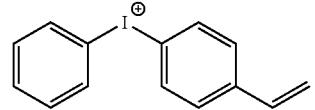

1-3

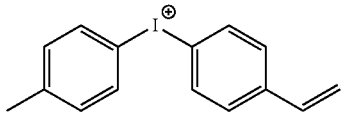

1-4

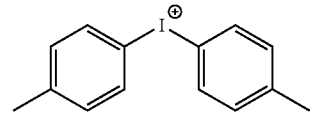

1-5

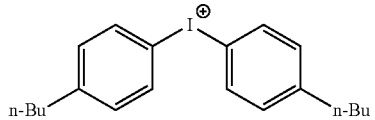

1-6

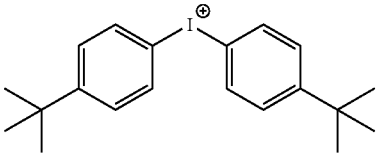

1-7

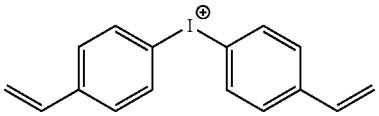

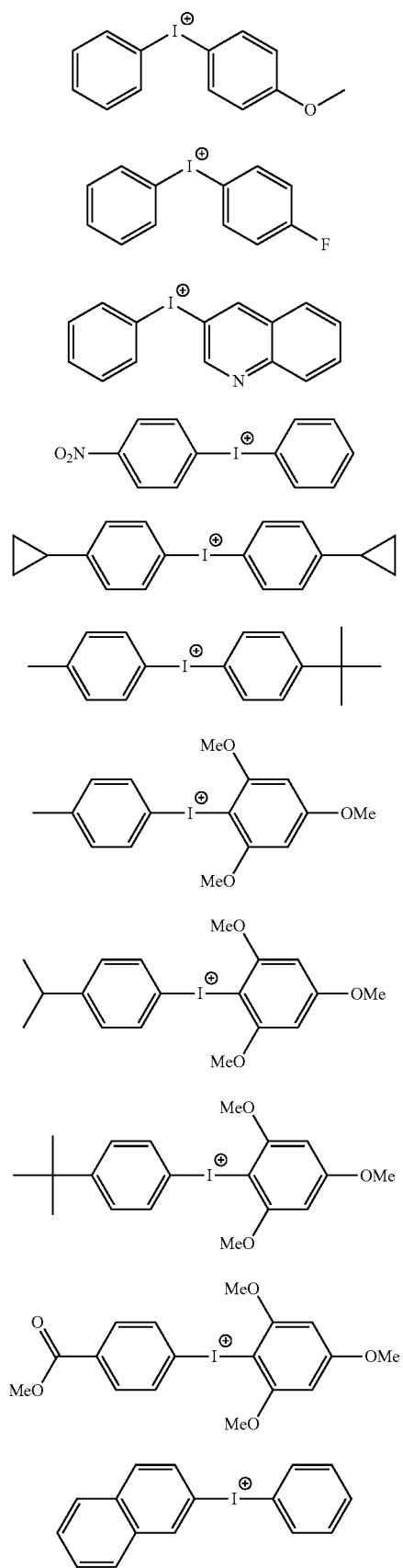
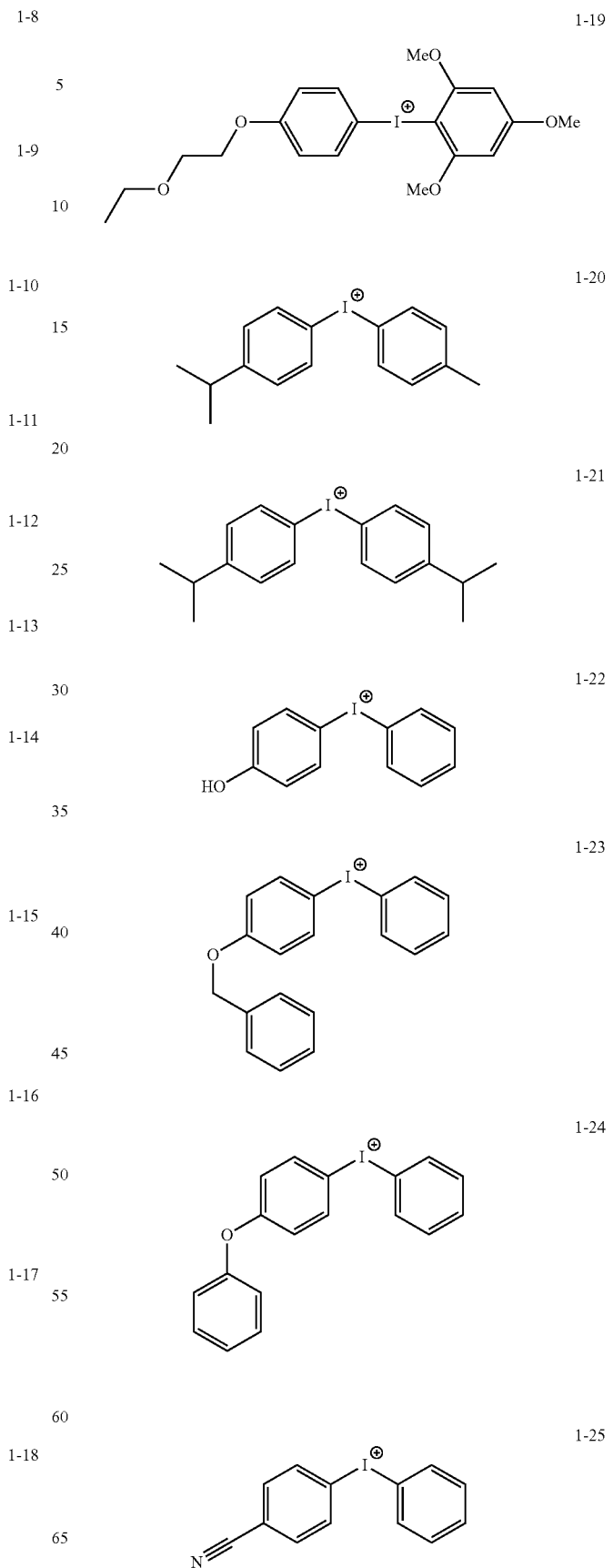

1-26 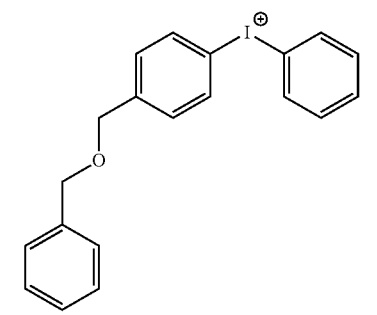
1-27 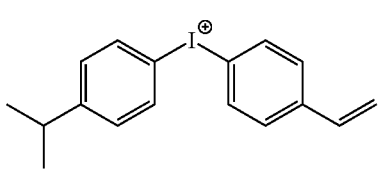
2-1 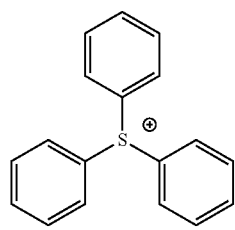
2-2 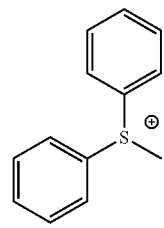
2-3 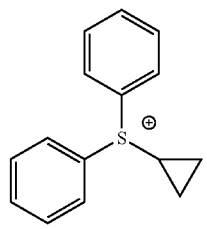
2-4 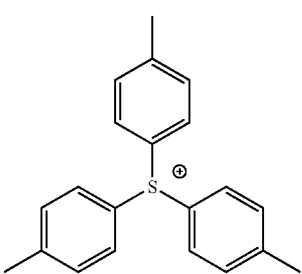
3-1 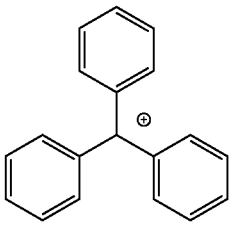
3-2 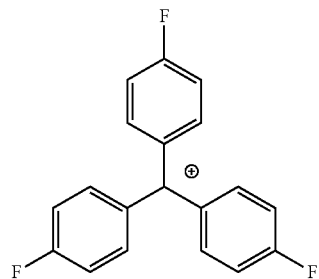
3-3 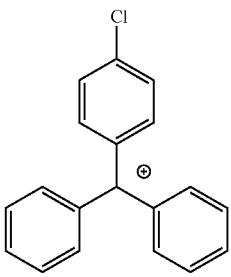
4-1 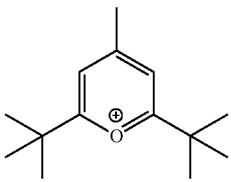
4-2 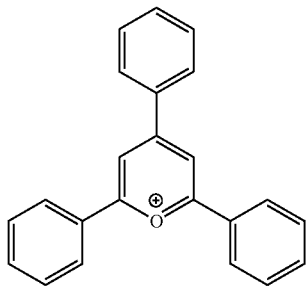
4-3 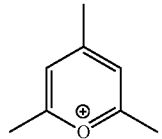

5-1 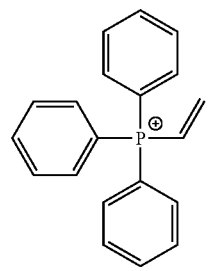
5-2 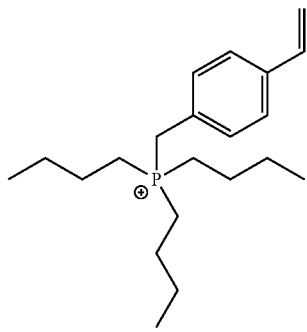
5-3 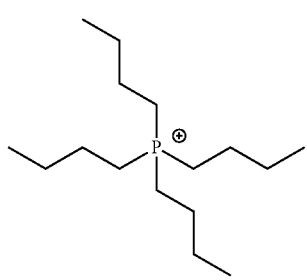
5-4 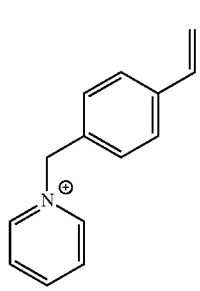
5-5 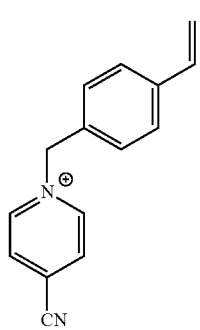
5-6 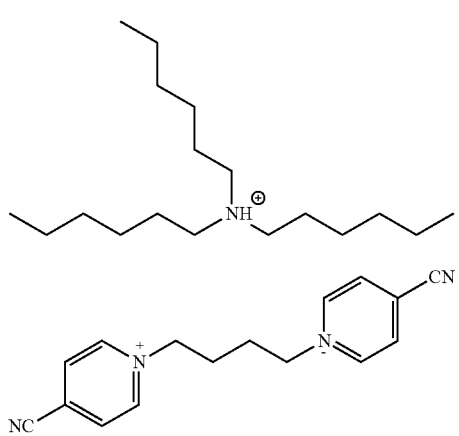
5-7
6-1
6-2
6-3
6-4

-continued
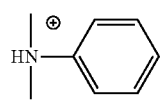
6-5
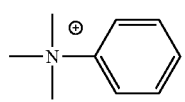
6-6
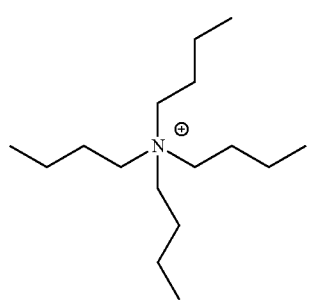
6-7
[Chemical Formula 1-1-1]
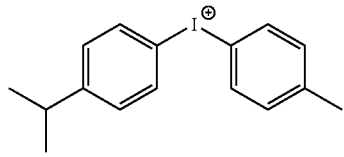
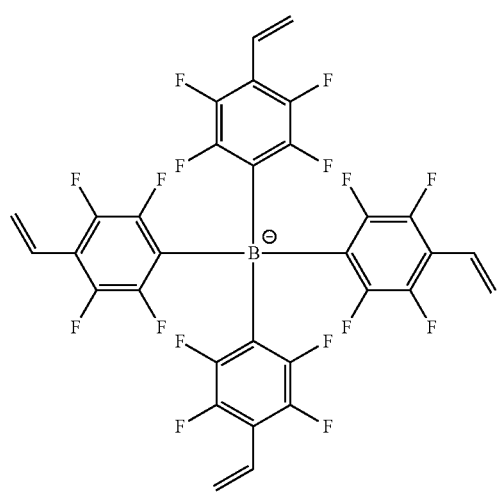
[Chemical Formula 1-1-2]
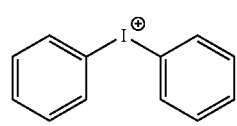
-continued
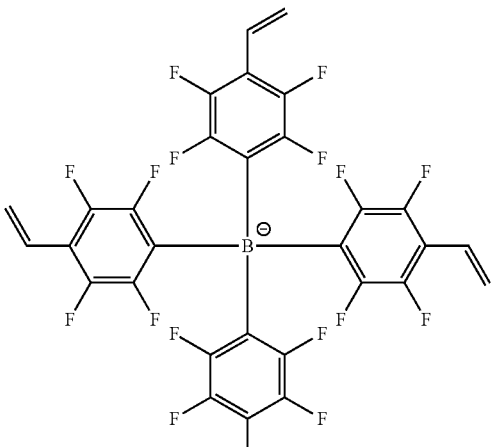
[Chemical Formula 1-1-3]
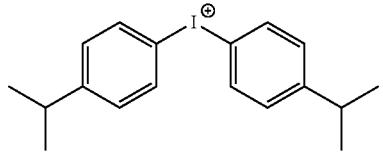
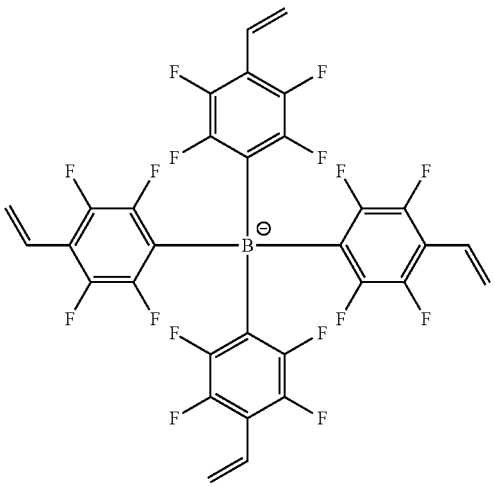
[Chemical Formula 1-1-4]
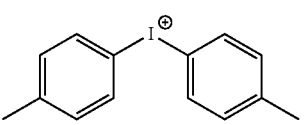

301
-continued
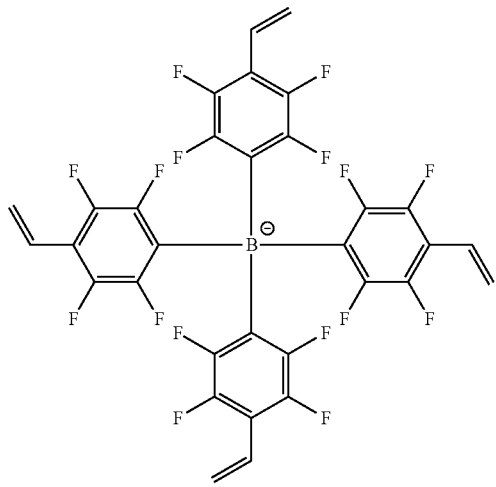
[Chemical Formula 1-1-5]
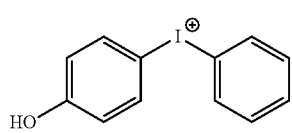
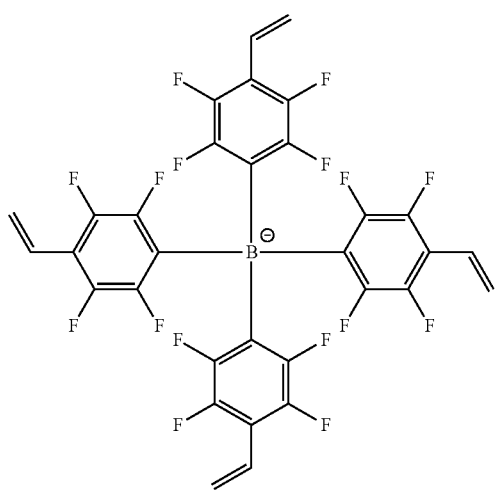
[Chemical Formula 1-1-6]
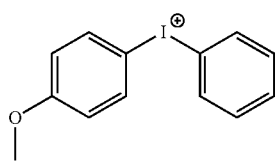
302
-continued
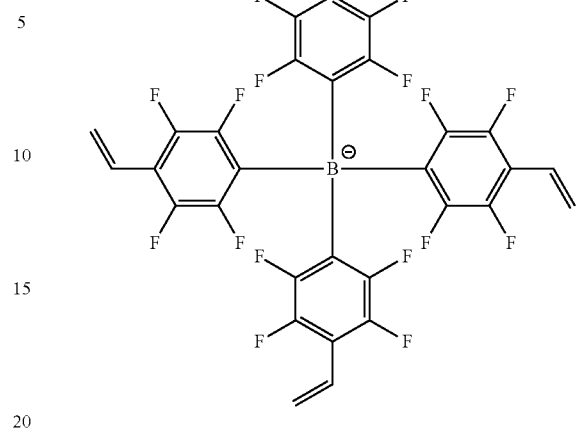
[Chemical Formula 1-1-7]
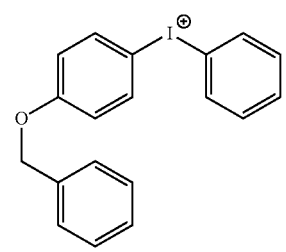
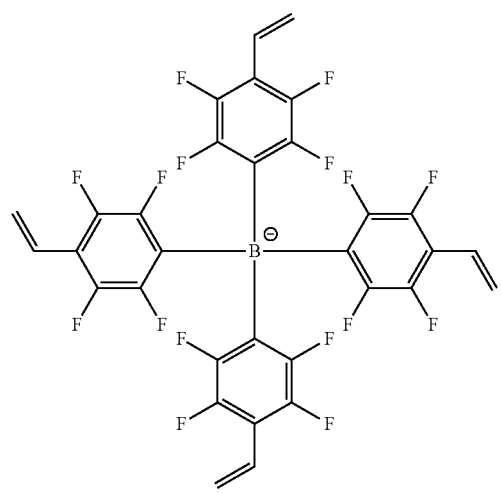
[Chemical Formula 1-1-8]
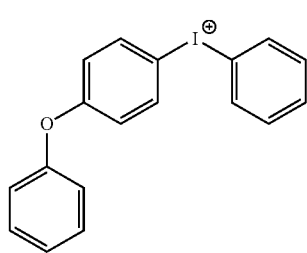

-continued
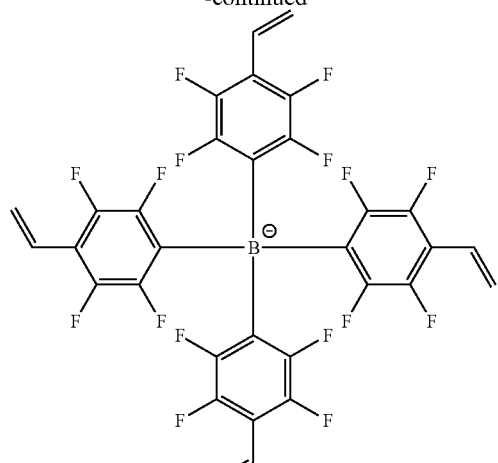
[Chemical Formula 1-1-9]
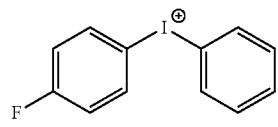
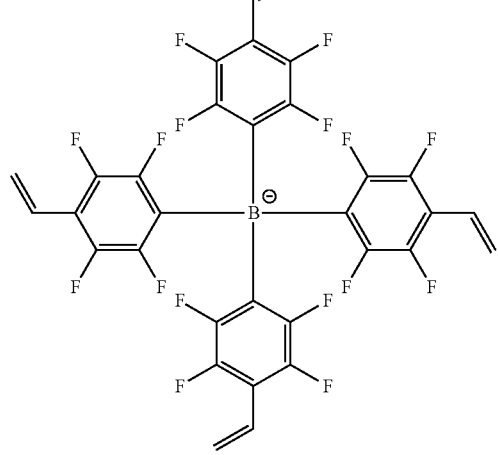
[Chemical Formula 1-1-10]
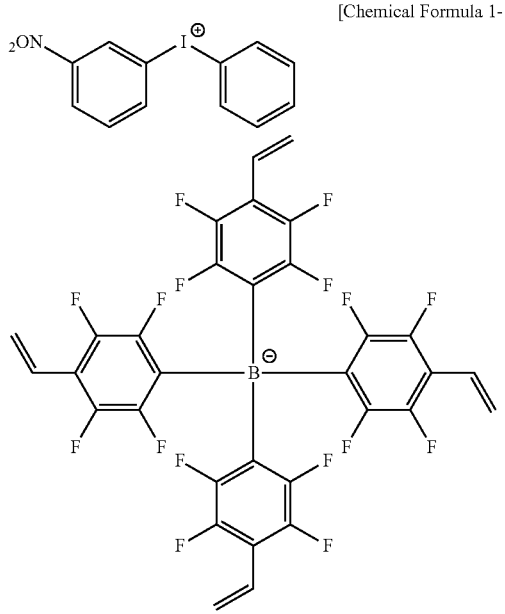
-continued
[Chemical Formula 1-1-11]
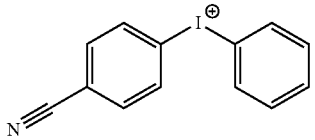
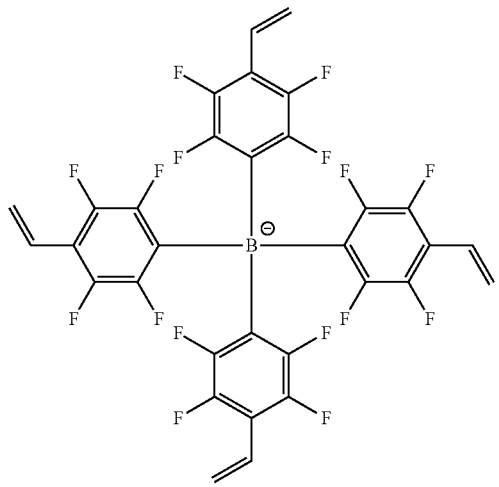
[Chemical Formula 1-1-12]
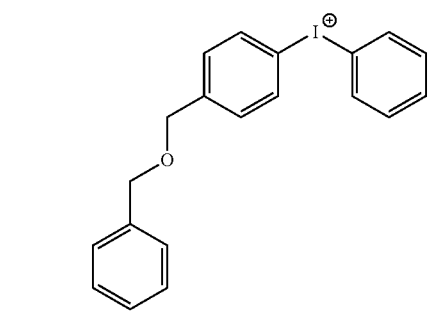
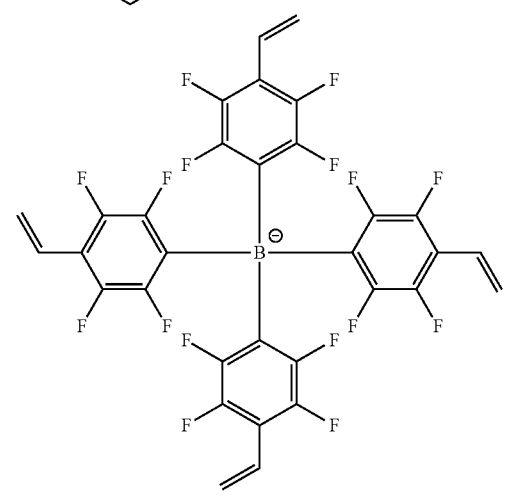
[Chemical Formula 1-1-14]
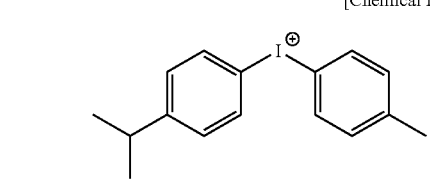

-continued
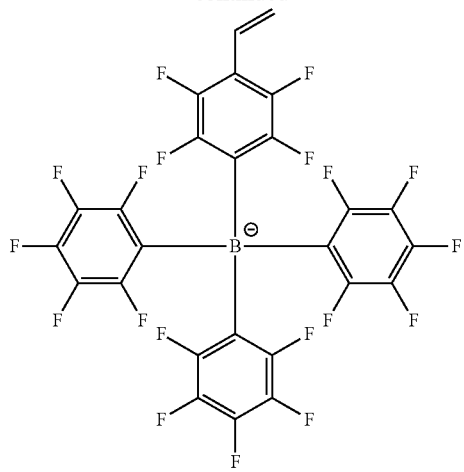
[Chemical Formula 1-1-15]
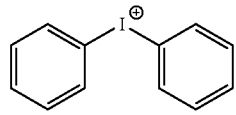
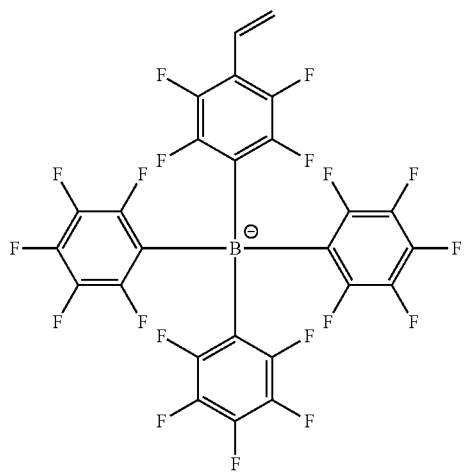
[Chemical Formula 1-1-16]
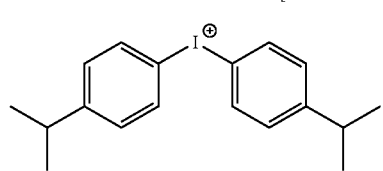
-continued
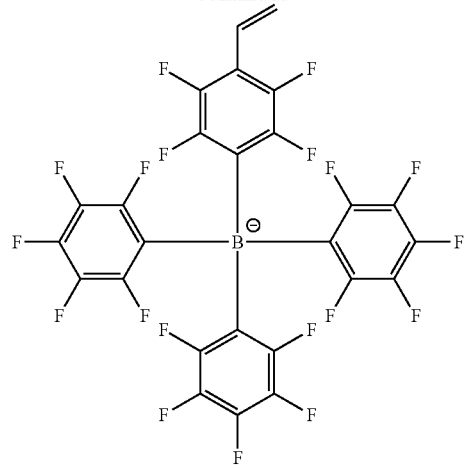
[Chemical Formula 1-1-17]
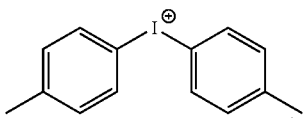
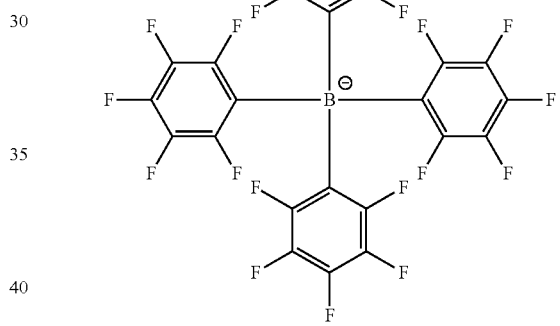
[Chemical Formula 1-1-18]
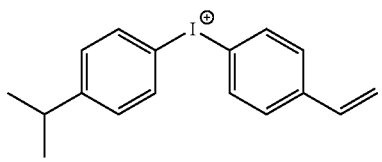
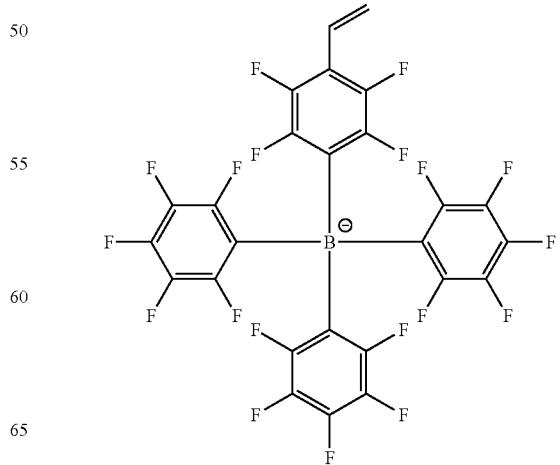

-continued
[Chemical Formula 1-1-19]
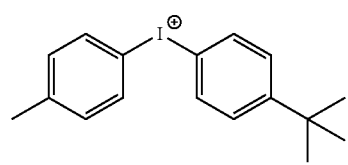
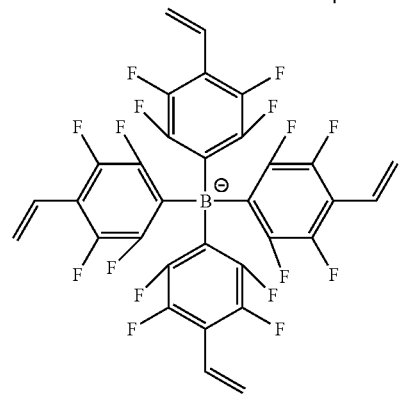
[Chemical Formula 1-1-20]
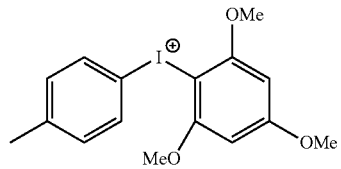
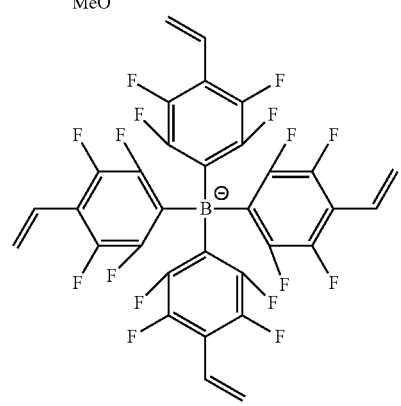
[Chemical Formula 1-1-21]
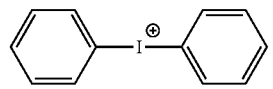
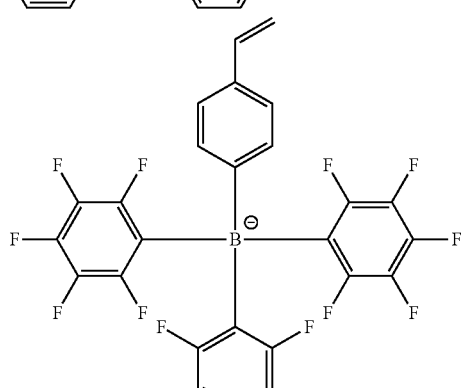
-continued
[Chemical Formula 1-1-21]
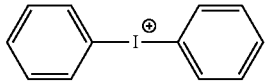
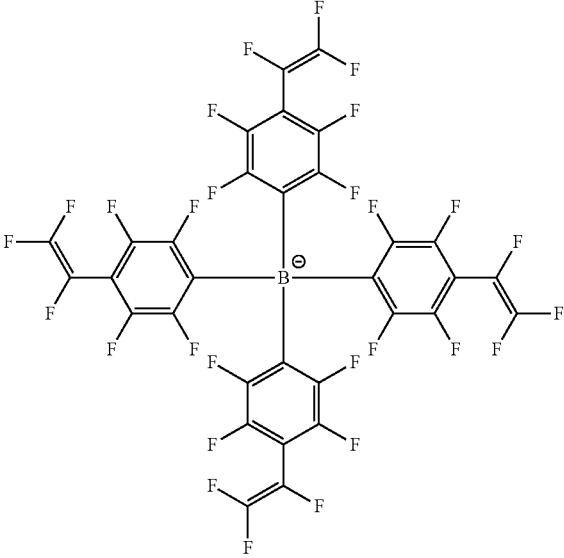
[Chemical Formula 1-1-22]
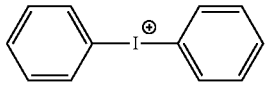
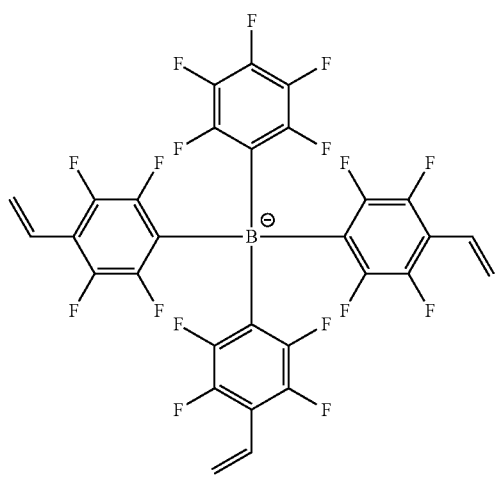
[Chemical Formula 1-1-23]
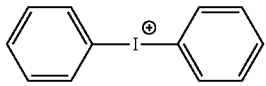

309
-continued
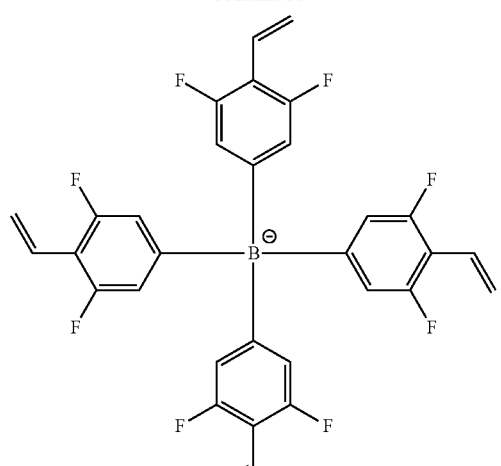
[Chemical Formula 1-1-24]
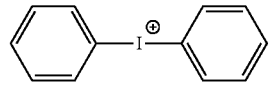
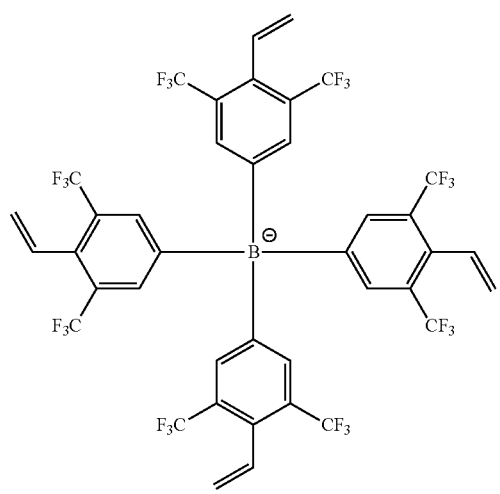
[Chemical Formula 1-1-25]
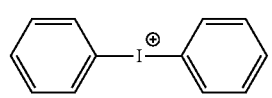
310
-continued
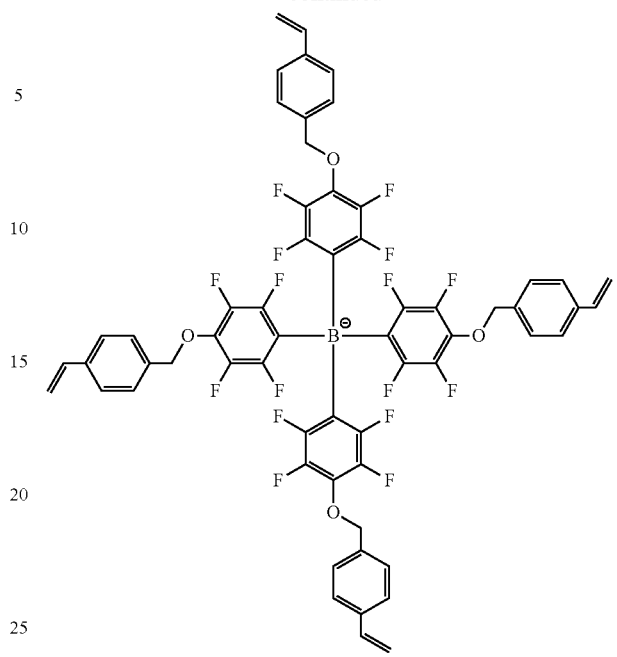
[Chemical Formula 1-1-26]
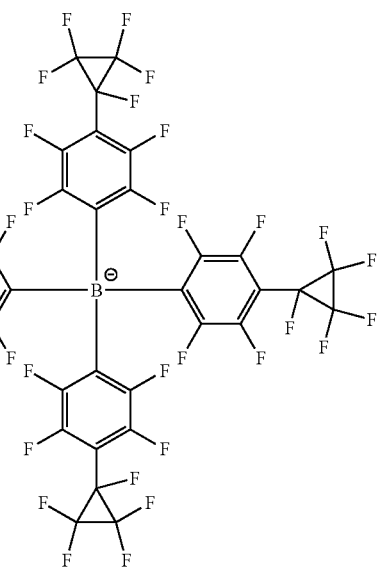
[Chemical Formula 1-2-1]
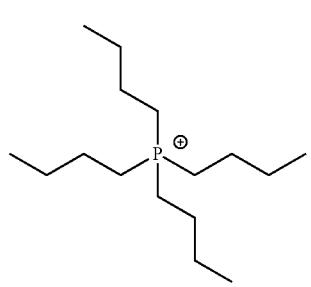

311
-continued
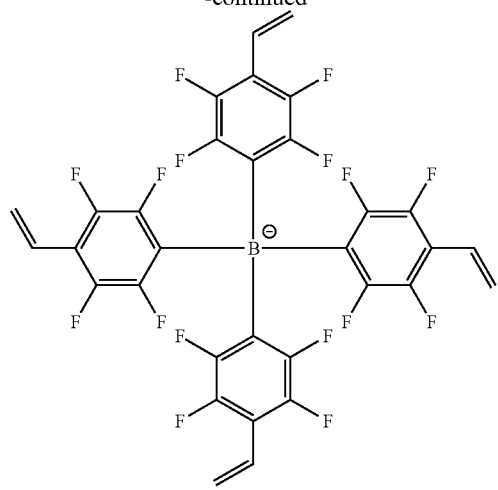
[Chemical Formula 1-2-3]
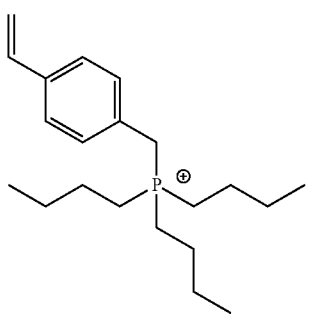
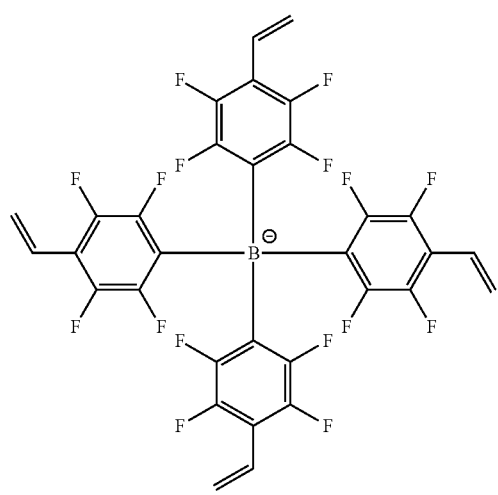
[Chemical Formula 1-2-4]
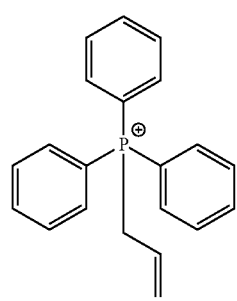
312
-continued
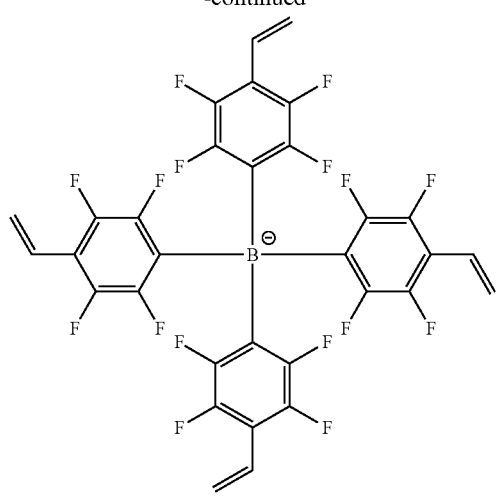
[Chemical Formula 1-2-5]
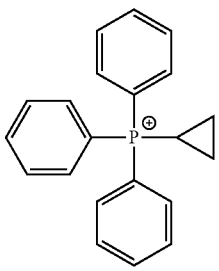
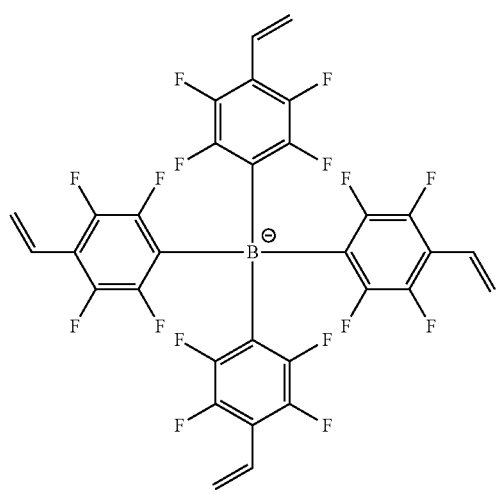
[Chemical Formula 1-3-1]
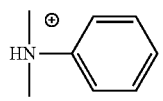

313
-continued
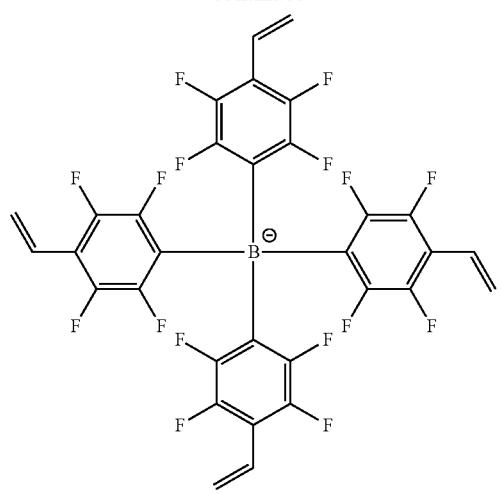
314
-continued
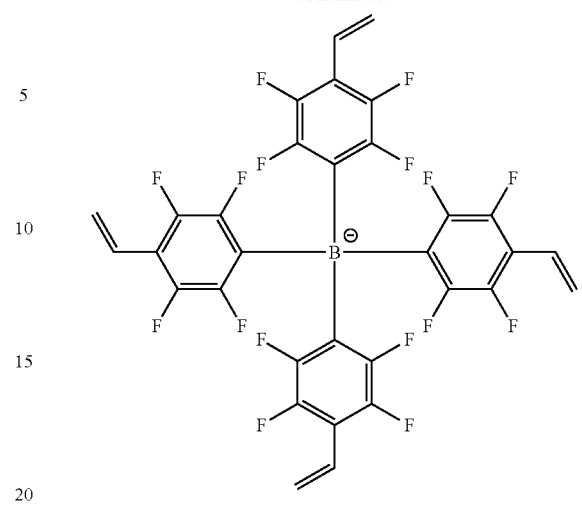
[Chemical Formula 1-3-2]
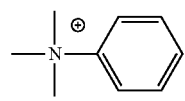
[Chemical Formula 1-3-4]
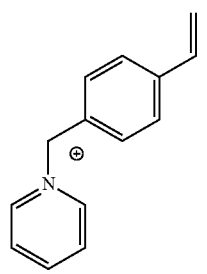
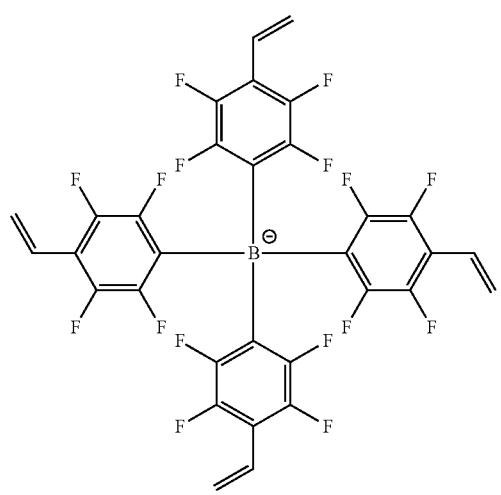
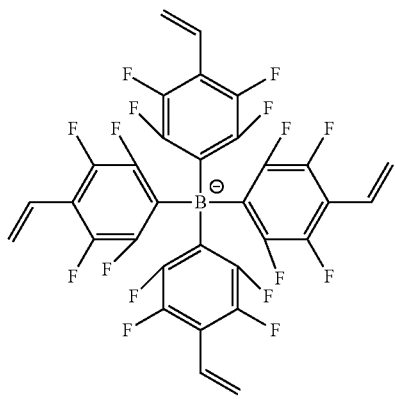
[Chemical Formula 1-3-3]
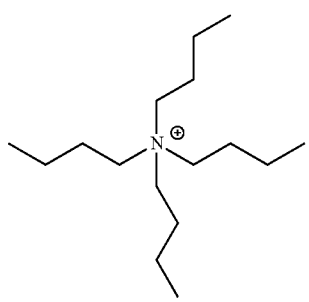
[Chemical Formula 1-4-1]
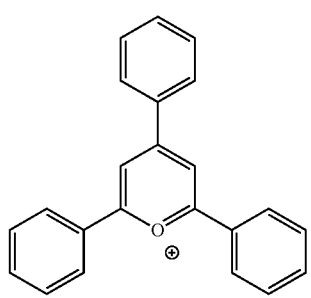

315
-continued
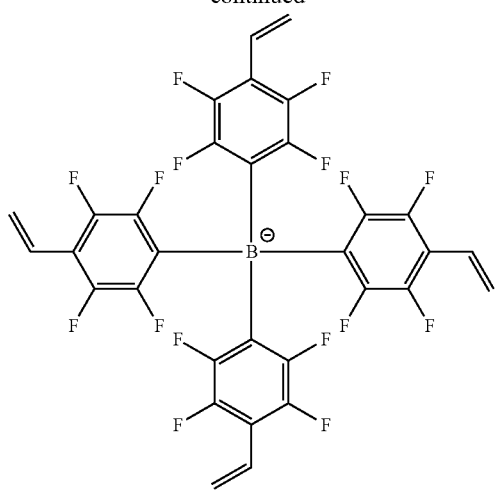
[Chemical Formula 1-5-1]
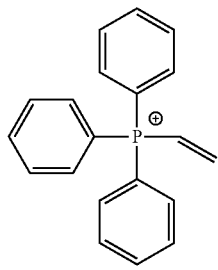
316
-continued
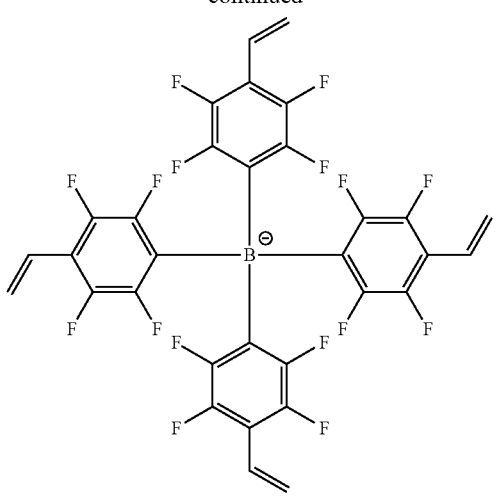
[Chemical Formula 1-5-3]
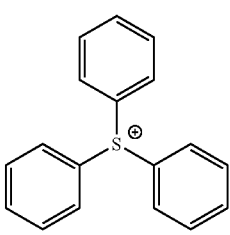
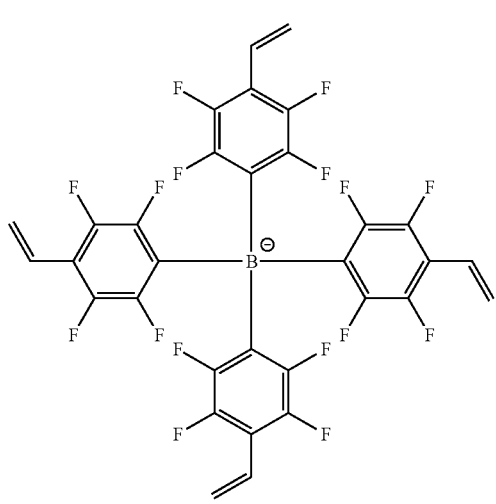
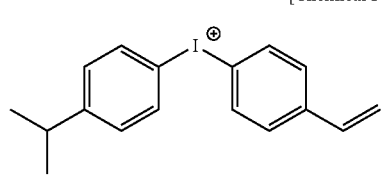
[Chemical Formula 1-5-2]
[Chemical Formula 1-5-4]
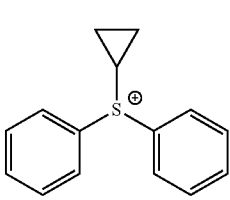

317
-continued

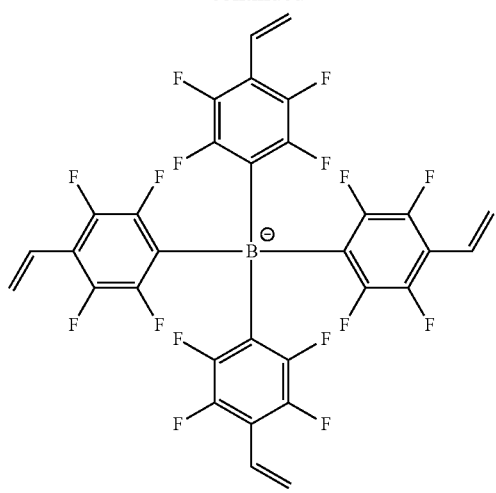

[Chemical Formula 1-5-5]

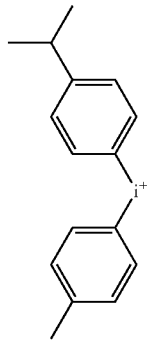

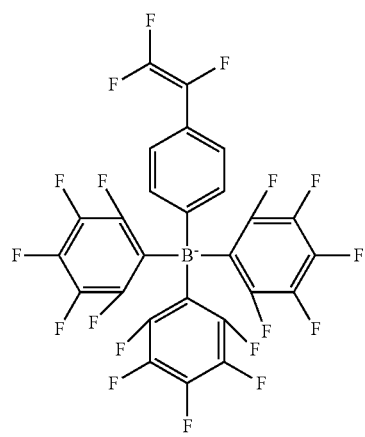

[Chemical Formula 1-5-6]

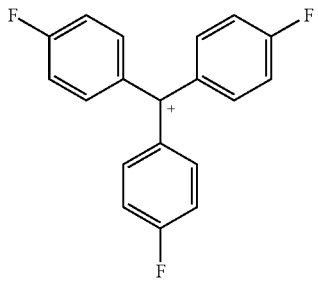

318
-continued

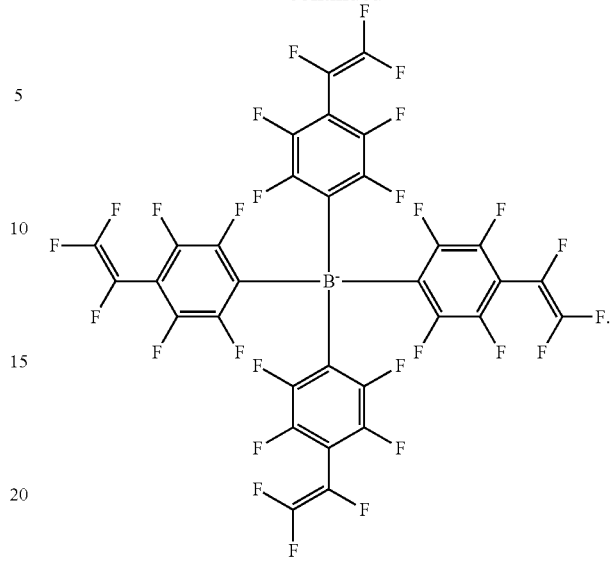

12. The coating composition of claim 1, wherein the ionic compound is selected from among the following structural formulae.

13. An organic light emitting device comprising:
a first electrode;
a second electrode; and
one or more organic material layers provided between the first electrode and the second electrode,
wherein one or more layers of the organic material layers comprise the coating composition of claim 1 or a cured material thereof.

14. The organic light emitting device of claim 13, wherein the organic material layer comprising the cured material of the coating composition is a hole transfer layer or a hole injection layer.

15. The organic light emitting device of claim 13, wherein the cured material of the coating composition is in a cured state by heat treating or light treating the coating composition.

16. A method for manufacturing an organic light emitting device comprising:
preparing a substrate;
forming a first electrode on the substrate;
forming one or more organic material layers on the first electrode; and
forming a second electrode on the organic material layers,
wherein the forming of the organic material layers comprises forming the one or more organic material layers using the coating composition of claim 1.

17. The method for manufacturing an organic light emitting device of claim 16, wherein the forming of the one or more organic material layers using the coating composition uses a spin coating method.

18. The method for manufacturing an organic light emitting device of claim 16, wherein the forming of the one or more organic material layers using the coating composition comprises coating the coating composition on the first electrode; and heat treating or light treating the coated coating composition.

19. The coating composition of claim 1, wherein the ionic compound is present at from 1% by weight to 50% by weight based on the compound represented by the following Chemical Formula 1.

* * * * *